United States Patent
Virgili-Bernado et al.

(10) Patent No.: US 10,703,765 B2
(45) Date of Patent: Jul. 7, 2020

(54) ALKYL AND ARYL DERIVATIVES OF 1-OXA-4,9-DIAZASPIRO UNDECANE COMPOUNDS HAVING MULTIMODAL ACTIVITY AGAINST PAIN

(71) Applicant: LABORATORIOS DEL DR. ESTEVE S.A., Barcelona (ES)

(72) Inventors: Marina Virgili-Bernado, Barcelona (ES); Monica Alonso-Xalma, Barcelona (ES); Carlos Alegret-Molina, Barcelona (ES); Carmen Almansa-Rosales, Barcelona (ES); Monica Garcia Lopez, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 15/314,595

(22) PCT Filed: Jun. 2, 2015

(86) PCT No.: PCT/EP2015/001113
§ 371 (c)(1),
(2) Date: Nov. 29, 2016

(87) PCT Pub. No.: WO2015/185207
PCT Pub. Date: Dec. 10, 2015

(65) Prior Publication Data
US 2017/0101420 A1    Apr. 13, 2017

(30) Foreign Application Priority Data
Jun. 2, 2014   (EP) ..................................... 14382207

(51) Int. Cl.
*C07D 498/10*    (2006.01)
*C07D 519/00*    (2006.01)

(52) U.S. Cl.
CPC ......... *C07D 498/10* (2013.01); *C07D 519/00* (2013.01)

(58) Field of Classification Search
CPC ............................. C07D 498/10; C07D 519/00
See application file for complete search history.

(56) References Cited

U.S. PATENT DOCUMENTS

| | | | |
|---|---|---|---|
| 3,481,942 A | 12/1969 | Loev | |
| 4,353,900 A * | 10/1982 | Clark | ................... C07D 498/10 514/230.8 |
| 6,114,541 A | 9/2000 | Abrecht | |
| 2009/0105290 A1 | 4/2009 | Sundermann | |
| 2009/0298807 A1 | 12/2009 | Alcaraz | |
| 2010/0120841 A1 | 5/2010 | Nakano et al. | |
| 2012/0264749 A1 | 10/2012 | Hadida-Ruah et al. | |
| 2017/0197984 A1 | 7/2017 | Virgili-Bernado et al. | |
| 2017/0313723 A1 | 11/2017 | Virgili-Bernado et al. | |
| 2019/0002475 A1 | 1/2019 | Virgili-Bernado et al. | |

FOREIGN PATENT DOCUMENTS

| | | | |
|---|---|---|---|
| DE | 102005030051 | 6/2005 | |
| EP | 1634873 | 3/2006 | |
| EP | 1847542 | 10/2007 | |
| EP | 1982714 | 10/2008 | |
| JP | WO 2007058322 A1 * | 5/2007 | ........... C07D 233/64 |
| WO | WO 93/13101 | 7/1993 | |
| WO | WO 2007/098961 | 9/2007 | |
| WO | WO-2007124136 A1 * | 11/2007 | ......... A61K 31/4468 |
| WO | WO 2008/105497 | 9/2008 | |
| WO | WO 2008/155132 | 12/2008 | |
| WO | WO 2009/032667 | 3/2009 | |
| WO | WO 2009/071657 | 6/2009 | |
| WO | WO 03/057698 | 7/2009 | |
| WO | WO 2009/0984496 | 8/2009 | |
| WO | WO 2012/125613 | 9/2012 | |
| WO | WO-2013028447 A1 * | 2/2013 | ........... C07D 498/10 |
| WO | WO 2015/017305 | 2/2015 | |
| WO | WO2015152368 | 10/2015 | |
| WO | WO 2015/185207 | 12/2015 | |
| WO | WO2015185208 | 12/2015 | |
| WO | WO2015185209 | 12/2015 | |
| WO | WO201678771 | 5/2016 | |
| WO | WO2017067664 | 4/2017 | |

OTHER PUBLICATIONS

Database Registry, XP002730855, Chemicalabstracts Server, May 12, 2010, datbase Accession No. 1222524-76-6.
International Search Report for PCT/E-2015/001113 dated Jul. 7, 2015.
Bornot et al., J. Med. Chem, 2013, 56, 1197-1210.
Chien, et al., Neuroscience Letters, 1995, 190, pp. 137-139.
Dickenson, et al., Eur J Pain 9, 113-116 (2005).
Friedman, et al., Agnew. Chem. Int. Ed. 2013, 52, pp. 9755-9758.
Goldber, et al., BMC Public Health. 11, 770 (2011).
Mao, et al., J. Pain 12, 157-166 (2011).

(Continued)

*Primary Examiner* — Sudhakar Katakam
(74) *Attorney, Agent, or Firm* — Hueschen and Sage

(57) ABSTRACT

The present invention relates to compounds of general formula (I) having dual pharmacological activity towards both the sigma (σ) receptor, and the μ-opiod receptor and more particularly to diazaspiro undecane compounds having this pharmacological activity, to processes of preparation of such compounds, to pharmaceutical compositions comprising them, and to their use in therapy, in particular for the treatment of pain.

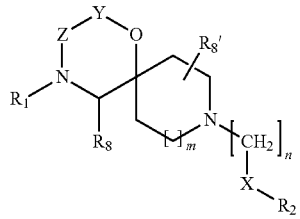

22 Claims, No Drawings

(56) References Cited

OTHER PUBLICATIONS

Turk, et al., Lancet 377, 2226-2235 (2011).
Zamanillo, et al., Eur. J. Pharmacol, 716, 78-93 (2013).
Clark, Journal of Medicinal Chemistry, 1983, 26, 855-861.
Kato, et al., Bioorganic & Medicinal Chemistry Letters, 2014, 24, 565-570.
Stocks, et al., Bioorganic & Medicinal Chemistry Letters, 2010, 20, 7458-7461.
Bowen, W. D. Pharmaceutica Acta Helvetiae 74 (2000), 211-218.
Hanner, et al., Proc. Natl. Acad. Sci., 1996, 93:8072-8077.
International Search Report for PCT/EP2016/001742 dated May 16, 2017.
Kaiser, et al., (1991) Neurotransmissions 7 (1): 1-5).
Quirion, et al., Trends Pharmacol. Sci., 1992, 13:85-86.
Ronsisvalle, et al., Pure Appl. Chem. 73, 1499-1509 (2001).
Snyder, et al., Neuropsychiatry 1989, 1, 7-15.
Walker, et al., Pharmacological Reviews, 1990, vol. 42, No. 4, 355-402.

\* cited by examiner

ALKYL AND ARYL DERIVATIVES OF 1-OXA-4,9-DIAZASPIRO UNDECANE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid) and more particularly to diazaspiro-undecane derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. Lancet 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. BMC Public Health. 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. Opioids in neuropathic pain: Clues from animal studies. Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 (σ) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. Neurosci. Lett. 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. Eur. J. Pharmacol, 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. J. Pain 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opiod receptor and to the σ$_1$ receptor.

The prior art document DE 10 2005 030051 A1 discloses compounds which are inhibitors of the μ-opioid receptor and differ from compounds of the present invention through the character of the bicyclic core.

Document WO 2008/155132 A1 disclose compounds which are inhibitors of the receptor and differ from compounds of the present invention through the character of the bicyclic core.

WO 2012/125613 A1 discloses compounds which are modulators of the ion channels and differ from compounds of the present invention through the invariable presence of carboxy group on the nitrogen atom of piperidine.

SUMMARY OF THE INVENTION

In this invention a family of structurally distinct diazaspiro undecane derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the σ$_1$ receptor and the μ-opioid receptor for use in the treatment of pain.

As this invention is aimed at providing a compound or a chemically related series of compounds which act as dual ligands of the σ$_1$ receptor and the μ-opioid receptor it is a very preferred embodiment if the compound has a binding expressed as K$_i$ which is preferably <1000 nM for both receptors, more preferably <500 nM, even more preferably <100 nM.

The invention is directed in a main aspect to a compound of general formula (I),

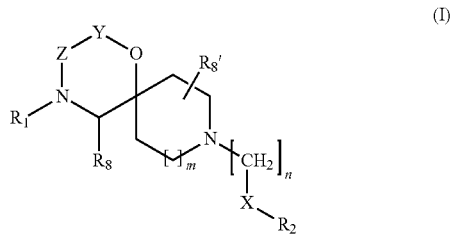

wherein R$^1$, R$^2$, R$^8$, R$^{8'}$, X, Y, Z, m and n are as defined below in the detailed description.

DETAILED DESCRIPTION OF THE INVENTION

The invention is directed to a family of structurally distinct diazaspiro undecane derivatives which have a dual pharmacological activity towards both the sigma (σ) receptor and the μ-opiod receptor, thus solving the above problem of identifying alternative or improved pain treatments by offering such dual compounds.

The invention is in one aspect directed to a compound having a dual activity binding to the σ$_1$ receptor and the μ-opioid receptor for use in the treatment of pain.

As this invention is aimed at providing a compound or a chemically related series of compounds which act as dual ligands of the σ$_1$ receptor and the μ-opioid receptor it is a preferred embodiment if the compound has a binding expressed as K$_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to μ-opioid receptor and to σ$_1$ receptor), thereby enhancing the opioid analgesia through the σ$_1$ activation without increasing the undesirable side effects. This supports the therapeutic value of a dual MOW σ$_1$ receptor compound whereby the σ$_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ opioid receptor agonists.

A dual compound that possess binding to both the μ-opiod receptor and to the σ$_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: σ$_1$ receptor antagonism and μ-opioid receptor agonism. It has to be noted, though, that both functionalities "antagonism" and "agonism" are also subdivided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while σ$_1$ receptor antagonists show outstanding effects in preclinical neuropathic pain models. Thus, the σ$_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem,* 56, 1197-1210 (2013)].

In a particular aspect, the present invention is directed to compounds of general formula (I):

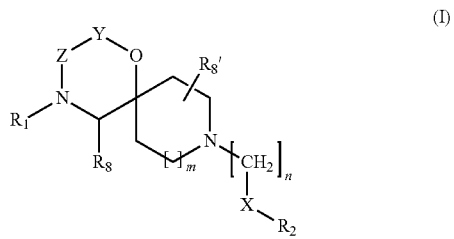

wherein

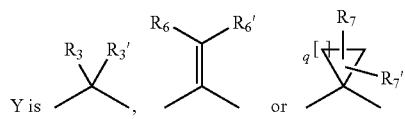

Z is —$CH_2$—, —C(O)— or —$CHR_9$—
m is 0 or 1
n is 1, 2 or 3
q is 1, 2, 3, 4, 5 or 6
$R_1$ is substituted or unsubstituted aryl, substituted or unsubstituted heterocyclyl, substituted or unsubstituted alkylaryl, substituted or unsubstituted alkylheterocyclyl or —(CH2)$_r$-W—$R_{1'}$;
r is 0, 1 or 2;
W is a bond, —$CH_2O$—, —$CH_2C(O)NR_5$—, —$CH_2C(O)O$—, —$CH_2C(O)$— or —$C(CH_3)_2O$—;
$R_{1'}$ is H, —CN, substituted or unsubstituted heterocyclyl, substituted or unsubstituted aryl, substituted or unsubstituted cycloalkyl or $R_5$;
X is a bond, —C(O)O—, —C(O)$NR_5$—, —C(O)—, —O— or —C($R_4R_{4'}$)—;
$R_2$ is H, substituted or unsubstituted aryl, substituted or unsubstituted heterocyclyl, substituted or unsubstituted cycloalkyl, substituted or unsubstituted $C_{1-6}$ alkyl, substituted or unsubstituted $C_{2-6}$ alkenyl or substituted or unsubstituted $C_{2-6}$ alkynyl,
$R_3$ and $R_{3'}$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl and —$CH_2R_4$;
$R_4$ is H, —$OR_5$, substituted or unsubstituted $C_{1-6}$ alkyl, substituted or unsubstituted $C_{2-6}$ alkenyl, substituted or unsubstituted $C_{2-6}$ alkynyl, —$COOR_5$, —$CONR_5R_{5'}$, —$NR_5COR_{5'}$, —$NR_5R_{5'''}$ or unsubstituted heterocyclyl, unsubstituted aryl, unsubstituted cycloalkyl;
$R_{4'}$ is H or substituted or unsubstituted $C_{1-6}$ alkyl, substituted or unsubstituted $C_{2-6}$ alkenyl or substituted or unsubstituted $C_{2-6}$ alkynyl;
$R_5$, $R_{5'}$ and $R_{5''}$ are independently selected from H, unsubstituted $C_{1-6}$ alkyl, unsubstituted $C_{2-6}$ alkenyl, unsubstituted $C_{2-6}$ alkynyl, unsubstituted aryl or unsubstituted alkylaryl;

$R_{5'''}$ is H, unsubstituted $C_{1-6}$ alkyl, unsubstituted $C_{2-6}$ alkenyl, unsubstituted $C_{2-6}$ alkynyl or -Boc;

$R_6$, $R_{6'}$, $R_7$ and $R_{7'}$ are independently selected from H, halogen, —$OR_5$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_{8'}$ are independently selected from H, —$OR_5$, halogen, substituted or unsubstituted $C_{1-6}$ alkyl, substituted or unsubstituted $C_{2-6}$ alkenyl or substituted or unsubstituted $C_{2-6}$ alkynyl;

$R_9$ is selected from H, substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

Please note that "or a corresponding salt thereof" does also mean "or a corresponding pharmaceutically acceptable salt thereof". This does apply to all below described embodiments and uses of "salt" being thus equivalent to "pharmaceutically acceptable salt".

In one embodiment the following proviso (P1) is applying:

when W is a bond, then $R_{1'}$ cannot be H, alkyl, alkenyl, alkynyl or cycloalkyl.

In another embodiment the following alternative proviso to above proviso P1 is applying:

when W is a bond, then $R_{1'}$ cannot be hydrogen, unsubstituted alkyl, unsubstituted alkenyl, unsubstituted alkynyl or unsubstituted cycloalkyl.

In another embodiment the following alternative proviso to above proviso P1 is applying:

when W is a bond, then $R_{1'}$ cannot be hydrogen, unsubstituted alkyl, unsubstituted alkenyl, unsubstituted alkynyl or substituted or unsubstituted cycloalkyl.

In another embodiment one or more of the the following compounds being further excluded:

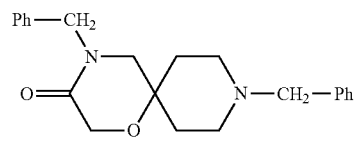

and/or

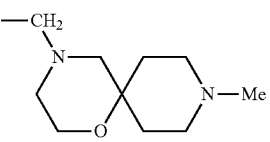

and/or

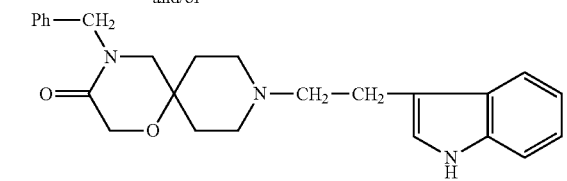

and/or

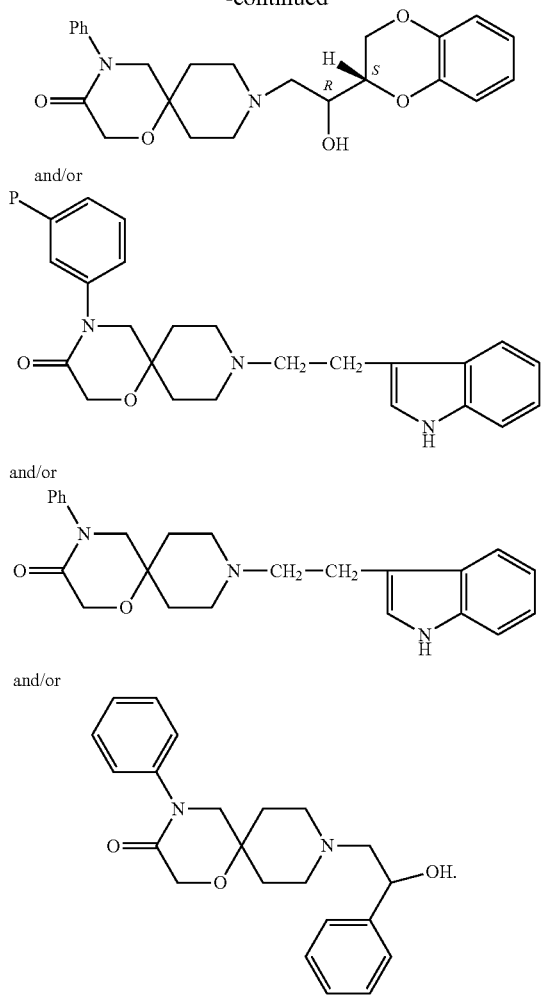

and/or

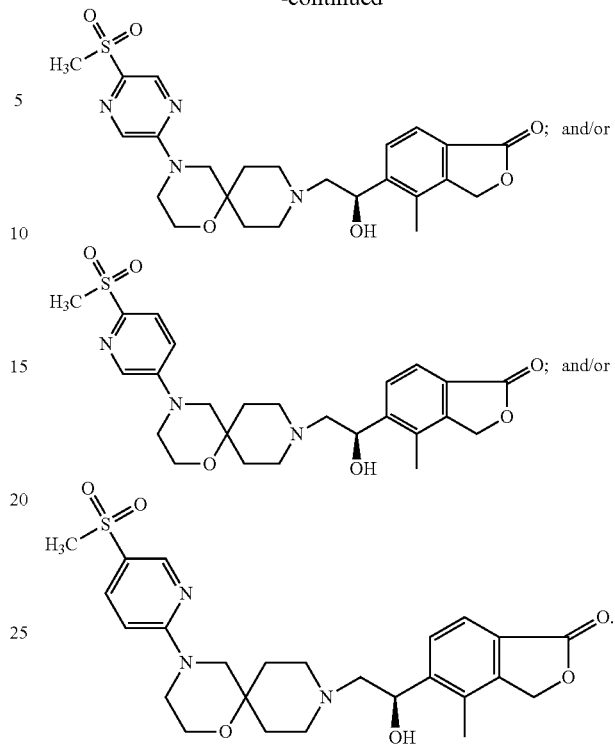

In a very preferred embodiment all of the above disclaimers (including all the compounds described above as excluded and either proviso P1 or on of its 2 alternatives) apply. This would then also apply to all below described embodiments (if still applicable).

In another embodiment of the compounds of the invention according to general Formula (I) as described above and herein, the following one or more—preferably all—of the following compounds are excluded:

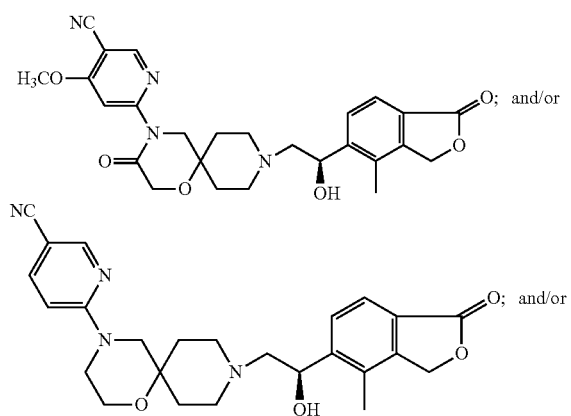

In another embodiment of the compounds of the invention according to general Formula (I) as described above and herein, the following proviso applies:

if —[CH$_2$]$_n$—X—R$_2$ is

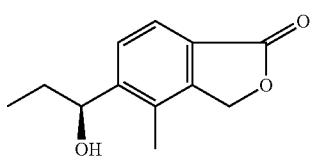

Y is

and Z is

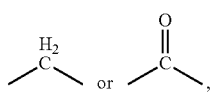

then R$_1$ may not be pyridine or pyrazine substituted with —CN or —SO$_2$CH3.

In the context of this invention, alkyl is understood as meaning saturated, linear or branched hydrocarbons, which may be unsubstituted or substituted once or several times. It encompasses e.g. —CH$_3$ and —CH$_2$—CH$_3$. In these radicals, C$_{1-2}$-alkyl represents C1- or C2-alkyl, C$_{1-3}$-alkyl represents C1-, C2- or C3-alkyl, C$_{1-4}$-alkyl represents C1-, C2-, C3- or C4-alkyl, C$_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH≡CH—$CH_3$. The alkenyl radicals are preferably vinyl (ethenyl), allyl (2-propenyl). Preferably in the context of this invention alkenyl is $C_{2-10}$-alkenyl or $C_{2-5}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl, alkenyl, alkynyl and O-alkyl—unless defined otherwise—the term substituted in the context of this invention is understood as meaning replacement of at least one hydrogen radical on a carbon atom by halogen (F, Cl, Br, I), $NR_5R_{5'''}$, $SR_5$, —$S(O)R_5$, —$S(O)_2R_5$, $OR_5$, —$C(O)OR_5$, —CN, $C(O)NR_5R_{5'}$, haloalkyl, haloalkoxy or —$OC_{1-4}$alkyl being unsubstituted or substituted by one or more of $OR_5$ or halogen (F, Cl, I, Br), being $R_4$, $R_{4'}$, $R_5$, $R_{5'}$, $R_{5''}$ and $R_{5'''}$ as defined above, and wherein when different radicals $R_1$ to $R_{8'}$ are present simultaneously in Formulas I to I''' they may be identical or different. More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$, when different radicals $R_1$ to $R_9$ are present simultaneously in Formula I, I', I'' or I''' they may be identical or different.

Most preferably in connection with alky, alkenyl, alkynyl or O-alkyl, substituted is understood in the context of this invention that any alky, alkenyl, alkynyl or O-alkyl which is substituted is substituted by one or more of halogen (F, Cl, I, Br), —$NR_5R_{5'''}$, —$SR_5$, —$OR_5$, —$C(O)OR_5$, —CN, $C(O)NR_5R_{5'}$, haloalkyl, haloalkoxy or —$OC_{1-4}$alkyl being unsubstituted or substituted by one or more of $OR_5$ or halogen (F, Cl, I, Br), being $R_4$, $R_{4'}$, $R_5$, $R_{5'}$, $R_{5''}$ and $R_{5'''}$ as defined above, and wherein when different radicals $R_1$ to $R_9$ are present simultaneously in Formulas I to I''' they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkyl is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkyl-aryl is understood as meaning an aryl group (see above) being connected to another atom through 1 to 4 (—$CH_2$—) groups. Most preferably alkyl-aryl is benzyl (i.e. —$CH_2$-phenyl).

In the context of this invention alkylheterocyclyl is understood as meaning an heterocyclyl group (see underneath) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group (see above) being connected to another atom through 1 to 4 (—CH$_2$—) groups. Most preferably alkylcycloalkyl is —CH$_2$-cyclopropyl.

In a general definition a heterocyclyl radical or group is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times. Examples include heteroaryls such as furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline. Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring. Preferred examples include imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, pyrazole, thiophene, indole, benzimidazole, pyrrolo[2,3b]pyridine, benzoxazole, oxopyrrolidine, pyrimidine.

In a more specific definition, a heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.
  the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;
  the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

Preferably, the aryl is a monocyclic aryl.
Preferably, the heteroaryl is a monocyclic heteroaryl.
Preferably, the non-aromatic heterocyclyl is a monocyclic non-aromatic heterocyclyl.
Preferably, the cycloalkyl is a monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl by halogen (F, Cl, Br, I), —R$_5$, —OR$_5$, —CN, —NO$_2$, —NR$_5$R$_{5'}$, —C(O)OR$_5$, NR$_5$C(O)R$_{5'}$, —C(O)NR$_5$R$_{5'}$, —NR$_5$S(O)$_2$R$_{5'}$, =O, —OCH$_2$CH$_2$OH, —NR$_5$C(O)NR$_5$R$_{5'''}$, —S(O)$_2$NR$_5$R$_{5'}$, —NR$_5$S(O)$_2$NR$_5$R$_{5'''}$, haloalkyl, haloalkoxy, —SR5, —S(O)R$_5$ or —S(O)$_2$R$_5$; NR$_x$R$_y$, with R$_x$ and R$_y$ independently being either H or a saturated or unsaturated, linear or branched, substituted or unsubstituted C$_{1-6}$-alkyl; a saturated or unsaturated, linear or branched, substituted or unsubstituted C$_{1-6}$-alkyl; a saturated or unsaturated, linear or branched, substituted or unsubstituted —O—C$_{1-6}$-alkyl (alkoxy); a saturated or unsaturated, linear or branched, substituted or unsubstituted —S—C$_{1-6}$-alkyl; a saturated or unsaturated, linear or branched, substituted or unsubstituted —C(O)—C$_{1-6}$-alkyl-group; a saturated or unsaturated, linear or branched, substituted or unsubstituted —C(O)—O—C$_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being R$_4$, R$_{4'}$, R$_5$, R$_{5'}$, R$_{5''}$ and R$_{5'''}$ as defined above, and wherein when different radicals R$_1$ to R$_9$ are present simultaneously in Formulas I to I''' they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted (also in an alyklaryl, alkylcycloalkyl or alkylheterocyclyl) is substituted by one or more of halogen (F, Cl, Br, I), —R$_5$, —OR$_5$, —CN, —NO$_2$, —NR$_5$R$_{5'''}$, —C(O)OR$_5$, NR$_5$C(O)R$_{5'}$, —C(O)NR$_5$R$_{5'}$, —NR$_5$S(O)$_2$R$_{5'}$, =O, —OCH$_2$CH$_2$OH, —NR$_5$C(O)NR$_5$R$_{5'''}$, —S(O)$_2$NR$_5$R$_{5'}$, —NR$_5$S(O)$_2$NR$_5$R$_{5'''}$, haloalkyl, —OC$_{1-4}$alkyl being unsubstituted or substituted by one or more of OR$_5$ or halogen (F, Cl, I, Br), —CN, or —C$_{1-4}$alkyl being unsubstituted or substituted by one or more of OR$_5$ or halogen (F, Cl, I, Br), being R$_4$, R$_{4'}$, R$_5$, R$_{5'}$, R$_{5''}$ and R$_{5'''}$ as defined above, and wherein when different radicals R$_1$ to R$_9$ are present simultaneously in Formulas I to I''' they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted (also in alkylaryl, alkyl-cycloalkyl or alkylheterocyclyl) is substituted by one or more of halogen (F, Cl, Br, I), —R$_5$, —OR$_5$, —CN, —NO$_2$, —NR$_5$R$_{5'''}$, NR$_5$C(O)R$_{5'}$, —C(O)NR$_5$R$_{5'}$, —NR$_5$S(O)$_2$R$_{5'}$, —OCH$_2$CH$_2$OH, —NR$_5$C(O)NR$_5$R$_{5'''}$, —S(O)$_2$NR$_5$R$_{5'}$, —NR$_5$S(O)$_2$NR$_5$R$_{5'''}$, haloalkyl, —OC$_{1-4}$alkyl being unsubstituted or substituted by one or more of OR$_5$ or halogen (F, Cl, I, Br), —CN, or —C$_{1-4}$alkyl being unsubstituted or substituted by one or more of OR$_5$ or halogen (F, Cl, I, Br), being R$_4$, R$_{4'}$, R$_5$, R$_{5'}$, R$_{5''}$ and R$_{5'''}$ as defined above, and wherein when different radicals R$_1$ to R$_9$ are present simultaneously in Formulas I to I''' they may be identical or different.

Additionally to the above-mentioned substitutions, in connection with cycloalkyl, or heterocycly namely non-aromatic heterocyclyl, substituted is also understood—unless defined otherwise—as meaning substitution of the ring-system of the cycloalkyl or; non-aromatic heterocyclyl with ▽ or =O.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH$_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those Derivatives that are converted in vivo to the compounds of the invention. Such Derivatives would readily occur to those skilled in the art, and include, depending on the functional groups present in the molecule and without limitation, the following Derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or of a nitrogen by $^{15}$N-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general formula I, is a compound wherein
Y is

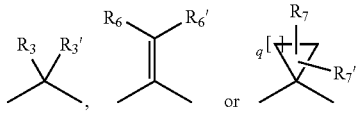

Z is —CH$_2$—, —C(O)— or —CHR$_9$—
m is 0 or 1
n is 1, 2 or 3
q is 1, 2, 3, 4, 5 or 6
R$_1$ is —(CH2)$_r$-W—R$_{1'}$
r is 0, 1 or 2
W is a bond, —CH$_2$O—, —CH$_2$C(O)NR$_5$—, —CH$_2$C(O)O—, —CH$_2$C(O)— or —C(CH$_3$)$_2$O—;
R$_{1'}$ is H, —CN, substituted or unsubstituted heterocyclyl, substituted or unsubstituted aryl, substituted or unsubstituted cycloalkyl or R$_5$;
X is a bond, —C(O)O—, —C(O)NR$_5$—, —C(O)—, —O— or —C(R$_4$R$_{4'}$)—;
R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl,
R$_3$ and R$_{3'}$ are independently selected from H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl and —CH$_2$R$_4$;
R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR$_5$R$_{5'''}$ or unsubstituted heterocyclyl, unsubstituted aryl, unsubstituted cycloalkyl;
R$_{4'}$ is H, substituted or unsubstituted C$_{1-6}$ alkyl, substituted or unsubstituted C$_{2-6}$ alkenyl or substituted or unsubstituted C$_{2-6}$ alkynyl;
R$_5$, R$_{5'}$ and R$_{5''}$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;

R$_{5'''}$ is H, unsubstituted C$_{1-6}$ alkyl, unsubstituted C$_{2-6}$ alkenyl, unsubstituted C$_{2-6}$ alkynyl or -Boc;
R$_6$, R$_{6'}$, R$_7$ and R$_{7'}$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;
R$_8$ and R$_{8'}$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl;
R$_9$ is selected from H, substituted or unsubstituted C$_{1-6}$ alkyl, substituted or unsubstituted C$_{2-6}$ alkenyl or substituted or unsubstituted C$_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof. In a very preferred embodiment of this embodiment r is 1 or 2 when W is a bond.

In another preferred embodiment of the compound according to the invention according to general formula I is a compound wherein
Y is

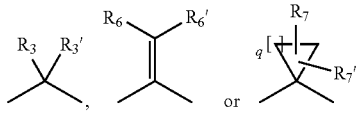

Z is —CH$_2$—, —C(O)— or —CHR$_9$—
m is 0 or 1
n is 1, 2 or 3
q is 1, 2, 3, 4, 5 or 6
R$_1$ is substituted or unsubstituted aryl, substituted or unsubstituted heterocyclyl, substituted or unsubstituted alkylaryl, or substituted or unsubstituted alkylheterocyclyl
X is a bond, —C(O)O—, —C(O)NR$_5$—, —C(O)—, —O— or —C(R$_4$R$_{4'}$)—;
R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl,
R$_3$ and R$_{3'}$ are independently selected from H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl and —CH$_2$R$_4$;
R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR$_5$R$_{5'''}$ or unsubstituted heterocyclyl, unsubstituted aryl, unsubstituted cycloalkyl;
R$_{4'}$ is H, substituted or unsubstituted C$_{1-6}$ alkyl, substituted or unsubstituted C$_{2-6}$ alkenyl or substituted or unsubstituted C$_{2-6}$ alkynyl;
R$_5$, R$_{5'}$ and R$_{5''}$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;
R$_{5'''}$ is H, unsubstituted C$_{1-6}$ alkyl, unsubstituted C$_{2-6}$ alkenyl, unsubstituted C$_{2-6}$ alkynyl or -Boc;
R$_6$, R$_{6'}$, R$_7$ and R$_{7'}$ are independently selected from H, halogen, —OR$_5$, substituted or unsubstituted C$_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_{8'}$ are independently selected from H, —OR$_5$, halogen, substituted or unsubstituted $C_{1-6}$ alkyl, substituted or unsubstituted $C_{2-6}$ alkenyl or substituted or unsubstituted $C_{2-6}$ alkynyl;

$R_9$ is selected from H, substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, In one embodiment the one or more of the following compounds are excluded:

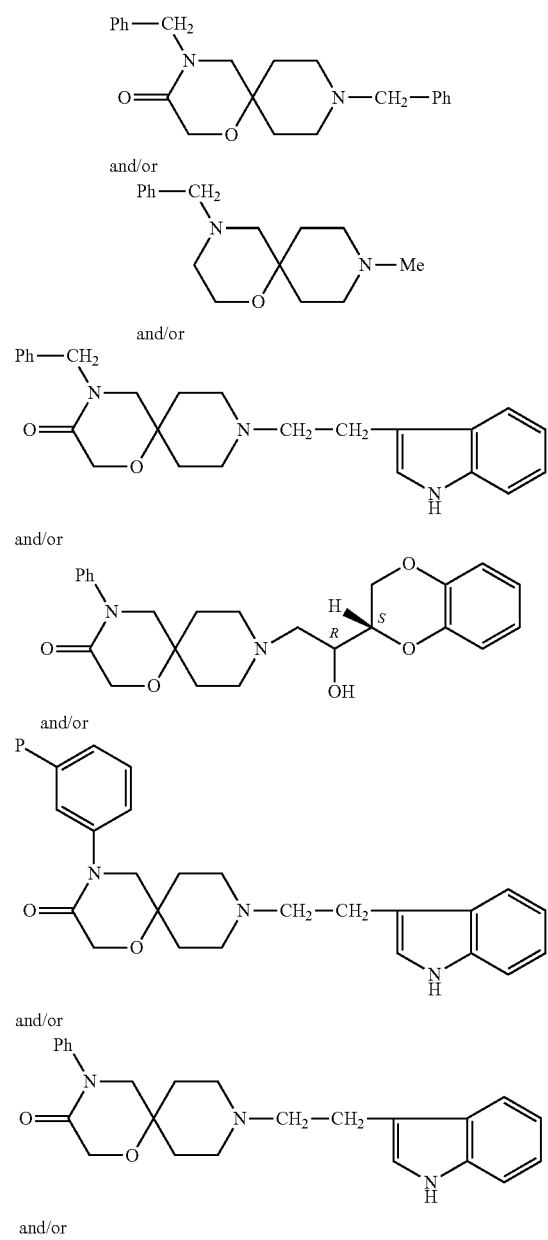

and/or

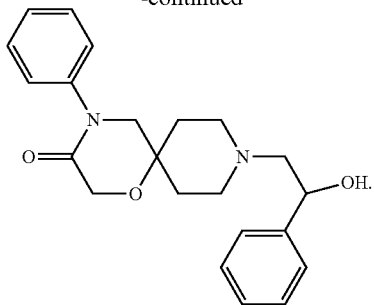

In a preferred embodiment (EMBODIMENT DA) of the compound according to the invention the compound is a compound according to Formula I

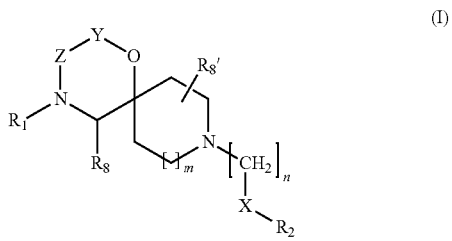

wherein
Y is

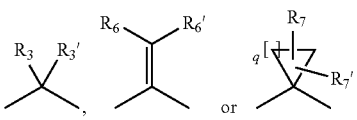

Z is —CH$_2$—, —C(O)— or —CHR$_9$—;
m is 0 or 1;
n is 1, 2 or 3;
q is 1, 2, 3, 4, 5 or 6;
$R_1$ is substituted or unsubstituted aryl, substituted or unsubstituted heterocyclyl, substituted or unsubstituted alkylaryl, substituted or unsubstituted alkylheterocyclyl or —(CH2)$_r$-W—R$_{1'}$;
r is 0, 1 or 2;
W is a bond, —CH$_2$O—, —CH$_2$C(O)NR$_5$—, —CH$_2$C(O)O—, —CH$_2$C(O)— or —C(CH$_3$)$_2$O—;
$R_{1'}$ is H, —CN, substituted or unsubstituted heterocyclyl, substituted or unsubstituted aryl, substituted or unsubstituted cycloalkyl or R$_5$;
wherein the aryl, heterocyclyl or cycloalkyl in R$_1$ or R$_{1'}$ if substituted (also in alkylaryl or alkylheterocyclyl) are substituted with substituents selected from —R$_5$, —OR$_5$, halogen, —CN, —NO$_2$, —NR$_5$R$_{5'''}$, —C(O)OR$_5$, NR$_5$C(O)R$_{5'}$, —C(O)NR$_5$R$_{5'}$, —NR$_5$S(O)$_2$R$_{5'}$, =O, —OCH$_2$CH$_2$OH, —NR$_5$C(O)NR$_{5'}$R$_{5''}$, —S(O)$_2$NR$_5$R$_{5'}$, —NR$_5$S(O)$_2$NR$_5$R$_{5''}$, haloalkyl, haloalkoxy, —SR5, —S(O)R$_5$ or —S(O)$_2$R$_5$;
X is a bond, —C(O)O—, —C(O)NR$_5$—, —C(O)—, —O— or —C(R$_4$R$_{4'}$)—;
$R_2$ is H, substituted or unsubstituted aryl, substituted or unsubstituted heterocyclyl, substituted or unsubstituted cycloalkyl, substituted or unsubstituted $C_{1-6}$ alkyl, substituted or unsubstituted $C_{2-6}$ alkenyl or substituted or unsubstituted $C_{2-6}$ alkynyl, wherein the aryl, heterocyclyl or cycloalkyl in R₂ if substituted also in alkylaryl or alkylheterocyclyl is substituted with substituents selected from —R₅, —OR₅, halogen, —CN, —NO₂, —NR₅R₅‴, —C(O)OR₅, —NR₅C(O)R₅', —C(O)NR₅R₅', —NR₅S(O)₂R₅', =O, —OCH₂CH₂OH, —NR₅C(O)NR₅R₅‴, —S(O)₂NR₅R₅', —NR₅S(O)₂NR₅R₅‴, haloalkyl, -haloalkoxy, —SR₅, —S(O)R₅ or —S(O)₂R₅

R₃ and R₃' are independently selected from H, substituted or unsubstituted C₁₋₆ alkyl, substituted or unsubstituted C₂₋₆ alkenyl, substituted or unsubstituted C₂₋₆ alkynyl, substituted or unsubstituted cycloalkyl, substituted or unsubstituted aryl, substituted or unsubstituted heterocyclyl, substituted or unsubstituted alkylaryl, substituted or unsubstituted alkylcycloalkyl and substituted or unsubstituted alkylheterocyclyl, wherein the aryl, cycloalkyl and heterocyclyl as defined in R₃ if substituted are substituted with substituents selected from —OR₅, halogen, —CN, haloalkyl, haloalkoxy, —SR₅, —S(O)R₅ or —S(O)₂R₅;

R₄ is H, —OR₅, substituted or unsubstituted C₁₋₆ alkyl, substituted or unsubstituted C₂₋₆ alkenyl, substituted or unsubstituted C₂₋₆ alkynyl, —COOR₅, —CONR₅R₅', —NR₅COR₅', —NR5R5'" or substituted or unsubstituted heterocyclyl, substituted or unsubstituted aryl, substituted or unsubstituted cycloalkyl, wherein the aryl, cycloalkyl and heterocyclyl as defined in R₄ if substituted are substituted with substituents selected from —OR₅, halogen, —CN, haloalkyl, haloalkoxy, —SR₅, —S(O)R₅ or —S(O)₂R₅;

R₄' is H, substituted or unsubstituted C₁₋₆ alkyl, substituted or unsubstituted C₂₋₆ alkenyl or substituted or unsubstituted C₂₋₆ alkynyl;

R₅, R₅' and R₅‴ are independently selected from H, unsubstituted C₁₋₆ alkyl, unsubstituted C₂₋₆ alkenyl, unsubstituted C₂₋₆ alkynyl, unsubstituted aryl or unsubstituted alkylaryl;

R₅‴ is H, unsubstituted C₁₋₆ alkyl, unsubstituted C₂₋₆ alkenyl, unsubstituted C₂₋₆ alkynyl or -Boc;

R₆, R₆', R₇ and R₇' are independently selected from H, halogen, —OR₅, substituted or unsubstituted C₁₋₆ alkyl, substituted or unsubstituted C₂₋₆ alkenyl, substituted or unsubstituted C₂₋₆ alkynyl, unsubstituted heterocyclyl, unsubstituted aryl and unsubstituted cycloalkyl;

R₈ and R₈' are independently selected from H, —OR₅, halogen, substituted or unsubstituted C₁₋₆ alkyl, substituted or unsubstituted C₂₋₆ alkenyl or substituted or unsubstituted C₂₋₆ alkynyl;

R₉ is selected from H, substituted or unsubstituted C₁₋₆ alkyl, substituted or unsubstituted C₂₋₆ alkenyl or substituted or unsubstituted C₂₋₆ alkynyl;

and wherein
the alkyl, alkenyl and alkynyl as defined in R₁, R₁', R₂, R₃, R₃', R₄, R₄', R₆, R₆', R₇, R₇', R₈, R₈' and R₉ if substituted are substituted with substituents selected from —OR₅, halogen, —CN, haloalkyl, haloalkoxy, —SR₅, —S(O)R₅, —S(O)₂R₅, C(O)OR₅ or C(O)NR₅R₅';

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In this EMBODIMENT DA the following proviso might apply:
"when W is a bond, then R₁' cannot be H, alkyl, alkenyl, alkynyl or cycloalkyl".

In this EMBODIMENT DA the following proviso might apply:

"the following compound being excluded from the general formula I:

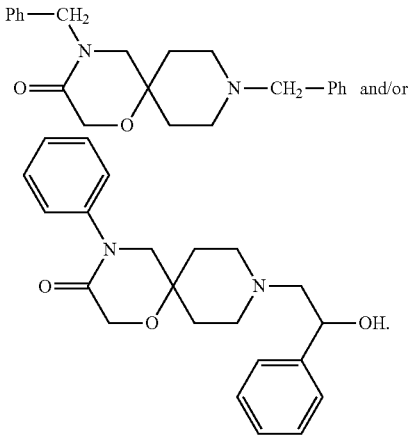

In another preferred embodiment (EMBODIMENT DB) of the compound according to the invention the compound is a compound according to Formula I

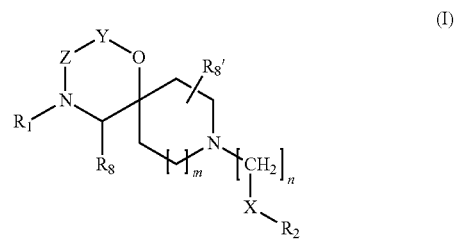

(I)

wherein
Y is

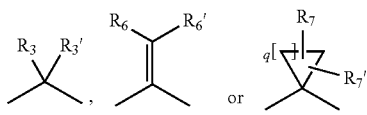

Z is —CH₂—, —C(O)— or —CHR₉—;
m is 0 or 1;
n is 1, 2 or 3;
q is 1, 2, 3, 4, 5 or 6;
R₁ is substituted or unsubstituted aryl, substituted or unsubstituted heterocyclyl, substituted or unsubstituted alkylaryl, substituted or unsubstituted alkylheterocyclyl, —(CH2)ᵣ-W—R₁', or —(CH2)ᵣ-R₁‴;
r is 0, 1 or 2;
W is a —CH₂O—, —CH₂C(O)NR₅—, —CH₂C(O)O—, —CH₂C(O)— or —C(CH₃)₂O—;
R₁' is H, —CN, substituted or unsubstituted heterocyclyl, substituted or unsubstituted aryl, substituted or unsubstituted cycloalkyl or R₅;
R₁‴ is —CN, substituted or unsubstituted heterocyclyl, substituted or unsubstituted aryl;
wherein the aryl, heterocyclyl or cycloalkyl in R₁, R₁' or R₁‴ if substituted (also in alkylaryl or alkylheterocyclyl) are substituted with substituents selected from —R₅, —OR₅, halogen, —CN, —NO₂, —NR₅R₅‴, —C(O)OR₅, NR₅C(O)

$R_{5'}$, —C(O)NR$_5$R$_{5'}$, —NR$_5$S(O)$_2$R$_{5'}$, =O, —OCH$_2$CH$_2$OH, —NR$_5$C(O)NR$_5$R$_{5'}$, —S(O)$_2$NR$_5$R$_{5'}$, —NR$_5$S(O)$_2$NR$_5$R$_{5''}$, haloalkyl, haloalkoxy, —SR5, —S(O)R$_5$ or —S(O)$_2$R$_5$;

X is a bond, —C(O)O—, —C(O)NR$_5$—, —C(O)—, —O— or —C(R$_4$R$_{4'}$)—;

R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl;

wherein the aryl, heterocyclyl or cycloalkyl in R$_2$ if substituted (also in alkylaryl or alkylheterocyclyl) is substituted with substituents selected from —R$_5$, —OR$_5$, halogen, —CN, —NO$_2$, —NR$_5$R$_{5'''}$, —C(O)OR$_5$, —NR$_5$C(O)R$_{5'}$, —C(O)NR$_5$R$_{5'}$, —NR$_5$S(O)$_2$R$_{5'}$, =O, —OCH$_2$CH$_2$OH, —NR$_5$C(O)NR$_5$R$_{5''}$, —S(O)$_2$NR$_5$R$_{5'}$, —NR$_5$S(O)$_2$NR$_5$R$_{5'''}$, haloalkyl, -haloalkoxy, —SR$_5$, —S(O)R$_5$ or —S(O)$_2$R$_5$ R$_3$ and R$_{3'}$ are independently selected from H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, and substituted or unsubstituted alkylcycloalkyl, wherein the aryl, cycloalkyl and heterocyclyl as defined in R$_3$ if substituted are substituted with substituents selected from —OR$_5$, halogen, —CN, haloalkyl, haloalkoxy, —SR$_5$, —S(O)R$_5$ or —S(O)$_2$R$_5$;

R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR5R5''' or substituted or unsubstituted heterocyclyl, substituted or unsubstituted aryl, substituted or unsubstituted cycloalkyl, wherein the aryl, cycloalkyl and heterocyclyl as defined in R$_4$ if substituted are substituted with substituents selected from —OR$_5$, halogen, —CN, haloalkyl, haloalkoxy, —SR$_5$, —S(O)R$_5$ or —S(O)$_2$R$_5$;

R$_{4'}$ is H, substituted or unsubstituted C$_{1-6}$ alkyl, substituted or unsubstituted C$_{2-6}$ alkenyl or substituted or unsubstituted C$_{2-6}$ alkynyl;

R$_5$, R$_{5'}$ and R$_{5''}$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;

R$_{5'''}$ is H, unsubstituted C$_{1-6}$ alkyl, unsubstituted C$_{2-6}$ alkenyl, unsubstituted C$_{2-6}$ alkynyl or -Boc;

R$_6$, R$_{6'}$, R$_7$ and R$_{7'}$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;

R$_8$ and R$_{8'}$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl;

R$_9$ is selected from H, substituted or unsubstituted C$_{1-6}$ alkyl, substituted or unsubstituted C$_{2-6}$ alkenyl or substituted or unsubstituted C$_{2-6}$ alkynyl;

and wherein the alkyl, alkenyl and alkynyl as defined in R$_1$, R$_{1'}$, R$_2$, R$_3$, R$_{3'}$, R$_4$, R$_{4'}$, R$_6$, R$_{6'}$, R$_7$, R$_{7'}$, R$_8$, R$_{8'}$ and R$_9$ if substituted are substituted with substituents selected from —OR$_5$, halogen, —CN, haloalkyl, haloalkoxy, —SR$_5$, —S(O)R$_5$, —S(O)$_2$R$_5$, C(O)OR$_5$ or C(O)NR$_5$R$_{5'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In this embodiment DB the following proviso might apply:

"the following compounds being excluded from the general formula I:

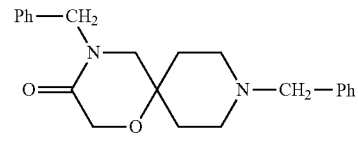

and/or

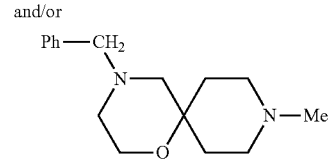

and/or

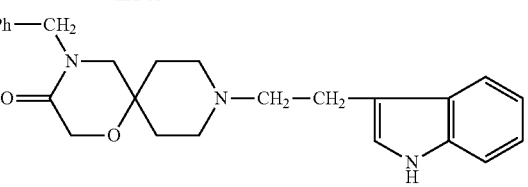

and/or

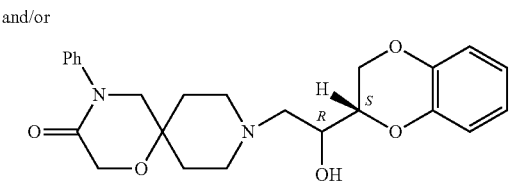

and/or

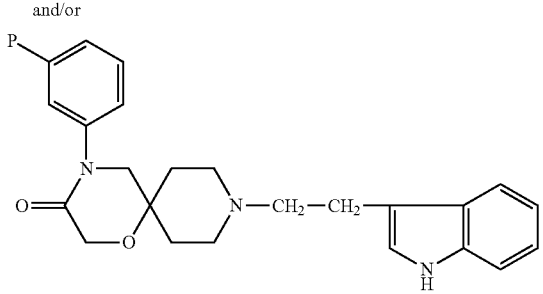

and/or

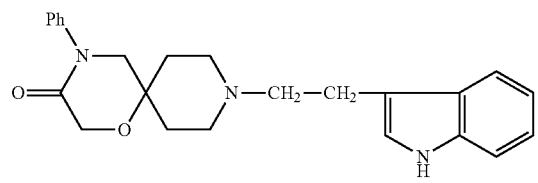

and/or

-continued

In another preferred embodiment (EMBODIMENT DC) of the compound according to the invention the compound is a compound according to Formula I (I)

wherein
Y is

Z is —CH$_2$—, —C(O)— or —CHR$_9$—;
m is 0 or 1;
n is 1, 2 or 3;
q is 1, 2, 3, 4, 5 or 6;
R$_1$ is substituted or unsubstituted aryl, substituted or unsubstituted heterocyclyl, substituted or unsubstituted alkylaryl, substituted or unsubstituted alkylheterocyclyl, —(CH2)$_r$-W—R$_1'$, or —(CH2)$_r$-R$_1''$;
r is 0, 1 or 2;
W is a —CH$_2$O—, —CH$_2$C(O)NR$_5$—, —CH$_2$C(O)O—, —CH$_2$C(O)— or —C(CH$_3$)$_2$O—;
R$_1'$ is H, —CN, substituted or unsubstituted heterocyclyl, substituted or unsubstituted aryl, substituted or unsubstituted cycloalkyl or R$_5$;
R$_1''$ is —CN, substituted or unsubstituted heterocyclyl, substituted or unsubstituted aryl;
wherein the aryl, heterocyclyl or cycloalkyl in R$_1$, R$_1'$ or R$_1''$ if substituted (also in alkylaryl or alkylheterocyclyl) are substituted with substituents selected from —R$_5$, —OR$_5$, halogen, —CN, —NO$_2$, —NR$_5$R$_5'''$, —C(O)OR$_5$, NR$_5$C(O)R$_5'$, —C(O)NR$_5$R$_5'$, —NR$_5$S(O)$_2$R$_5'$, =O, —OCH$_2$CH$_2$OH, —NR$_5$C(O)NR$_5$R$_5'''$, —S(O)$_2$NR$_5$R$_5'$, —NR$_5$S(O)$_2$NR$_5$R$_5'''$, haloalkyl, haloalkoxy, —SR5, —S(O)R$_5$ or —S(O)$_2$R$_5$;
X is a bond, —C(O)O—, —C(O)NR$_5$—, —C(O)—, —O— or —C(R$_4$R$_4'$)—;
R$_2$ is substituted or unsubstituted aryl, substituted or unsubstituted monocyclic heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl;
wherein the aryl, heterocyclyl or cycloalkyl in R$_2$ if substituted (also in alkylaryl or alkylheterocyclyl) is substituted with substituents selected from —R$_5$, —OR$_5$, halogen, —CN, —NO$_2$, —NR$_5$R$_5'''$, —C(O)OR$_5$, —NR$_5$C(O)R$_5'$, —C(O)NR$_5$R$_5'$, —NR$_5$S(O)$_2$R$_5'$, =O, —OCH$_2$CH$_2$OH, —NR$_5$C(O)NR$_5$R$_5'''$, —S(O)$_2$NR$_5$R$_5'$, —NR$_5$S(O)$_2$NR$_5$R$_5'''$, haloalkyl, -haloalkoxy, —SR$_5$, —S(O)R$_5$ or —S(O)$_2$R$_5$ R$_3$ and R$_3'$ are independently selected from H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl and substituted or unsubstituted alkylcycloalkyl;
wherein the aryl, cycloalkyl and heterocyclyl as defined in R$_3$ if substituted are substituted with substituents selected from —OR$_5$, halogen, —CN, haloalkyl, haloalkoxy, —SR$_5$, —S(O)R$_5$ or —S(O)$_2$R$_5$;
R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_5'$, —NR$_5$COR$_5'$, —NR5R5''' or substituted or unsubstituted heterocyclyl, substituted or unsubstituted aryl, substituted or unsubstituted cycloalkyl, wherein the aryl, cycloalkyl and heterocyclyl as defined in R$_4$ if substituted are substituted with substituents selected from —OR$_5$, halogen, —CN, haloalkyl, haloalkoxy, —SR$_5$, —S(O)R$_5$ or —S(O)$_2$R$_5$;
R$_4'$ is H, substituted or unsubstituted C$_{1-6}$ alkyl, substituted or unsubstituted C$_{2-6}$ alkenyl or substituted or unsubstituted C$_{2-6}$ alkynyl;
R$_5$, R$_5'$ and R$_5''$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;
R$_5'''$ is H, unsubstituted C$_{1-6}$ alkyl, unsubstituted C$_{2-6}$ alkenyl, unsubstituted C$_{2-6}$ alkynyl or -Boc;
R$_6$, R$_6'$, R$_7$ and R$_7'$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;
R$_8$ and R$_8'$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl;
R$_9$ is selected from H, substituted or unsubstituted C$_{1-6}$ alkyl, substituted or unsubstituted C$_{2-6}$ alkenyl or substituted or unsubstituted C$_{2-6}$ alkynyl;
and wherein
the alkyl, alkenyl and alkynyl as defined in R$_1$, R$_1'$, R$_2$, R$_3$, R$_3'$, R$_4$, R$_4'$, R$_6$, R$_6'$, R$_7$, R$_7'$, R$_8$, R$_8'$ and R$_9$ if substituted are substituted with substituents selected from —OR$_5$, halogen, —CN, haloalkyl, haloalkoxy, —SR$_5$, —S(O)R$_5$, —S(O)$_2$R$_5$, C(O)OR$_5$ or C(O)NR$_5$R$_5'$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In this EMBODIMENT DC the following proviso might apply:

"the following compound being excluded from the general formula I:

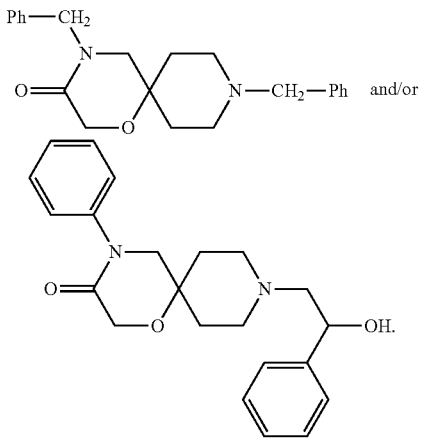

In another preferred embodiment of the compound according to the invention of general formula I is a compound wherein
Y is

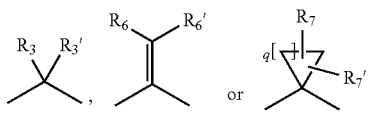

Z is —CH$_2$—, —C(O)— or —CHR$_9$—
m is 0 or 1
n is 1, 2 or 3
q is 1, 2, 3, 4, 5 or 6
R$_1$ is substituted or unsubstituted aryl, substituted or unsubstituted heterocyclyl, substituted or unsubstituted alkylaryl, substituted or unsubstituted alkylheterocyclyl or —(CH2)$_r$-W—R$_1$;
r is 0, 1 or 2
W is a bond, —CH$_2$O—, —CH$_2$C(O)NR$_5$—, —CH$_2$C(O)O—, —CH$_2$C(O)— or —C(CH$_3$)$_2$O—;
R$_{1'}$ is H, —CN, substituted or unsubstituted heterocyclyl, substituted or unsubstituted aryl (–), substituted or unsubstituted cycloalkyl or R$_5$;
with the proviso that when W is a bond, then R$_{1'}$ cannot be H, alkyl, alkenyl, alkynyl or cycloalkyl;
X is a bond;
R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl;
R$_3$ and R$_{3'}$ are independently selected from H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl and —CH$_2$R$_4$;
R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR$_5$R$_{5'''}$ or unsubstituted heterocyclyl, unsubstituted aryl, unsubstituted cycloalkyl;
R$_5$, R$_{5'}$ and R$_{5''}$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;

R$_{5'''}$ is H, unsubstituted C$_{1-6}$ alkyl, unsubstituted C$_{2-6}$ alkenyl, unsubstituted C$_{2-6}$ alkynyl or -Boc
R$_6$, R$_{6'}$, R$_7$ and R$_{7'}$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;
R$_8$ and R$_{8'}$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl;
R$_9$ is selected from H, substituted or unsubstituted C$_{1-6}$ alkyl, substituted or unsubstituted C$_{2-6}$ alkenyl or substituted or unsubstituted C$_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment the following compounds are excluded:

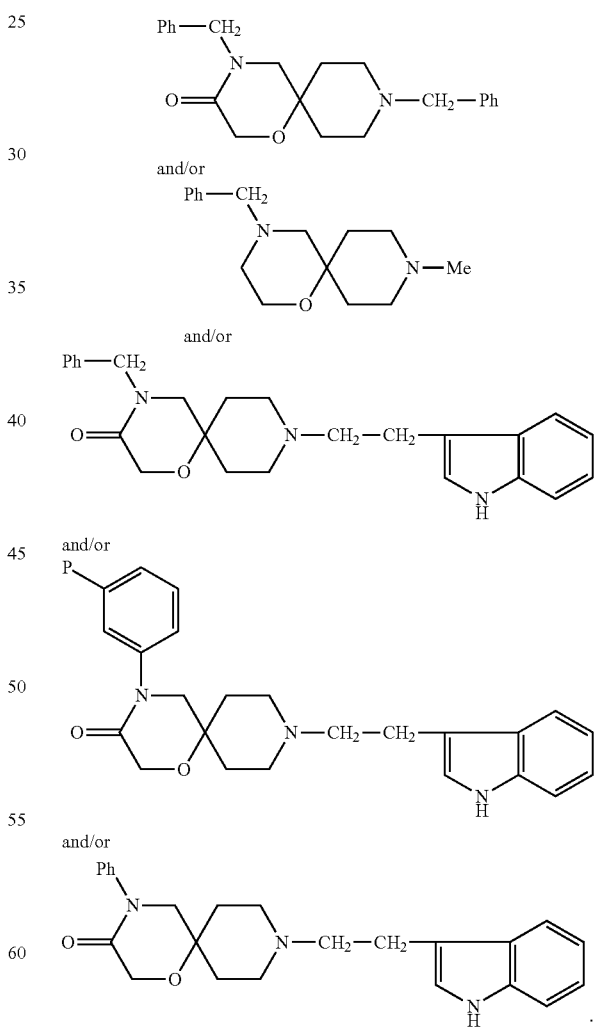

In another preferred embodiment of the compound according to the invention of general formula I is a compound wherein
Y is

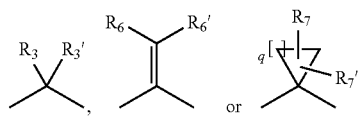

Z is —CH$_2$—, —C(O)— or —CHR$_9$—;
m is 0 or 1;
n is 1, 2 or 3;
q is 1, 2, 3, 4, 5 or 6;
R$_1$ is substituted or unsubstituted aryl, substituted or unsubstituted heterocyclyl, substituted or unsubstituted alkylaryl, substituted or unsubstituted alkylheterocyclyl or —(CH2)$_r$-W—R$_{1'}$;
r is 0, 1 or 2
W is a bond, —CH$_2$O—, —CH$_2$C(O)NR$_5$—, —CH$_2$C(O)O—, —CH$_2$C(O)— or —C(CH$_3$)$_2$O—;
R$_{1'}$ is H, —CN, substituted or unsubstituted heterocyclyl, substituted or unsubstituted aryl (-), substituted or unsubstituted cycloalkyl or R$_5$;
with the proviso that when W is a bond, then R$_{1'}$ cannot be H, alkyl, alkenyl, alkynyl or cycloalkyl;
X is —C(R$_4$R$_{4'}$)—;
R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl;
R$_3$ and R$_{3'}$ are independently selected from H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl and —CH$_2$R$_4$;
R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR$_5$R$_{5'''}$ or unsubstituted heterocyclyl, unsubstituted aryl, unsubstituted cycloalkyl;
R$_{4'}$ is H, substituted or unsubstituted C$_{1-6}$ alkyl, substituted or unsubstituted C$_{2-6}$ alkenyl or substituted or unsubstituted C$_{2-6}$ alkynyl;
R$_5$, R$_{5'}$ and R$_{5''}$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;
R$_{5'''}$ is H, unsubstituted C$_{1-6}$ alkyl, unsubstituted C$_{2-6}$ alkenyl, unsubstituted C$_{2-6}$ alkynyl or -Boc
R$_6$, R$_{6'}$, R$_7$ and R$_{7'}$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;
R$_8$ and R$_{8'}$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl;
R$_9$ is selected from H, substituted or unsubstituted C$_{1-6}$ alkyl, substituted or unsubstituted C$_{2-6}$ alkenyl or substituted or unsubstituted C$_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment the following compounds are excluded:

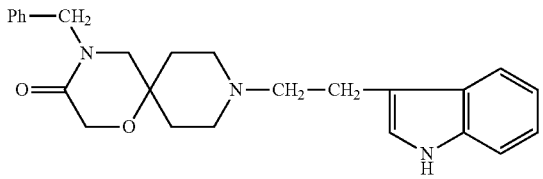

and/or

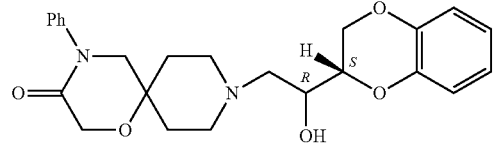

and/or

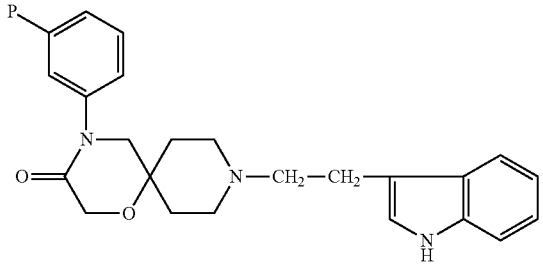

and/or

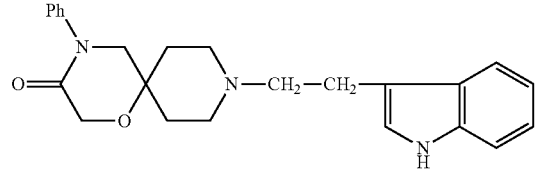

and/or

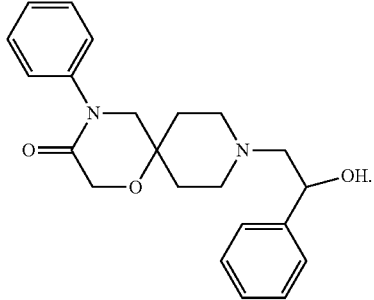

In another embodiment of the compound according to the invention of general formula I is a compound
wherein
Y is

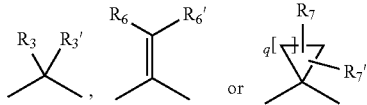

Z is —CH$_2$—, —C(O)— or —CHR$_9$—;
m is 0 or 1;
n is 1, 2 or 3;
q is 1, 2, 3, 4, 5 or 6;
R$_1$ is substituted or unsubstituted aryl, substituted or unsubstituted heterocyclyl, substituted or unsubstituted alkylaryl, substituted or unsubstituted alkylheterocyclyl or —(CH2)$_r$-W—R$_{1'}$;
r is 0, 1 or 2
W is a bond, —CH$_2$O—, —CH$_2$C(O)NR$_{5'}$—, —CH$_2$C(O)O—, —CH$_2$C(O)— or —C(CH$_3$)$_2$O—;
R$_{1'}$ is H, —CN, substituted or unsubstituted heterocyclyl, substituted or unsubstituted aryl, substituted or unsubstituted cycloalkyl or R$_5$;
with the proviso that when W is a bond, then R$_{1'}$ cannot be H, alkyl, alkenyl, alkynyl or cycloalkyl;
X is —C(O)O—, —C(O)NR$_5$—, —C(O)— or —O—;
R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl;
R$_3$ and R$_{3'}$ are independently selected from H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl and —CH$_2$R$_4$;
R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR$_5$R$_{5'''}$ or unsubstituted heterocyclyl, unsubstituted aryl, unsubstituted cycloalkyl;
R$_{4'}$ is H, substituted or unsubstituted C$_{1-6}$ alkyl, substituted or unsubstituted C$_{2-6}$ alkenyl or substituted or unsubstituted C$_{2-6}$ alkynyl;
R$_5$, R$_{5'}$ and R$_{5''}$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;
R$_{5'''}$ is H, unsubstituted C$_{1-6}$ alkyl, unsubstituted C$_{2-6}$ alkenyl, unsubstituted C$_{2-6}$ alkynyl or -Boc
R$_6$, R$_{6'}$, R$_7$ and R$_{7'}$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;
R$_8$ and R$_{8'}$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl;
R$_9$ is selected from H, substituted or unsubstituted C$_{1-6}$ alkyl, substituted or unsubstituted C$_{2-6}$ alkenyl or substituted or unsubstituted C$_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound
wherein
Y is

Z is —CH$_2$—, —C(O)— or —CHR$_9$—;
m is 0 or 1;
n is 1, 2 or 3;
R$_1$ is substituted or unsubstituted aryl, substituted or unsubstituted heterocyclyl, substituted or unsubstituted alkylaryl, substituted or unsubstituted alkylheterocyclyl or —(CH2)$_r$-W—R$_{1'}$;
r is 0, 1 or 2
W is a bond, —CH$_2$O—, —CH$_2$C(O)NR$_{5'}$—, —CH$_2$C(O)O—, —CH$_2$C(O)— or —C(CH$_3$)$_2$O—;
R$_{1'}$ is H, —CN, substituted or unsubstituted heterocyclyl, substituted or unsubstituted aryl (–), substituted or unsubstituted cycloalkyl or R$_5$;
X is a bond, —C(O)O—, —C(O)NR$_5$—, —C(O)—, —O— or —C(R$_4$R$_{4'}$)—;
R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl;
R$_3$ and R$_{3'}$ are independently selected from H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl and —CH$_2$R$_4$;
R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR$_5$R$_{5'''}$ or unsubstituted heterocyclyl, unsubstituted aryl, unsubstituted cycloalkyl;
R$_{4'}$ is H, substituted or unsubstituted C$_{1-6}$ alkyl, substituted or unsubstituted C$_{2-6}$ alkenyl or substituted or unsubstituted C$_{2-6}$ alkynyl;
R$_5$, R$_{5'}$ and R$_{5''}$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;
R$_{5'''}$ is H, unsubstituted C$_{1-6}$ alkyl, unsubstituted C$_{2-6}$ alkenyl, unsubstituted C$_{2-6}$ alkynyl or -Boc
R$_6$, R$_{6'}$, R$_7$ and R$_{7'}$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;
R$_8$ and R$_{8'}$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl;
R$_9$ is selected from H, substituted or unsubstituted C$_{1-6}$ alkyl, substituted or unsubstituted C$_{2-6}$ alkenyl or substituted or unsubstituted C$_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment the following compounds are excluded

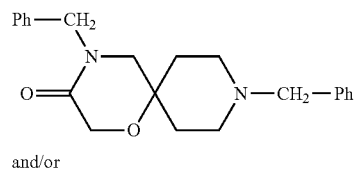

and/or

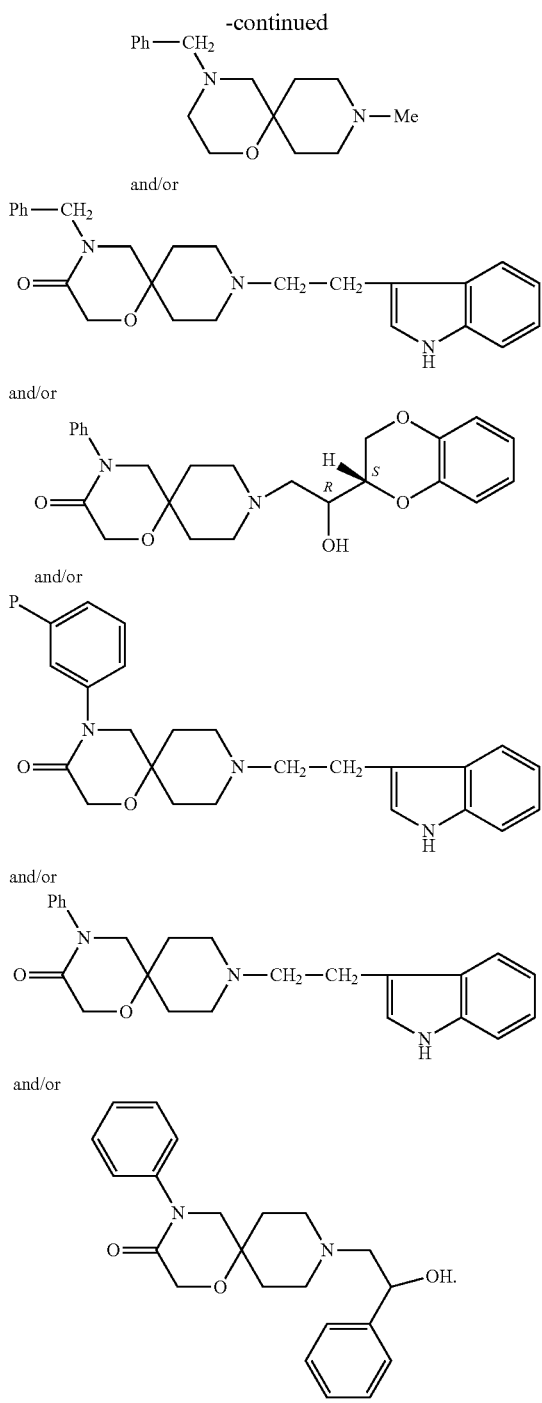

and/or and/or and/or and/or and/or

In another preferred embodiment of the compound according to the invention of general formula I is a compound
wherein
Y is

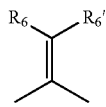

Z is —CH$_2$—, —C(O)— or —CHR$_9$—;
m is 0 or 1;
n is 1, 2 or 3;
R$_1$ is substituted or unsubstituted aryl, substituted or unsubstituted heterocyclyl, substituted or unsubstituted alkylaryl, substituted or unsubstituted alkylheterocyclyl or —(CH2)$_r$-W—R$_{1'}$;
r is 0, 1 or 2
W is a bond, —CH$_2$O—, —CH$_2$C(O)NR$_{5'}$—, —CH$_2$C(O)O—, —CH$_2$C(O)— or —C(CH$_3$)$_2$O—;
R$_{1'}$ is H, —CN, substituted or unsubstituted heterocyclyl, substituted or unsubstituted aryl, substituted or unsubstituted cycloalkyl or R$_5$;
X is a bond, —C(O)O—, —C(O)NR$_5$—, —C(O)—, —O— or —C(R$_4$R$_{4'}$)—;
R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl;
R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR$_5$R$_{5''}$ or unsubstituted heterocyclyl, unsubstituted aryl, unsubstituted cycloalkyl;
R$_{4'}$ is H, substituted or unsubstituted C$_{1-6}$ alkyl, substituted or unsubstituted C$_{2-6}$ alkenyl or substituted or unsubstituted C$_{2-6}$ alkynyl;
R$_5$, R$_{5'}$ and R$_{5''}$ are independently selected from H, unsubstituted C$_{1-6}$ alkyl, unsubstituted C$_{2-6}$ alkenyl, unsubstituted C$_{2-6}$ alkynyl, unsubstituted aryl or unsubstituted alkylaryl;
R$_{5'''}$ is H, unsubstituted C$_{1-6}$ alkyl, unsubstituted C$_{2-6}$ alkenyl, unsubstituted C$_{2-6}$ alkynyl or -Boc
R$_6$, R$_{6'}$, R$_7$ and R$_{7'}$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl;
R$_8$ and R$_{8'}$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl;
R$_9$ is selected from H, substituted or unsubstituted C$_{1-6}$ alkyl, substituted or unsubstituted C$_{2-6}$ alkenyl or substituted or unsubstituted C$_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound
wherein
Y is

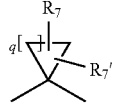

Z is —CH₂—, —C(O)— or —CHR₉—;
m is 0 or 1;
n is 1, 2 or 3;
q is 1, 2, 3, 4, 5 or 6;
R₁ is substituted or unsubstituted aryl, substituted or unsubstituted heterocyclyl, substituted or unsubstituted alkylaryl, substituted or unsubstituted alkylheterocyclyl or —(CH2)ᵣ-W—R₁·;
r is 0, 1 or 2
W is a bond, —CH₂O—, —CH₂C(O)NR₅·—, —CH₂C(O)O—, —CH₂C(O)— or —C(CH₃)₂O—;
R₁· is H, —CN, substituted or unsubstituted heterocyclyl, substituted or unsubstituted aryl (-), substituted or unsubstituted cycloalkyl or R₅;
X is a bond, —C(O)O—, —C(O)NR₅—, —C(O)—, —O— or —C(R₄R₄·)—;
R₂ is H, substituted or unsubstituted aryl, substituted or unsubstituted heterocyclyl, substituted or unsubstituted cycloalkyl, substituted or unsubstituted C₁₋₆ alkyl, substituted or unsubstituted C₂₋₆ alkenyl or substituted or unsubstituted C₂₋₆ alkynyl;
R₄ is H, —OR₅, substituted or unsubstituted C₁₋₆ alkyl, substituted or unsubstituted C₂₋₆ alkenyl, substituted or unsubstituted C₂₋₆ alkynyl, —COOR₅, —CONR₅R₅·, —NR₅COR₅·, —NR₅R₅‴ or unsubstituted heterocyclyl, unsubstituted aryl, unsubstituted cycloalkyl;
R₄· is H, substituted or unsubstituted C₁₋₆ alkyl, substituted or unsubstituted C₂₋₆ alkenyl or substituted or unsubstituted C₂₋₆ alkynyl;
R₅, R₅· and R₅‴ are independently selected from H, unsubstituted C₁₋₆ alkyl, unsubstituted C₂₋₆ alkenyl, unsubstituted C₂₋₆ alkynyl, unsubstituted aryl or unsubstituted alkylaryl;
R₅‴ is H, unsubstituted C₁₋₆ alkyl, unsubstituted C₂₋₆ alkenyl, unsubstituted C₂₋₆ alkynyl or -Boc
R₇ and R₇· are independently selected from H, halogen, —OR₅, substituted or unsubstituted C₁₋₆ alkyl, substituted or unsubstituted C₂₋₆ alkenyl, substituted or unsubstituted C₂₋₆ alkynyl, unsubstituted heterocyclyl, unsubstituted aryl and unsubstituted cycloalkyl;
R₈ and R₈· are independently selected from H, —OR₅, halogen, substituted or unsubstituted C₁₋₆ alkyl, substituted or unsubstituted C₂₋₆ alkenyl or substituted or unsubstituted C₂₋₆ alkynyl;
R₉ is selected from H, substituted or unsubstituted C₁₋₆ alkyl, substituted or unsubstituted C₂₋₆ alkenyl or substituted or unsubstituted C₂₋₆ alkynyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment the compound according to the invention according to general formula I is a compound of formula I'

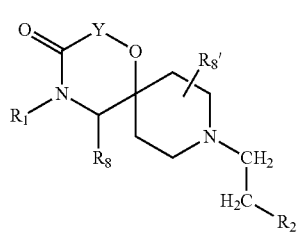

(I')

wherein
Y is

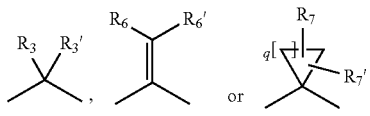

q is 1, 2, 3, 4, 5 or 6;
R₁ is substituted or unsubstituted aryl, substituted or unsubstituted heterocyclyl, substituted or unsubstituted alkylaryl, substituted or unsubstituted alkylheterocyclyl or —(CH2)ᵣ-W—R₁·;
r is 0, 1 or 2
W is a bond, —CH₂O—, —CH₂C(O)NR₅·—, —CH₂C(O)O—, —CH₂C(O)— or —C(CH₃)₂O—;
R₁· is H, —CN, substituted or unsubstituted heterocyclyl, substituted or unsubstituted aryl (-), substituted or unsubstituted cycloalkyl or R₅;
R₂ is H, substituted or unsubstituted aryl, substituted or unsubstituted heterocyclyl, substituted or unsubstituted cycloalkyl, substituted or unsubstituted C₁₋₆ alkyl, substituted or unsubstituted C₂₋₆ alkenyl or substituted or unsubstituted C₂₋₆ alkynyl;
R₃ and R₃· are independently selected from H, substituted or unsubstituted C₁₋₆ alkyl, substituted or unsubstituted C₂₋₆ alkenyl, substituted or unsubstituted C₂₋₆ alkynyl, substituted or unsubstituted cycloalkyl and —CH₂R₄;
R₅, R₅· and R₅‴ are independently selected from H, unsubstituted C₁₋₆ alkyl, unsubstituted C₂₋₆ alkenyl, unsubstituted C₂₋₆ alkynyl, unsubstituted aryl or unsubstituted alkylaryl;
R₅‴ is H, unsubstituted C₁₋₆ alkyl, unsubstituted C₂₋₆ alkenyl, unsubstituted C₂₋₆ alkynyl or -Boc
R₆, R₆·, R₇ and R₇· are independently selected from H, halogen, —OR₅, substituted or unsubstituted C₁₋₆ alkyl, substituted or unsubstituted C₂₋₆ alkenyl, substituted or unsubstituted C₂₋₆ alkynyl, unsubstituted heterocyclyl, unsubstituted aryl and unsubstituted cycloalkyl;
R₈ and R₈· are independently selected from H, —OR₅, halogen, substituted or unsubstituted C₁₋₆ alkyl, substituted or unsubstituted C₂₋₆ alkenyl or substituted or unsubstituted C₂₋₆ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment of the above embodiment of formula I' the following compounds are excluded

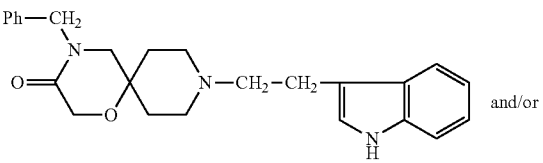

and/or

-continued

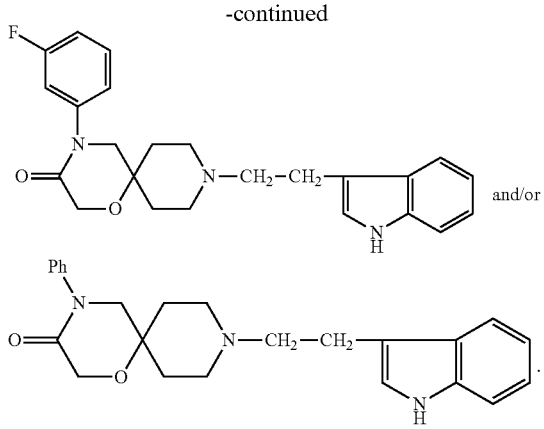

and/or

In another preferred embodiment the compound according to the invention of general formula I is a compound of formula I''

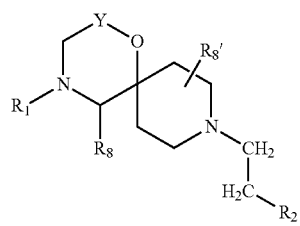

wherein
Y is

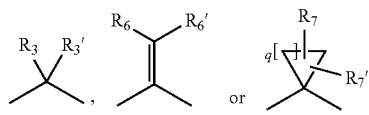

q is 1, 2, 3, 4, 5 or 6;
R₁ is substituted or unsubstituted aryl, substituted or unsubstituted heterocyclyl, substituted or unsubstituted alkylaryl, substituted or unsubstituted alkylheterocyclyl or —(CH2)$_r$-W—R₁·;
r is 0, 1 or 2
W is a bond, —CH₂O—, —CH₂C(O)NR₅·—, —CH₂C(O)O—, —CH₂C(O)— or —C(CH₃)₂O—;
R₁· is H, —CN, substituted or unsubstituted heterocyclyl, substituted or unsubstituted aryl (-), substituted or unsubstituted cycloalkyl or R₅;
R₂ is H, substituted or unsubstituted aryl, substituted or unsubstituted heterocyclyl, substituted or unsubstituted cycloalkyl, substituted or unsubstituted C₁₋₆ alkyl, substituted or unsubstituted C₂₋₆ alkenyl or substituted or unsubstituted C₂₋₆ alkynyl;
R₃ and R₃· are independently selected from H, substituted or unsubstituted C₁₋₆ alkyl, substituted or unsubstituted C₂₋₆ alkenyl, substituted or unsubstituted C₂₋₆ alkynyl, substituted or unsubstituted cycloalkyl and —CH₂R₄;
R₅, R₅· and R₅·· are independently selected from H, unsubstituted C₁₋₆ alkyl, unsubstituted C₂₋₆ alkenyl, unsubstituted C₂₋₆ alkynyl, unsubstituted aryl or unsubstituted alkylaryl;

R₅··· is H, unsubstituted C₁₋₆ alkyl, unsubstituted C₂₋₆ alkenyl, unsubstituted C₂₋₆ alkynyl or -Boc
R₆, R₆·, R₇ and R₇· are independently selected from H, halogen, —OR₅, substituted or unsubstituted C₁₋₆ alkyl, substituted or unsubstituted C₂₋₆ alkenyl, substituted or unsubstituted C₂₋₆ alkynyl, unsubstituted heterocyclyl, unsubstituted aryl and unsubstituted cycloalkyl;
R₈ and R₈· are independently selected from H, —OR₅, halogen, substituted or unsubstituted C₁₋₆ alkyl, substituted or unsubstituted C₂₋₆ alkenyl or substituted or unsubstituted C₂₋₆ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, In another preferred embodiment the compound according to the invention of general formula I is a compound of formula I'''

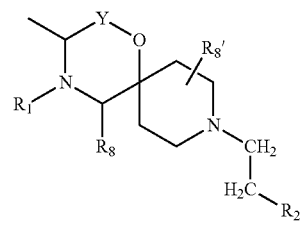

wherein
Y is

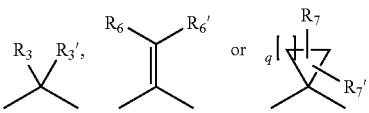

q is 1, 2, 3, 4, 5 or 6;
R₁ is substituted or unsubstituted aryl, substituted or unsubstituted heterocyclyl, substituted or unsubstituted alkylaryl, substituted or unsubstituted alkylheterocyclyl or —(CH2)$_r$-W—R₁·;
r is 0, 1 or 2
W is a bond, —CH₂O—, —CH₂C(O)NR₅·—, —CH₂C(O)O—, —CH₂C(O)— or —C(CH₃)₂O—;
R₁· is H, —CN, substituted or unsubstituted heterocyclyl, substituted or unsubstituted aryl (-), substituted or unsubstituted cycloalkyl or R₅;
R₂ is H, substituted or unsubstituted aryl, substituted or unsubstituted heterocyclyl, substituted or unsubstituted cycloalkyl, substituted or unsubstituted C₁₋₆ alkyl, substituted or unsubstituted C₂₋₆ alkenyl or substituted or unsubstituted C₂₋₆ alkynyl;
R₃ and R₃· are independently selected from H, substituted or unsubstituted C₁₋₆ alkyl, substituted or unsubstituted C₂₋₆ alkenyl, substituted or unsubstituted C₂₋₆ alkynyl, substituted or unsubstituted cycloalkyl and —CH₂R₄;
R₅, R₅· and R₅·· are independently selected from H, unsubstituted C₁₋₆ alkyl, unsubstituted C₂₋₆ alkenyl, unsubstituted C₂₋₆ alkynyl, unsubstituted aryl or unsubstituted alkylaryl;

$R_{5'''}$ is H, unsubstituted $C_{1-6}$ alkyl, unsubstituted $C_{2-6}$ alkenyl, unsubstituted $C_{2-6}$ alkynyl or -Boc $R_6$, $R_{6'}$, $R_7$ and $R_{7'}$ are independently selected from H, halogen, —$OR_5$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_{8'}$ are independently selected from H, —$OR_5$, halogen, substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein
Y is

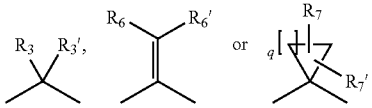

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein
Y is

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein
Y is

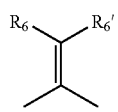

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein
Y is

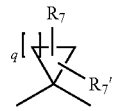

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein $R_1$ is substituted or unsubstituted aryl, substituted or unsubstituted heterocyclyl, substituted or unsubstituted alkylaryl, substituted or unsubstituted alkylheterocyclyl or —$(CH2)_r$—W—$R_{1'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein
W is a bond, —$CH_2O$—, —$CH_2C(O)NR_{5'}$—, —$CH_2C(O)O$—, —$CH_2C(O)$— or —$C(CH_3)_2O$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein
$R_{1'}$ is H, —CN, substituted or unsubstituted heterocyclyl, substituted or unsubstituted aryl, substituted or unsubstituted cycloalkyl or $R_5$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein
X is a bond, —C(O)O—, —C(O)$NR_5$—, —C(O)—, —O— or —C($R_4R_{4'}$)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein $R_2$ is H, substituted or unsubstituted aryl, substituted or unsubstituted heterocyclyl, substituted or unsubstituted cycloalkyl, substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein $R_3$ and $R_{3'}$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl and —$CH_2R_4$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein $R_3$ and $R_{3'}$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, and substituted or unsubstituted alkylcycloalkyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein $R_4$ is H, —$OR_5$, substituted or unsubstituted $C_{1-6}$ alkyl, substituted or unsubstituted $C_{2-6}$ alkenyl, substituted or unsubstituted $C_{2-6}$ alkynyl, —$COOR_5$, —$CONR_5R_{5'}$, —$NR_5COR_{5'}$, —$NR_5R_{5'''}$ or unsubstituted heterocyclyl, unsubstituted aryl, unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, the compound is a compound, wherein $R_4$ is H, —$OR_5$, substituted or unsubstituted $C_{1-6}$ alkyl, substituted or unsubstituted $C_{2-6}$ alkenyl, substituted or unsubstituted $C_{2-6}$ alkynyl, —$COOR_5$, —$CONR_5R_{5'}$, —$NR_5COR_{5'}$, —$NR_5R_{5'''}$ or substituted or unsubstituted heterocyclyl, substituted or unsubstituted aryl, substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein $R_{4'}$ is H, substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein $R_5$, $R_{5'}$ and $R_{5''}$ are independently selected from H, unsubstituted $C_{1-6}$ alkyl, unsubstituted $C_{2-6}$ alkenyl, unsubstituted $C_{2-6}$ alkynyl, unsubstituted aryl or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein $R_{5'''}$ is H, unsubstituted $C_{1-6}$ alkyl, unsubstituted $C_{2-6}$ alkenyl, unsubstituted $C_{2-6}$ alkynyl or -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein $R_6$, $R_{6'}$, $R_7$ and $R_{7'}$ are independently selected from H, halogen, —$OR_5$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I''' the compound is a compound, wherein $R_8$ and $R_{8'}$ are independently selected from H, —$OR_5$, halogen, substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I'" the compound is a compound, wherein $R_9$ is H, substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein Z is —CH$_2$—, —C(O)— or —CHR$_9$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I'" the compound is a compound, wherein m is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I the compound is a compound, wherein n is 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I'" the compound is a compound, wherein q is 1, 2, 3, 4, 5 or 6;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I'" the compound is a compound, wherein r is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, I', I" or I'" the compound is a compound, wherein $R_1$ is substituted or unsubstituted aryl, substituted or unsubstituted heterocyclyl, substituted or unsubstituted alkylaryl, substituted or unsubstituted alkylheterocyclyl or —(CH2)$_r$-W—R$_1$;

wherein the aryl is selected from phenyl, naphtyl, or anthracene; preferably is napthyl and phenyl; more preferably is phenyl; and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine, pyrazine, indazole, benzodioxane, thiazole, benzothiazole, morpholine, tetrahydropyrane, pyrazole, imidazole, and/or the alkyl is $C_{1-6}$ alkyl like methyl, ethyl, propyl, butyl, pentyl, hexyl, more preferably the alkyl is methyl, and/or $R_1$, is H, —CN, substituted or unsubstituted heterocyclyl, substituted or unsubstituted aryl, substituted or unsubstituted cycloalkyl or $R_5$; wherein wherein the aryl is selected from phenyl, naphtyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is morpholine or tetrahydropyrane, and/or the cycloalkyl is $C_{3-5}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_2$ is H, substituted or unsubstituted aryl, substituted or unsubstituted heterocyclyl, substituted or unsubstituted cycloalkyl, substituted or unsubstituted $C_{1-6}$ alkyl, substituted or unsubstituted $C_{2-6}$ alkenyl or substituted or unsubstituted $C_{2-6}$ alkynyl;

wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine, piperidine, thiazole, morpholine, tetrahydropyrane, pyrazole, thiophene, indole, benzimidazole, pyrrolo[2,3b]pyridine, benzoxazole, oxopyrrolidine, pyrimidine;

and/or the $C_{1-6}$ alkyl is preferably selected from methyl, ethyl, propyl, butyl, pentyl, hexyl, isopropyl, or 2-methylpropyl, more preferably the $C_{1-6}$ alkyl is methyl, isopropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; preferably the cycloalkyl is cyclopropyl;

and/or $R_3$ and $R_{3'}$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl and —CH$_2$R$_4$; wherein the $C_{1-6}$ alkyl is preferably selected from methyl, ethyl, propyl, butyl, pentyl, hexyl, isopropyl, or 2-methylpropyl, the $C_{1-6}$ alkyl is preferably methyl, ethyl, isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_4$ (for Formula I) is H, —OR$_5$, substituted or unsubstituted $C_{1-6}$ alkyl, substituted or unsubstituted $C_{2-6}$ alkenyl, substituted or unsubstituted $C_{2-6}$ alkynyl, —COOR$_5$, —CONR$_5$R$_5$, —NR$_5$COR$_{5'}$, —NR$_5$R$_{5'}$— or unsubstituted heterocyclyl, unsubstituted aryl, unsubstituted cycloalkyl;

wherein the $C_{1-6}$ alkyl is preferably selected from methyl, ethyl, propyl, butyl, pentyl, hexyl, isopropyl, or 2-methylpropyl, preferably the $C_{1-6}$ alkyl is methyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphtyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, preferably is tetrahydropyrane;

and/or $R_{4'}$ (for Formula I) is H or substituted or unsubstituted $C_{1-6}$ alkyl, substituted or unsubstituted $C_{2-6}$ alkenyl or substituted or unsubstituted $C_{2-6}$ alkynyl; wherein wherein the $C_{1-6}$ alkyl is preferably selected from methyl, ethyl, propyl, butyl, pentyl, hexyl, isopropyl, or 2-methylpropyl, preferably the $C_{1-6}$ alkyl is methyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or $R_5$, $R_{5'}$ and $R_{5''}$ are independently selected from H, unsubstituted $C_{1-6}$ alkyl, unsubstituted $C_{2-6}$ alkenyl, unsubstituted $C_{2-6}$ alkynyl, unsubstituted aryl or unsubstituted alkylaryl;

wherein the alkyl is $C_{1-6}$ alkyl like methyl, ethyl, propyl, butyl, pentyl, hexyl, more preferably the alkyl is methyl or ethyl;

and/or the C$_{1-6}$ alkyl is preferably selected from methyl, ethyl, propyl, butyl, pentyl, hexyl, isopropyl, or 2-methylpropyl, more preferably the C$_{1-6}$ alkyl is methyl, ethyl, or isopropyl;

and/or the C$_{2-6}$-alkenyl, is preferably selected from ethylene, propylene, butylene, pentylene or hexylene;

and/or the C$_{2-6}$-alkynyl is preferably selected from ethyne, propyne, butyne, pentyne or hexyne;

and/or the aryl is selected from phenyl, naphtyl, or anthracene; preferably is napthyl and phenyl; preferably phenyl and/or R$_{5'''}$ is H, unsubstituted C$_{1-6}$ alkyl, unsubstituted C$_{2-6}$ alkenyl, unsubstituted C$_{2-6}$ alkynyl or -Boc, wherein the C$_{1-6}$ alkyl is preferably selected from methyl, ethyl, propyl, butyl, pentyl, hexyl, isopropyl, or 2-methylpropyl, more preferably the C$_{1-6}$ alkyl is methyl;

and/or the C$_{2-6}$-alkenyl, is preferably selected from ethylene, propylene, butylene, pentylene or hexylene;

and/or the C$_{2-6}$-alkynyl is preferably selected from ethyne, propyne, butyne, pentyne or hexyne;

and/or

R$_6$, R$_{6'}$, R$_7$ and R$_{7'}$ are independently selected from H, halogen, —OR$_5$, substituted or unsubstituted C$_{1-6}$ alkyl, substituted or unsubstituted C$_{2-6}$ alkenyl, substituted or unsubstituted C$_{2-6}$ alkynyl, unsubstituted heterocyclyl, unsubstituted aryl and unsubstituted cycloalkyl; wherein the C$_{1-6}$ alkyl is preferably selected from methyl, ethyl, propyl, butyl, pentyl, hexyl, isopropyl, or 2-methylpropyl, more preferably the C$_{1-6}$ alkyl is methyl or ethyl, and/or the C$_{2-6}$-alkenyl, is preferably selected from ethylene, propylene, butylene, pentylene or hexylene;

and/or the C$_{2-6}$-alkynyl is preferably selected from ethyne, propyne, butyne, pentyne or hexyne;

and/or the cycloalkyl is C$_{3-8}$ cycloalkyl like cyclopropyl, cyclobutyl, cyclopentyl, cyclohexyl, cycloheptyl, or cyclooctyl; preferably is C$_{3-7}$ cycloalkyl like cyclopropyl, cyclobutyl, cyclopentyl, cyclohexyl, or cycloheptyl; more preferably from C$_{3-6}$ cycloalkyl like cyclopropyl, cyclobutyl, cyclopentyl or cyclohexyl;

and/or the aryl is selected from phenyl, naphtyl, or anthracene; preferably is napthyl and phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is tetrahydropyrane, and/or R$_8$ and R$_{8'}$ are independently selected from H, —OR$_5$, halogen, substituted or unsubstituted C$_{1-6}$ alkyl, substituted or unsubstituted C$_{2-6}$ alkenyl or substituted or unsubstituted C$_{2-6}$ alkynyl, wherein the C$_{1-6}$ alkyl is preferably selected from methyl, ethyl, propyl, butyl, pentyl, hexyl, isopropyl, or 2-methylpropyl, and/or the C$_{2-6}$-alkenyl, is preferably selected from ethylene, propylene, butylene, pentylene or hexylene;

and/or the C$_{2-6}$-alkynyl is preferably selected from ethyne, propyne, butyne, pentyne or hexyne;

and/or

R$_9$ is H or substituted or unsubstituted C$_{1-6}$ alkyl, substituted or unsubstituted C$_{2-6}$ alkenyl or substituted or unsubstituted C$_{2-6}$ alkynyl); wherein wherein the C$_{1-6}$ alkyl is preferably selected from methyl, ethyl, propyl, butyl, pentyl, hexyl, isopropyl, or 2-methylpropyl, preferably the C$_{1-6}$ alkyl is methyl, and/or the C$_{2-6}$-alkenyl, is preferably selected from ethylene, propylene, butylene, pentylene or hexylene;

and/or the C$_{2-6}$-alkynyl is preferably selected from ethyne, propyne, butyne, pentyne or hexyne;

and/or

Z (for Formula I) is —CH$_2$—, —C(O)— or —CHR$_9$—;

and/or m is 0 or 1, preferably m is 1;

and/or n is 1, 2 or 3, preferably n is 2;

and/or q is 1, 2, 3, 4, 5 or 6, preferably q is 1;

and/or r is 0, 1 or 2;

and/or

W is a bond, —CH$_2$O—, —CH$_2$C(O)NR$_{5'}$—, —CH$_2$C(O)O—, —CH$_2$C(O)— or —C(CH$_3$)$_2$O—;

and/or

X (for Formula I) is a bond, —C(O)O—, —C(O)NR$_5$—, —C(O)—, —O— or —C(R$_4$R$_{4'}$)—;

preferably X is a bond o —C(R$_4$R$_{4'}$)—;

and/or

Y is

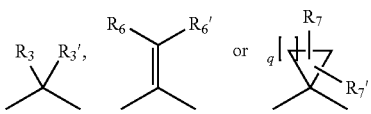

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I, I', I" or I''' the compound is a compound, wherein in $R_1$ as defined in any of the above embodiments, the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine, pyrazine, indazole, benzodioxane, thiazole, benzothiazole, morpholine, tetrahydropyrane, pyrazole, imidazole, and/or the alkyl is $C_{1-6}$ alkyl like methyl, ethyl, propyl, butyl, pentyl, hexyl, more preferably the alkyl is methyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I, I', I" or I'" the compound is a compound, wherein in $R_{1'}$ as defined in any of the above embodiments, the aryl is selected from phenyl, naphtyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is morpholine or tetrahydropyrane, and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, In another preferred embodiment of the invention according to general formulas I, I', I" or I'" the compound is a compound, wherein in $R_2$ as defined in any of the above embodiments, the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is pyridine, piperidine, thiazole, morpholine, tetrahydropyrane, pyrazole, thiophene, indole, benzimidazole, pyrrolo[2,3b]pyridine, benzoxazole, oxopyrrolidine, pyrimidine;

and/or the $C_{1-6}$ alkyl is preferably selected from methyl, ethyl, propyl, butyl, pentyl, hexyl, isopropyl, or 2-methylpropyl, more preferably the $C_{1-6}$ alkyl is methyl, isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; preferably the cycloalkyl is cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I, I', I" or I'" the compound is a compound, wherein in $R_3$ or $R_{3'}$ as defined in any of the above embodiments, the alkyl is $C_{1-6}$ alkyl like methyl, ethyl, propyl, butyl, pentyl, hexyl, the alkyl is preferably methyl or ethyl;

and/or the $C_{1-6}$ alkyl is preferably selected from methyl, ethyl, propyl, butyl, pentyl, hexyl, isopropyl, or 2-methylpropyl, the $C_{1-6}$ alkyl is preferably methyl, ethyl, isopropyl;

the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I the compound is a compound, wherein in $R_4$ as defined in any of the above embodiments, the $C_{1-6}$ alkyl is preferably selected from methyl, ethyl, propyl, butyl, pentyl, hexyl, isopropyl, or 2-methylpropyl, preferably the $C_{1-6}$ alkyl is methyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphtyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, preferably is tetrahydropyrane;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I the compound is a compound, wherein in $R_{4'}$ as defined in any of the above embodiments, the $C_{1-6}$ alkyl is preferably selected from methyl, ethyl, propyl, butyl, pentyl, hexyl, isopropyl, or 2-methylpropyl, preferably the $C_{1-6}$ alkyl is methyl, and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I, I', I" or I'" the compound is a compound, wherein in $R_5$, $R_{5'}$ or $R_{5''}$ as defined in any of the above embodiments, the alkyl is $C_{1-6}$ alkyl like methyl, ethyl, propyl, butyl, pentyl, hexyl, more preferably the alkyl is methyl or ethyl;

and/or the $C_{1-6}$ alkyl is preferably selected from methyl, ethyl, propyl, butyl, pentyl, hexyl, isopropyl, or 2-methylpropyl, more preferably the $C_{1-6}$ alkyl is methyl, ethyl, or isopropyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; preferably phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I, I', I" or I''' the compound is a compound, wherein in $R_{5'''}$ as defined in any of the above embodiments, the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I, I', I" or I''' the compound is a compound, wherein in $R_6$, $R_{6'}$, $R_7$ or $R_{7'}$ as defined in any of the above embodiments, the $C_{1-6}$ alkyl is preferably selected from methyl, ethyl, propyl, butyl, pentyl, hexyl, isopropyl, or 2-methylpropyl, more preferably the $C_{1-6}$ alkyl is methyl or ethyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphtyl, or anthracene; preferably is napthyl and phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocycle is tetrahydropyrane, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I, I', I" or I''' the compound is a compound, wherein in $R_8$ or $R_{8'}$ as defined in any of the above embodiments, the $C_{1-6}$ alkyl is preferably selected from methyl, ethyl, propyl, butyl, pentyl, hexyl, isopropyl, or 2-methylpropyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formulas I, I', I" or I''' the compound is a compound, wherein in $R_9$ as defined in any of the above embodiments, the $C_{1-6}$ alkyl is preferably selected from methyl, ethyl, propyl, butyl, pentyl, hexyl, isopropyl, or 2-methylpropyl, preferably the $C_{1-6}$ alkyl is methyl, and/or the $C_{2-6}$-alkenyl, is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment $R_1$ is a substituted or unsubstituted group selected from phenyl, benzyl, pyridine, methylpyridine, pyrazine, indazole, benzodioxane, thiazole, methylthiazole, benzothiazole, morpholine-2-oxoethyl, tetrahydro-2H-pyrane-2yl-oxyethyl, methyltetrahydropyrane, pyrazole, methylpyrazole, imidazole, methylimidazole, hydroxyethyl, methyl-3-propanoate, hydroxypropyl, N-methyl-3-propanamide, 3-methoxypropyl, 3-propanenitrile and N,N-dimethyl-3-propanamide.

In another preferred embodiment $R_1$ is substituted or unsubstituted phenyl, substituted or unsubstituted benzyl, substituted or unsubstituted pyridine or substituted or unsubstituted methylpyridine.

In a most preferred embodiment $R_1$ is substituted or unsubstituted phenyl, substituted or unsubstituted benzyl or substituted or unsubstituted pyridine.

In a preferred embodiment $R_{1'}$ is preferably H, —CN, substituted or unsubstituted heterocyclyl, or $R_5$.

In another preferred embodiment $R_{1'}$ is H, —CN, substituted or unsubstituted morpholine, substituted or unsubstituted tetrahydropyrane, or unsubstituted methyl.

In a preferred embodiment $R_2$ is substituted or unsubstituted phenyl, substituted or unsubstituted pyridine, substituted or unsubstituted thiazole, substituted or unsubstituted methyl, substituted or unsubstituted isopropyl, substituted or unsubstituted O-isopropyl, substituted or unsubstituted morpholine, substituted or unsubstituted piperidine;

In a preferred embodiment $R_2$ is substituted or unsubstituted phenyl, substituted or unsubstituted pyridine, substituted or unsubstituted thiazole, unsubstituted methyl, unsubstituted isopropyl, unsubstituted O-isopropyl, substituted or unsubstituted morpholine, substituted or unsubstituted piperidine;

In another preferred embodiment $R_2$ is substituted or unsubstituted phenyl or substituted or unsubstituted pyridine.

In a preferred embodiment $R_3$ is preferably H, substituted or unsubstituted methyl, substituted or unsubstituted ethyl, substituted or unsubstituted isopropyl, substituted or unsubstituted methoxymethyl, methylacetate, ethanol, —$CH_2COOH$, N,N-dimethylacetamide, benzyloxymethyl, —$CH_2OH$, substituted or unsubstituted methyltetrahydropyrane, 4-methoxypropyl or hydroxypropyl.

In a preferred embodiment $R_3$ is preferably H, unsubstituted methyl, unsubstituted ethyl, unsubstituted isopropyl, unsubstituted methoxymethyl, methylacetate, ethanol, —$CH_2COOH$, N,N-dimethylacetamide, benzyloxymethyl, —$CH_2OH$, substituted or unsubstituted methyltetrahydropyrane, 4-methoxypropyl or hydroxypropyl.

In another preferred embodiment $R_{3'}$ is preferably H or substituted or unsubstituted methyl, preferably unsubstituted methyl.

In particular preferred embodiment $R_3$ is H or methyl, while $R_{3'}$ is H or substituted or unsubstituted methyl, preferably unsubstituted methyl.

In another particular preferred embodiment $R_3$ is substituted or unsubstituted methyl while $R_{3'}$ is hydrogen, preferably $R_3$ is unsubstituted methyl while $R_{3'}$ is hydrogen.

In a most preferred embodiment $R_3$ and $R_{3'}$ are both hydrogen.

In a preferred embodiment $R_4$ is hydroxyl, substituted or unsubstituted methyl, substituted or unsubstituted tetrahydropyrane. $R_4$ is preferably hydroxyl or unsubstituted methyl.

In another preferred embodiment $R_{4'}$ is hydrogen or substituted or unsubstituted methyl, preferably hydrogen or unsubstituted methyl.

In particular preferred embodiment $R_{4'}$ is hydrogen;

In another particular preferred embodiment $R_4$ is hydroxyl, while $R_{4'}$ is hydrogen;

In a most preferred embodiment $R_4$ and $R_{4'}$ are both hydrogen.

In a preferred embodiment $R_5$ is H, unsubstituted methyl, unsubstituted ethyl, unsubstituted isopropyl or unsubstituted phenyl.

In another preferred embodiment $R_{5'}$ is H or unsubstituted methyl.

In a preferred embodiment $R_6$, $R_{6'}$, $R_7$ and $R_{7'}$ are independently selected from H, substituted or unsubstituted $C_{1-6}$ alkyl or unsubstituted heterocyclyl.

In another preferred embodiment $R_6$ is H, substituted or unsubstituted methyl, substituted or unsubstituted ethyl, or unsubstituted tetrahydropyrane, while $R_{6'}$ is hydrogen or substituted or unsubstituted methyl.

In particularly preferred embodiment $R_6$ and $R_{6'}$ are both hydrogen.

In another particularly preferred embodiment $R_6$ and $R_{6'}$ are both substituted or unsubstituted methyl.

In still another particularly preferred embodiment $R_6$ is substituted or unsubstituted ethyl and $R_{6'}$ is hydrogen.

In a preferred embodiment $R_7$ and $R_{7'}$ are both hydrogen.

In a preferred embodiment $R_5$ and $R_{5'}$ are preferably both hydrogen.

In another preferred embodiment $R_9$ is substituted or unsubstituted methyl.

In a preferred embodiment

Y is

In another preferred embodiment m is 1.

In an particular embodiment n is 2.

In a preferred embodiment q is 1.

In another preferred embodiment

X is a bond.

In an particular embodiment

X is —$C(R_4R_{4'})$—.

In an particular embodiment the halogen is fluorine, chlorine, iodine or bromine.

In an particular embodiment the halogen is fluorine or chlorine.

In an particular embodiment

Z is —$CH_2$—.

In an particular embodiment

Z is —$CHR_9$—.

In an particular embodiment

Z is —$CH(CH_3)$—.

In an particular embodiment

Z is —$C(O)$—.

In a preferred further embodiment, the compounds of the general formula I are selected from

| EX | Chemical name |
|---|---|
| 1 | 4-(4-methoxyphenyl)-2-methyl-9-phenethyl-1-oxa-4,9-diazaspiro[5.5]undecan-3-one |
| 2 | 9-benzyl-4-(2-methoxyphenyl)-1-oxa-4,9-diazaspiro[5.5]undecan-3-one |
| 3 | 9-benzyl-4-phenyl-1-oxa-4,9-diazaspiro[5.5]undecan-3-one |
| 4 | 4-(2-methoxyphenyl)-9-phenethyl-1-oxa-4,9-diazaspiro[5.5]undecan-3-one |
| 5 | 9-phenethyl-4-phenyl-1-oxa-4,9-diazaspiro[5.5]undecan-3-one |
| 6 | 9-benzyl-4-(3-methoxyphenyl)-1-oxa-4,9-diazaspiro[5.5]undecan-3-one |

-continued

| EX | Chemical name |
|---|---|
| 7 | 2-benzyl-9-phenyl-6-oxa-2,9-diazaspiro[4.5]decan-8-one |
| 8 | 4-(3-methoxyphenyl)-9-phenethyl-1-oxa-4,9-diazaspiro[5.5]undecan-3-one |
| 9 | 2-methyl-9-phenethyl-4-phenyl-1-oxa-4,9-diazaspiro[5.5]undecan-3-one |
| 10a | (R)-2-methyl-9-phenethyl-4-phenyl-1-oxa-4,9-diazaspiro[5.5]undecan-3-one |
| 10b | (S)-2-methyl-9-phenethyl-4-phenyl-1-oxa-4,9-diazaspiro[5.5]undecan-3-one |
| 11 | 2-(methoxymethyl)-9-phenethyl-4-phenyl-1-oxa-4,9-diazaspiro[5.5]undecan-3-one |
| 12a | (S)-2-(methoxymethyl)-9-phenethyl-4-phenyl-1-oxa-4,9-diazaspiro[5.5]undecan-3-one |
| 12b | (R)-2-(methoxymethyl)-9-phenethyl-4-phenyl-1-oxa-4,9-diazaspiro[5.5]undecan-3-one |
| 13 | 2-ethyl-9-phenethyl-4-phenyl-1-oxa-4,9-diazaspiro[5.5]undecan-3-one |
| 14 | methyl 2-(3-oxo-9-phenethyl-4-phenyl-1-oxa-4,9-diazaspiro[5.5]undecan-2-yl)acetate |
| 15 | 4-(3-methoxyphenyl)-2-methyl-9-phenethyl-1-oxa-4,9-diazaspiro[5.5]undecan-3-one |
| 16 | 9-benzyl-2-methyl-4-phenyl-1-oxa-4,9-diazaspiro[5.5]undecan-3-one |
| 17 | 2-isopropyl-9-phenethyl-4-phenyl-1-oxa-4,9-diazaspiro[5.5]undecan-3-one |
| 18 | 2,2-dimethyl-9-phenethyl-4-phenyl-1-oxa-4,9-diazaspiro[5.5]undecan-3-one |
| 19 | 2-(benzyloxymethyl)-9-phenethyl-4-phenyl-1-oxa-4,9-diazaspiro[5.5]undecan-3-one |
| 20 | 2-methyl-4-(1-methyl-1H-pyrazol-3-yl)-9-phenethyl-1-oxa-4,9-diazaspiro[5.5]undecan-3-one |
| 21 | 2-methylene-9-phenethyl-4-phenyl-1-oxa-4,9-diazaspiro[5.5]undecan-3-one |
| 22 | 4-(2-fluorophenyl)-2-methylene-9-phenethyl-1-oxa-4,9-diazaspiro[5.5]undecan-3-one |
| 23 | 2-methyl-9-(2-(5-nitropyridin-2-yl)ethyl)-4-phenyl-1-oxa-4,9-diazaspiro[5.5]undecan-3-one |
| 24 | 4-(2-fluorophenyl)-2-methyl-9-(2-(5-nitropyridin-2-yl)ethyl)-1-oxa-4,9-diazaspiro[5.5]undecan-3-one |
| 25 | 4-(2-fluorophenyl)-2-methyl-9-(2-(3-nitropyridin-2-yl)ethyl)-1-oxa-4,9-diazaspiro[5.5]undecan-3-one |
| 26 | 2-methyl-4-phenyl-9-(2-(pyrimidin-2-yl)ethyl)-1-oxa-4,9-diazaspiro[5.5]undecan-3-one |
| 27 | 2-methyl-9-(2-(2-nitropyridin-3-yl)ethyl)-4-phenyl-1-oxa-4,9-diazaspiro[5.5]undecan-3-one |
| 28 | 2-methyl-4-phenyl-9-(2-(4-(trifluoromethyl)pyridin-2-yl)ethyl)-1-oxa-4,9-diazaspiro[5.5]undecan-3-one |
| 29 | 9-(2-(6-aminopyridin-2-yl)ethyl)-2-methyl-4-phenyl-1-oxa-4,9-diazaspiro[5.5]undecan-3-one |
| 30 | 9-(2-(4-aminopyridin-2-yl)ethyl)-2-methyl-4-phenyl-1-oxa-4,9-diazaspiro[5.5]undecan-3-one |
| 31 | 4-(2-fluorophenyl)-2-methyl-9-(2-(6-(trifluoromethyl)pyridin-2-yl)ethyl)-1-oxa-4,9-diazaspiro[5.5]undecan-3-one |
| 32 | 9-(2-(2-aminopyridin-4-yl)ethyl)-2-methyl-4-phenyl-1-oxa-4,9-diazaspiro[5.5]undecan-3-one |
| 33 | 2-methyl-4-phenyl-9-(2-(3-(trifluoromethyl)pyridin-2-yl)ethyl)-1-oxa-4,9-diazaspiro[5.5]undecan-3-one |
| 34 | 2-methyl-4-phenyl-9-(2-(5-(trifluoromethyl)pyridin-2-yl)ethyl)-1-oxa-4,9-diazaspiro[5.5]undecan-3-one |
| 35 | 9-(2-(4-methoxypyridin-2-yl)ethyl)-2-methyl-4-phenyl-1-oxa-4,9-diazaspiro[5.5]undecan-3-one |
| 36 | 6-(2-(2-methyl-3-oxo-4-phenyl-1-oxa-4,9-diazaspiro[5.5]undecan-9-yl)ethyl)nicotinonitrile |
| 37 | 9-(2-(3-chloropyridin-2-yl)ethyl)-2-methyl-4-phenyl-1-oxa-4,9-diazaspiro[5.5]undecan-3-one |
| 38 | 9-(2-(5-chloropyridin-2-yl)ethyl)-2-methyl-4-phenyl-1-oxa-4,9-diazaspiro[5.5]undecan-3-one |
| 39 | 4-(2-fluorophenyl)-2-isopropyl-9-(2-(2-nitropyridin-3-yl)ethyl)-1-oxa-4,9-diazaspiro[5.5]undecan-3-one |
| 40 | 2-methyl-4-phenyl-9-(2-(2-(trifluoromethyl)pyridin-4-yl)ethyl)-1-oxa-4,9-diazaspiro[5.5]undecan-3-one |
| 41 | 2-(2-(2-methyl-3-oxo-4-phenyl-1-oxa-4,9-diazaspiro[5.5]undecan-9-yl)ethyl)isonicotinonitrile |
| 42 | 9-(2-(6-aminopyridin-2-yl)ethyl)-2-methyl-4-(4-(trifluoromethyl)pyridin-3-yl)-1-oxa-4,9-diazaspiro[5.5]undecan-3-one |
| 43 | 2-methyl-9-(2-(2-nitropyridin-3-yl)ethyl)-4-(4-(trifluoromethyl)pyridin-3-yl)-1-oxa-4,9-diazaspiro[5.5]undecan-3-one |
| 44 | 9-(2-(3-chloropyridin-2-yl)ethyl)-2-methyl-4-(4-(trifluoromethyl)pyridin-3-yl)-1-oxa-4,9-diazaspiro[5.5]undecan-3-one |
| 45 | 9-(2-(3-chloropyridin-2-yl)ethyl)-2-methyl-4-((5-(trifluoromethyl)pyridin-2-yl)methyl)-1-oxa-4,9-diazaspiro[5.5]undecan-3-one |
| 46 | 9-(2-(3-chloropyridin-2-yl)ethyl)-4-((5-fluoropyridin-2-yl)methyl)-2-methyl-1-oxa-4,9-diazaspiro[5.5]undecan-3-one |
| 47 | 9-(2-(3-fluoropyridin-2-yl)ethyl)-4-((5-fluoropyridin-2-yl)methyl)-2-methyl-1-oxa-4,9-diazaspiro[5.5]undecan-3-one |

-continued

| EX | Chemical name |
|---|---|
| 48 | 9-(2-(3-fluoropyridin-2-yl)ethyl)-2-methyl-4-(2-(trifluoromethyl)pyridin-3-yl)-1-oxa-4,9-diazaspiro[5.5]undecan-3-one |
| 49 | 4-((5-fluoropyridin-2-yl)methyl)-2-methyl-9-(2-(6-(trifluoromethyl)pyridin-2-yl)ethyl)-1-oxa-4,9-diazaspiro[5.5]undecan-3-one |
| 50 | 9-(2-(3-chloropyridin-4-yl)ethyl)-2-methyl-4-phenyl-1-oxa-4,9-diazaspiro[5.5]undecan-3-one |
| 51 | 9-(2-fluorophenethyl)-2-methyl-4-phenyl-1-oxa-4,9-diazaspiro[5.5]undecan-3-one |
| 52 | 9-(4-methoxyphenethyl)-4-phenyl-1-oxa-4,9-diazaspiro[5.5]undecan-3-one |
| 53 | 2-methyl-4-phenyl-9-(2-(thiophen-2-yl)ethyl)-1-oxa-4,9-diazaspiro[5.5]undecan-3-one |
| 54 | 9-(3-fluorophenethyl)-2-methyl-4-phenyl-1-oxa-4,9-diazaspiro[5.5]undecan-3-one |
| 55 | 9-(4-fluorophenethyl)-2-methyl-4-phenyl-1-oxa-4,9-diazaspiro[5.5]undecan-3-one |
| 56 | 9-(2-(1H-pyrazol-1-yl)ethyl)-2-methyl-4-phenyl-1-oxa-4,9-diazaspiro[5.5]undecan-3-one |
| 57 | 9-(2-methoxyphenethyl)-2-methyl-4-phenyl-1-oxa-4,9-diazaspiro[5.5]undecan-3-one |
| 58 | 2-methyl-4-phenyl-9-(2-(pyridin-2-yl)ethyl)-1-oxa-4,9-diazaspiro[5.5]undecan-3-one |
| 59 | 2-methyl-4-phenyl-9-((tetrahydro-2H-pyran-4-yl)methyl)-1-oxa-4,9-diazaspiro[5.5]undecan-3-one |
| 60 | 2-methyl-4-phenyl-9-(3-phenylpropyl)-1-oxa-4,9-diazaspiro[5.5]undecan-3-one |
| 61 | 2-methyl-9-(2-(4-methylthiazol-5-yl)ethyl)-4-phenyl-1-oxa-4,9-diazaspiro[5.5]undecan-3-one |
| 62 | 9-(2-(1H-indol-1-yl)ethyl)-2-methyl-4-phenyl-1-oxa-4,9-diazaspiro[5.5]undecan-3-one |
| 63 | 9-(2-(1H-benzo[d]imidazol-1-yl)ethyl)-2-methyl-4-phenyl-1-oxa-4,9-diazaspiro[5.5]undecan-3-one |
| 64 | methyl 3-(2-methyl-3-oxo-4-phenyl-1-oxa-4,9-diazaspiro[5.5]undecan-9-yl)propanoate |
| 65 | 2-methyl-9-(2-morpholinoethyl)-4-phenyl-1-oxa-4,9-diazaspiro[5.5]undecan-3-one |
| 66 | 2-methyl-9-(4-nitrophenethyl)-4-phenyl-1-oxa-4,9-diazaspiro[5.5]undecan-3-one |
| 67 | 2-methyl-9-(3-nitrophenethyl)-4-phenyl-1-oxa-4,9-diazaspiro[5.5]undecan-3-one |
| 68 | 2-methyl-9-(2-nitrophenethyl)-4-phenyl-1-oxa-4,9-diazaspiro[5.5]undecan-3-one |
| 69 | 9-(2-(1H-pyrrolo[2,3-b]pyridin-1-yl)ethyl)-2-methyl-4-phenyl-1-oxa-4,9-diazaspiro[5.5]undecan-3-one |
| 70 | methyl 4-(2-(2-methyl-3-oxo-4-phenyl-1-oxa-4,9-diazaspiro[5.5]undecan-9-yl)ethyl)benzoate |
| 71 | 2-(2-methyl-3-oxo-4-phenyl-1-oxa-4,9-diazaspiro[5.5]undecan-9-yl)-N-phenylacetamide |
| 72 | 2-methyl-9-(2-phenoxyethyl)-4-phenyl-1-oxa-4,9-diazaspiro[5.5]undecan-3-one |
| 73 | 2-methyl-4-phenyl-9-(2-(pyridin-3-yl)ethyl)-1-oxa-4,9-diazaspiro[5.5]undecan-3-one |
| 74 | 3-(2-(2-methyl-3-oxo-4-phenyl-1-oxa-4,9-diazaspiro[5.5]undecan-9-yl)ethyl)benzo[d]oxazol-2(3H)-one |
| 75 | 3-(2-(2-methyl-3-oxo-4-phenyl-1-oxa-4,9-diazaspiro[5.5]undecan-9-yl)ethyl)benzonitrile |
| 76 | 4-(2-(2-methyl-3-oxo-4-phenyl-1-oxa-4,9-diazaspiro[5.5]undecan-9-yl)ethyl)benzonitrile |
| 77 | 9-(2-(3,5-dimethyl-1H-pyrazol-1-yl)ethyl)-2-methyl-4-phenyl-1-oxa-4,9-diazaspiro[5.5]undecan-3-one |
| 78 | 2-methyl-9-(2-morpholino-2-oxoethyl)-4-phenyl-1-oxa-4,9-diazaspiro[5.5]undecan-3-one |
| 79 | 9-(2-methoxyphenethyl)-4-(pyridin-2-ylmethyl)-1-oxa-4,9-diazaspiro[5.5]undecan-3-one |
| 80 | (Z)-4-(2-fluorophenyl)-9-phenethyl-2-((tetrahydro-2H-pyran-4-yl)methylene)-1-oxa-4,9-diazaspiro[5.5]undecan-3-one |
| 81 | 4-(2-fluorophenyl)-9-isopentyl-2-methyl-1-oxa-4,9-diazaspiro[5.5]undecan-3-one |
| 82 | 9-(cyclopropylmethyl)-4-(2-fluorophenyl)-2-methyl-1-oxa-4,9-diazaspiro[5.5]undecan-3-one |
| 83 | 4-(2-fluorophenyl)-9-(3-methoxyphenethyl)-2-methyl-1-oxa-4,9-diazaspiro[5.5]undecan-3-one |
| 84 | 9-(2-(pyridin-2-yl)ethyl)-4-(pyridin-2-ylmethyl)-1-oxa-4,9-diazaspiro[5.5]undecan-3-one |
| 85 | 4-(2-fluorophenyl)-9-phenethyl-2-(propan-2-ylidene)-1-oxa-4,9-diazaspiro[5.5]undecan-3-one |
| 86 | 9-phenethyl-4-(pyridin-2-ylmethyl)-1-oxa-4,9-diazaspiro[5.5]undecan-3-one |
| 87 | 4-benzyl-9-(2-methoxyphenethyl)-1-oxa-4,9-diazaspiro[5.5]undecane |

-continued

| EX | Chemical name |
|---|---|
| 88 | 2-methyl-9-phenethyl-4-(thiazol-4-yl)-1-oxa-4,9-diazaspiro[5.5]undecan-3-one |
| 89 | 4-(2-fluorophenyl)-9-(2-(6-fluoropyridin-2-yl)ethyl)-2-methyl-1-oxa-4,9-diazaspiro[5.5]undecan-3-one |
| 90 | 12-phenyl-8-[2-(pyridin-2-yl)ethyl]-4-oxa-8,12-diazadispiro[2.1.5.3]tridecan-13-one |
| 91 | 4-(2-fluorophenyl)-2-methyl-9-(2-(6-(trifluoromethyl)pyridin-3-yl)ethyl)-1-oxa-4,9-diazaspiro[5.5]undecan-3-one |
| 92 | 8-(3-nitrophenethyl)-12-phenyl-4-oxa-8,12-diazadispiro[2.1.5.3]tridecan-13-one |
| 93 | N-methyl-3-(2-(2-methyl-3-oxo-4-phenyl-1-oxa-4,9-diazaspiro[5.5]undecan-9-yl)ethyl)benzenesulfonamide |
| 94 | 9-(2-(5-fluoropyridin-2-yl)ethyl)-2-methyl-4-phenyl-1-oxa-4,9-diazaspiro[5.5]undecan-3-one |
| 95 | 2-methyl-4-phenyl-9-(2-(thiazol-2-yl)ethyl)-1-oxa-4,9-diazaspiro[5.5]undecan-3-one |
| 96 | 9-(2-(3-fluoropyridin-2-yl)ethyl)-2-methyl-4-phenyl-1-oxa-4,9-diazaspiro[5.5]undecan-3-one |
| 97 | 8-(2-oxo-2-phenylethyl)-12-phenyl-4-oxa-8,12-diazadispiro[2.1.5.3]tridecan-13-one |
| 98 | 9-(2-(pyridin-2-yl)ethyl)-4-((5-(trifluoromethyl)pyridin-2-yl)methyl)-1-oxa-4,9-diazaspiro[5.5]undecan-3-one |
| 99 | 9-(2-oxo-2-phenylethyl)-4-((5-(trifluoromethyl)pyridin-2-yl)methyl)-1-oxa-4,9-diazaspiro[5.5]undecan-3-one |
| 100 | N-methyl-3-(2-methyl-3-oxo-4-phenyl-1-oxa-4,9-diazaspiro[5.5]undecan-9-yl)-N-phenylpropanamide |
| 101 | 2-methyl-9-(2-(pyridin-2-yl)ethyl)-4-(4-(trifluoromethyl)pyridin-3-yl)-1-oxa-4,9-diazaspiro[5.5]undecan-3-one |
| 102 | 9-(2-(6-methoxypyridin-2-yl)ethyl)-2-methyl-4-phenyl-1-oxa-4,9-diazaspiro[5.5]undecan-3-one |
| 103 | 9-(3-nitrophenethyl)-4-((5-(trifluoromethyl)pyridin-2-yl)methyl)-1-oxa-4,9-diazaspiro[5.5]undecan-3-one |
| 104 | 4-((6-aminopyridin-2-yl)methyl)-9-phenethyl-1-oxa-4,9-diazaspiro[5.5]undecan-3-one |
| 105 | 4-((5-chloropyridin-2-yl)methyl)-9-phenethyl-1-oxa-4,9-diazaspiro[5.5]undecan-3-one |
| 106 | tert-butyl (4-(2-(3-oxo-4-((5-(trifluoromethyl)pyridin-2-yl)methyl)-1-oxa-4,9-diazaspiro[5.5]undecan-9-yl)ethyl)thiazol-2-yl)carbamate |
| 107 | N-methyl-4-(2-(2-methyl-3-oxo-4-phenyl-1-oxa-4,9-diazaspiro[5.5]undecan-9-yl)ethyl)benzenesulfonamide |
| 108 | 4-(2-(2-methyl-3-oxo-4-phenyl-1-oxa-4,9-diazaspiro[5.5]undecan-9-yl)ethyl)benzenesulfonamide |
| 109 | 12-(4-methoxybenzyl)-8-phenethyl-4-oxa-8,12-diazadispiro[2.1.5.3]tridecan-13-one hydrochloride |
| 110 | 2-methyl-9-(2-(3-nitro-1H-pyrazol-1-yl)ethyl)-4-phenyl-1-oxa-4,9-diazaspiro[5.5]undecan-3-one |
| 111 | 9-(2-(6-methoxypyridin-3-yl)ethyl)-2-methyl-4-phenyl-1-oxa-4,9-diazaspiro[5.5]undecan-3-one |
| 112 | 2-methyl-4-phenyl-9-(2-(5-(trifluoromethyl)pyridin-3-yl)ethyl)-1-oxa-4,9-diazaspiro[5.5]undecan-3-one |
| 113 | 9-(2-(6-chloropyridin-3-yl)ethyl)-2-methyl-4-phenyl-1-oxa-4,9-diazaspiro[5.5]undecan-3-one |
| 114 | 9-(2-(5-fluoropyridin-3-yl)ethyl)-2-methyl-4-phenyl-1-oxa-4,9-diazaspiro[5.5]undecan-3-one |
| 115 | 9-(2-(5-chloropyridin-3-yl)ethyl)-2-methyl-4-phenyl-1-oxa-4,9-diazaspiro[5.5]undecan-3-one |
| 116 | tert-butyl (1-(2-(2-methyl-3-oxo-4-phenyl-1-oxa-4,9-diazaspiro[5.5]undecan-9-yl)ethyl)-1H-pyrazol-5-yl)carbamate |
| 117 | tert-butyl (4-(2-(4-(2-fluorophenyl)-2-isopropyl-3-oxo-1-oxa-4,9-diazaspiro[5.5]undecan-9-yl)ethyl)thiazol-2-yl)carbamate |
| 118 | tert-butyl (4-(2-(13-oxo-12-phenyl-4-oxa-8,12-diazadispiro[2.1.5.3]tridecan-8-yl)ethyl)thiazol-2-yl)carbamate |
| 119 | 8-(3-nitrophenethyl)-12-{[5-(trifluoromethyl)pyridin-2-yl]methyl}-4-oxa-8,12-diazadispiro[2.1.5.3]tridecan-13-one |
| 120 | tert-butyl (4-(2-(13-oxo-12-{[5-(trifluoromethyl)pyridin-2-yl]methyl}-4-oxa-8,12-diazadispiro[2.1.5.3]tridecan-8-yl)ethyl)thiazol-2-yl)carbamate |
| 121 | tert-butyl (4-(2-(2-methyl-3-oxo-4-(4-(trifluoromethyl)pyridin-3-yl)-1-oxa-4,9-diazaspiro[5.5]undecan-9-yl)ethyl)thiazol-2-yl)carbamate |
| 122 | 9-(2-isopropoxyethyl)-2-methyl-4-phenyl-1-oxa-4,9-diazaspiro[5.5]undecan-3-one |
| 123 | 6-(2-(2-methyl-3-oxo-4-phenyl-1-oxa-4,9-diazaspiro[5.5]undecan-9-yl)ethyl)picolinonitrile |
| 124 | 2-methyl-9-(2-morpholino-2-oxoethyl)-4-((5-(trifluoromethyl)pyridin-2-yl)methyl)-1-oxa-4,9-diazaspiro[5.5]undecan-3-one |
| 125 | 9-(2-isopropoxyethyl)-2-methyl-4-((5-(trifluoromethyl)pyridin-2-yl)methyl)-1-oxa-4,9-diazaspiro[5.5]undecan-3-one |
| 126 | 9-(2-fluorophenethyl)-2-methyl-4-(4-(trifluoromethyl)pyridin-3-yl)-1-oxa-4,9-diazaspiro[5.5]undecan-3-one |

-continued

| EX | Chemical name |
|---|---|
| 127a | (S)-9-(2-fluorophenethyl)-2-methyl-4-(4-(trifluoromethyl)pyridin-3-yl)-1-oxa-4,9-diazaspiro[5.5]undecan-3-one hydrochloride |
| 127b | (R)-9-(2-fluorophenethyl)-2-methyl-4-(4-(trifluoromethyl)pyridin-3-yl)-1-oxa-4,9-diazaspiro[5.5]undecan-3-one hydrochloride |
| 128 | 2-methyl-9-(2-oxo-2-(piperidin-1-yl)ethyl)-4-((5-(trifluoromethyl)pyridin-2-yl)methyl)-1-oxa-4,9-diazaspiro[5.5]undecan-3-one |
| 129 | 2-methyl-9-(2-oxo-2-(piperidin-1-yl)ethyl)-4-phenyl-1-oxa-4,9-diazaspiro[5.5]undecan-3-one |
| 130 | 9-(2-fluorophenethyl)-2-methyl-4-(2-(trifluoromethyl)pyridin-3-yl)-1-oxa-4,9-diazaspiro[5.5]undecan-3-one |
| 131 | 2-methyl-4-phenyl-9-(2-(tetrahydro-2H-pyran-4-yl)ethyl)-1-oxa-4,9-diazaspiro[5.5]undecan-3-one |
| 132 | 9-(3-methoxyphenethyl)-4-phenyl-1-oxa-4,9-diazaspiro[5.5]undecan-3-one |
| 133 | 2-methyl-4-phenyl-9-(2-(pyridin-4-yl)ethyl)-1-oxa-4,9-diazaspiro[5.5]undecan-3-one |
| 134 | 4-(2-fluorophenyl)-2-(methoxymethyl)-9-(2-(pyridin-2-yl)ethyl)-1-oxa-4,9-diazaspiro[5.5]undecan-3-one |
| 135 | 4-(2-fluorophenyl)-2-(methoxymethyl)-9-(2-methoxyphenethyl)-1-oxa-4,9-diazaspiro[5.5]undecan-3-one |
| 136 | 9-(2-fluorophenethyl)-4-(2-fluorophenyl)-2-(methoxymethyl)-1-oxa-4,9-diazaspiro[5.5]undecan-3-one |
| 137 | 4-(2-fluorophenyl)-2-isopropyl-9-(2-methoxyphenethyl)-1-oxa-4,9-diazaspiro[5.5]undecan-3-one |
| 138 | 4-benzyl-9-(2-(pyridin-2-yl)ethyl)-1-oxa-4,9-diazaspiro[5.5]undecane |
| 139 | 4-(2-fluorophenyl)-2-(propan-2-ylidene)-9-(2-(pyridin-2-yl)ethyl)-1-oxa-4,9-diazaspiro[5.5]undecan-3-one |
| 140 | tert-butyl (4-(2-(4-(2-fluorophenyl)-2-methyl-3-oxo-1-oxa-4,9-diazaspiro[5.5]undecan-9-yl)ethyl)thiazol-2-yl)carbamate |
| 141 | 4-(2-fluorophenyl)-9-(2-(4-methylthiazol-5-yl)ethyl)-2-(propan-2-ylidene)-1-oxa-4,9-diazaspiro[5.5]undecan-3-one |
| 142 | (Z)-4-(2-fluorophenyl)-2-(3-methoxypropylidene)-9-phenethyl-1-oxa-4,9-diazaspiro[5.5]undecan-3-one |
| 143 | ethyl 3-(2-(4-(2-fluorophenyl)-2-methyl-3-oxo-1-oxa-4,9-diazaspiro[5.5]undecan-9-yl)ethyl)benzoate |
| 144 | 3-(2-methyl-3-oxo-4-phenyl-1-oxa-4,9-diazaspiro[5.5]undecan-9-yl)-N-phenylpropanamide |
| 145 | 2-methyl-4-phenyl-9-(2-(pyridin-3-yloxy)ethyl)-1-oxa-4,9-diazaspiro[5.5]undecan-3-one |
| 146 | 2-methyl-9-(2-(2-oxopyrrolidin-1-yl)ethyl)-4-phenyl-1-oxa-4,9-diazaspiro[5.5]undecan-3-one |
| 147 | 9-(2-(1H-pyrazol-4-yl)ethyl)-2-methyl-4-phenyl-1-oxa-4,9-diazaspiro[5.5]undecan-3-one |
| 148 | 8-(2-fluorophenethyl)-12-(4-methoxybenzyl)-4-oxa-8,12-diazadispiro[2.1.5.3]tridecan-13-one |
| 149 | 2-phenethyl-9-phenyl-6-oxa-2,9-diazaspiro[4.5]decan-8-one |
| 150 | 9-(2-hydroxy-2-phenylethyl)-2-methyl-4-phenyl-1-oxa-4,9-diazaspiro[5.5]undecan-3-one |
| 151a | (R)-9-((R)-2-hydroxy-2-phenylethyl)-2-methyl-4-phenyl-1-oxa-4,9-diazaspiro[5.5]undecan-3-one |
| 151b | (R)-9-((S)-2-hydroxy-2-phenylethyl)-2-methyl-4-phenyl-1-oxa-4,9-diazaspiro[5.5]undecan-3-one |
| 151c | (S)-9-((S)-2-hydroxy-2-phenylethyl)-2-methyl-4-phenyl-1-oxa-4,9-diazaspiro[5.5]undecan-3-one |
| 151d | (S)-9-((R)-2-hydroxy-2-phenylethyl)-2-methyl-4-phenyl-1-oxa-4,9-diazaspiro[5.5]undecan-3-one |
| 152 | 4-benzyl-2-methyl-9-phenethyl-1-oxa-4,9-diazaspiro[5.5]undecan-3-one |
| 153 | 4-benzyl-9-phenethyl-1-oxa-4,9-diazaspiro[5.5]undecan-3-one |
| 154 | 4-(2-fluorobenzyl)-2-methyl-9-phenethyl-1-oxa-4,9-diazaspiro[5.5]undecan-3-one |
| 155 | 4-(3-fluorobenzyl)-2-methyl-9-phenethyl-1-oxa-4,9-diazaspiro[5.5]undecan-3-one |
| 156 | 2-methyl-4,9-diphenethyl-1-oxa-4,9-diazaspiro[5.5]undecan-3-one |
| 157 | 2-methyl-9-phenethyl-4-(pyridin-2-ylmethyl)-1-oxa-4,9-diazaspiro[5.5]undecan-3-one |
| 158 | 4-(4-fluorobenzyl)-2-methyl-9-phenethyl-1-oxa-4,9-diazaspiro[5.5]undecan-3-one |
| 159 | 2-methyl-9-phenethyl-4-(pyridin-3-ylmethyl)-1-oxa-4,9-diazaspiro[5.5]undecan-3-one |
| 160 | 2-methyl-9-phenethyl-4-(thiazol-2-ylmethyl)-1-oxa-4,9-diazaspiro[5.5]undecan-3-one |
| 161 | 2-methyl-9-phenethyl-4-(thiazol-5-ylmethyl)-1-oxa-4,9-diazaspiro[5.5]undecan-3-one |
| 162 | 2-methyl-9-phenethyl-4-(pyridin-4-ylmethyl)-1-oxa-4,9-diazaspiro[5.5]undecan-3-one |
| 163 | 2-methyl-9-phenethyl-4-((tetrahydro-2H-pyran-4-yl)methyl)-1-oxa-4,9-diazaspiro[5.5]undecan-3-one |

| EX | Chemical name |
|---|---|
| 164 | 2-methyl-9-phenethyl-4-(thiazol-4-ylmethyl)-1-oxa-4,9-diazaspiro[5.5]undecan-3-one |
| 165 | 9-phenethyl-4-(pyridin-4-ylmethyl)-1-oxa-4,9-diazaspiro[5.5]undecan-3-one |
| 166 | 4-(3-methoxybenzyl)-9-phenethyl-1-oxa-4,9-diazaspiro[5.5]undecan-3-one |
| 167 | 9-phenethyl-4-(thiazol-4-ylmethyl)-1-oxa-4,9-diazaspiro[5.5]undecan-3-one |
| 168 | 4-((1-benzyl-1H-imidazol-2-yl)methyl)-9-phenethyl-1-oxa-4,9-diazaspiro[5.5]undecan-3-one |
| 169 | 9-phenethyl-4-(2-(pyridin-2-yl)ethyl)-1-oxa-4,9-diazaspiro[5.5]undecan-3-one |
| 170 | 2-methyl-4-(2-morpholino-2-oxoethyl)-9-phenethyl-1-oxa-4,9-diazaspiro[5.5]undecan-3-one |
| 171 | 2-methyl-4-((1-methyl-1H-pyrazol-3-yl)methyl)-9-phenethyl-1-oxa-4,9-diazaspiro[5.5]undecan-3-one |
| 172 | 2-methyl-4-((1-methyl-1H-imidazol-2-yl)methyl)-9-phenethyl-1-oxa-4,9-diazaspiro[5.5]undecan-3-one |
| 173 | 4-((3-fluoropyridin-2-yl)methyl)-2-methyl-9-phenethyl-1-oxa-4,9-diazaspiro[5.5]undecan-3-one |
| 174 | 2-methyl-9-phenethyl-4-((6-(trifluoromethyl)pyridin-2-yl)methyl)-1-oxa-4,9-diazaspiro[5.5]undecan-3-one |
| 175 | 2-methyl-9-phenethyl-4-(2-(pyridin-3-yl)ethyl)-1-oxa-4,9-diazaspiro[5.5]undecan-3-one |
| 176 | 4-((5-fluoropyridin-2-yl)methyl)-9-phenethyl-1-oxa-4,9-diazaspiro[5.5]undecan-3-one |
| 177 | 9-phenethyl-4-((5-(trifluoromethyl)pyridin-2-yl)methyl)-1-oxa-4,9-diazaspiro[5.5]undecan-3-one |
| 178 | 9-phenethyl-4-(2-(pyridin-4-yl)ethyl)-1-oxa-4,9-diazaspiro[5.5]undecan-3-one |
| 179 | 4-(3-nitrobenzyl)-9-phenethyl-1-oxa-4,9-diazaspiro[5.5]undecan-3-one |
| 180 | 12-(3-methoxypropyl)-8-phenethyl-4-oxa-8,12-diazadispiro[2.1.5.3]tridecan-13-one |
| 181 | 3-[13-oxo-8-phenethyl-4-oxa-8,12-diazadispiro[2.1.5.3]tridecan-12-yl]propanenitrile |
| 182 | N,N-dimethyl-3-[13-oxo-8-phenethyl-4-oxa-8,12-diazadispiro[2.1.5.3]tridecan-12-yl]propanamide |
| 183 | 4-(2-hydroxy-2-methylpropyl)-2-methyl-9-phenethyl-1-oxa-4,9-diazaspiro[5.5]undecan-3-one |
| 184 | 12-(2-methoxyethyl)-8-phenethyl-4-oxa-8,12-diazadispiro[2.1.5.3]tridecan-13-one |
| 185 | 12-(2-((tetrahydro-2H-pyran-2-yl)oxy)ethyl)-8-phenethyl-4-oxa-8,12-diazadispiro[2.1.5.3]tridecan-13-one |
| 186 | methyl 3-(13-oxo-8-phenethyl-4-oxa-8,12-diazadispiro[2.1.5.3]tridecan-12-yl)propanoate |
| 187 | 8-phenethyl-12-{[5-(trifluoromethyl)pyridin-2-yl]methyl}-4-oxa-8,12-diazadispiro[2.1.5.3]tridecan-13-one |
| 188 | 9-benzyl-4-(4-fluorophenyl)-1-oxa-4,9-diazaspiro[5.5]undecan-3-one |
| 189 | 4-(2-fluorophenyl)-9-phenethyl-1-oxa-4,9-diazaspiro[5.5]undecan-3-one |
| 190 | 4-(4-fluorophenyl)-9-phenethyl-1-oxa-4,9-diazaspiro[5.5]undecan-3-one |
| 191 | 4-(3-fluorophenyl)-9-phenethyl-1-oxa-4,9-diazaspiro[5.5]undecan-3-one |
| 192 | 4-(2-fluorophenyl)-2-methyl-9-phenethyl-1-oxa-4,9-diazaspiro[5.5]undecan-3-one |
| 193 | 4-(2-chlorophenyl)-2-methyl-9-phenethyl-1-oxa-4,9-diazaspiro[5.5]undecan-3-one |
| 194 | 2-methyl-9-phenethyl-4-(pyridin-3-yl)-1-oxa-4,9-diazaspiro[5.5]undecan-3-one |
| 195 | 2-methyl-9-phenethyl-4-(pyrazin-2-yl)-1-oxa-4,9-diazaspiro[5.5]undecan-3-one |
| 196 | 2-methyl-9-phenethyl-4-(pyridin-2-yl)-1-oxa-4,9-diazaspiro[5.5]undecan-3-one |
| 197 | ethyl 3-(2-methyl-3-oxo-9-phenethyl-1-oxa-4,9-diazaspiro[5.5]undecan-4-yl)benzoate |
| 198 | 3-(2-methyl-3-oxo-9-phenethyl-1-oxa-4,9-diazaspiro[5.5]undecan-4-yl)benzonitrile |
| 199 | 2-methyl-4-(3-nitrophenyl)-9-phenethyl-1-oxa-4,9-diazaspiro[5.5]undecan-3-one |
| 200 | 2-methyl-4-(1-methyl-1H-indazol-3-yl)-9-phenethyl-1-oxa-4,9-diazaspiro[5.5]undecan-3-one |
| 201 | 2-methyl-4-(1-methyl-1H-indazol-6-yl)-9-phenethyl-1-oxa-4,9-diazaspiro[5.5]undecan-3-one |
| 202 | 4-(benzo[d][1,3]dioxol-5-yl)-2-methyl-9-phenethyl-1-oxa-4,9-diazaspiro[5.5]undecan-3-one |
| 203 | 4-(benzo[d]thiazol-6-yl)-2-methyl-9-phenethyl-1-oxa-4,9-diazaspiro[5.5]undecan-3-one |
| 204 | 4-(benzo[d]thiazol-2-yl)-2-methyl-9-phenethyl-1-oxa-4,9-diazaspiro[5.5]undecan-3-one |
| 205 | 2-methyl-9-phenethyl-4-(pyridin-4-yl)-1-oxa-4,9-diazaspiro[5.5]undecan-3-one |
| 206 | 4-(2-methoxyphenyl)-2-methyl-9-phenethyl-1-oxa-4,9-diazaspiro[5.5]undecan-3-one |
| 207 | 2-methyl-9-phenethyl-4-(6-(trifluoromethyl)pyridin-2-yl)-1-oxa-4,9-diazaspiro[5.5]undecan-3-one |
| 208 | 4-(3-fluoropyridin-2-yl)-2-methyl-9-phenethyl-1-oxa-4,9-diazaspiro[5.5]undecan-3-one |

| EX | Chemical name |
|---|---|
| 209 | 2-methyl-9-phenethyl-4-(thiazol-2-yl)-1-oxa-4,9-diazaspiro[5.5]undecan-3-one |
| 210 | 2-methyl-4-(1-methyl-1H-pyrazol-4-yl)-9-phenethyl-1-oxa-4,9-diazaspiro[5.5]undecan-3-one |
| 211 | 4-(6-methoxypyridin-2-yl)-2-methyl-9-phenethyl-1-oxa-4,9-diazaspiro[5.5]undecan-3-one |
| 212 | 2-methyl-9-phenethyl-4-(6-(trifluoromethyl)pyridin-3-yl)-1-oxa-4,9-diazaspiro[5.5]undecan-3-one |
| 213 | 4-(2-fluoropyridin-3-yl)-2-methyl-9-phenethyl-1-oxa-4,9-diazaspiro[5.5]undecan-3-one |
| 214 | 2-methyl-9-phenethyl-4-(4-(trifluoromethyl)pyridin-3-yl)-1-oxa-4,9-diazaspiro[5.5]undecan-3-one |
| 215 | 2-methyl-9-phenethyl-4-(2-(trifluoromethyl)pyridin-3-yl)-1-oxa-4,9-diazaspiro[5.5]undecan-3-one |
| 216 | 4-(5-fluoropyridin-3-yl)-2-methyl-9-phenethyl-1-oxa-4,9-diazaspiro[5.5]undecan-3-one |
| 217 | 2-methyl-9-phenethyl-4-(5-(trifluoromethyl)pyridin-3-yl)-1-oxa-4,9-diazaspiro[5.5]undecan-3-one |
| 218 | 2-methyl-9-phenethyl-4-(3-(trifluoromethyl)pyridin-2-yl)-1-oxa-4,9-diazaspiro[5.5]undecan-3-one |
| 219 | 8-(2-fluorophenethyl)-12-(2-(trifluoromethyl)pyridin-3-yl)-4-oxa-8,12-diazadispiro[2.1.5.3]tridecan-13-one |
| 220 | 8-(2-fluorophenethyl)-12-(3-(trifluoromethyl)pyridin-2-yl)-4-oxa-8,12-diazadispiro[2.1.5.3]tridecan-13-one hydrochloride |
| 221 | 9-(2-fluorophenethyl)-2-methyl-4-(3-(trifluoromethyl)pyridin-2-yl)-1-oxa-4,9-diazaspiro[5.5]undecan-3-one |
| 222a | (R)-9-(2-fluorophenethyl)-2-methyl-4-(3-(trifluoromethyl)pyridin-2-yl)-1-oxa-4,9-diazaspiro[5.5]undecan-3-one hydrochloride |
| 222b | (S)-9-(2-fluorophenethyl)-2-methyl-4-(3-(trifluoromethyl)pyridin-2-yl)-1-oxa-4,9-diazaspiro[5.5]undecan-3-one hydrochloride |
| 223 | 8-(2-fluorophenethyl)-12-(4-(trifluoromethyl)pyridin-3-yl)-4-oxa-8,12-diazadispiro[2.1.5.3]tridecan-13-one hydrochloride |
| 224 | 12-(2-Fluorophenyl)-8-phenethyl-4-oxa-8,12-diazadispiro[2.1.5.3]tridecan-13-one |
| 225 | 8-phenethyl-12-phenyl-4-oxa-8,12-diazadispiro[2.1.5.3]tridecan-13-one |
| 226 | 9-(3-aminophenethyl)-2-methyl-4-phenyl-1-oxa-4,9-diazaspiro[5.5]undecan-3-one |
| 227 | 4-(3-aminophenyl)-2-methyl-9-phenethyl-1-oxa-4,9-diazaspiro[5.5]undecan-3-one |
| 228 | 9-(4-aminophenethyl)-2-methyl-4-phenyl-1-oxa-4,9-diazaspiro[5.5]undecan-3-one |
| 229 | 9-(2-aminophenethyl)-2-methyl-4-phenyl-1-oxa-4,9-diazaspiro[5.5]undecan-3-one |
| 230 | 9-(2-(5-aminopyridin-2-yl)ethyl)-4-(2-fluorophenyl)-2-methyl-1-oxa-4,9-diazaspiro[5.5]undecan-3-one |
| 231 | 8-(3-aminophenethyl)-12-phenyl-4-oxa-8,12-diazadispiro[2.1.5.3]tridecan-13-one |
| 232 | 9-(2-(3-aminopyridin-2-yl)ethyl)-4-(2-fluorophenyl)-2-methyl-1-oxa-4,9-diazaspiro[5.5]undecan-3-one |
| 233 | 4-(3-aminobenzyl)-9-phenethyl-1-oxa-4,9-diazaspiro[5.5]undecan-3-one |
| 234 | 9-(2-(2-aminopyridin-3-yl)ethyl)-2-methyl-4-phenyl-1-oxa-4,9-diazaspiro[5.5]undecan-3-one |
| 235 | 9-(3-aminophenethyl)-4-((5-(trifluoromethyl)pyridin-2-yl)methyl)-1-oxa-4,9-diazaspiro[5.5]undecan-3-one |
| 236 | 9-(2-(5-aminopyridin-2-yl)ethyl)-2-methyl-4-phenyl-1-oxa-4,9-diazaspiro[5.5]undecan-3-one |
| 237 | 9-(2-(3-amino-1H-pyrazol-1-yl)ethyl)-2-methyl-4-phenyl-1-oxa-4,9-diazaspiro[5.5]undecan-3-one |
| 238 | 9-(2-(2-aminopyridin-3-yl)ethyl)-4-(2-fluorophenyl)-2-isopropyl-1-oxa-4,9-diazaspiro[5.5]undecan-3-one |
| 239 | 8-(3-aminophenethyl)-12-{[5-(trifluoromethyl)pyridin-2-yl]methyl}-4-oxa-8,12-diazadispiro[2.1.5.3]tridecan-13-one |
| 240 | 9-(2-(2-aminopyridin-3-yl)ethyl)-2-methyl-4-(4-(trifluoromethyl)pyridin-3-yl)-1-oxa-4,9-diazaspiro[5.5]undecan-3-one |
| 241 | N-(4-(2-(2-methyl-3-oxo-4-phenyl-1-oxa-4,9-diazaspiro[5.5]undecan-9-yl)ethyl)phenyl)acetamide |
| 242 | N-(3-(2-methyl-3-oxo-9-phenethyl-1-oxa-4,9-diazaspiro[5.5]undecan-4-yl)phenyl)acetamide |
| 243 | N-(3-(2-(2-methyl-3-oxo-4-phenyl-1-oxa-4,9-diazaspiro[5.5]undecan-9-yl)ethyl)phenyl)acetamide |
| 244a | (S)—N-(3-(2-(2-methyl-3-oxo-4-phenyl-1-oxa-4,9-diazaspiro[5.5]undecan-9-yl)ethyl)phenyl)acetamide |
| 244b | (R)—N-(3-(2-(2-methyl-3-oxo-4-phenyl-1-oxa-4,9-diazaspiro[5.5]undecan-9-yl)ethyl)phenyl)acetamide |
| 245 | N-(2-(2-(2-methyl-3-oxo-4-phenyl-1-oxa-4,9-diazaspiro[5.5]undecan-9-yl)ethyl)phenyl)acetamide |
| 246 | N-[3-(2-{13-oxo-12-phenyl-4-oxa-8,12-diazadispiro[2.1.5.3]tridecan-8-yl}ethyl)phenyl]acetamide |

-continued

| EX | Chemical name |
|---|---|
| 247 | N-(3-(2-(2-methyl-3-oxo-4-phenyl-1-oxa-4,9-diazaspiro[5.5]undecan-9-yl)ethyl)phenyl)isobutyramide |
| 248 | 1,1-dimethyl-3-(3-(2-(2-methyl-3-oxo-4-phenyl-1-oxa-4,9-diazaspiro[5.5]undecan-9-yl)ethyl)phenyl)urea |
| 249 | N-(3-((3-oxo-9-phenethyl-1-oxa-4,9-diazaspiro[5.5]undecan-4-yl)methyl)phenyl)acetamide |
| 250 | N-(2-(2-(4-(2-fluorophenyl)-2-methyl-3-oxo-1-oxa-4,9-diazaspiro[5.5]undecan-9-yl)ethyl)pyridin-3-yl)acetamide |
| 251 | N-(3-(2-(3-oxo-4-((5-(trifluoromethyl)pyridin-2-yl)methyl)-1-oxa-4,9-diazaspiro[5.5]undecan-9-yl)ethyl)phenyl)acetamide |
| 252 | N-(6-(2-(2-methyl-3-oxo-4-phenyl-1-oxa-4,9-diazaspiro[5.5]undecan-9-yl)ethyl)pyridin-3-yl)acetamide |
| 253 | N-(2-(2-(2-methyl-3-oxo-4-phenyl-1-oxa-4,9-diazaspiro[5.5]undecan-9-yl)ethyl)pyridin-4-yl)acetamide |
| 254 | N-(6-(2-(2-methyl-3-oxo-4-phenyl-1-oxa-4,9-diazaspiro[5.5]undecan-9-yl)ethyl)pyridin-2-yl)acetamide |
| 255 | N-(4-(2-(2-methyl-3-oxo-4-phenyl-1-oxa-4,9-diazaspiro[5.5]undecan-9-yl)ethyl)pyridin-2-yl)acetamide |
| 256 | N-(3-(2-(2-methyl-3-oxo-4-phenyl-1-oxa-4,9-diazaspiro[5.5]undecan-9-yl)ethyl)phenyl)methanesulfonamide |
| 257 | N-(2-(2-(2-methyl-3-oxo-4-phenyl-1-oxa-4,9-diazaspiro[5.5]undecan-9-yl)ethyl)phenyl)methanesulfonamide |
| 258 | N-(4-(2-(2-methyl-3-oxo-4-phenyl-1-oxa-4,9-diazaspiro[5.5]undecan-9-yl)ethyl)phenyl)methanesulfonamide |
| 259 | N-(3-((3-oxo-9-phenethyl-1-oxa-4,9-diazaspiro[5.5]undecan-4-yl)methyl)phenyl)methanesulfonamide |
| 260 | N-[3-(2-{13-oxo-12-phenyl-4-oxa-8,12-diazadispiro[2.1.5.3]tridecan-8-yl}ethyl)phenyl]methanesulfonamide |
| 261 | N-(3-(2-(2-methyl-3-oxo-4-phenyl-1-oxa-4,9-diazaspiro[5.5]undecan-9-yl)ethyl)phenyl)propane-2-sulfonamide |
| 262 | 1-(3-(2-(2-methyl-3-oxo-4-phenyl-1-oxa-4,9-diazaspiro[5.5]undecan-9-yl)ethyl)phenyl)urea |
| 263 | {3-[2-(13-oxo-12-{[5-(trifluoromethyl)pyridin-2-yl]methyl}-4-oxa-8,12-diazadispiro[2.1.5.3]tridecan-8-yl)ethyl]phenyl}urea |
| 264 | 1-(6-(2-(2-methyl-3-oxo-4-phenyl-1-oxa-4,9-diazaspiro[5.5]undecan-9-yl)ethyl)pyridin-2-yl)urea |
| 265 | N-[3-(2-{2-methyl-3-oxo-4-phenyl-1-oxa-4,9-diazaspiro[5.5]undecan-9-yl}ethyl)phenyl]aminosulfonamide |
| 266 | 3-(2-(2-methyl-3-oxo-4-phenyl-1-oxa-4,9-diazaspiro[5.5]undecan-9-yl)ethyl)benzamide |
| 267 | 4-(2-(2-methyl-3-oxo-4-phenyl-1-oxa-4,9-diazaspiro[5.5]undecan-9-yl)ethyl)benzoic acid |
| 268 | 3-(2-methyl-3-oxo-9-phenethyl-1-oxa-4,9-diazaspiro[5.5]undecan-4-yl)benzoic acid |
| 269 | 3-(2-methyl-3-oxo-4-phenyl-1-oxa-4,9-diazaspiro[5.5]undecan-9-yl)propanoic acid |
| 270 | 2-(3-oxo-9-phenethyl-4-phenyl-1-oxa-4,9-diazaspiro[5.5]undecan-2-yl)acetic acid |
| 271 | N,N-dimethyl-3-(2-methyl-3-oxo-9-phenethyl-1-oxa-4,9-diazaspiro[5.5]undecan-4-yl)benzamide |
| 272 | N,N-dimethyl-2-(3-oxo-9-phenethyl-4-phenyl-1-oxa-4,9-diazaspiro[5.5]undecan-2-yl)acetamide |
| 273 | N,N-dimethyl-4-(2-(2-methyl-3-oxo-4-phenyl-1-oxa-4,9-diazaspiro[5.5]undecan-9-yl)ethyl)benzamide |
| 274 | N-methyl-4-(2-(2-methyl-3-oxo-4-phenyl-1-oxa-4,9-diazaspiro[5.5]undecan-9-yl)ethyl)benzamide |
| 275 | N-methyl-3-[13-oxo-8-phenethyl-4-oxa-8,12-diazadispiro[2.1.5.3]tridecan-12-yl]propanamide |
| 276 | 3-(2-(4-(2-fluorophenyl)-2-methyl-3-oxo-1-oxa-4,9-diazaspiro[5.5]undecan-9-yl)ethyl)-N-methylbenzamide |
| 277 | 8-(2-hydroxy-2-phenylethyl)-12-phenyl-4-oxa-8,12-diazadispiro[2.1.5.3]tridecan-13-one |
| 278 | 9-(2-hydroxy-2-phenylethyl)-4-((5-(trifluoromethyl)pyridin-2-yl)methyl)-1-oxa-4,9-diazaspiro[5.5]undecan-3-one |
| 279 | 12-(3-hydroxypropyl)-8-phenethyl-4-oxa-8,12-diazadispiro[2.1.5.3]tridecan-13-one |
| 280 | 9-(2-(6-aminopyridin-3-yl)ethyl)-2-methyl-4-phenyl-1-oxa-4,9-diazaspiro[5.5]undecan-3-one |
| 281 | 4-(2-fluorophenyl)-9-(2-(2-hydroxyethoxy)phenethyl)-2-isopropyl-1-oxa-4,9-diazaspiro[5.5]undecan-3-one |
| 282 | 4-(2-fluorophenyl)-9-(3-(2-hydroxyethoxy)phenethyl)-2-methyl-1-oxa-4,9-diazaspiro[5.5]undecan-3-one |
| 283 | 2-(hydroxymethyl)-9-phenethyl-4-phenyl-1-oxa-4,9-diazaspiro[5.5]undecan-3-one |
| 284 | 4-((1H-imidazol-2-yl)methyl)-9-phenethyl-1-oxa-4,9-diazaspiro[5.5]undecan-3-one |

| EX | Chemical name |
|---|---|
| 285 | 9-benzyl-4-(2-hydroxyphenyl)-1-oxa-4,9-diazaspiro[5.5]undecan-3-one |
| 286 | 4-(2-hydroxyphenyl)-9-phenethyl-1-oxa-4,9-diazaspiro[5.5]undecan-3-one |
| 287 | 9-benzyl-4-(3-hydroxyphenyl)-1-oxa-4,9-diazaspiro[5.5]undecan-3-one |
| 288 | 4-(3-hydroxyphenyl)-9-phenethyl-1-oxa-4,9-diazaspiro[5.5]undecan-3-one |
| 289 | 9-(2-hydroxyphenethyl)-4-phenyl-1-oxa-4,9-diazaspiro[5.5]undecan-3-one |
| 290 | 9-(4-hydroxyphenethyl)-4-phenyl-1-oxa-4,9-diazaspiro[5.5]undecan-3-one |
| 291 | 9-(3-hydroxyphenethyl)-4-phenyl-1-oxa-4,9-diazaspiro[5.5]undecan-3-one |
| 292 | 4-(2-(4-phenyl-1-oxa-4,9-diazaspiro[5.5]undecan-9-yl)ethyl)phenol |
| 293 | 4-(4-hydroxyphenyl)-2-methyl-9-phenethyl-1-oxa-4,9-diazaspiro[5.5]undecan-3-one |
| 294 | 4-(3-hydroxyphenyl)-2-methyl-9-phenethyl-1-oxa-4,9-diazaspiro[5.5]undecan-3-one |
| 295 | 9-(2-hydroxyphenethyl)-2-methyl-4-phenyl-1-oxa-4,9-diazaspiro[5.5]undecan-3-one |
| 296 | 4-(2-hydroxyphenyl)-2-methyl-9-phenethyl-1-oxa-4,9-diazaspiro[5.5]undecan-3-one |
| 297 | 4-(2-fluorophenyl)-9-(2-hydroxyphenethyl)-2-isopropyl-1-oxa-4,9-diazaspiro[5.5]undecan-3-one |
| 298 | 4-(2-fluorophenyl)-9-(3-hydroxyphenethyl)-2-methyl-1-oxa-4,9-diazaspiro[5.5]undecan-3-one |
| 299 | 2-(2-(4-benzyl-1-oxa-4,9-diazaspiro[5.5]undecan-9-yl)ethyl)phenol |
| 300 | 9-(2-hydroxyphenethyl)-4-(pyridin-2-ylmethyl)-1-oxa-4,9-diazaspiro[5.5]undecan-3-one |
| 301 | 4-(2-fluorophenyl)-2-(hydroxymethyl)-9-(2-hydroxyphenethyl)-1-oxa-4,9-diazaspiro[5.5]undecan-3-one |
| 302 | 4-(2-fluorophenyl)-2-(3-hydroxypropyl)-9-phenethyl-1-oxa-4,9-diazaspiro[5.5]undecan-3-one |
| 303 | 9-(2-(2-aminothiazol-4-yl)ethyl)-4-(2-fluorophenyl)-2-methyl-1-oxa-4,9-diazaspiro[5.5]undecan-3-one |
| 304 | 9-(2-(2-aminothiazol-4-yl)ethyl)-4-((5-(trifluoromethyl)pyridin-2-yl)methyl)-1-oxa-4,9-diazaspiro[5.5]undecan-3-one |
| 305 | 9-(2-(5-amino-1H-pyrazol-1-yl)ethyl)-2-methyl-4-phenyl-1-oxa-4,9-diazaspiro[5.5]undecan-3-one |
| 306 | 9-(2-(2-aminothiazol-4-yl)ethyl)-4-(2-fluorophenyl)-2-isopropyl-1-oxa-4,9-diazaspiro[5.5]undecan-3-one |
| 307 | 8-[2-(2-aminothiazol-4-yl)ethyl]-12-phenyl-4-oxa-8,12-diazadispiro[2.1.5.3]tridecan-13-one |
| 308 | 8-[2-(2-aminothiazol-4-yl)ethyl]-12-{[5-(trifluoromethyl)pyridin-2-yl]methyl}-4-oxa-8,12-diazadispiro[2.1.5.3]tridecan-13-one |
| 309 | 9-(2-(2-aminothiazol-4-yl)ethyl)-2-methyl-4-(4-(trifluoromethyl)pyridin-3-yl)-1-oxa-4,9-diazaspiro[5.5]undecan-3-one |
| 310 | 12-(2-hydroxyethyl)-8-phenethyl-4-oxa-8,12-diazadispiro[2.1.5.3]tridecan-13-one |
| 311 | 4-(2-fluorophenyl)-9-phenethyl-2-((tetrahydro-2H-pyran-4-yl)methyl)-1-oxa-4,9-diazaspiro[5.5]undecan-3-one |
| 312 | 4-(2-fluorophenyl)-2-isopropyl-9-phenethyl-1-oxa-4,9-diazaspiro[5.5]undecan-3-one |
| 313 | 4-(2-fluorophenyl)-2-isopropyl-9-(2-(pyridin-2-yl)ethyl)-1-oxa-4,9-diazaspiro[5.5]undecan-3-one |
| 314 | 4-(2-fluorophenyl)-2-(3-methoxypropyl)-9-phenethyl-1-oxa-4,9-diazaspiro[5.5]undecan-3-one |
| 315 | N-methyl-2-(2-methyl-3-oxo-4-phenyl-1-oxa-4,9-diazaspiro[5.5]undecan-9-yl)-N-phenylacetamide |
| 316 | 3-(9-phenethyl-1-oxa-4,9-diazaspiro[5.5]undecan-4-yl)phenol |
| 317 | 9-phenethyl-4-phenyl-1-oxa-4,9-diazaspiro[5.5]undecane |
| 318 | 3-(9-benzyl-1-oxa-4,9-diazaspiro[5.5]undecan-4-yl)phenol |
| 319 | 2-(methoxymethyl)-9-phenethyl-4-phenyl-1-oxa-4,9-diazaspiro[5.5]undecane |
| 320 | 9-(3-methoxyphenethyl)-4-phenyl-1-oxa-4,9-diazaspiro[5.5]undecane |
| 321 | 2-(2-(4-phenyl-1-oxa-4,9-diazaspiro[5.5]undecan-9-yl)ethyl)phenol |
| 322 | 3-(2-(4-phenyl-1-oxa-4,9-diazaspiro[5.5]undecan-9-yl)ethyl)phenol |
| 323 | 2-(9-phenethyl-4-phenyl-1-oxa-4,9-diazaspiro[5.5]undecan-2-yl)ethanol |
| 324 | 4-benzyl-9-phenethyl-1-oxa-4,9-diazaspiro[5.5]undecane |
| 325 | 9-phenethyl-4-(thiazol-4-ylmethyl)-1-oxa-4,9-diazaspiro[5.5]undecane |
| 326 | 9-(2-methoxyphenethyl)-4-(pyridin-2-ylmethyl)-1-oxa-4,9-diazaspiro[5.5]undecane |
| 327 | 2-methyl-4-((1-methyl-1H-imidazol-2-yl)methyl)-9-phenethyl-1-oxa-4,9-diazaspiro[5.5]undecane |
| 328 | 2-methyl-4-((1-methyl-1H-pyrazol-3-yl)methyl)-9-phenethyl-1-oxa-4,9-diazaspiro[5.5]undecane |
| 329 | 2-(2-(4-(pyridin-2-ylmethyl)-1-oxa-4,9-diazaspiro[5.5]undecan-9-yl)ethyl)phenol |
| 330 | 2-methyl-9-phenethyl-4-(pyridin-2-ylmethyl)-1-oxa-4,9-diazaspiro[5.5]undecane |
| 331 | 2-methyl-9-phenethyl-4-(2-(pyridin-3-yl)ethyl)-1-oxa-4,9-diazaspiro[5.5]undecane |
| 332 | 9-(4-methoxyphenethyl)-4-phenyl-1-oxa-4,9-diazaspiro[5.5]undecane |
| 333 | 4-(3-methoxyphenyl)-9-phenethyl-1-oxa-4,9-diazaspiro[5.5]undecane |

| EX | Chemical name |
|---|---|
| 334 | 9-(2-methoxyphenethyl)-4-phenyl-1-oxa-4,9-diazaspiro[5.5]undecane |
| 335 | 4-benzyl-2-methyl-9-phenethyl-1-oxa-4,9-diazaspiro[5.5]undecane |
| 336 | 9-phenethyl-4-(pyridin-2-ylmethyl)-1-oxa-4,9-diazaspiro[5.5]undecane |
| 337 | 4,9-diphenethyl-1-oxa-4,9-diazaspiro[5.5]undecane |
| 338 | 3-(2-(4-benzyl-1-oxa-4,9-diazaspiro[5.5]undecan-9-yl)ethyl)aniline |
| 339 | N-(3-(2-(4-benzyl-1-oxa-4,9-diazaspiro[5.5]undecan-9-yl)ethyl)phenyl)acetamide |
| 340 | 3-methyl-9-phenethyl-4-phenyl-1-oxa-4,9-diazaspiro[5.5]undecane | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a further preferred further embodiment, the compounds of the general formula I are selected from

| EX | Chemical name |
|---|---|
| 1 | 4-(4-methoxyphenyl)-2-methyl-9-phenethyl-1-oxa-4,9-diazaspiro[5.5]undecan-3-one |
| 2 | 9-benzyl-4-(2-methoxyphenyl)-1-oxa-4,9-diazaspiro[5.5]undecan-3-one |
| 3 | 9-benzyl-4-phenyl-1-oxa-4,9-diazaspiro[5.5]undecan-3-one |
| 4 | 4-(2-methoxyphenyl)-9-phenethyl-1-oxa-4,9-diazaspiro[5.5]undecan-3-one |
| 5 | 9-phenethyl-4-phenyl-1-oxa-4,9-diazaspiro[5.5]undecan-3-one |
| 6 | 9-benzyl-4-(3-methoxyphenyl)-1-oxa-4,9-diazaspiro[5.5]undecan-3-one |
| 7 | 2-benzyl-9-phenyl-6-oxa-2,9-diazaspiro[4.5]decan-8-one |
| 8 | 4-(3-methoxyphenyl)-9-phenethyl-1-oxa-4,9-diazaspiro[5.5]undecan-3-one |
| 9 | 2-methyl-9-phenethyl-4-phenyl-1-oxa-4,9-diazaspiro[5.5]undecan-3-one |
| 10a | (R)-2-methyl-9-phenethyl-4-phenyl-1-oxa-4,9-diazaspiro[5.5]undecan-3-one |
| 10b | (S)-2-methyl-9-phenethyl-4-phenyl-1-oxa-4,9-diazaspiro[5.5]undecan-3-one |
| 11 | 2-(methoxymethyl)-9-phenethyl-4-phenyl-1-oxa-4,9-diazaspiro[5.5]undecan-3-one |
| 12a | (S)-2-(methoxymethyl)-9-phenethyl-4-phenyl-1-oxa-4,9-diazaspiro[5.5]undecan-3-one |
| 12b | (R)-2-(methoxymethyl)-9-phenethyl-4-phenyl-1-oxa-4,9-diazaspiro[5.5]undecan-3-one |
| 13 | 2-ethyl-9-phenethyl-4-phenyl-1-oxa-4,9-diazaspiro[5.5]undecan-3-one |
| 14 | methyl 2-(3-oxo-9-phenethyl-4-phenyl-1-oxa-4,9-diazaspiro[5.5]undecan-2-yl)acetate |
| 15 | 4-(3-methoxyphenyl)-2-methyl-9-phenethyl-1-oxa-4,9-diazaspiro[5.5]undecan-3-one |
| 16 | 9-benzyl-2-methyl-4-phenyl-1-oxa-4,9-diazaspiro[5.5]undecan-3-one |
| 17 | 2-isopropyl-9-phenethyl-4-phenyl-1-oxa-4,9-diazaspiro[5.5]undecan-3-one |
| 18 | 2,2-dimethyl-9-phenethyl-4-phenyl-1-oxa-4,9-diazaspiro[5.5]undecan-3-one |
| 19 | 2-(benzyloxymethyl)-9-phenethyl-4-phenyl-1-oxa-4,9-diazaspiro[5.5]undecan-3-one |
| 20 | 2-methyl-4-(1-methyl-1H-pyrazol-3-yl)-9-phenethyl-1-oxa-4,9-diazaspiro[5.5]undecan-3-one |
| 21 | 2-methylene-9-phenethyl-4-phenyl-1-oxa-4,9-diazaspiro[5.5]undecan-3-one |
| 22 | 4-(2-fluorophenyl)-2-methylene-9-phenethyl-1-oxa-4,9-diazaspiro[5.5]undecan-3-one |
| 23 | 2-methyl-9-(2-(5-nitropyridin-2-yl)ethyl)-4-phenyl-1-oxa-4,9-diazaspiro[5.5]undecan-3-one |
| 24 | 4-(2-fluorophenyl)-2-methyl-9-(2-(5-nitropyridin-2-yl)ethyl)-1-oxa-4,9-diazaspiro[5.5]undecan-3-one |
| 25 | 4-(2-fluorophenyl)-2-methyl-9-(2-(3-nitropyridin-2-yl)ethyl)-1-oxa-4,9-diazaspiro[5.5]undecan-3-one |
| 26 | 2-methyl-4-phenyl-9-(2-(pyrimidin-2-yl)ethyl)-1-oxa-4,9-diazaspiro[5.5]undecan-3-one |
| 27 | 2-methyl-9-(2-(2-nitropyridin-3-yl)ethyl)-4-phenyl-1-oxa-4,9-diazaspiro[5.5]undecan-3-one |
| 28 | 2-methyl-4-phenyl-9-(2-(4-(trifluoromethyl)pyridin-2-yl)ethyl)-1-oxa-4,9-diazaspiro[5.5]undecan-3-one |
| 29 | 9-(2-(6-aminopyridin-2-yl)ethyl)-2-methyl-4-phenyl-1-oxa-4,9-diazaspiro[5.5]undecan-3-one |
| 30 | 9-(2-(4-aminopyridin-2-yl)ethyl)-2-methyl-4-phenyl-1-oxa-4,9-diazaspiro[5.5]undecan-3-one |
| 31 | 4-(2-fluorophenyl)-2-methyl-9-(2-(6-(trifluoromethyl)pyridin-2-yl)ethyl)-1-oxa-4,9-diazaspiro[5.5]undecan-3-one |
| 32 | 9-(2-(2-aminopyridin-4-yl)ethyl)-2-methyl-4-phenyl-1-oxa-4,9-diazaspiro[5.5]undecan-3-one |

-continued

| EX | Chemical name |
|---|---|
| 33 | 2-methyl-4-phenyl-9-(2-(3-(trifluoromethyl)pyridin-2-yl)ethyl)-1-oxa-4,9-diazaspiro[5.5]undecan-3-one |
| 34 | 2-methyl-4-phenyl-9-(2-(5-(trifluoromethyl)pyridin-2-yl)ethyl)-1-oxa-4,9-diazaspiro[5.5]undecan-3-one |
| 35 | 9-(2-(4-methoxypyridin-2-yl)ethyl)-2-methyl-4-phenyl-1-oxa-4,9-diazaspiro[5.5]undecan-3-one |
| 36 | 6-(2-(2-methyl-3-oxo-4-phenyl-1-oxa-4,9-diazaspiro[5.5]undecan-9-yl)ethyl)nicotinonitrile |
| 37 | 9-(2-(3-chloropyridin-2-yl)ethyl)-2-methyl-4-phenyl-1-oxa-4,9-diazaspiro[5.5]undecan-3-one |
| 38 | 9-(2-(5-chloropyridin-2-yl)ethyl)-2-methyl-4-phenyl-1-oxa-4,9-diazaspiro[5.5]undecan-3-one |
| 39 | 4-(2-fluorophenyl)-2-isopropyl-9-(2-(2-nitropyridin-3-yl)ethyl)-1-oxa-4,9-diazaspiro[5.5]undecan-3-one |
| 40 | 2-methyl-4-phenyl-9-(2-(2-(trifluoromethyl)pyridin-4-yl)ethyl)-1-oxa-4,9-diazaspiro[5.5]undecan-3-one |
| 41 | 2-(2-(2-methyl-3-oxo-4-phenyl-1-oxa-4,9-diazaspiro[5.5]undecan-9-yl)ethyl)isonicotinonitrile |
| 42 | 9-(2-(6-aminopyridin-2-yl)ethyl)-2-methyl-4-(4-(trifluoromethyl)pyridin-3-yl)-1-oxa-4,9-diazaspiro[5.5]undecan-3-one |
| 43 | 2-methyl-9-(2-(2-nitropyridin-3-yl)ethyl)-4-(4-(trifluoromethyl)pyridin-3-yl)-1-oxa-4,9-diazaspiro[5.5]undecan-3-one |
| 44 | 9-(2-(3-chloropyridin-2-yl)ethyl)-2-methyl-4-(4-(trifluoromethyl)pyridin-3-yl)-1-oxa-4,9-diazaspiro[5.5]undecan-3-one |
| 45 | 9-(2-(3-chloropyridin-2-yl)ethyl)-2-methyl-4-((5-(trifluoromethyl)pyridin-2-yl)methyl)-1-oxa-4,9-diazaspiro[5.5]undecan-3-one |
| 46 | 9-(2-(3-chloropyridin-2-yl)ethyl)-4-((5-fluoropyridin-2-yl)methyl)-2-methyl-1-oxa-4,9-diazaspiro[5.5]undecan-3-one |
| 47 | 9-(2-(3-fluoropyridin-2-yl)ethyl)-4-((5-fluoropyridin-2-yl)methyl)-2-methyl-1-oxa-4,9-diazaspiro[5.5]undecan-3-one |
| 48 | 9-(2-(3-fluoropyridin-2-yl)ethyl)-2-methyl-4-(2-(trifluoromethyl)pyridin-3-yl)-1-oxa-4,9-diazaspiro[5.5]undecan-3-one |
| 49 | 4-((5-fluoropyridin-2-yl)methyl)-2-methyl-9-(2-(6-(trifluoromethyl)pyridin-2-yl)ethyl)-1-oxa-4,9-diazaspiro[5.5]undecan-3-one |
| 50 | 9-(2-(3-chloropyridin-4-yl)ethyl)-2-methyl-4-phenyl-1-oxa-4,9-diazaspiro[5.5]undecan-3-one |
| 51 | 9-(2-fluorophenethyl)-2-methyl-4-phenyl-1-oxa-4,9-diazaspiro[5.5]undecan-3-one |
| 52 | 9-(4-methoxyphenethyl)-4-phenyl-1-oxa-4,9-diazaspiro[5.5]undecan-3-one |
| 53 | 2-methyl-4-phenyl-9-(2-(thiophen-2-yl)ethyl)-1-oxa-4,9-diazaspiro[5.5]undecan-3-one |
| 54 | 9-(3-fluorophenethyl)-2-methyl-4-phenyl-1-oxa-4,9-diazaspiro[5.5]undecan-3-one |
| 55 | 9-(4-fluorophenethyl)-2-methyl-4-phenyl-1-oxa-4,9-diazaspiro[5.5]undecan-3-one |
| 56 | 9-(2-(1H-pyrazol-1-yl)ethyl)-2-methyl-4-phenyl-1-oxa-4,9-diazaspiro[5.5]undecan-3-one |
| 57 | 9-(2-methoxyphenethyl)-2-methyl-4-phenyl-1-oxa-4,9-diazaspiro[5.5]undecan-3-one |
| 58 | 2-methyl-4-phenyl-9-(2-(pyridin-2-yl)ethyl)-1-oxa-4,9-diazaspiro[5.5]undecan-3-one |
| 59 | 2-methyl-4-phenyl-9-((tetrahydro-2H-pyran-4-yl)methyl)-1-oxa-4,9-diazaspiro[5.5]undecan-3-one |
| 60 | 2-methyl-4-phenyl-9-(3-phenylpropyl)-1-oxa-4,9-diazaspiro[5.5]undecan-3-one |
| 61 | 2-methyl-9-(2-(4-methylthiazol-5-yl)ethyl)-4-phenyl-1-oxa-4,9-diazaspiro[5.5]undecan-3-one |
| 62 | 9-(2-(1H-indol-1-yl)ethyl)-2-methyl-4-phenyl-1-oxa-4,9-diazaspiro[5.5]undecan-3-one |
| 63 | 9-(2-(1H-benzo[d]imidazol-1-yl)ethyl)-2-methyl-4-phenyl-1-oxa-4,9-diazaspiro[5.5]undecan-3-one |
| 64 | methyl 3-(2-methyl-3-oxo-4-phenyl-1-oxa-4,9-diazaspiro[5.5]undecan-9-yl)propanoate |
| 65 | 2-methyl-9-(2-morpholinoethyl)-4-phenyl-1-oxa-4,9-diazaspiro[5.5]undecan-3-one |
| 66 | 2-methyl-9-(4-nitrophenethyl)-4-phenyl-1-oxa-4,9-diazaspiro[5.5]undecan-3-one |
| 67 | 2-methyl-9-(3-nitrophenethyl)-4-phenyl-1-oxa-4,9-diazaspiro[5.5]undecan-3-one |
| 68 | 2-methyl-9-(2-nitrophenethyl)-4-phenyl-1-oxa-4,9-diazaspiro[5.5]undecan-3-one |
| 69 | 9-(2-(1H-pyrrolo[2,3-b]pyridin-1-yl)ethyl)-2-methyl-4-phenyl-1-oxa-4,9-diazaspiro[5.5]undecan-3-one |
| 70 | methyl 4-(2-(2-methyl-3-oxo-4-phenyl-1-oxa-4,9-diazaspiro[5.5]undecan-9-yl)ethyl)benzoate |
| 71 | 2-(2-methyl-3-oxo-4-phenyl-1-oxa-4,9-diazaspiro[5.5]undecan-9-yl)-N-phenylacetamide |

-continued

| EX | Chemical name |
|---|---|
| 72 | 2-methyl-9-(2-phenoxyethyl)-4-phenyl-1-oxa-4,9-diazaspiro[5.5]undecan-3-one |
| 73 | 2-methyl-4-phenyl-9-(2-(pyridin-3-yl)ethyl)-1-oxa-4,9-diazaspiro[5.5]undecan-3-one |
| 74 | 3-(2-(2-methyl-3-oxo-4-phenyl-1-oxa-4,9-diazaspiro[5.5]undecan-9-yl)ethyl)benzo[d]oxazol-2(3H)-one |
| 75 | 3-(2-(2-methyl-3-oxo-4-phenyl-1-oxa-4,9-diazaspiro[5.5]undecan-9-yl)ethyl)benzonitrile |
| 76 | 4-(2-(2-methyl-3-oxo-4-phenyl-1-oxa-4,9-diazaspiro[5.5]undecan-9-yl)ethyl)benzonitrile |
| 77 | 9-(2-(3,5-dimethyl-1H-pyrazol-1-yl)ethyl)-2-methyl-4-phenyl-1-oxa-4,9-diazaspiro[5.5]undecan-3-one |
| 78 | 2-methyl-9-(2-morpholino-2-oxoethyl)-4-phenyl-1-oxa-4,9-diazaspiro[5.5]undecan-3-one |
| 79 | 9-(2-methoxyphenethyl)-4-(pyridin-2-ylmethyl)-1-oxa-4,9-diazaspiro[5.5]undecan-3-one |
| 80 | (Z)-4-(2-fluorophenyl)-9-phenethyl-2-((tetrahydro-2H-pyran-4-yl)methylene)-1-oxa-4,9-diazaspiro[5.5]undecan-3-one |
| 81 | 4-(2-fluorophenyl)-9-isopentyl-2-methyl-1-oxa-4,9-diazaspiro[5.5]undecan-3-one |
| 82 | 9-(cyclopropylmethyl)-4-(2-fluorophenyl)-2-methyl-1-oxa-4,9-diazaspiro[5.5]undecan-3-one |
| 83 | 4-(2-fluorophenyl)-9-(3-methoxyphenethyl)-2-methyl-1-oxa-4,9-diazaspiro[5.5]undecan-3-one |
| 84 | 9-(2-(pyridin-2-yl)ethyl)-4-(pyridin-2-ylmethyl)-1-oxa-4,9-diazaspiro[5.5]undecan-3-one |
| 85 | 4-(2-fluorophenyl)-9-phenethyl-2-(propan-2-ylidene)-1-oxa-4,9-diazaspiro[5.5]undecan-3-one |
| 86 | 9-phenethyl-4-(pyridin-2-ylmethyl)-1-oxa-4,9-diazaspiro[5.5]undecan-3-one |
| 87 | 4-benzyl-9-(2-methoxyphenethyl)-1-oxa-4,9-diazaspiro[5.5]undecane |
| 88 | 2-methyl-9-phenethyl-4-(thiazol-4-yl)-1-oxa-4,9-diazaspiro[5.5]undecan-3-one |
| 89 | 4-(2-fluorophenyl)-9-(2-(6-fluoropyridin-2-yl)ethyl)-2-methyl-1-oxa-4,9-diazaspiro[5.5]undecan-3-one |
| 90 | 12-phenyl-8-[2-(pyridin-2-yl)ethyl]-4-oxa-8,12-diazadispiro[2.1.5.3]tridecan-13-one |
| 91 | 4-(2-fluorophenyl)-2-methyl-9-(2-(6-(trifluoromethyl)pyridin-3-yl)ethyl)-1-oxa-4,9-diazaspiro[5.5]undecan-3-one |
| 92 | 8-(3-nitrophenethyl)-12-phenyl-4-oxa-8,12-diazadispiro[2.1.5.3]tridecan-13-one |
| 93 | N-methyl-3-(2-(2-methyl-3-oxo-4-phenyl-1-oxa-4,9-diazaspiro[5.5]undecan-9-yl)ethyl)benzenesulfonamide |
| 94 | 9-(2-(5-fluoropyridin-2-yl)ethyl)-2-methyl-4-phenyl-1-oxa-4,9-diazaspiro[5.5]undecan-3-one |
| 95 | 2-methyl-4-phenyl-9-(2-(thiazol-2-yl)ethyl)-1-oxa-4,9-diazaspiro[5.5]undecan-3-one |
| 96 | 9-(2-(3-fluoropyridin-2-yl)ethyl)-2-methyl-4-phenyl-1-oxa-4,9-diazaspiro[5.5]undecan-3-one |
| 97 | 8-(2-oxo-2-phenylethyl)-12-phenyl-4-oxa-8,12-diazadispiro[2.1.5.3]tridecan-13-one |
| 98 | 9-(2-(pyridin-2-yl)ethyl)-4-((5-(trifluoromethyl)pyridin-2-yl)methyl)-1-oxa-4,9-diazaspiro[5.5]undecan-3-one |
| 99 | 9-(2-oxo-2-phenylethyl)-4-((5-(trifluoromethyl)pyridin-2-yl)methyl)-1-oxa-4,9-diazaspiro[5.5]undecan-3-one |
| 100 | N-methyl-3-(2-methyl-3-oxo-4-phenyl-1-oxa-4,9-diazaspiro[5.5]undecan-9-yl)-N-phenylpropanamide |
| 101 | 2-methyl-9-(2-(pyridin-2-yl)ethyl)-4-(4-(trifluoromethyl)pyridin-3-yl)-1-oxa-4,9-diazaspiro[5.5]undecan-3-one |
| 102 | 9-(2-(6-methoxypyridin-2-yl)ethyl)-2-methyl-4-phenyl-1-oxa-4,9-diazaspiro[5.5]undecan-3-one |
| 103 | 9-(3-nitrophenethyl)-4-((5-(trifluoromethyl)pyridin-2-yl)methyl)-1-oxa-4,9-diazaspiro[5.5]undecan-3-one |
| 104 | 4-((6-aminopyridin-2-yl)methyl)-9-phenethyl-1-oxa-4,9-diazaspiro[5.5]undecan-3-one |
| 105 | 4-((5-chloropyridin-2-yl)methyl)-9-phenethyl-1-oxa-4,9-diazaspiro[5.5]undecan-3-one |
| 106 | tert-butyl (4-(2-(3-oxo-4-((5-(trifluoromethyl)pyridin-2-yl)methyl)-1-oxa-4,9-diazaspiro[5.5]undecan-9-yl)ethyl)thiazol-2-yl)carbamate |
| 107 | N-methyl-4-(2-(2-methyl-3-oxo-4-phenyl-1-oxa-4,9-diazaspiro[5.5]undecan-9-yl)ethyl)benzenesulfonamide |
| 108 | 4-(2-(2-methyl-3-oxo-4-phenyl-1-oxa-4,9-diazaspiro[5.5]undecan-9-yl)ethyl)benzenesulfonamide |
| 109 | 12-(4-methoxybenzyl)-8-phenethyl-4-oxa-8,12-diazadispiro[2.1.5.3]tridecan-13-one hydrochloride |
| 110 | 2-methyl-9-(2-(3-nitro-1H-pyrazol-1-yl)ethyl)-4-phenyl-1-oxa-4,9-diazaspiro[5.5]undecan-3-one |
| 111 | 9-(2-(6-methoxypyridin-3-yl)ethyl)-2-methyl-4-phenyl-1-oxa-4,9-diazaspiro[5.5]undecan-3-one |

-continued

| EX | Chemical name |
|---|---|
| 112 | 2-methyl-4-phenyl-9-(2-(5-(trifluoromethyl)pyridin-3-yl)ethyl)-1-oxa-4,9-diazaspiro[5.5]undecan-3-one |
| 113 | 9-(2-(6-chloropyridin-3-yl)ethyl)-2-methyl-4-phenyl-1-oxa-4,9-diazaspiro[5.5]undecan-3-one |
| 114 | 9-(2-(5-fluoropyridin-3-yl)ethyl)-2-methyl-4-phenyl-1-oxa-4,9-diazaspiro[5.5]undecan-3-one |
| 115 | 9-(2-(5-chloropyridin-3-yl)ethyl)-2-methyl-4-phenyl-1-oxa-4,9-diazaspiro[5.5]undecan-3-one |
| 116 | tert-butyl (1-(2-(2-methyl-3-oxo-4-phenyl-1-oxa-4,9-diazaspiro[5.5]undecan-9-yl)ethyl)-1H-pyrazol-5-yl)carbamate |
| 117 | tert-butyl (4-(2-(4-(2-fluorophenyl)-2-isopropyl-3-oxo-1-oxa-4,9-diazaspiro[5.5]undecan-9-yl)ethyl)thiazol-2-yl)carbamate |
| 118 | tert-butyl (4-(2-(13-oxo-12-phenyl-4-oxa-8,12-diazadispiro[2.1.5.3]tridecan-8-yl)ethyl)thiazol-2-yl)carbamate |
| 119 | 8-(3-nitrophenethyl)-12-{[5-(trifluoromethyl)pyridin-2-yl]methyl}-4-oxa-8,12-diazadispiro[2.1.5.3]tridecan-13-one |
| 120 | tert-butyl (4-(2-(13-oxo-12-{[5-(trifluoromethyl)pyridin-2-yl]methyl}-4-oxa-8,12-diazadispiro[2.1.5.3]tridecan-8-yl)ethyl)thiazol-2-yl)carbamate |
| 121 | tert-butyl (4-(2-(2-methyl-3-oxo-4-(4-(trifluoromethyl)pyridin-3-yl)-1-oxa-4,9-diazaspiro[5.5]undecan-9-yl)ethyl)thiazol-2-yl)carbamate |
| 122 | 9-(2-isopropoxyethyl)-2-methyl-4-phenyl-1-oxa-4,9-diazaspiro[5.5]undecan-3-one |
| 123 | 6-(2-(2-methyl-3-oxo-4-phenyl-1-oxa-4,9-diazaspiro[5.5]undecan-9-yl)ethyl)picolinonitrile |
| 124 | 2-methyl-9-(2-morpholino-2-oxoethyl)-4-((5-(trifluoromethyl)pyridin-2-yl)methyl)-1-oxa-4,9-diazaspiro[5.5]undecan-3-one |
| 125 | 9-(2-isopropoxyethyl)-2-methyl-4-((5-(trifluoromethyl)pyridin-2-yl)methyl)-1-oxa-4,9-diazaspiro[5.5]undecan-3-one |
| 126 | 9-(2-fluorophenethyl)-2-methyl-4-(4-(trifluoromethyl)pyridin-3-yl)-1-oxa-4,9-diazaspiro[5.5]undecan-3-one |
| 127a | (S)-9-(2-fluorophenethyl)-2-methyl-4-(4-(trifluoromethyl)pyridin-3-yl)-1-oxa-4,9-diazaspiro[5.5]undecan-3-one hydrochloride |
| 127b | (R)-9-(2-fluorophenethyl)-2-methyl-4-(4-(trifluoromethyl)pyridin-3-yl)-1-oxa-4,9-diazaspiro[5.5]undecan-3-one hydrochloride |
| 128 | 2-methyl-9-(2-oxo-2-(piperidin-1-yl)ethyl)-4-((5-(trifluoromethyl)pyridin-2-yl)methyl)-1-oxa-4,9-diazaspiro[5.5]undecan-3-one |
| 129 | 2-methyl-9-(2-oxo-2-(piperidin-1-yl)ethyl)-4-phenyl-1-oxa-4,9-diazaspiro[5.5]undecan-3-one |
| 130 | 9-(2-fluorophenethyl)-2-methyl-4-(2-(trifluoromethyl)pyridin-3-yl)-1-oxa-4,9-diazaspiro[5.5]undecan-3-one |
| 131 | 2-methyl-4-phenyl-9-(2-(tetrahydro-2H-pyran-4-yl)ethyl)-1-oxa-4,9-diazaspiro[5.5]undecan-3-one |
| 132 | 9-(3-methoxyphenethyl)-4-phenyl-1-oxa-4,9-diazaspiro[5.5]undecan-3-one |
| 133 | 2-methyl-4-phenyl-9-(2-(pyridin-4-yl)ethyl)-1-oxa-4,9-diazaspiro[5.5]undecan-3-one |
| 134 | 4-(2-fluorophenyl)-2-(methoxymethyl)-9-(2-(pyridin-2-yl)ethyl)-1-oxa-4,9-diazaspiro[5.5]undecan-3-one |
| 135 | 4-(2-fluorophenyl)-2-(methoxymethyl)-9-(2-methoxyphenethyl)-1-oxa-4,9-diazaspiro[5.5]undecan-3-one |
| 136 | 9-(2-fluorophenethyl)-4-(2-fluorophenyl)-2-(methoxymethyl)-1-oxa-4,9-diazaspiro[5.5]undecan-3-one |
| 137 | 4-(2-fluorophenyl)-2-isopropyl-9-(2-methoxyphenethyl)-1-oxa-4,9-diazaspiro[5.5]undecan-3-one |
| 138 | 4-benzyl-9-(2-(pyridin-2-yl)ethyl)-1-oxa-4,9-diazaspiro[5.5]undecane |
| 139 | 4-(2-fluorophenyl)-2-(propan-2-ylidene)-9-(2-(pyridin-2-yl)ethyl)-1-oxa-4,9-diazaspiro[5.5]undecan-3-one |
| 140 | tert-butyl (4-(2-(4-(2-fluorophenyl)-2-methyl-3-oxo-1-oxa-4,9-diazaspiro[5.5]undecan-9-yl)ethyl)thiazol-2-yl)carbamate |
| 141 | 4-(2-fluorophenyl)-9-(2-(4-methylthiazol-5-yl)ethyl)-2-(propan-2-ylidene)-1-oxa-4,9-diazaspiro[5.5]undecan-3-one |
| 142 | (Z)-4-(2-fluorophenyl)-2-(3-methoxypropylidene)-9-phenethyl-1-oxa-4,9-diazaspiro[5.5]undecan-3-one |
| 143 | ethyl 3-(2-(4-(2-fluorophenyl)-2-methyl-3-oxo-1-oxa-4,9-diazaspiro[5.5]undecan-9-yl)ethyl)benzoate |
| 144 | 3-(2-methyl-3-oxo-4-phenyl-1-oxa-4,9-diazaspiro[5.5]undecan-9-yl)-N-phenylpropanamide |
| 145 | 2-methyl-4-phenyl-9-(2-(pyridin-3-yloxy)ethyl)-1-oxa-4,9-diazaspiro[5.5]undecan-3-one |
| 146 | 2-methyl-9-(2-(2-oxopyrrolidin-1-yl)ethyl)-4-phenyl-1-oxa-4,9-diazaspiro[5.5]undecan-3-one |
| 147 | 9-(2-(1H-pyrazol-4-yl)ethyl)-2-methyl-4-phenyl-1-oxa-4,9-diazaspiro[5.5]undecan-3-one |
| 148 | 8-(2-fluorophenethyl)-12-(4-methoxybenzyl)-4-oxa-8,12-diazadispiro[2.1.5.3]tridecan-13-one |
| 149 | 2-phenethyl-9-phenyl-6-oxa-2,9-diazaspiro[4.5]decan-8-one |
| 150 | 9-(2-hydroxy-2-phenylethyl)-2-methyl-4-phenyl-1-oxa-4,9-diazaspiro[5.5]undecan-3-one |

| EX | Chemical name |
|---|---|
| 151a | (R)-9-((R)-2-hydroxy-2-phenylethyl)-2-methyl-4-phenyl-1-oxa-4,9-diazaspiro[5.5]undecan-3-one |
| 151b | (R)-9-((S)-2-hydroxy-2-phenylethyl)-2-methyl-4-phenyl-1-oxa-4,9-diazaspiro[5.5]undecan-3-one |
| 151c | (S)-9-((S)-2-hydroxy-2-phenylethyl)-2-methyl-4-phenyl-1-oxa-4,9-diazaspiro[5.5]undecan-3-one |
| 151d | (S)-9-((R)-2-hydroxy-2-phenylethyl)-2-methyl-4-phenyl-1-oxa-4,9-diazaspiro[5.5]undecan-3-one |
| 152 | 4-benzyl-2-methyl-9-phenethyl-1-oxa-4,9-diazaspiro[5.5]undecan-3-one |
| 153 | 4-benzyl-9-phenethyl-1-oxa-4,9-diazaspiro[5.5]undecan-3-one |
| 154 | 4-(2-fluorobenzyl)-2-methyl-9-phenethyl-1-oxa-4,9-diazaspiro[5.5]undecan-3-one |
| 155 | 4-(3-fluorobenzyl)-2-methyl-9-phenethyl-1-oxa-4,9-diazaspiro[5.5]undecan-3-one |
| 156 | 2-methyl-4,9-diphenethyl-1-oxa-4,9-diazaspiro[5.5]undecan-3-one |
| 157 | 2-methyl-9-phenethyl-4-(pyridin-2-ylmethyl)-1-oxa-4,9-diazaspiro[5.5]undecan-3-one |
| 158 | 4-(4-fluorobenzyl)-2-methyl-9-phenethyl-1-oxa-4,9-diazaspiro[5.5]undecan-3-one |
| 159 | 2-methyl-9-phenethyl-4-(pyridin-3-ylmethyl)-1-oxa-4,9-diazaspiro[5.5]undecan-3-one |
| 160 | 2-methyl-9-phenethyl-4-(thiazol-2-ylmethyl)-1-oxa-4,9-diazaspiro[5.5]undecan-3-one |
| 161 | 2-methyl-9-phenethyl-4-(thiazol-5-ylmethyl)-1-oxa-4,9-diazaspiro[5.5]undecan-3-one |
| 162 | 2-methyl-9-phenethyl-4-(pyridin-4-ylmethyl)-1-oxa-4,9-diazaspiro[5.5]undecan-3-one |
| 163 | 2-methyl-9-phenethyl-4-((tetrahydro-2H-pyran-4-yl)methyl)-1-oxa-4,9-diazaspiro[5.5]undecan-3-one |
| 164 | 2-methyl-9-phenethyl-4-(thiazol-4-ylmethyl)-1-oxa-4,9-diazaspiro[5.5]undecan-3-one |
| 165 | 9-phenethyl-4-(pyridin-4-ylmethyl)-1-oxa-4,9-diazaspiro[5.5]undecan-3-one |
| 166 | 4-(3-methoxybenzyl)-9-phenethyl-1-oxa-4,9-diazaspiro[5.5]undecan-3-one |
| 167 | 9-phenethyl-4-(thiazol-4-ylmethyl)-1-oxa-4,9-diazaspiro[5.5]undecan-3-one |
| 168 | 4-((1-benzyl-1H-imidazol-2-yl)methyl)-9-phenethyl-1-oxa-4,9-diazaspiro[5.5]undecan-3-one |
| 169 | 9-phenethyl-4-(2-(pyridin-2-yl)ethyl)-1-oxa-4,9-diazaspiro[5.5]undecan-3-one |
| 170 | 2-methyl-4-(2-morpholino-2-oxoethyl)-9-phenethyl-1-oxa-4,9-diazaspiro[5.5]undecan-3-one |
| 171 | 2-methyl-4-((1-methyl-1H-pyrazol-3-yl)methyl)-9-phenethyl-1-oxa-4,9-diazaspiro[5.5]undecan-3-one |
| 172 | 2-methyl-4-((1-methyl-1H-imidazol-2-yl)methyl)-9-phenethyl-1-oxa-4,9-diazaspiro[5.5]undecan-3-one |
| 173 | 4-((3-fluoropyridin-2-yl)methyl)-2-methyl-9-phenethyl-1-oxa-4,9-diazaspiro[5.5]undecan-3-one |
| 174 | 2-methyl-9-phenethyl-4-((6-(trifluoromethyl)pyridin-2-yl)methyl)-1-oxa-4,9-diazaspiro[5.5]undecan-3-one |
| 175 | 2-methyl-9-phenethyl-4-(2-(pyridin-3-yl)ethyl)-1-oxa-4,9-diazaspiro[5.5]undecan-3-one |
| 176 | 4-((5-fluoropyridin-2-yl)methyl)-9-phenethyl-1-oxa-4,9-diazaspiro[5.5]undecan-3-one |
| 177 | 9-phenethyl-4-((5-(trifluoromethyl)pyridin-2-yl)methyl)-1-oxa-4,9-diazaspiro[5.5]undecan-3-one |
| 178 | 9-phenethyl-4-(2-(pyridin-4-yl)ethyl)-1-oxa-4,9-diazaspiro[5.5]undecan-3-one |
| 179 | 4-(3-nitrobenzyl)-9-phenethyl-1-oxa-4,9-diazaspiro[5.5]undecan-3-one |
| 180 | 12-(3-methoxypropyl)-8-phenethyl-4-oxa-8,12-diazadispiro[2.1.5.3]tridecan-13-one |
| 181 | 3-[13-oxo-8-phenethyl-4-oxa-8,12-diazadispiro[2.1.5.3]tridecan-12-yl]propanenitrile |
| 182 | N,N-dimethyl-3-[13-oxo-8-phenethyl-4-oxa-8,12-diazadispiro[2.1.5.3]tridecan-12-yl]propanamide |
| 183 | 4-(2-hydroxy-2-methylpropyl)-2-methyl-9-phenethyl-1-oxa-4,9-diazaspiro[5.5]undecan-3-one |
| 184 | 12-(2-methoxyethyl)-8-phenethyl-4-oxa-8,12-diazadispiro[2.1.5.3]tridecan-13-one |
| 185 | 12-(2-((tetrahydro-2H-pyran-2-yl)oxy)ethyl)-8-phenethyl-4-oxa-8,12-diazadispiro[2.1.5.3]tridecan-13-one |
| 186 | methyl 3-(13-oxo-8-phenethyl-4-oxa-8,12-diazadispiro[2.1.5.3]tridecan-12-yl)propanoate |
| 187 | 8-phenethyl-12-{[5-(trifluoromethyl)pyridin-2-yl]methyl}-4-oxa-8,12-diazadispiro[2.1.5.3]tridecan-13-one |
| 188 | 9-benzyl-4-(4-fluorophenyl)-1-oxa-4,9-diazaspiro[5.5]undecan-3-one |
| 189 | 4-(2-fluorophenyl)-9-phenethyl-1-oxa-4,9-diazaspiro[5.5]undecan-3-one |
| 190 | 4-(4-fluorophenyl)-9-phenethyl-1-oxa-4,9-diazaspiro[5.5]undecan-3-one |
| 191 | 4-(3-fluorophenyl)-9-phenethyl-1-oxa-4,9-diazaspiro[5.5]undecan-3-one |
| 192 | 4-(2-fluorophenyl)-2-methyl-9-phenethyl-1-oxa-4,9-diazaspiro[5.5]undecan-3-one |

| EX | Chemical name |
|---|---|
| 193 | 4-(2-chlorophenyl)-2-methyl-9-phenethyl-1-oxa-4,9-diazaspiro[5.5]undecan-3-one |
| 194 | 2-methyl-9-phenethyl-4-(pyridin-3-yl)-1-oxa-4,9-diazaspiro[5.5]undecan-3-one |
| 195 | 2-methyl-9-phenethyl-4-(pyrazin-2-yl)-1-oxa-4,9-diazaspiro[5.5]undecan-3-one |
| 196 | 2-methyl-9-phenethyl-4-(pyridin-2-yl)-1-oxa-4,9-diazaspiro[5.5]undecan-3-one |
| 197 | ethyl 3-(2-methyl-3-oxo-9-phenethyl-1-oxa-4,9-diazaspiro[5.5]undecan-4-yl)benzoate |
| 198 | 3-(2-methyl-3-oxo-9-phenethyl-1-oxa-4,9-diazaspiro[5.5]undecan-4-yl)benzonitrile |
| 199 | 2-methyl-4-(3-nitrophenyl)-9-phenethyl-1-oxa-4,9-diazaspiro[5.5]undecan-3-one |
| 200 | 2-methyl-4-(1-methyl-1H-indazol-3-yl)-9-phenethyl-1-oxa-4,9-diazaspiro[5.5]undecan-3-one |
| 201 | 2-methyl-4-(1-methyl-1H-indazol-6-yl)-9-phenethyl-1-oxa-4,9-diazaspiro[5.5]undecan-3-one |
| 202 | 4-(benzo[d][1,3]dioxol-5-yl)-2-methyl-9-phenethyl-1-oxa-4,9-diazaspiro[5.5]undecan-3-one |
| 203 | 4-(benzo[d]thiazol-6-yl)-2-methyl-9-phenethyl-1-oxa-4,9-diazaspiro[5.5]undecan-3-one |
| 204 | 4-(benzo[d]thiazol-2-yl)-2-methyl-9-phenethyl-1-oxa-4,9-diazaspiro[5.5]undecan-3-one |
| 205 | 2-methyl-9-phenethyl-4-(pyridin-4-yl)-1-oxa-4,9-diazaspiro[5.5]undecan-3-one |
| 206 | 4-(2-methoxyphenyl)-2-methyl-9-phenethyl-1-oxa-4,9-diazaspiro[5.5]undecan-3-one |
| 207 | 2-methyl-9-phenethyl-4-(6-(trifluoromethyl)pyridin-2-yl)-1-oxa-4,9-diazaspiro[5.5]undecan-3-one |
| 208 | 4-(3-fluoropyridin-2-yl)-2-methyl-9-phenethyl-1-oxa-4,9-diazaspiro[5.5]undecan-3-one |
| 209 | 2-methyl-9-phenethyl-4-(thiazol-2-yl)-1-oxa-4,9-diazaspiro[5.5]undecan-3-one |
| 210 | 2-methyl-4-(1-methyl-1H-pyrazol-4-yl)-9-phenethyl-1-oxa-4,9-diazaspiro[5.5]undecan-3-one |
| 211 | 4-(6-methoxypyridin-2-yl)-2-methyl-9-phenethyl-1-oxa-4,9-diazaspiro[5.5]undecan-3-one |
| 212 | 2-methyl-9-phenethyl-4-(6-(trifluoromethyl)pyridin-3-yl)-1-oxa-4,9-diazaspiro[5.5]undecan-3-one |
| 213 | 4-(2-fluoropyridin-3-yl)-2-methyl-9-phenethyl-1-oxa-4,9-diazaspiro[5.5]undecan-3-one |
| 214 | 2-methyl-9-phenethyl-4-(4-(trifluoromethyl)pyridin-3-yl)-1-oxa-4,9-diazaspiro[5.5]undecan-3-one |
| 215 | 2-methyl-9-phenethyl-4-(2-(trifluoromethyl)pyridin-3-yl)-1-oxa-4,9-diazaspiro[5.5]undecan-3-one |
| 216 | 4-(5-fluoropyridin-3-yl)-2-methyl-9-phenethyl-1-oxa-4,9-diazaspiro[5.5]undecan-3-one |
| 217 | 2-methyl-9-phenethyl-4-(5-(trifluoromethyl)pyridin-3-yl)-1-oxa-4,9-diazaspiro[5.5]undecan-3-one |
| 218 | 2-methyl-9-phenethyl-4-(3-(trifluoromethyl)pyridin-2-yl)-1-oxa-4,9-diazaspiro[5.5]undecan-3-one |
| 219 | 8-(2-fluorophenethyl)-12-(2-(trifluoromethyl)pyridin-3-yl)-4-oxa-8,12-diazadispiro[2.1.5.3]tridecan-13-one |
| 220 | 8-(2-fluorophenethyl)-12-(3-(trifluoromethyl)pyridin-2-yl)-4-oxa-8,12-diazadispiro[2.1.5.3]tridecan-13-one hydrochloride |
| 221 | 9-(2-fluorophenethyl)-2-methyl-4-(3-(trifluoromethyl)pyridin-2-yl)-1-oxa-4,9-diazaspiro[5.5]undecan-3-one |
| 222a | (R)-9-(2-fluorophenethyl)-2-methyl-4-(3-(trifluoromethyl)pyridin-2-yl)-1-oxa-4,9-diazaspiro[5.5]undecan-3-one hydrochloride |
| 222b | (S)-9-(2-fluorophenethyl)-2-methyl-4-(3-(trifluoromethyl)pyridin-2-yl)-1-oxa-4,9-diazaspiro[5.5]undecan-3-one hydrochloride |
| 223 | 8-(2-fluorophenethyl)-12-(4-(trifluoromethyl)pyridin-3-yl)-4-oxa-8,12-diazadispiro[2.1.5.3]tridecan-13-one hydrochloride |
| 224 | 12-(2-Fluorophenyl)-8-phenethyl-4-oxa-8,12-diazadispiro[2.1.5.3]tridecan-13-one |
| 225 | 8-phenethyl-12-phenyl-4-oxa-8,12-diazadispiro[2.1.5.3]tridecan-13-one |
| 226 | 9-(3-aminophenethyl)-2-methyl-4-phenyl-1-oxa-4,9-diazaspiro[5.5]undecan-3-one |
| 227 | 4-(3-aminophenyl)-2-methyl-9-phenethyl-1-oxa-4,9-diazaspiro[5.5]undecan-3-one |
| 228 | 9-(4-aminophenethyl)-2-methyl-4-phenyl-1-oxa-4,9-diazaspiro[5.5]undecan-3-one |
| 229 | 9-(2-aminophenethyl)-2-methyl-4-phenyl-1-oxa-4,9-diazaspiro[5.5]undecan-3-one |
| 230 | 9-(2-(5-aminopyridin-2-yl)ethyl)-4-(2-fluorophenyl)-2-methyl-1-oxa-4,9-diazaspiro[5.5]undecan-3-one |
| 231 | 8-(3-aminophenethyl)-12-phenyl-4-oxa-8,12-diazadispiro[2.1.5.3]tridecan-13-one |
| 232 | 9-(2-(3-aminopyridin-2-yl)ethyl)-4-(2-fluorophenyl)-2-methyl-1-oxa-4,9-diazaspiro[5.5]undecan-3-one |

-continued

| EX | Chemical name |
|---|---|
| 233 | 4-(3-aminobenzyl)-9-phenethyl-1-oxa-4,9-diazaspiro[5.5]undecan-3-one |
| 234 | 9-(2-(2-aminopyridin-3-yl)ethyl)-2-methyl-4-phenyl-1-oxa-4,9-diazaspiro[5.5]undecan-3-one |
| 235 | 9-(3-aminophenethyl)-4-((5-(trifluoromethyl)pyridin-2-yl)methyl)-1-oxa-4,9-diazaspiro[5.5]undecan-3-one |
| 236 | 9-(2-(5-aminopyridin-2-yl)ethyl)-2-methyl-4-phenyl-1-oxa-4,9-diazaspiro[5.5]undecan-3-one |
| 237 | 9-(2-(3-amino-1H-pyrazol-1-yl)ethyl)-2-methyl-4-phenyl-1-oxa-4,9-diazaspiro[5.5]undecan-3-one |
| 238 | 9-(2-(2-aminopyridin-3-yl)ethyl)-4-(2-fluorophenyl)-2-isopropyl-1-oxa-4,9-diazaspiro[5.5]undecan-3-one |
| 239 | 8-(3-aminophenethyl)-12-{[5-(trifluoromethyl)pyridin-2-yl]methyl}-4-oxa-8,12-diazadispiro[2.1.5.3]tridecan-13-one |
| 240 | 9-(2-(2-aminopyridin-3-yl)ethyl)-2-methyl-4-(4-(trifluoromethyl)pyridin-3-yl)-1-oxa-4,9-diazaspiro[5.5]undecan-3-one |
| 241 | N-(4-(2-(2-methyl-3-oxo-4-phenyl-1-oxa-4,9-diazaspiro[5.5]undecan-9-yl)ethyl)phenyl)acetamide |
| 242 | N-(3-(2-methyl-3-oxo-9-phenethyl-1-oxa-4,9-diazaspiro[5.5]undecan-4-yl)phenyl)acetamide |
| 243 | N-(3-(2-(2-methyl-3-oxo-4-phenyl-1-oxa-4,9-diazaspiro[5.5]undecan-9-yl)ethyl)phenyl)acetamide |
| 244a | (S)-N-(3-(2-(2-methyl-3-oxo-4-phenyl-1-oxa-4,9-diazaspiro[5.5]undecan-9-yl)ethyl)phenyl)acetamide |
| 244b | (R)-N-(3-(2-(2-methyl-3-oxo-4-phenyl-1-oxa-4,9-diazaspiro[5.5]undecan-9-yl)ethyl)phenyl)acetamide |
| 245 | N-(2-(2-(2-methyl-3-oxo-4-phenyl-1-oxa-4,9-diazaspiro[5.5]undecan-9-yl)ethyl)phenyl)acetamide |
| 246 | N-[3-(2-{13-oxo-12-phenyl-4-oxa-8,12-diazadispiro[2.1.5.3]tridecan-8-yl}ethyl)phenyl]acetamide |
| 247 | N-(3-(2-(2-methyl-3-oxo-4-phenyl-1-oxa-4,9-diazaspiro[5.5]undecan-9-yl)ethyl)phenyl)isobutyramide |
| 248 | 1,1-dimethyl-3-(3-(2-(2-methyl-3-oxo-4-phenyl-1-oxa-4,9-diazaspiro[5.5]undecan-9-yl)ethyl)phenyl)urea |
| 249 | N-(3-((3-oxo-9-phenethyl-1-oxa-4,9-diazaspiro[5.5]undecan-4-yl)methyl)phenyl)acetamide |
| 250 | N-(2-(2-(4-(2-fluorophenyl)-2-methyl-3-oxo-1-oxa-4,9-diazaspiro[5.5]undecan-9-yl)ethyl)pyridin-3-yl)acetamide |
| 251 | N-(3-(2-(3-oxo-4-((5-(trifluoromethyl)pyridin-2-yl)methyl)-1-oxa-4,9-diazaspiro[5.5]undecan-9-yl)ethyl)phenyl)acetamide |
| 252 | N-(6-(2-(2-methyl-3-oxo-4-phenyl-1-oxa-4,9-diazaspiro[5.5]undecan-9-yl)ethyl)pyridin-3-yl)acetamide |
| 253 | N-(2-(2-(2-methyl-3-oxo-4-phenyl-1-oxa-4,9-diazaspiro[5.5]undecan-9-yl)ethyl)pyridin-4-yl)acetamide |
| 254 | N-(6-(2-(2-methyl-3-oxo-4-phenyl-1-oxa-4,9-diazaspiro[5.5]undecan-9-yl)ethyl)pyridin-2-yl)acetamide |
| 255 | N-(4-(2-(2-methyl-3-oxo-4-phenyl-1-oxa-4,9-diazaspiro[5.5]undecan-9-yl)ethyl)pyridin-2-yl)acetamide |
| 256 | N-(3-(2-(2-methyl-3-oxo-4-phenyl-1-oxa-4,9-diazaspiro[5.5]undecan-9-yl)ethyl)phenyl)methanesulfonamide |
| 257 | N-(2-(2-(2-methyl-3-oxo-4-phenyl-1-oxa-4,9-diazaspiro[5.5]undecan-9-yl)ethyl)phenyl)methanesulfonamide |
| 258 | N-(4-(2-(2-methyl-3-oxo-4-phenyl-1-oxa-4,9-diazaspiro[5.5]undecan-9-yl)ethyl)phenyl)methanesulfonamide |
| 259 | N-(3-((3-oxo-9-phenethyl-1-oxa-4,9-diazaspiro[5.5]undecan-4-yl)methyl)phenyl)methanesulfonamide |
| 260 | N-[3-(2-{13-oxo-12-phenyl-4-oxa-8,12-diazadispiro[2.1.5.3]tridecan-8-yl}ethyl)phenyl]methanesulfonamide |
| 261 | N-(3-(2-(2-methyl-3-oxo-4-phenyl-1-oxa-4,9-diazaspiro[5.5]undecan-9-yl)ethyl)phenyl)propane-2-sulfonamide |
| 262 | 1-(3-(2-(2-methyl-3-oxo-4-phenyl-1-oxa-4,9-diazaspiro[5.5]undecan-9-yl)ethyl)phenyl)urea |
| 263 | {3-[2-(13-oxo-12-{[5-(trifluoromethyl)pyridin-2-yl]methyl}-4-oxa-8,12-diazadispiro[2.1.5.3]tridecan-8-yl)ethyl]phenyl}urea |
| 264 | 1-(6-(2-(2-methyl-3-oxo-4-phenyl-1-oxa-4,9-diazaspiro[5.5]undecan-9-yl)ethyl)pyridin-2-yl)urea |
| 265 | N-[3-(2-{2-methyl-3-oxo-4-phenyl-1-oxa-4,9-diazaspiro[5.5]undecan-9-yl}ethyl)phenyl]aminosulfonamide |
| 266 | 3-(2-(2-methyl-3-oxo-4-phenyl-1-oxa-4,9-diazaspiro[5.5]undecan-9-yl)ethyl)benzamide |
| 267 | 4-(2-(2-methyl-3-oxo-4-phenyl-1-oxa-4,9-diazaspiro[5.5]undecan-9-yl)ethyl)benzoic acid |
| 268 | 3-(2-methyl-3-oxo-9-phenethyl-1-oxa-4,9-diazaspiro[5.5]undecan-4-yl)benzoic acid |
| 269 | 3-(2-methyl-3-oxo-4-phenyl-1-oxa-4,9-diazaspiro[5.5]undecan-9-yl)propanoic acid |
| 270 | 2-(3-oxo-9-phenethyl-4-phenyl-1-oxa-4,9-diazaspiro[5.5]undecan-2-yl)acetic acid |

| EX | Chemical name |
|---|---|
| 271 | N,N-dimethyl-3-(2-methyl-3-oxo-9-phenethyl-1-oxa-4,9-diazaspiro[5.5]undecan-4-yl)benzamide |
| 272 | N,N-dimethyl-2-(3-oxo-9-phenethyl-4-phenyl-1-oxa-4,9-diazaspiro[5.5]undecan-2-yl)acetamide |
| 273 | N,N-dimethyl-4-(2-(2-methyl-3-oxo-4-phenyl-1-oxa-4,9-diazaspiro[5.5]undecan-9-yl)ethyl)benzamide |
| 274 | N-methyl-4-(2-(2-methyl-3-oxo-4-phenyl-1-oxa-4,9-diazaspiro[5.5]undecan-9-yl)ethyl)benzamide |
| 275 | N-methyl-3-[13-oxo-8-phenethyl-4-oxa-8,12-diazadispiro[2.1.5.3]tridecan-12-yl]propanamide |
| 276 | 3-(2-(4-(2-fluorophenyl)-2-methyl-3-oxo-1-oxa-4,9-diazaspiro[5.5]undecan-9-yl)ethyl)-N-methylbenzamide |
| 277 | 8-(2-hydroxy-2-phenylethyl)-12-phenyl-4-oxa-8,12-diazadispiro[2.1.5.3]tridecan-13-one |
| 278 | 9-(2-hydroxy-2-phenylethyl)-4-((5-(trifluoromethyl)pyridin-2-yl)methyl)-1-oxa-4,9-diazaspiro[5.5]undecan-3-one |
| 279 | 12-(3-hydroxypropyl)-8-phenethyl-4-oxa-8,12-diazadispiro[2.1.5.3]tridecan-13-one |
| 280 | 9-(2-(6-aminopyridin-3-yl)ethyl)-2-methyl-4-phenyl-1-oxa-4,9-diazaspiro[5.5]undecan-3-one |
| 281 | 4-(2-fluorophenyl)-9-(2-(2-hydroxyethoxy)phenethyl)-2-isopropyl-1-oxa-4,9-diazaspiro[5.5]undecan-3-one |
| 282 | 4-(2-fluorophenyl)-9-(3-(2-hydroxyethoxy)phenethyl)-2-methyl-1-oxa-4,9-diazaspiro[5.5]undecan-3-one |
| 283 | 2-(hydroxymethyl)-9-phenethyl-4-phenyl-1-oxa-4,9-diazaspiro[5.5]undecan-3-one |
| 284 | 4-((1H-imidazol-2-yl)methyl)-9-phenethyl-1-oxa-4,9-diazaspiro[5.5]undecan-3-one |
| 285 | 9-benzyl-4-(2-hydroxyphenyl)-1-oxa-4,9-diazaspiro[5.5]undecan-3-one |
| 286 | 4-(2-hydroxyphenyl)-9-phenethyl-1-oxa-4,9-diazaspiro[5.5]undecan-3-one |
| 287 | 9-benzyl-4-(3-hydroxyphenyl)-1-oxa-4,9-diazaspiro[5.5]undecan-3-one |
| 288 | 4-(3-hydroxyphenyl)-9-phenethyl-1-oxa-4,9-diazaspiro[5.5]undecan-3-one |
| 289 | 9-(2-hydroxyphenethyl)-4-phenyl-1-oxa-4,9-diazaspiro[5.5]undecan-3-one |
| 290 | 9-(4-hydroxyphenethyl)-4-phenyl-1-oxa-4,9-diazaspiro[5.5]undecan-3-one |
| 291 | 9-(3-hydroxyphenethyl)-4-phenyl-1-oxa-4,9-diazaspiro[5.5]undecan-3-one |
| 292 | 4-(2-(4-phenyl-1-oxa-4,9-diazaspiro[5.5]undecan-9-yl)ethyl)phenol |
| 293 | 4-(4-hydroxyphenyl)-2-methyl-9-phenethyl-1-oxa-4,9-diazaspiro[5.5]undecan-3-one |
| 294 | 4-(3-hydroxyphenyl)-2-methyl-9-phenethyl-1-oxa-4,9-diazaspiro[5.5]undecan-3-one |
| 295 | 9-(2-hydroxyphenethyl)-2-methyl-4-phenyl-1-oxa-4,9-diazaspiro[5.5]undecan-3-one |
| 296 | 4-(2-hydroxyphenyl)-2-methyl-9-phenethyl-1-oxa-4,9-diazaspiro[5.5]undecan-3-one |
| 297 | 4-(2-fluorophenyl)-9-(2-hydroxyphenethyl)-2-isopropyl-1-oxa-4,9-diazaspiro[5.5]undecan-3-one |
| 298 | 4-(2-fluorophenyl)-9-(3-hydroxyphenethyl)-2-methyl-1-oxa-4,9-diazaspiro[5.5]undecan-3-one |
| 299 | 2-(2-(4-benzyl-1-oxa-4,9-diazaspiro[5.5]undecan-9-yl)ethyl)phenol |
| 300 | 9-(2-hydroxyphenethyl)-4-(pyridin-2-ylmethyl)-1-oxa-4,9-diazaspiro[5.5]undecan-3-one |
| 301 | 4-(2-fluorophenyl)-2-(hydroxymethyl)-9-(2-hydroxyphenethyl)-1-oxa-4,9-diazaspiro[5.5]undecan-3-one |
| 302 | 4-(2-fluorophenyl)-2-(3-hydroxypropyl)-9-phenethyl-1-oxa-4,9-diazaspiro[5.5]undecan-3-one |
| 303 | 9-(2-(2-aminothiazol-4-yl)ethyl)-4-(2-fluorophenyl)-2-methyl-1-oxa-4,9-diazaspiro[5.5]undecan-3-one |
| 304 | 9-(2-(2-aminothiazol-4-yl)ethyl)-4-((5-(trifluoromethyl)pyridin-2-yl)methyl)-1-oxa-4,9-diazaspiro[5.5]undecan-3-one |
| 305 | 9-(2-(5-amino-1H-pyrazol-1-yl)ethyl)-2-methyl-4-phenyl-1-oxa-4,9-diazaspiro[5.5]undecan-3-one |
| 306 | 9-(2-(2-aminothiazol-4-yl)ethyl)-4-(2-fluorophenyl)-2-isopropyl-1-oxa-4,9-diazaspiro[5.5]undecan-3-one |
| 307 | 8-[2-(2-aminothiazol-4-yl)ethyl]-12-phenyl-4-oxa-8,12-diazadispiro[2.1.5.3]tridecan-13-one |
| 308 | 8-[2-(2-aminothiazol-4-yl)ethyl]-12-{[5-(trifluoromethyl)pyridin-2-yl]methyl}-4-oxa-8,12-diazadispiro[2.1.5.3]tridecan-13-one |
| 309 | 9-(2-(2-aminothiazol-4-yl)ethyl)-2-methyl-4-(4-(trifluoromethyl)pyridin-3-yl)-1-oxa-4,9-diazaspiro[5.5]undecan-3-one |
| 310 | 12-(2-hydroxyethyl)-8-phenethyl-4-oxa-8,12-diazadispiro[2.1.5.3]tridecan-13-one |
| 311 | 4-(2-fluorophenyl)-9-phenethyl-2-((tetrahydro-2H-pyran-4-yl)methyl)-1-oxa-4,9-diazaspiro[5.5]undecan-3-one |
| 312 | 4-(2-fluorophenyl)-2-isopropyl-9-phenethyl-1-oxa-4,9-diazaspiro[5.5]undecan-3-one |
| 313 | 4-(2-fluorophenyl)-2-isopropyl-9-(2-(pyridin-2-yl)ethyl)-1-oxa-4,9-diazaspiro[5.5]undecan-3-one |

-continued

| EX | Chemical name |
|---|---|
| 314 | 4-(2-fluorophenyl)-2-(3-methoxypropyl)-9-phenethyl-1-oxa-4,9-diazaspiro[5.5]undecan-3-one |
| 315 | N-methyl-2-(2-methyl-3-oxo-4-phenyl-1-oxa-4,9-diazaspiro[5.5]undecan-9-yl)-N-phenylacetamide |
| 316 | 3-(9-phenethyl-1-oxa-4,9-diazaspiro[5.5]undecan-4-yl)phenol |
| 317 | 9-phenethyl-4-phenyl-1-oxa-4,9-diazaspiro[5.5]undecane |
| 318 | 3-(9-benzyl-1-oxa-4,9-diazaspiro[5.5]undecan-4-yl)phenol |
| 319 | 2-(methoxymethyl)-9-phenethyl-4-phenyl-1-oxa-4,9-diazaspiro[5.5]undecane |
| 320 | 9-(3-methoxyphenethyl)-4-phenyl-1-oxa-4,9-diazaspiro[5.5]undecane |
| 321 | 2-(2-(4-phenyl-1-oxa-4,9-diazaspiro[5.5]undecan-9-yl)ethyl)phenol |
| 322 | 3-(2-(4-phenyl-1-oxa-4,9-diazaspiro[5.5]undecan-9-yl)ethyl)phenol |
| 323 | 2-(9-phenethyl-4-phenyl-1-oxa-4,9-diazaspiro[5.5]undecan-2-yl)ethanol |
| 324 | 4-benzyl-9-phenethyl-1-oxa-4,9-diazaspiro[5.5]undecane |
| 325 | 9-phenethyl-4-(thiazol-4-ylmethyl)-1-oxa-4,9-diazaspiro[5.5]undecane |
| 326 | 9-(2-methoxyphenethyl)-4-(pyridin-2-ylmethyl)-1-oxa-4,9-diazaspiro[5.5]undecane |
| 327 | 2-methyl-4-((1-methyl-1H-imidazol-2-yl)methyl)-9-phenethyl-1-oxa-4,9-diazaspiro[5.5]undecane |
| 328 | 2-methyl-4-((1-methyl-1H-pyrazol-3-yl)methyl)-9-phenethyl-1-oxa-4,9-diazaspiro[5.5]undecane |
| 329 | 2-(2-(4-(pyridin-2-ylmethyl)-1-oxa-4,9-diazaspiro[5.5]undecan-9-yl)ethyl)phenol |
| 330 | 2-methyl-9-phenethyl-4-(pyridin-2-ylmethyl)-1-oxa-4,9-diazaspiro[5.5]undecane |
| 331 | 2-methyl-9-phenethyl-4-(2-(pyridin-3-yl)ethyl)-1-oxa-4,9-diazaspiro[5.5]undecane |
| 332 | 9-(4-methoxyphenethyl)-4-phenyl-1-oxa-4,9-diazaspiro[5.5]undecane |
| 333 | 4-(3-methoxyphenyl)-9-phenethyl-1-oxa-4,9-diazaspiro[5.5]undecane |
| 334 | 9-(2-methoxyphenethyl)-4-phenyl-1-oxa-4,9-diazaspiro[5.5]undecane |
| 335 | 4-benzyl-2-methyl-9-phenethyl-1-oxa-4,9-diazaspiro[5.5]undecane |
| 336 | 9-phenethyl-4-(pyridin-2-ylmethyl)-1-oxa-4,9-diazaspiro[5.5]undecane |
| 337 | 4,9-diphenethyl-1-oxa-4,9-diazaspiro[5.5]undecane |
| 338 | 3-(2-(4-benzyl-1-oxa-4,9-diazaspiro[5.5]undecan-9-yl)ethyl)aniline |
| 339 | N-(3-(2-(4-benzyl-1-oxa-4,9-diazaspiro[5.5]undecan-9-yl)ethyl)phenyl)acetamide |
| 340 | 3-methyl-9-phenethyl-4-phenyl-1-oxa-4,9-diazaspiro[5.5]undecane |
| 341 | 8-(2,5-difluorophenethyl)-12-(2-(trifluoromethyl)pyridin-3-yl)-4-oxa-8,12-diazadispiro[2.1.5.3]tridecan-13-one |
| 342 | 8-(2,5-difluorophenethyl)-12-(4-(trifluoromethyl)pyridin-3-yl)-4-oxa-8,12-diazadispiro[2.1.5.3]tridecan-13-one |
| 343 | 8-(2,5-difluorophenethyl)-12-(3-(trifluoromethyl)pyridin-2-yl)-4-oxa-8,12-diazadispiro[2.1.5.3]tridecan-13-one |
| 344 | 12-benzyl-8-(2-(3-fluoropyridin-2-yl)ethyl)-4-oxa-8,12-diazadispiro[2.1.5.3]tridecane |
| 345 | 8-(2-(3-fluoropyridin-2-yl)ethyl)-12-(3-methylpyridin-2-yl)-4-oxa-8,12-diazadispiro[2.1.5.3]tridecane |
| 346 | methyl 3-(12-benzyl-13-oxo-4-oxa-8,12-diazadispiro[2.1.5.3]tridecan-8-yl)propanoate |
| 347 | methyl 3-(12-benzyl-4-oxa-8,12-diazadispiro[2.1.5.3]tridecan-8-yl)propanoate |
| 348 | methyl 3-(13-oxo-12-phenyl-4-oxa-8,12-diazadispiro[2.1.5.3]tridecan-8-yl)propanoate |
| 349 | (R)-2-benzyl-9-phenyl-6-oxa-2,9-diazaspiro[4.5]decan-8-one |
| 350 | (S)-2-benzyl-9-phenyl-6-oxa-2,9-diazaspiro[4.5]decan-8-one | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another very preferred embodiment of the compound according to the invention according to general formula I' the compound is selected from examples 1, 4, 5, 8 to 15, 17 to 70, 73 to 77, 79 to 81, 83 to 86, 88 to 96, 98, 101 to 121, 123, 126 to 127b, 130 to 137, 139 to 143, 146 to 149, 152 to 187, 189 to 268, 270 to 276, 279 to 284, 286, 288 to 298 and 300 to 314, and 315;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another very preferred embodiment of the compound according to the invention according to general formula I' the compound is selected from examples 1, 4, 5, 8 to 15, 17 to 70, 73 to 77, 79 to 81, 83 to 86, 88 to 96, 98, 101 to 121, 123, 126 to 127b, 130 to 137, 139 to 143, 146 to 149, 152 to 187, 189 to 268, 270 to 276, 279 to 284, 286, 288 to 298, 300 to 315, 341 to 343, 346 and 348;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I" the compound is selected from examples 87, 138, 299, 316, 317, and 319 to 339;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I''' the compound is selected from examples 87, 138, 299, 316, 317, 319 to 339, 344, 345 and 347;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to general formula I''' the compound is the compound of example 340; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a preferred embodiment of the compound according to the invention according to general formula I, I'. I'' or I''' wherein $R_1$ is substituted or unsubstituted aryl, substituted or unsubstituted heterocyclyl, substituted or unsubstituted alkylaryl, substituted or unsubstituted alkylheterocyclyl or —(CH2)$_r$-W—$R_1$;

wherein the aryl, heterocyclyl or cycloalkyl in $R_1$ or $R_{1'}$ if substituted (also in alkylaryl or alkylheterocyclyl) are substituted with substituents selected from —$R_5$, —$OR_5$, halogen, —CN, —$NO_2$, —$NR_5R_{5'''}$, —C(O)O$R_5$, $NR_5$C(O)$NR_{5'}$, —C(O)$NR_5R_{5'}$, —$NR_5$S(O)$_2R_{5'}$, =O, —OCH$_2$CH$_2$OH, —$NR_5$C(O)$NR_5R_{5'''}$, —S(O)$_2NR_5R_{5'}$, —$NR_5$S(O)$_2NR_5R_{5'''}$, haloalkyl, haloalkoxy, —$SR_5$, —S(O)$R_5$ or —S(O)$_2R_5$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention the compound of general formulas I, I', I'' and I'''

$R_1$ is H, —CN, substituted or unsubstituted heterocyclyl, substituted or unsubstituted aryl, substituted or unsubstituted cycloalkyl or $R_5$;

wherein the aryl, heterocyclyl or cycloalkyl in $R_1$ if substituted are substituted with substituents selected from —$R_5$, —$OR_5$, halogen, —CN, —$NO_2$, —$NR_5R_{5'''}$, —C(O)O$R_5$, $NR_5$C(O)$R_{5'}$, —C(O)$NR_5R_{5'}$, —$NR_5$S(O)$_2R_{5'}$, =O, —OCH$_2$CH$_2$OH, —$NR_5$C(O)$NR_5R_{5'''}$, —S(O)$_2NR_5R_{5'}$, —$NR_5$S(O)$_2NR_5R_{5'''}$, haloalkyl, haloalkoxy, —$SR_5$, —S(O)$R_5$ or —S(O)$_2R_5$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention the compound of general formulas I, I', I'' and I'''

$R_2$ is H, substituted or unsubstituted aryl, substituted or unsubstituted heterocyclyl, substituted or unsubstituted cycloalkyl, substituted or unsubstituted $C_{1-6}$ alkyl, substituted or unsubstituted $C_{2-6}$ alkenyl or substituted or unsubstituted $C_{2-6}$ alkynyl;

wherein the aryl, heterocyclyl or cycloalkyl in R2 if substituted is substituted with substituents selected from —$R_5$, —$OR_5$, halogen, —CN, —$NO_2$, —$NR_5R_{5'''}$, —C(O)O$R_5$, —$NR_5$C(O)$R_{5'}$, —C(O)$NR_5R_{5'}$, —$NR_5$S(O)$_2R_{5'}$, =O, —OCH$_2$CH$_2$OH, —$NR_5$C(O)$NR_5R_{5'''}$, —S(O)$_2NR_5R_{5'}$, —$NR_5$S(O)$_2NR_5R_{5'''}$, haloalkyl, -haloalkoxy, —$SR_5$, —S(O)$R_5$ or —S(O)$_2R_5$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I, I', I'' and I''' wherein $R_3$ and $R_{3'}$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl and —CH$_2R_4$;

wherein the cycloalkyl as defined in $R_3$ if substituted are substituted with substituents selected from —$OR_5$, halogen, —CN, haloalkyl, haloalkoxy, —$SR_5$, —S(O)$R_5$ or —S(O)$_2R_5$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I, I', I'' and I''' wherein $R_3$ and $R_{3'}$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, wherein the aryl, cycloalkyl and heterocyclyl as defined in $R_3$ if substituted (also in alkylaryl or alkylheterocyclyl) are substituted with substituents selected from —$OR_5$, halogen, —CN, haloalkyl, haloalkoxy, —$SR_5$, —S(O)$R_5$ or —S(O)$_2R_5$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound according to general formulas I wherein $R_4$ is H, —$OR_5$, substituted or unsubstituted $C_{1-6}$ alkyl, substituted or unsubstituted $C_{2-6}$ alkenyl, substituted or unsubstituted $C_{2-6}$ alkynyl, —COO$R_5$, —CON$R_5R_{5'}$, —$NR_5$CO$R_{5'}$, —$NR_5R_{5'''}$ or unsubstituted heterocyclyl, unsubstituted aryl, unsubstituted cycloalkyl;

wherein the aryl, cycloalkyl and heterocyclyl as defined in $R_4$ if substituted are substituted with substituents selected from —$OR_5$, halogen, —CN, haloalkyl, haloalkoxy, —$SR_5$, —S(O)$R_5$ or —S(O)$_2R_5$;

In another embodiment of the invention in the compound according to general formulas I wherein $R_4$ is H, —$OR_5$, substituted or unsubstituted $C_{1-6}$ alkyl, substituted or unsubstituted $C_{2-6}$ alkenyl, substituted or unsubstituted $C_{2-6}$ alkynyl, —COO$R_5$, —CON$R_5R_{5'}$, —$NR_5$CO$R_{5'}$, —NR5R5''' or substituted or unsubstituted heterocyclyl, substituted or unsubstituted aryl, substituted or unsubstituted cycloalkyl wherein the aryl, cycloalkyl and heterocyclyl as defined in $R_4$ if substituted are substituted with substituents selected from —$OR_5$, halogen, —CN, haloalkyl, haloalkoxy, —$SR_5$, —S(O)$R_5$ or —S(O)$_2R_5$;

In an embodiment of the invention in the compound of general formulas I, I', I'' and I''' the alkyl, alkenyl and alkynyl as defined in $R_1$, $R_{1'}$, $R_2$, $R_3$, $R_{3'}$, $R_4$, $R_{4'}$, $R_6$, $R_{6'}$, $R_7$, $R_{7'}$, $R_8$, $R_{8'}$ and $R_9$ if substituted are substituted with substituents selected from —$OR_5$, halogen, —CN, haloalkoxy, —$SR_5$, —$S(O)R_5$, —$S(O)_2R_5$, $C(O)OR_5$ or $C(O)NR_5R_{5'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In an embodiment of the invention in the compound of general formulas I, I', I" and I'"
the halogen is fluorine, chlorine, iodine or bromine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a most preferred embodiment of the invention in the compound according to general formulas I, I', I" and I'"
the halogen is fluorine or chlorine optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In an embodiment of the invention in the compound of general formulas I, I', I" and I'"
the haloalkyl is —$CF_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment of the invention in the compound of general formulas I, I', I" and I'"
the haloalkoxy is —$OCF_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In an embodiment of the invention in the compound of general formula I

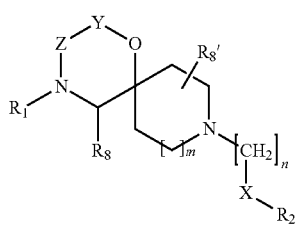

(I)

wherein
Y is

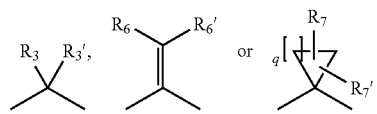

Z is —$CH_2$—, —$C(O)$— or —$CHR_9$—;
m is 0 or 1;
n is 1, 2 or 3;
q is 1, 2, 3, 4, 5 or 6;
$R_1$ is substituted or unsubstituted aryl, substituted or unsubstituted heterocyclyl, substituted or unsubstituted alkylaryl, substituted or unsubstituted alkylheterocyclyl or —$(CH2)_r$—W—$R_{1'}$;
r is 0, 1 or 2
W is a bond, —$CH_2O$—, —$CH_2C(O)NR_{5'}$—, —$CH_2C(O)O$—, —$CH_2C(O)$— or —$C(CH_3)_2O$—;
$R_{1'}$ is H, —CN, substituted or unsubstituted heterocyclyl, substituted or unsubstituted aryl, substituted or unsubstituted cycloalkyl or $R_5$;

wherein the aryl, heterocyclyl or cycloalkyl in $R_1$ or $R_{1'}$ (also in alkylaryl or alkylheterocyclyl) if substituted are substituted with substituents selected from —$R_5$, —$OR_5$, halogen, —CN, —$NO_2$, —$NR_5R_{5'''}$, —$C(O)OR_5$, $NR_5C(O)R_{5'}$, —$C(O)NR_5R_{5'}$, —$NR_5S(O)_2R_{5'}$, =O, —$OCH_2CH_2OH$, —$NR_5C(O)NR_5R_{5''}$, —$S(O)_2NR_5R_{5'}$, —$NR_5S(O)_2NR_5R_{5''}$, haloalkyl, haloalkoxy, —SR5, —$S(O)R_5$ or —$S(O)_2R_5$;

X is a bond, —$C(O)O$—, —$C(O)NR_5$—, —$C(O)$—, —O— or —$C(R_4R_{4'})$—;

$R_2$ is H, substituted or unsubstituted aryl, substituted or unsubstituted heterocyclyl, substituted or unsubstituted cycloalkyl, substituted or unsubstituted $C_{1-6}$ alkyl, substituted or unsubstituted $C_{2-6}$ alkenyl or substituted or unsubstituted $C_{2-6}$ alkynyl;

wherein the aryl, heterocyclyl or cycloalkyl in R2 if substituted is substituted with substituents selected from —$R_5$, —$OR_5$, halogen, —CN, —$NO_2$, —$NR_5R_{5'''}$, —$C(O)OR_5$, —$NR_5C(O)R_{5'}$, —$C(O)NR_5R_{5'}$, —$NR_5S(O)_2R_{5'}$, =O, —$OCH_2CH_2OH$, —$NR_5C(O)NR_5R_{5''}$, —$S(O)_2NR_5R_{5'}$, —$NR_5S(O)_2NR_5R_{5''}$, haloalkyl, -haloalkoxy, —$SR_5$, —$S(O)R_5$ or —$S(O)_2R_5$;

$R_3$ and $R_{3'}$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, substituted or unsubstituted alkylcycloalkyl, wherein the aryl, cycloalkyl and heterocyclyl as defined in $R_3$ if substituted (also in alkylaryl, alkylcycloalkyl or alkylheterocyclyl) are substituted with substituents selected from —$OR_5$, halogen, —CN, haloalkyl, haloalkoxy, —$SR_5$, —$S(O)R_5$ or —$S(O)_2R_5$;

$R_4$ is H, —$OR_5$, substituted or unsubstituted $C_{1-6}$ alkyl, substituted or unsubstituted $C_{2-6}$ alkenyl, substituted or unsubstituted $C_{2-6}$ alkynyl, —$COOR_5$, —$CONR_5R_{5'}$, —$NR_5COR_{5'}$, —NR5R5'" or substituted or unsubstituted heterocyclyl, substituted or unsubstituted aryl, substituted or unsubstituted cycloalkyl wherein the aryl, cycloalkyl and heterocyclyl as defined in $R_4$ if substituted are substituted with substituents selected from —$OR_5$, halogen, —CN, haloalkyl, haloalkoxy, —$SR_5$, —$S(O)R_5$ or —$S(O)_2R_5$;

$R_{4'}$ is H, substituted or unsubstituted $C_{1-6}$ alkyl, substituted or unsubstituted $C_{2-6}$ alkenyl or substituted or unsubstituted $C_{2-6}$ alkynyl;

$R_5$, $R_{5'}$ and $R_{5''}$ are independently selected from H, unsubstituted $C_{1-6}$ alkyl, unsubstituted $C_{2-6}$ alkenyl, unsubstituted $C_{2-6}$ alkynyl, unsubstituted aryl or unsubstituted alkylaryl;

$R_{5'''}$ is H, unsubstituted $C_{1-6}$ alkyl, unsubstituted $C_{2-6}$ alkenyl, unsubstituted $C_{2-6}$ alkynyl or -Boc $R_6$, $R_{6'}$, $R_7$ and $R_{7'}$ are independently selected from H, halogen, —$OR_5$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_{8'}$ are independently selected from H, —$OR_5$, halogen, substituted or unsubstituted $C_{1-6}$ alkyl, substituted or unsubstituted $C_{2-6}$ alkenyl or substituted or unsubstituted $C_{2-6}$ alkynyl;

$R_9$ is selected from H, substituted or unsubstituted $C_{1-6}$ alkyl, substituted or unsubstituted $C_{2-6}$ alkenyl or substituted or unsubstituted $C_{2-6}$ alkynyl;

and/or wherein the alkyl, alkenyl and alkynyl as defined in $R_1$, $R_{1'}$, $R_2$, $R_3$, $R_{3'}$, $R_4$, $R_{4'}$, $R_6$, $R_{6'}$, $R_7$, $R_{7'}$, $R_8$, $R_{8'}$ and $R_9$ if substituted are substituted with substituents selected from —$OR_5$, halogen, —CN, haloalkyl, haloalkoxy, —$SR_5$, —$S(O)R_5$, —$S(O)_2R_5$, $C(O)OR_5$ or $C(O)NR_5R_{5'}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, with the proviso that when W is a bond, then $R_{1'}$ cannot be H, unsubstituted alkyl, unsubstituted alkenyl, unsubstituted alkynyl or substituted or unsubstituted cycloalkyl;

with the following compounds being excluded from the general formula I:

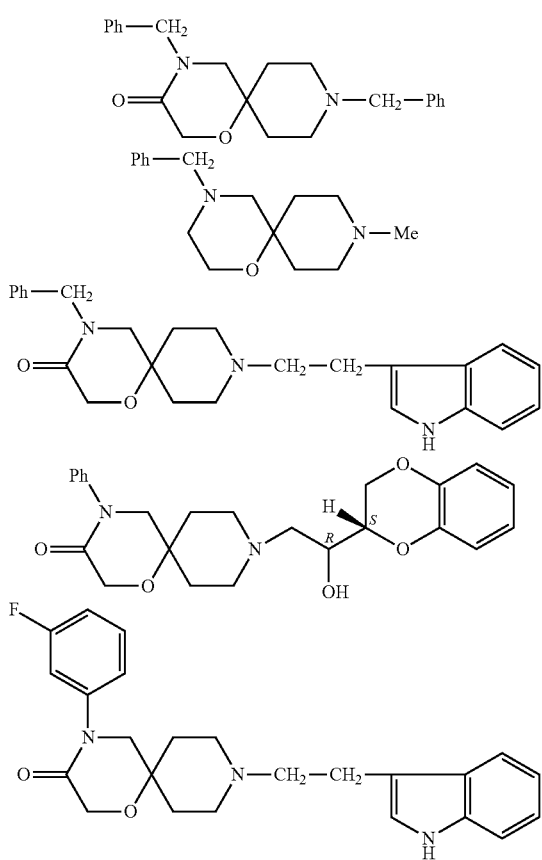

-continued

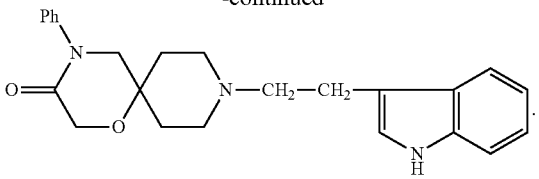

In an embodiment of the invention in the compound of general formula I

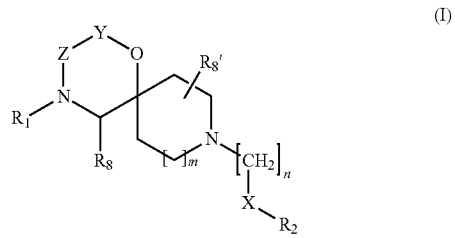

(I)

wherein
Y is

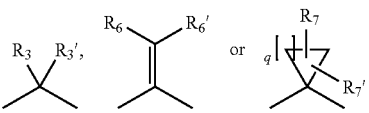

Z is —$CH_2$—, —$C(O)$— or —$CHR_9$—;
m is 0 or 1;
n is 1, 2 or 3;
q is 1, 2, 3, 4, 5 or 6;
$R_1$ is substituted or unsubstituted aryl, substituted or unsubstituted heterocyclyl, substituted or unsubstituted alkylaryl, substituted or unsubstituted alkylheterocyclyl or —$(CH2)_r$-W—$R_{1'}$;
r is 0, 1 or 2
W is a bond, —$CH_2O$—, —$CH_2C(O)NR_{5'}$—, —$CH_2C(O)O$—, —$CH_2C(O)$— or —$C(CH_3)_2O$—;
$R_{1'}$ is H, —CN, substituted or unsubstituted heterocyclyl, substituted or unsubstituted aryl (–), substituted or unsubstituted cycloalkyl or $R_5$;
X is a bond, —$C(O)O$—, —$C(O)NR_5$—, —$C(O)$—, —O— or —$C(R_4R_{4'})$—;
$R_2$ is H, substituted or unsubstituted aryl, substituted or unsubstituted heterocyclyl, substituted or unsubstituted cycloalkyl, substituted or unsubstituted $C_{1-6}$ alkyl, substituted or unsubstituted $C_{2-6}$ alkenyl or substituted or unsubstituted $C_{2-6}$ alkynyl;
$R_3$ and $R_{3'}$ are independently selected from H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, substituted or unsubstituted alkylcycloalkyl,
$R_4$ is H, —$OR_5$, substituted or unsubstituted $C_{1-6}$ alkyl, substituted or unsubstituted $C_{2-6}$ alkenyl, substituted or unsubstituted $C_{2-6}$ alkynyl, —$COOR_5$, —$CONR_5R_{5'}$, —$NR_5COR_{5'}$, —$NR5R5'''$ or substituted or unsubstituted heterocyclyl, substituted or unsubstituted aryl, substituted or unsubstituted cycloalkyl $R_{4'}$ is H, substituted or unsubstituted $C_{1-6}$ alkyl, substituted or unsubstituted $C_{2-6}$ alkenyl or substituted or unsubstituted $C_{2-6}$ alkynyl;

$R_5$, $R_{5'}$ and $R_{5''}$ are independently selected from H, unsubstituted $C_{1-6}$ alkyl, unsubstituted $C_{2-6}$ alkenyl, unsubstituted $C_{2-6}$ alkynyl, unsubstituted aryl or unsubstituted alkylaryl;

$R_{5'''}$ is H, unsubstituted $C_{1-6}$ alkyl, unsubstituted $C_{2-6}$ alkenyl, unsubstituted $C_{2-6}$ alkynyl or -Boc $R_6$, $R_{6'}$, $R_7$ and $R_{7'}$ are independently selected from H, halogen, —$OR_5$, substituted or unsubstituted $C_{1-6}$ alkyl, substituted or unsubstituted $C_{2-6}$ alkenyl, substituted or unsubstituted $C_{2-6}$ alkynyl, unsubstituted heterocyclyl, unsubstituted aryl and unsubstituted cycloalkyl;

$R_8$ and $R_{8'}$ are independently selected from H, —$OR_5$, halogen, substituted or unsubstituted $C_{1-6}$ alkyl, substituted or unsubstituted $C_{2-6}$ alkenyl or substituted or unsubstituted $C_{2-6}$ alkynyl;

$R_9$ is selected from H, substituted or unsubstituted $C_{1-6}$ alkyl, substituted or unsubstituted $C_{2-6}$ alkenyl or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof, with the proviso that when W is a bond, then $R_{1'}$ cannot be H, unsubstituted alkyl, unsubstituted alkenyl, unsubstituted alkynyl or substituted or unsubstituted cycloalkyl;

with the following compounds being excluded from the general formula I:

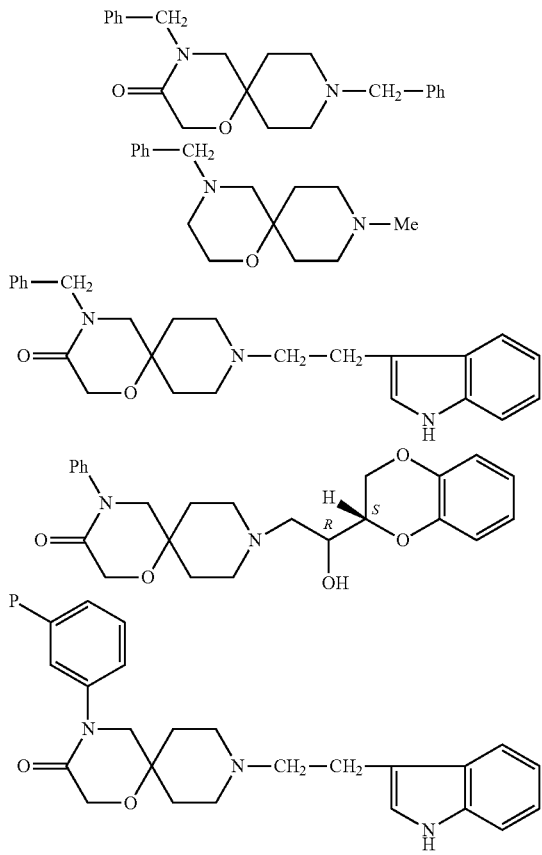

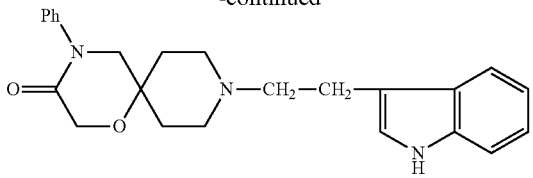

-continued

In addition to the two embodiments above, also the following compound may be excluded:

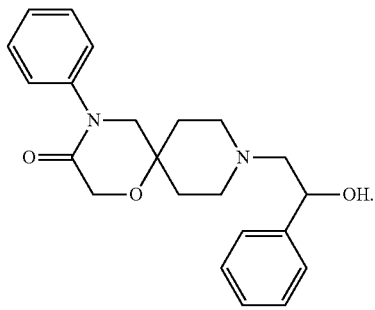 [SMILES: O=C1COC2(CCN(CC(O)c3ccccc3)CC2)CN1c1ccccc1]

As this invention is aimed at providing a compound or a chemically related series of compounds which act as dual ligands of the $\sigma_1$ receptor and the µ-opiod receptor it is a very preferred embodiment in which the compounds are selected which act as dual ligands of the $\sigma_1$ receptor and the µ-opiod receptor and especially compounds which have a binding expressed as $K_i$ which is preferably <1000 nM for both receptors, more preferably <500 nM, even more preferably <100 nM.

In the following the phrase "compound of the invention" is used. This is to be understood as any compound according to the invention as described above according to general formulas I, I', I" or I'".

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to formula I,

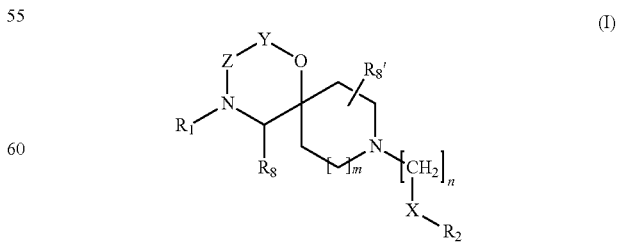

(I)

wherein $R_1$, $R_2$, $R_8$, $R_{8'}$, X, Y, Z, m and n are as already defined above in the description, wherein a compound of formula (VIIIH') or its suitable salt like the hydrochloride

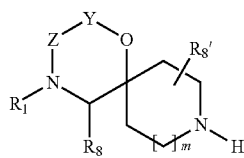
(VIIIH')

wherein $R_1$, $R_8$, $R_{8'}$, Y, Z and m are already defined in above in the description, is reacted with a compound according to formula IX, X or XI.

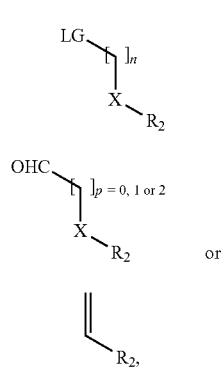
(IX)

(X)

or (XI)

wherein $R_2$, X and n are as already defined in above in the description, and wherein LG is a leaving group, leading to a compound according to formula (I)

A particular embodiment is a process for the preparation of a compound of general formula Ia

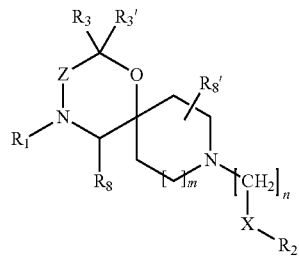
(Ia)

wherein
$R_1$, $R_2$, $R_3$, $R_{3'}$, $R_8$, $R_{8'}$, X, m, n and Z are as already defined above in the description;
which comprises the steps of
(a) reacting a compound of formula Va

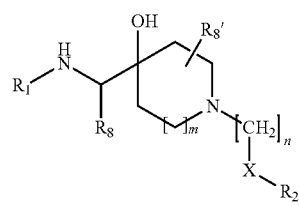
(Va)

with a compound of formula VI

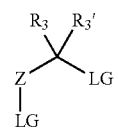
(VI)

wherein LG is a leaving group, $R_3$, $R_{3'}$ and Z are as already defined above in the description;
to obtain a compound of formula VIIa

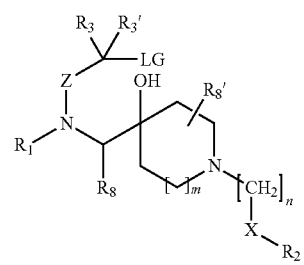
(VIIa)

and (b) carrying out a cyclisation of the resulting compound in a suitable solvent, in the presence of a strong base and at a temperature comprised between −78° C. and the reflux temperature;
wherein the hydrogen, the blocking agent or the —(CH2)n-X—R2 group defined as A in the above general Markush formulae Iax', Vax' and VIIax' may be introduced in any step during the process.

Another particular embodiment of the invention is a process for the preparation of a compound of general formula Icx

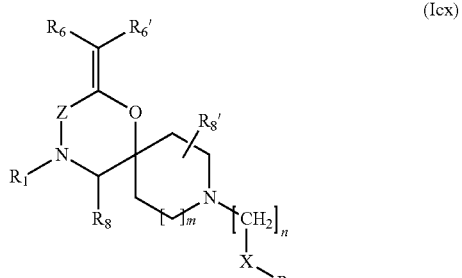
(Icx)

wherein
$R_1$, $R_2$, $R_6$, $R_{6'}$, $R_8$, $R_{8'}$, X, m, n and Z are as defined in the preceeding claims;
which comprises the dehydration of a compound of formula XIXx

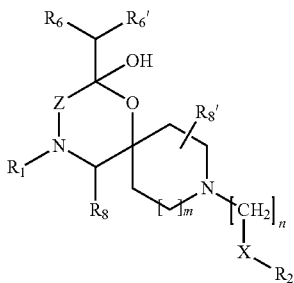 (XIXx)

A further embodiment of the invention is a process for the preparation of a compound of general formula Ifx

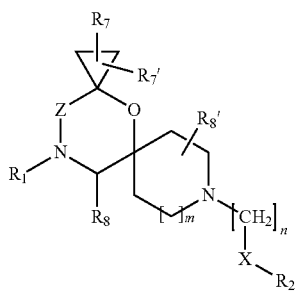 (Ifx)

wherein
R$_1$, R$_2$, R$_8$, R$_{8'}$, m, n, X and Z are already defined above in the description, and R$_7$ and R$_{7'}$ are hydrogen;

which comprises the cyclopropanation of a compound of formula Icx

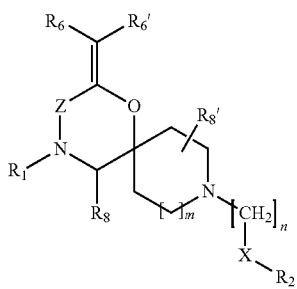 (Icx)

wherein
R$_1$, R$_2$, R$_8$, R$_{8'}$, m, n, X and Z are already defined above in the description;
R$_6$ and R$_{6'}$ are hydrogen;

A further embodiment of the invention is a process for the preparation of a compound of general formula Icx

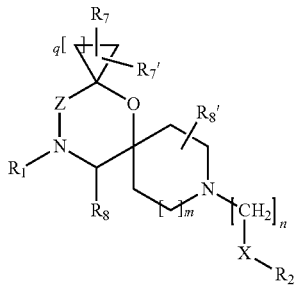 (Iox)

wherein
R$_1$, R$_2$, R$_8$, R$_{8'}$, m, n, q, X and Z are already defined above in the description;
which comprises reacting a compound of formula Ikx

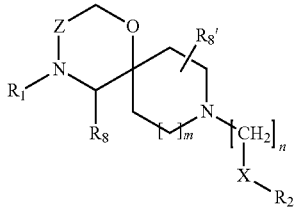 (Ikx)

wherein
R$_1$, R$_2$, R$_8$, R$_{8'}$, m, n, X and Z are already defined above in the description;
with a compound of formula XXXIV

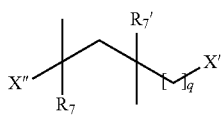 (XXXIV)

wherein
R$_7$, R$_{7'}$ and q are already defined above in the description,
X' and X" independently represent a leaving group;

Preparation of the hydrochloride salt: To a solution of the free base in a suitable solvent, preferably in anhydrous diethyl ether, HCl is added and the mixture is stirred, preferably at r.t. and preferably for 1 h. The solids are filtered and dried, preferably under vacuum, to give the corresponding HCl salt.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formulas I, I', I" or I''' or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formulas I, I', I" or I'" or a pharmaceutically acceptable salt or isomer thereof, for use as a medicament for the treatment of pain.

Preferably the pain is medium to severe pain, visceral pain, chronic pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis)

Scheme 1:

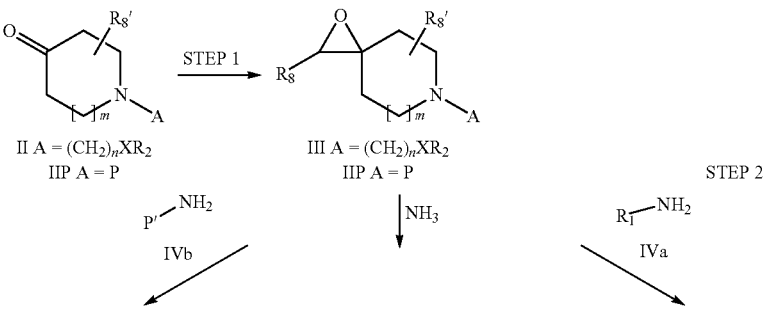

-continued

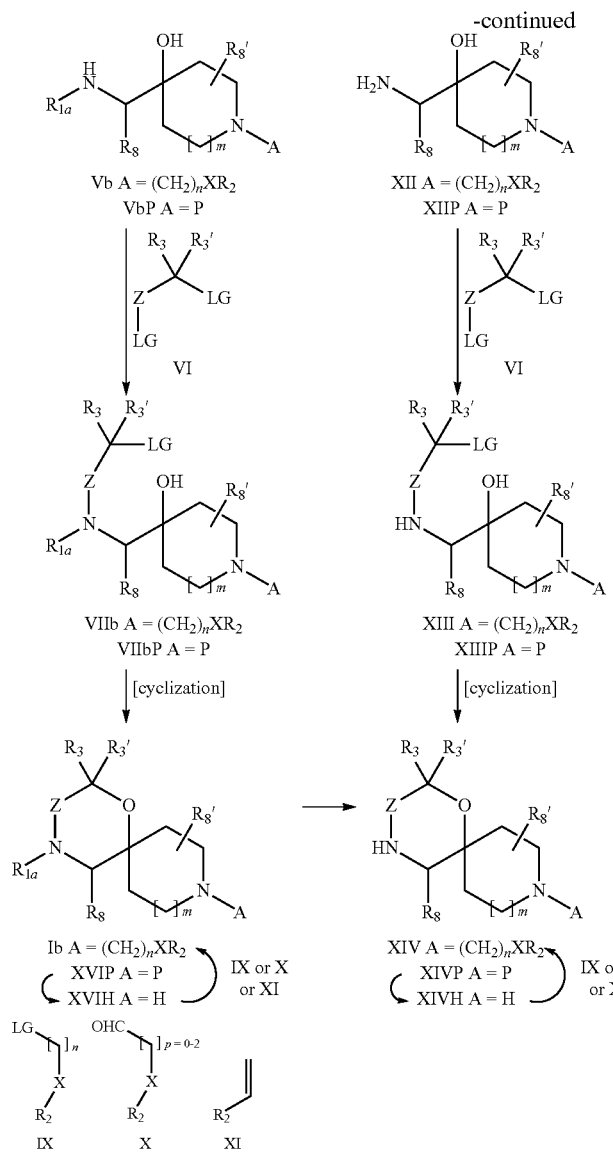
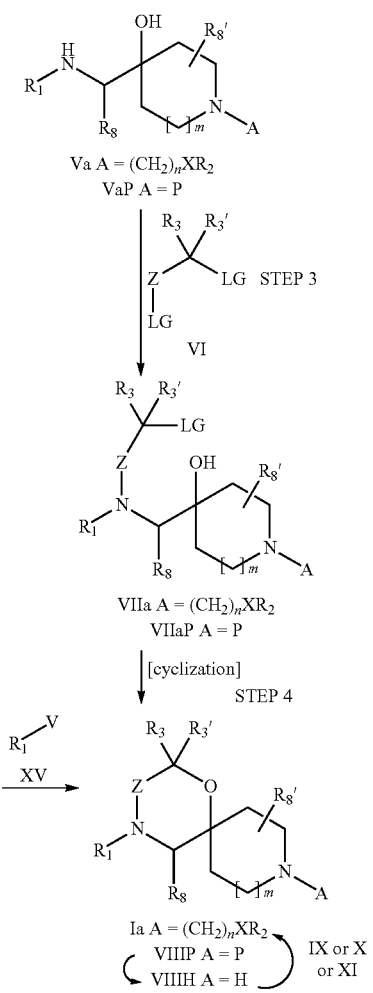

A 4-step process is described for the preparation of compounds of general formula (I) wherein Y is $CR_3R_{3'}$ (compounds of formula Ia) starting from a ketone of formula II, as shown in the following scheme:

wherein $R_1$, $R_2$, $R_3$, $R_{3'}$, $R_8$, $R_{8'}$, X, Z, m and n have the meanings as defined above for a compound of formula (I), p represents 0, 1 or 2, LG represents a leaving group such such as halogen, mesylate, tosylate or triflate, with the proviso that when Z=CO it can only be chloro or bromo, V represents an aldehyde or another leaving group (such as halogen, mesylate, tosylate or triflate), P represents a suitable protecting group (preferably Boc) and $R_{1a}$ represents a $R_1$ group that can be used as a protecting group (preferably 4-methoxybenzyl or benzyl).

The 4 step-process is carried out as described below:

Step1:

When $R_8$=H, a compound of formula III is prepared by treating a compound of formula II with a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C. The compounds of formula III wherein $R_8 \neq H$ can be prepared from compounds of formula II in a two-step process, comprising an olefination under typical Wittig reaction conditions followed by an epoxidation using a suitable oxidizing agent such as a peracid (as for example m-chloroperbenzoic acid), or hydrogen peroxide (optionally in the presence of a metal catalyst).

Step2:

A compound of formula Va is prepared by reacting a compound of formula III with an amine of formula IVa, in a suitable solvent such as an alcohol, preferably ethanol-water mixtures, at a suitable temperature comprised between room temperature and the reflux temperature.

Step3:

A compound of formula VIIa is prepared by reacting a compound of formula Va with a compound of formula VI. Depending on the meaning of Z, the compound of formula VI can be of different nature and different reaction conditions will apply:

a) When Z represents CO, VI is an acylating agent. The acylation reaction is carried out in a suitable solvent, such as dichloromethane or ethyl acetate-water mixtures; in the presence of an organic base such as triethylamine or diisopropylethylamine or an inorganic base such as $K_2CO_3$; and at a suitable temperature, preferably comprised between −78° C. and room temperature.

b) When Z represents $CH_2$ or $CHR_9$, VI is an alkylating agent. The alkylation reaction may be carried out in a suitable solvent, such as acetonitrile, dichloromethane, tetrahydrofuran, 1,4-dioxane or dimethylformamide; in the presence of an inorganic base such as $K_2CO_3$, $Cs_2CO_3$ or NaH, or an organic base such as triethylamine or diisopropylethylamine, at a suitable temperature comprised between room temperature and the reflux temperature. The OH group present may need protection previous to the alkylation reaction.

Step4:

The intramolecular cyclization of a compound of formula VIIa renders a compound of formula Ia. The cyclization reaction is carried out in a suitable solvent, such as tetrahydrofuran; in the presence of a strong base such as potassium tert-butoxide or sodium hydride; and at a suitable temperature, comprised between −78° C. and the reflux temperature, preferably cooling.

Alternatively, the group $(CH_2)_nXR_2$ can be incorporated in the last step of the synthesis by reaction of a compound of formula VIIIH with a compound of formula IX, X or XI, as shown in Scheme 1. A compound of formula VIIIH is obtained by deprotection of a compound of formula VIIIP, wherein P represents a suitable protecting group, preferably Boc (tert-butoxycarbonyl). When the protecting group is Boc, the deprotection can be conducted by adding a solution of a strong acid such as HCl, in a suitable solvent such as diethyl ether, 1,4-dioxane or methanol, or with trifluoroacetic acid in dichloromethane. A compound of formula VIIIP is prepared from a compound of formula IIP following the same sequence described for the synthesis of compounds of formula Ia.

The alkylation reaction between a compound of formula VIIIH (or a suitable salt such as trifluoroacetate or hydrochloride) and a compound of formula IX is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$, at a suitable temperature comprised between room temperature and the reflux temperature, preferably heating, or alternatively, the reactions can be carried out in a microwave reactor. Additionally, an activating agent such as NaI can be used.

The reductive amination reaction between a compound of formula VIIIH and a compound of formula X is carried out in the presence of a reductive reagent, preferably sodium triacetoxyborohydride, in an aprotic solvent, preferably tetrahydrofuran or dichloroethane, optionally in the presence of an acid, preferably acetic acid.

The condensation reaction between a compound of general formula VIIIH and a compound of formula XI is preferably carried out in a suitable solvent, such as isopropanol, n-butanol or 2-methoxyethanol, optionally in the presence of an organic base such as triethylamine or diisopropylethylamine, at a suitable temperature comprised between room temperature and the reflux temperature, preferably heating, or alternatively, the reactions can be carried out in a microwave reactor.

In another alternative approach, the $R_1$ substituent can be incorporated later in the sequence by the reaction of a compound of formula XIV with a compound of formula XV. Depending on the meaning of $R_1$ and Z, V can be of different nature and different reaction conditions will apply:

a) When Z is $CH_2$ and $R_1$ is not aryl or heterocyclyl, compound XV is an alkylating agent and V represents a leaving group such as halogen, mesylate, tosylate or triflate. The alkylation reaction is carried out under the same reaction conditions described above for the reaction of a compound of formula VIIIH and a compound of formula IX.

Alternatively, when Z is $CH_2$, compound XV can be an aldehyde wherein V represents a C(O)—H group. The reductive amination reaction is carried out under the same reaction conditions described above for the reaction of a compound of formula VIIIH and a compound of formula X.

b) When Z is C(O) and $R_1$ is not aryl or heterocyclyl, compound XV is an alkylating agent and V represents a leaving group such as halogen, mesylate, tosylate or triflate. This alkylation reaction is carried out in an aprotic solvent, preferably dimethylformamide, in the presence of an inorganic base such as NaH, at a suitable temperature, preferably between room temperature and 60° C.

c) When $R_1$ is aryl or heterocyclyl, compound XV is an arylating agent and V represents halogen (preferably bromo or iodo) or triflate. This arylation reaction is carried out under catalytic conditions using a palladium or copper catalyst, in the presence of a suitable ligand and a suitable base, in a suitable solvent, and at a suitable temperature, preferably heating at the reflux temperature or in a microwave reactor. When using copper catalysts such as copper(I) iodide, trans-1,2-cyclohexanediamine is the preferred ligand, potassium phosphate is used preferably as the base and 1,4-dioxane is the solvent of choice. When using palladium catalysts such as tris(dibenzylideneacetone)dipalladium(0) or palladium diacetate, 4,5-bis(diphenylphosphino)-9,9-dimethylxanthene (Xantphos) or BINAP are the preferred ligands, cessium carbonate or sodium tert-butoxide are used preferably as the base and 1,4-dioxane or toluene are the solvents of choice.

A compound of formula XIV is synthesized following an analogous sequence as described for the synthesis of compounds of formula Ia, but effecting step 2 using ammonia instead of an amine. Alternatively, a compound of formula XIV can be prepared by reaction of a compound of formula XIVH (prepared from a compound of formula XIVP, wherein P represents a suitable protecting group) with a compound of formula IX, X or XI, as described above.

Additionally, a compound of formula XIV can be prepared from a compound of formula Ib, wherein $R_{1a}$ represents a $R_1$ group that can be used as a protecting group. When Z is C(O), $R_{1a}$ is preferably a 4-methoxybenzyl group and the deprotection reaction is carried out with cerium ammonium nitrate in a suitable solvent such as mixtures of acetonitrile-water or by heating in trifluoroacetic acid or hydrochloric acid. When Z is —CH2- or CHR9-, $R_{1a}$ is preferably a 4-methoxybenzyl or a benzyl group, and the deprotection reaction is preferably carried out by hydrogenation under hydrogen atmosphere and metal catalysis, preferably by the use of palladium over charcoal as catalyst in a suitable solvent such as methanol or ethanol, optionally in the presence of an acid such as acetic acid or hydrochloric acid.

A compound of formula Ib is synthesized from a compound of formula III following an analogous sequence as described for the synthesis of compounds of formula Ia. Alternatively, a compound of formula Ib can be prepared by reaction of a compound of formula XVIIH (prepared from a compound of formula XVIP, wherein P represents a suitable protecting group) with a compound of formula IX, X or XI, as described above.

The compounds of general formula II, IIP, IVa, IVb, VI, IX, X, XI and XV wherein $R_1$, $R_{1a}$, $R_2$, $R_3$, $R_{3'}$, $R_{8'}$, LG, P, V, X, Z, m, n and p have the meanings as defined above, are commercially available or can be prepared by conventional methods described in the bibliography.

Scheme 2

The preparation of compounds of general formula (I) wherein Y is

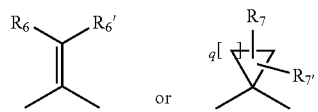

is described in the following scheme:

Scheme 2

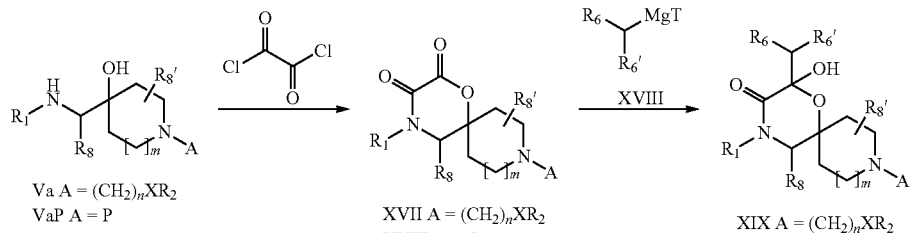

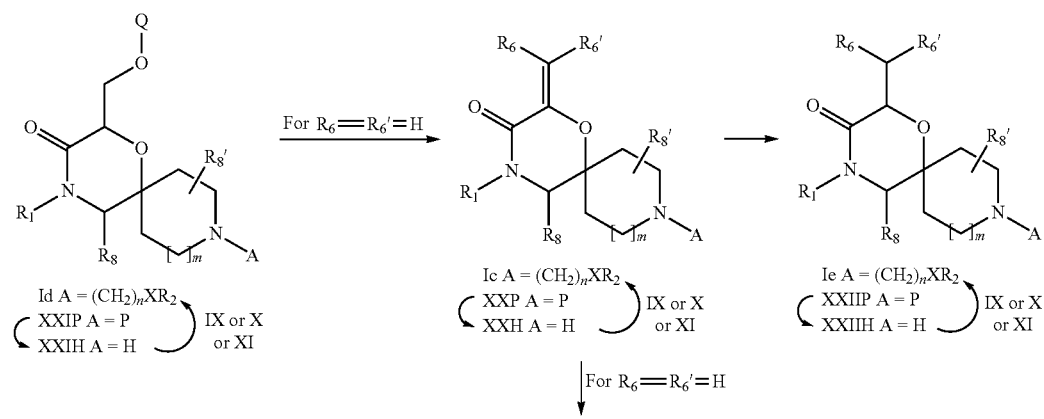

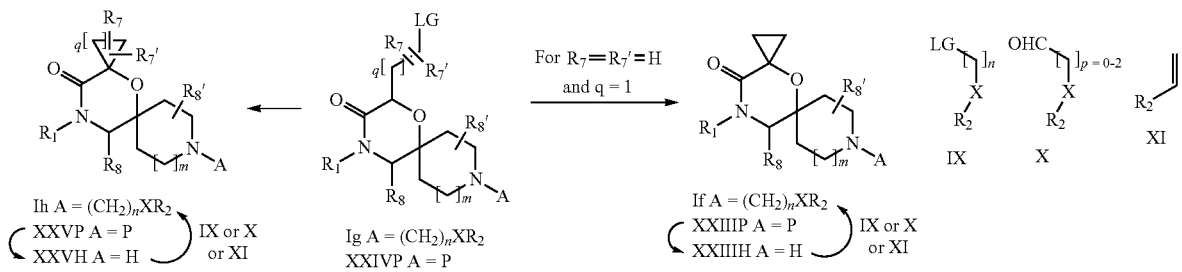

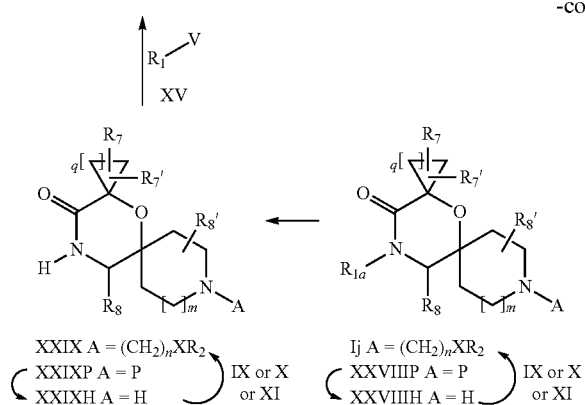
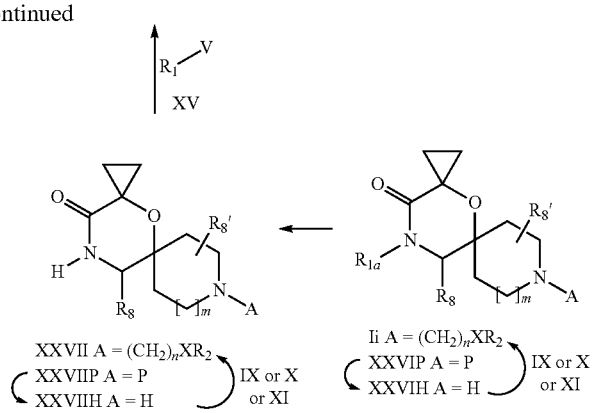

wherein $R_1$, $R_2$, $R_6$, $R_{6'}$, $R_7$, $R_{7'}$, $R_8$, $R_{8'}$, X, m, n and q have the meanings as defined above for a compound of formula (I), p represents 0, 1 or 2, LG represents a leaving group such as halogen, mesylate, tosylate or triflate, V represents an aldehyde or another leaving group (such as halogen, mesylate, tosylate or triflate), P represents a suitable protecting group (preferably Boc), $R_{1a}$ represents a $R_1$ group that can be used as a protecting group (preferably 4-methoxybenzyl), T represents chloro, bromo or iodo and Q represents methyl or benzyl.

Compounds of formula Ic can be prepared in a 3-step process starting from a compound of formula Va:

Step1:
A compound of formula XVII is prepared by treating a compound of formula Va with oxalyl chloride, in a suitable solvent such as dichloromethane, in the presence of a base such as triethylamine, at a suitable temperature, preferably comprised between 0° C. and room temperature. Additionally, an activating agent such as 4-dimethylaminopyridine can be used.

Step2:
A compound of formula XIX is prepared by reacting a compound of formula XVII with a Grignard reagent of formula XVIII, in an aprotic solvent such as tetrahydrofuran, at a suitable temperature, preferably at room temperature.

Step3:
A compound of formula Ic is prepared by reacting a compound of formula XIX with a dehydrating agent such as boron trifluoride diethyl etherate, in a suitable solvent such as dichloromethane, at a suitable temperature, preferably at room temperature.

Alternatively, a compound of formula Ic wherein $R_6$=$R_{6'}$=H can be prepared from a compound of formula Id wherein Q represents methyl or benzyl. The elimination reaction is carried out in the presence of a base, such as potassium tert-butoxide, in a suitable solvent, such as tetrahydrofuran.

Compounds of formula Ie can be prepared from compounds of formula Ic. The reduction reaction is preferably carried out by hydrogenation under hydrogen atmosphere and metal catalysis, preferably by the use of palladium over charcoal as catalyst in a suitable solvent such as methanol or ethanol, optionally in the presence of an acid such as acetic acid or hydrochloric acid.

Compounds of formula If can be prepared from compounds of formula Ic wherein $R_6$=$R_{6'}$=H. The cyclopropanation reaction is carried out using a suitable methyl-transfer reagent such as trimethylsulfoxonium iodide or trimethylsulfonium iodide, in a suitable aprotic solvent such as dimethylsulfoxide, and in the presence of a strong base such as sodium hydride or potassium tert-butoxide, at a suitable temperature, preferably comprised between room temperature and 60° C. Alternatively, typical Simmons-Smith reaction conditions could be used, comprising the treatment of a compound of formula Ic with diiodomethane, a zinc source such as zinc-copper, zinc iodide or diethylzinc, in a suitable aprotic solvent, such as diethyl ether.

Alternatively, a compound of formula If can be prepared from a compound of formula Ig wherein $R_7$=$R_{7'}$=H and q=1 by treatment with a strong base such as lithium diisopropylamide or potassium tert-butoxide, in an aprotic solvent such as tetrahydrofuran, at a suitable temperature, preferably cooling at 0° C. And analogously, compounds of formula Ih can be prepared from compounds of formula Ig under the same reaction conditions.

In another alternative approach, the $R_1$ substituent can be incorporated later in the synthesis. Thus, compounds of formula If and Ih can be prepared from compounds of formula Ii and Ij, respectively, following the reaction conditions described in Scheme 1 for the preparation of compounds of formula Ia from compounds of formula Ib.

In addition, the group $(CH_2)_n XR_2$ can be incorporated in the last step of the synthesis to prepare compounds of formula Ic, Id, Ie, If, Ih, Ii and Ij from suitable protected precursors, by deprotection followed by reaction with a compound of formula IX, X or XI, as described in Scheme 1 for the preparation of compounds of formula Ia.

The compounds of general formula Id and Ig can be prepared by the procedures described in Scheme 1 using suitable starting materials. The compounds of general formula Ii and Ij can be prepared from a compound of formula Vb following the procedures described in Schemes 1 and 2.

The compounds of general formula IX, X, XI, XV and XVIII wherein $R_1$, $R_2$, $R_6$, $R_{6'}$, LG, T, V, X, n and p have the meanings as defined above, are commercially available or can be prepared by conventional methods described in the bibliography.

Scheme 3 and Scheme 4

Compounds of formula (I) can also be prepared starting from other compounds of formula (I), as described in Schemes 3 and 4 below.

Compounds of formula Im, In and Io can be prepared from a compound of formula Ik as shown in Scheme 3:

Scheme 3

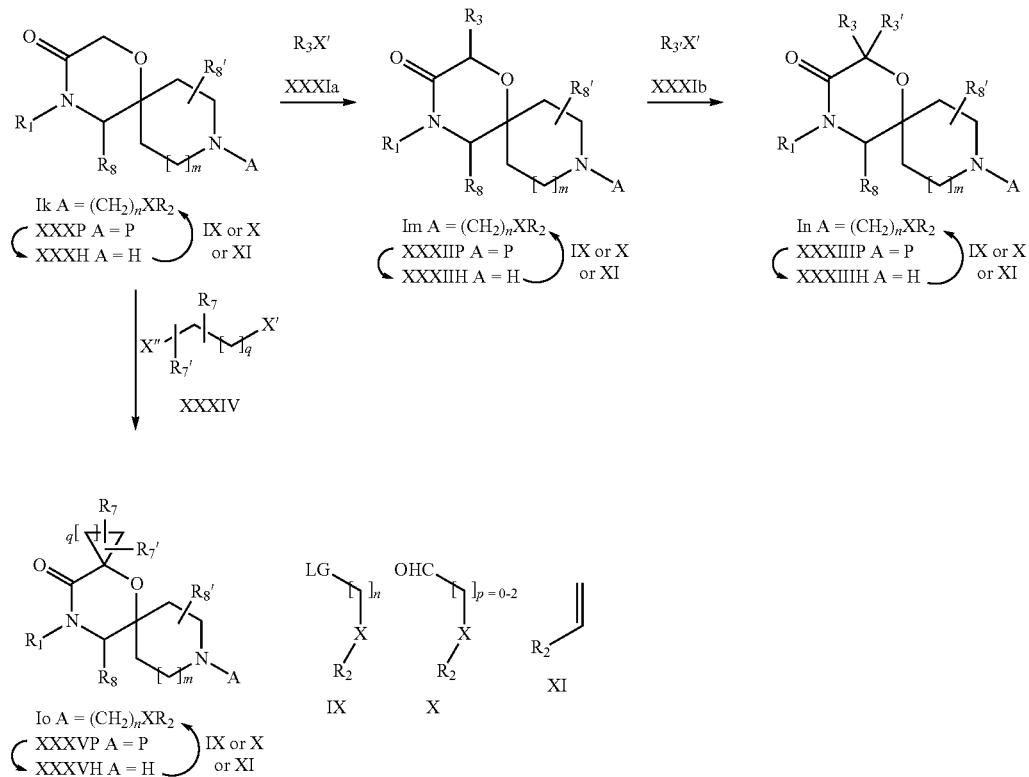

wherein $R_1$, $R_2$, $R_3$, $R_{3'}$, $R_7$, $R_{7'}$, $R_8$, $R_{8'}$, X, m, n and q have the meanings as defined above for a compound of formula (I), p represents 0, 1 or 2, LG, X' and X" independently represent a leaving group such as halogen, mesylate, tosylate or triflate, and P represents a suitable protecting group (preferably Boc).

A compound of formula Im can be prepared by treating a compound of formula Ik with an alkylating agent of formula XXXIa in the presence of a strong base such as lithium diisopropylamide or potassium tert-butoxide, in an aprotic solvent such as tetrahydrofuran, at a suitable temperature, preferably comprised between −78° C. and room temperature. A second alkylation can be performed under the same reaction conditions to prepare a compound of formula In. An analogous double-alkylation process can be used for the preparation of compounds of formula Io, by reacting a compound of formula Ik with an alkylating agent of formula XXXIV.

In addition, the group $(CH_2)_nXR_2$ can be incorporated in the last step of the synthesis to prepare compounds of formula Im, In and Io from suitable protected precursors, by deprotection followed by reaction with a compound of formula IX, X or XI, under the reaction conditions described in Scheme 1 for the preparation of compounds of formula Ia.

The compounds of general formula Ik and Im can be prepared by the procedures described in Scheme 1 using suitable starting materials.

Scheme 4 shows the preparation of compounds of formula (I) wherein Z is $CH_2$ from the corresponding compounds of formula (I) wherein Z is C(O):

Scheme 4

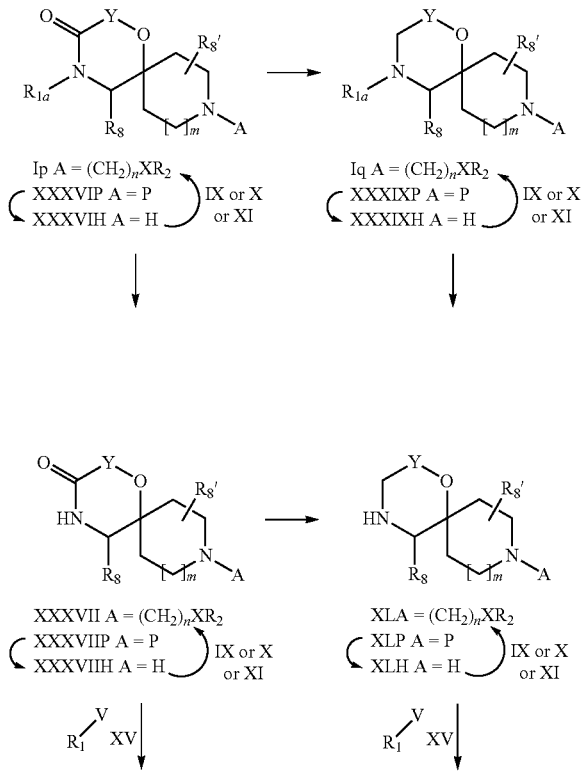

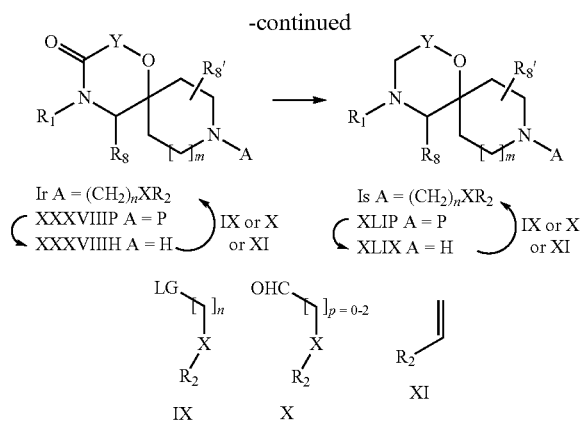

wherein $R_1$, $R_2$, $R_8$, $R_{8'}$, X, Y, m and n have the meanings as defined above for a compound of formula (I), p represents 0, 1 or 2, LG represents a leaving group such as halogen, mesylate, tosylate or triflate, V represents an aldehyde or another leaving group (such as halogen, mesylate, tosylate or triflate), P represents a suitable protecting group (preferably Boc) and $R_{1a}$ represents a $R_1$ group that can be used as a protecting group (preferably 4-methoxybenzyl or benzyl).

The reduction reaction of a compound of formula Ir to yield a compound of formula Is can be performed using a suitable reducing agent such as lithium aluminium hydride, borane-tetrahydrofuran complex or borane-dimethyl sulphide complex, in a suitable solvent such as tetrahydrofuran, at a suitable temperature comprised between room temperature and the reflux temperature, preferably heating.

The compounds of general formula Ir can be prepared by the procedures described in Scheme 1 and Scheme 2 using suitable starting materials, or they can be prepared from a compound of formula Ip or XXXVII. The deprotection of a compound of formula Ip to give a compound of formula XXXVII and the subsequent reaction with a compound of formula XV to yield a compound of formula Ir are performed following the procedures described in Scheme 1.

The compounds of general formula Ip and XXXVII can be prepared according to the procedures described in Scheme 1 using suitable starting materials.

The reduction reaction can also be performed on a suitable precursor (compounds of formula Ip or XXXVII) or a protected derivative wherein A=P. When P represents Boc, borane is the preferred reducing agent. Accordingly, the compounds of general formula Is may be prepared from a compound of formula Iq or XL following an analogous procedure to the one described above.

In addition, the group $(CH_2)_nXR_2$ may be incorporated at different stages of the synthesis to prepare compounds of formula Is from suitable precursors and compounds of formula IX, X and XI, following similar reaction conditions as described in Scheme 1 for the preparation of compounds of formula Ia.

The compounds of general formula IX, X, XI, XV, XXXIa, XXXIb and XXXIV wherein $R_1$, $R_2$, $R_3$, $R_{3'}$, $R_7$, $R_{7'}$, LG, X, X', X", n, p and q have the meanings as defined above, are commercially available or can be prepared by conventional methods described in the bibliography.

Moreover, certain compounds of the present invention can also be obtained starting from other compounds of formula (I) by appropriate conversion reactions of functional groups, in one or several steps, using well-known reactions in organic chemistry under standard experimental conditions. As a way of example, some of these conversions include the demethylation of a methoxy group to yield an hydroxy group, the reduction of a nitro group to yield an amino group, the acylation or sulfonylation of an amino group to yield an acylamino or sulfonylamino group, the conversion of an amino group into an ureido or sulfamido group, the hydrolysis of an ester to yield a carboxylic acid, the conversion of an acid or an ester to an amide, and the reduction of a ketone or an ester to yield the corresponding hydroxyl compound.

In addition, a compound of formula I that shows chirality can also be obtained by resolution of a racemic compound of formula I either by chiral preparative HPLC or by crystallization of a diastereomeric salt or co-crystal. Alternatively, the resolution step can be carried out at a previous stage, using any suitable intermediate.

Examples

All solvents used for synthesis were p. a. quality.

The following abbreviations are used in the examples:
ACN: acetonitrile
AcOH: acetic acid
Boc: tert-butoxycarbonyl
CAN: cerium ammonium nitrate
DCM: dichloromethane
DEA: diethylamine
DIPEA: diisopropylethylamine
DMF: dimethylformamide
DMSO: dimethylsulfoxide
Eq: equivalent
EtOH: ethanol
EX: example
h: hour/s
HPLC: high performance liquid chromatography
IPA: isopropanol
INT: intermediate
LDA: lithium diisopropylamide
MeOH: methanol
MS: mass spectrometry
Min.: minutes
Quant: quantitative
Ret.: retention
r.t.: room temperature
Sat: saturated
s.m.: starting material
TFA: trifluoroacetic acid
THF: tetrahydrofuran
Wt: weight The following method was used to determine the HPLC-MS spectrums:
Column: Xbridge $C_{18}$ XP 30×4.6 mm, 2.5 um
Temperature: 40° C.
Flow: 2.0 mL/min
Gradient: $NH_4HCO_3$ pH 8: ACN (95:5)---0.5 min---(95:5)---6.5 min---(0:100)---1 min---(0:100)
Sample dissolved aprox. 1 mg/mL in $NH_4HCO_3$ pH 8/ACN Alternatively, methods B or C were used in some cases:
Method B:
Column: Xbridge $C_{18}$ XP 30×4.6 mm, 2.5 um
Temperature: 25° C.
Flow: 2.0 mL/min
Gradient: $NH_4HCO_3$ pH 8: ACN (95:5)---7 min---(0:100)---3 min---(0:100)
Sample dissolved aprox. 1 mg/mL in MeOH
Method C:
Column: Gemini-NX 30×4.6 mm, 3 um
Temperature: 40° C.

Flow: 2.0 mL/min

Gradient: NH$_4$HCO$_3$ pH 8: ACN (95:5)---0.5 min---(95:5)---6.5 min---(0:100)---1 min---(0:100)

Sample dissolved aprox. 1 mg/mL in NH$_4$HCO$_3$ pH 8/ACN

Synthesis of Intermediates

Intermediate 1A: tert-butyl 1-oxa-6-azaspiro[2.5]octane-6-carboxylate

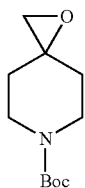 [SMILES: CC(C)(C)OC(=O)N1CCC2(CC1)CO2]

To a suspension of trimethylsulfoxonium iodide (24.3 g, 110 mmol) and NaH (4.4 g, 60 wt % in mineral oil, 110 mmol) in DMSO (140 mL), a solution of tert-butyl 4-oxopiperidine-1-carboxylate (20.0 g, 100 mmol) in DMSO (140 mL) was added dropwise. The reaction mixture was stirred at r.t. for 30 min, then heated at 50° C. for 1 h. After cooling to r.t., ice was slowly added, and the reaction mixture was extracted three times with ethyl acetate. The organic phases were combined, washed with water, dried over MgSO$_4$ and concentrated under vacuum to give the title compound (17.6 g, 82% yield) as a white solid. HPLC retention time: 3.31 min; MS: 158 (M+H−56).

This method was used for the preparation of intermediates 1B-1D using suitable starting materials:

| INT | Structure | Chemical name | Ret time (min) | MS (M + H) |
|-----|-----------|---------------|----------------|------------|
| 1B | | 6-phenethyl-1-oxa-6-azaspiro[2.5]octane | 3.36 | 218 |
| 1C | 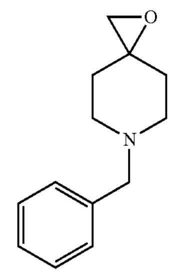 [SMILES: c1ccc(CN2CCC3(CC2)CO3)cc1] | 6-benzyl-1-oxa-6-azaspiro[2.5]octane | 3.21 (method B) | 204 |
| 1D | 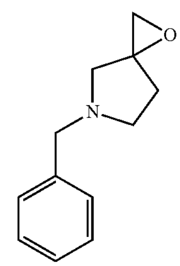 [SMILES: c1ccc(CN2CCC3(CO3)C2)cc1] | 5-benzyl-1-oxa-5-azaspiro[2.4]heptane | 2.94 | 190 |

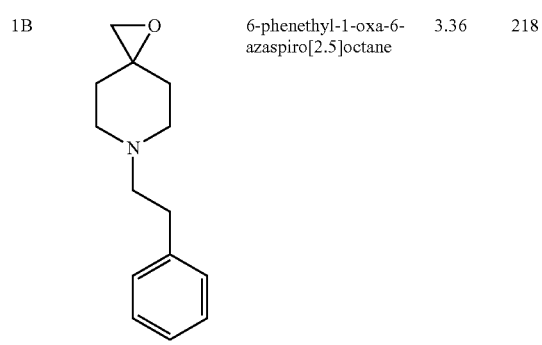

Intermediate 2A: tert-butyl 4-hydroxy-4-((phenylamino)methyl)piperidine-1-carboxylate

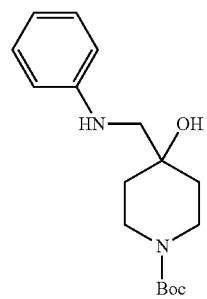 [SMILES: CC(C)(C)OC(=O)N1CCC(O)(CNc2ccccc2)CC1]

To a solution of intermediate 1A (5.0 g, 23.4 mmol) in a mixture of ethanol-water 9:1 (103 mL), aniline (2.14 mL, 23.4 mmol) was added. The reaction mixture was heated to 100° C. overnight in an autoclave reactor. The solvent was removed under vacuum and the residue was purified by flash chromatography, silica gel, gradient dichloromethane to methanol:dichloromethane (1:4) to give the title compound (4.90 g, 68% yield) as an oil. HPLC retention time: 4.14 min; MS: 251 (M+H−56).

This method was used for the preparation of intermediates 2B-2L using suitable starting materials:

| INT | Structure | Chemical name | s.m. | Ret time (min) | MS (M + H) |
|---|---|---|---|---|---|
| 2B | 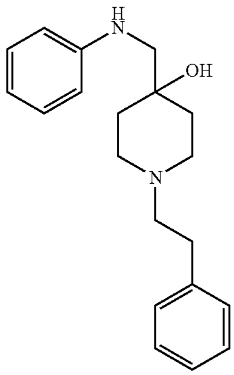 [SMILES: OC1(CNc2ccccc2)CCN(CCc2ccccc2)CC1] | 1-phenethyl-4-((phenylamino)methyl)piperidin-4-ol | 1B | 3.64 | 311 |
| 2C | 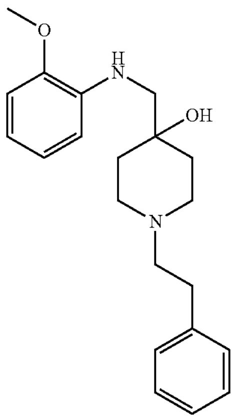 [SMILES: COc1ccccc1NCC1(O)CCN(CCc2ccccc2)CC1] | 4-(((2-methoxyphenyl)amino)methyl)-1-phenethylpiperidin-4-ol | 1B | 4.00 (method B) | 341 |
| 2D | 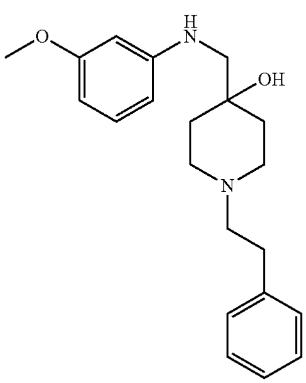 [SMILES: COc1cccc(NCC2(O)CCN(CCc3ccccc3)CC2)c1] | 4-(((3-methoxyphhenyl)amino)methyl)-1-phenethylpiperidin-4-ol | 1B | 3.63 | 341 |
| 2E | 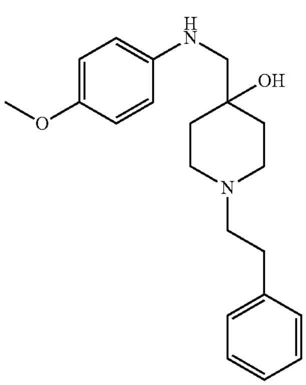 [SMILES: COc1ccc(NCC2(O)CCN(CCc3ccccc3)CC2)cc1] | 4-(((4-methoxyphenyl)amino)methyl)-1-phenethylpiperidin-4-ol | 1B | 3.49 | 341 |

| INT | Structure | Chemical name | s.m. | Ret time (min) | MS (M + H) |
|---|---|---|---|---|---|
| 2F | 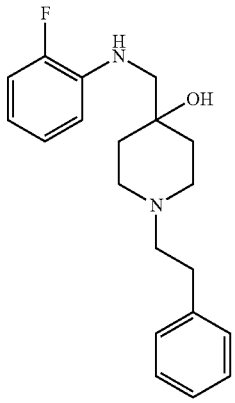 [SMILES: OC1(CNc2ccccc2F)CCN(CCc2ccccc2)CC1] | 4-(((2-fluorophenyl)amino)methyl)-1-phenethylpiperidin-4-ol | 1B | 4.01 | 329 |
| 2G | 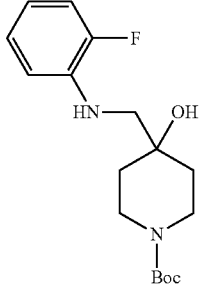 [SMILES: CC(C)(C)OC(=O)N1CCC(O)(CNc2ccccc2F)CC1] | tert-butyl 4-(((2-fluorophenyl)amino)methyl)-4-hydroxypiperidine-1-carboxylate | 1A | 4.37 | 269 (M + H − 56) |
| 2H | 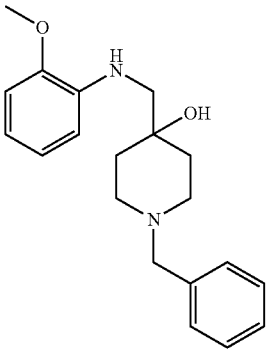 [SMILES: COc1ccccc1NCC1(O)CCN(Cc2ccccc2)CC1] | 1-benzyl-4-(((2-methoxyphenyl)amino)methyl)piperidin-4-ol | 1C | 4.11 (method B) | 327 |
| 2I | 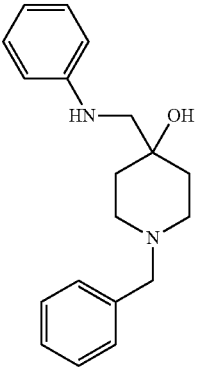 [SMILES: OC1(CNc2ccccc2)CCN(Cc2ccccc2)CC1] | 1-benzyl-4-((phenylamino)methyl)piperidin-4-ol | 1C | 3.85 (method B) | 297 |

-continued

| INT | Structure | Chemical name | s.m. | Ret time (min) | MS (M + H) |
|---|---|---|---|---|---|
| 2J | 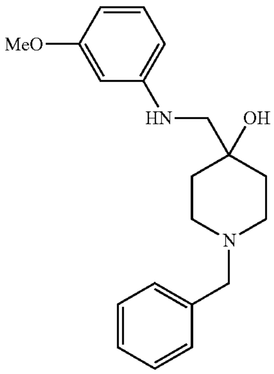 [SMILES: COc1cccc(NCC2(O)CCN(Cc3ccccc3)CC2)c1] | 1-benzyl-4-(((3-methoxyphenyl)amino)methyl)piperidin-4-ol | 1C | 3.82 (method B) | 327 |
| 2K | 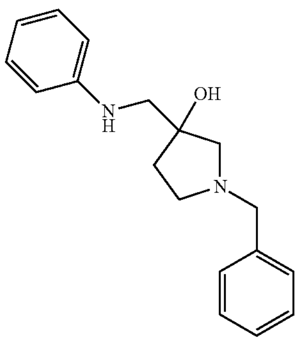 [SMILES: OC1(CNc2ccccc2)CCN(Cc2ccccc2)C1] | 1-benzyl-3-((phenylamino)methyl)pyrrolidin-3-ol | 1D | ¹H-RMN (300 MHz) | (1*) |
| 2L | 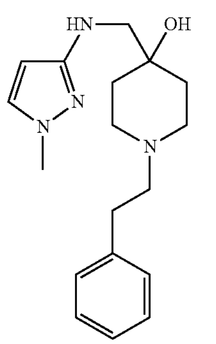 [SMILES: Cn1ccc(NCC2(O)CCN(CCc3ccccc3)CC2)n1] | 4-(((1-methyl-1H-pyrazol-3-yl)amino)methyl)-1-phenethylpiperidin-4-ol | 1B | 2.75 | 315 |

(1*) ¹H-RMN (300 MHz, CDCl₃) δ: 7.32 (d, 4H), 7.27 (m, 1H), 7.17 (m, 2H), 6.71 (m, 1H), 6.64 (m, 2H), 4.14 (broad s, 1H), 3.64 (m, 2H), 3.23 (s, 2H), 2.90 (m, 1H), 2.76 (m, 1H), 2.42-2.51 (m, 2H), 1.88-2.06 (m, 2H)

Intermediate 2M: tert-butyl 4-(aminomethyl)-4-hydroxypiperidine-1-carboxylate

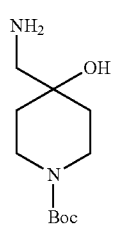

A mixture of intermediate 1A (10.0 g, 46.9 mmol) and ammonia solution (201 mL, 7 M solution in methanol, 1.4 mol) was stirred at r.t. overnight. The solvent was removed under vacuum and the residue was purified by flash chromatography, silica gel, gradient dichloromethane to methanol:dichloromethane (1:4) to give the title compound (7.4 g, 69% yield) as a white solid. HPLC retention time: 2.15 min; MS: 131 (M+H−100).

This method was used for the preparation of intermediates 2N-2O using suitable starting materials:

| INT | Structure | Chemical name | s.m. | Ret time (min) | MS (M + H) |
|---|---|---|---|---|---|
| 2N | H₂N—⟨piperidine with OH, N-phenethyl⟩ | 4-(aminomethyl)-1-phenethylpiperidin-4-ol | 1B | 2.19 | 235 |
| 2O | H₂N—⟨piperidine with OH, N-benzyl⟩ | 4-(aminomethyl)-1-benzylpiperidin-4-ol | 1C | 1.77 | 221 |

Intermediate 2P: tert-butyl 4-hydroxy-4-(((4-methoxybenzyl)amino)methyl) piperidine-1-carboxylate

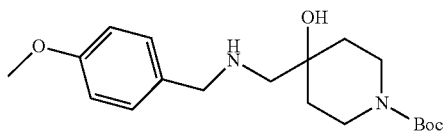 [SMILES: COc1ccc(CNCC2(O)CCN(C(=O)OC(C)(C)C)CC2)cc1]

To a solution of intermediate 1A (9.1 g, 42.5 mmol) in a mixture of ethanol-water 9:1 (205 mL), 4-methoxybenzylamine (5.8 g, 42.5 mmol) was added. The reaction mixture was heated at 100° C. overnight in a sealed tube. The solvent was removed under vacuum and the residue was purified by flash chromatography, silica gel, gradient dichloromethane to methanol:dichloromethane (1:4) to give the title compound (9.3 g, 63% yield). HPLC retention time: 3.80 min; MS: 351 (M+H).

This method was used for the preparation of intermediates 2Q-2R using suitable starting materials:

| INT | Structure | Chemical name | s.m. | Ret time (min) | MS (M + H) |
|---|---|---|---|---|---|
| 2Q | ⟨pyridin-2-ylmethylamino piperidine-Boc⟩ | tert-butyl 4-hydroxy-4-(((pyridin-2-ylmethyl)amino)methyl) piperidine-1-carboxylate | 1A | 3.14 | 322 |
| 2R | ⟨benzylamino methyl piperidine-Boc⟩ | tert-butyl 4-((benzylamino)methyl)-4-hydroxypiperidine-1-carboxylate | 1A | 3.90 | 321 |

Intermediate 3A: tert-butyl 2-methyl-3-oxo-4-phenyl-1-oxa-4,9-diazaspiro[5.5]undecane-9-carboxylate

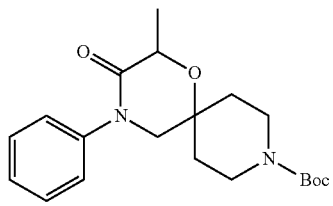 [SMILES: CC1OC2(CCN(C(=O)OC(C)(C)C)CC2)CN(c2ccccc2)C1=O]

Step 1. tert-Butyl 4-((2-chloro-N-phenylpropanamido)methyl)-4-hydroxypiperidine-1-carboxylate: To a solution of intermediate 2A (4.90 g, 16.0 mmol) and triethylamine (5.3 mL, 38.4 mmol) in dichloromethane (180 mL), 2-chloropropionyl chloride (2.3 mL, 24.0 mmol) was added dropwise at 0° C. The reaction mixture was stirred at r.t. for 1 h. Dichloromethane was then added, and the organic phase was washed with NaHCO$_3$ sat solution, dried over MgSO$_4$, filtered and concentrated to dryness to give the title compound (6.6 g). HPLC retention time: 4.37 min; MS: 297 (M+H−100).

Step 2. Title compound: A solution of the crude product obtained in step 1 in THF (280 mL) was cooled to −78° C. using a dry ice/acetone bath. After addition of potassium tert-butoxide solution (25 mL, 1M in THF, 25 mmol), the reaction mixture was stirred at −78° C. for 30 min and then 4 h at −30° C. NaHCO$_3$ sat solution was then added and the aqueous phase was extracted with dichloromethane. The organic phases were combined, dried over MgSO$_4$, filtered and concentrated under vacuum. The residue was purified by flash chromatography, silica gel, gradient dichloromethane to methanol:dichloromethane (1:4) to give the title compound (4.56 g, 79% yield for the 2 steps). HPLC retention time: 4.23 min; MS: 361 (M+H).

This method was used for the preparation of intermediates 3B-3F using suitable starting materials:

| INT | Structure | Chemical name | s.m. | Ret time (min) | MS (M + H) |
|---|---|---|---|---|---|
| 3B | 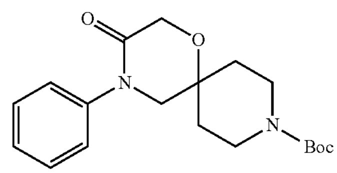 [SMILES: CC(C)(C)OC(=O)N1CCC2(CC1)CN(c1ccccc1)C(=O)CO2] | tert-butyl 3-oxo-4-phenyl-1-oxa-4,9-diazaspiro[5.5]undecane-9-carboxylate | 2A | 3.85 | 347 |
| 3C | 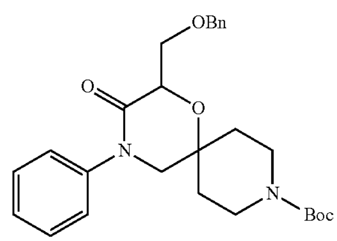 [SMILES: CC(C)(C)OC(=O)N1CCC2(CC1)CN(c1ccccc1)C(=O)C(COCc1ccccc1)O2] | tert-butyl 2-((benzyloxy)methyl)-3-oxo-4-phenyl-1-oxa-4,9-diazaspiro[5.5]undecane-9-carboxylate | 2A | 4.96 | 467 |
| 3D | 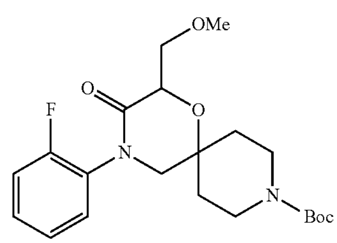 [SMILES: COCC1OC2(CCN(C(=O)OC(C)(C)C)CC2)CN(c2ccccc2F)C1=O] | tert-butyl 4-(2-fluorophenyl)-2-(methoxymethyl)-3-oxo-1-oxa-4,9-diazaspiro[5.5]undecane-9-carboxylate | 2G | 4.14 | 409 |
| 3E | 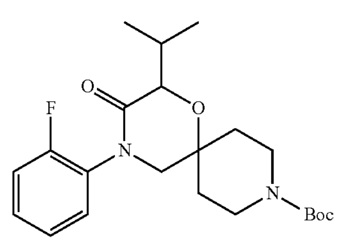 [SMILES: CC(C)C1OC2(CCN(C(=O)OC(C)(C)C)CC2)CN(c2ccccc2F)C1=O] | tert-butyl 4-(2-fluorophenyl)-2-isopropyl-3-oxo-1-oxa-4,9-diazaspiro[5.5]undecane-9-carboxylate | 2G | 5.13 | 407 |

| INT | Structure | Chemical name | s.m. | Ret time (min) | MS (M + H) |
|---|---|---|---|---|---|
| 3F | 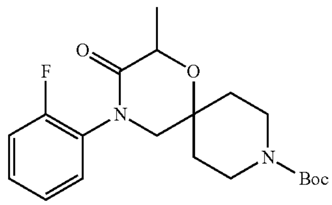 [SMILES: CC1OC2(CCN(C(=O)OC(C)(C)C)CC2)CN(c2ccccc2F)C1=O] | tert-butyl 4-(2-fluorophenyl)-2-methyl-3-oxo-1-oxa-4,9-diazaspiro[5.5]undecane-9-carboxylate | 2G | 4.39 | 379.1 |

Intermediate 3G: tert-butyl 3-oxo-1-oxa-4,9-diazaspiro[5.5]undecane-9-carboxylate

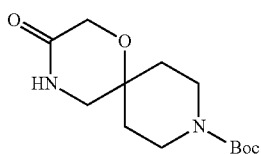 [SMILES: CC(C)(C)OC(=O)N1CCC2(CC1)CNC(=O)CO2]

Step 1. tert-Butyl 4-((2-chloroacetamido)methyl)-4-hydroxypiperidine-1-carboxylate: To a solution of intermediate 2M (1.0 g, 4.34 mmol) in ethyl acetate (9 mL), a solution of K₂CO₃ (1.67 g, 12.11 mmol) in water (7 mL) was added. After cooling to 0° C., chloroacetyl chloride (0.47 mL, 5.91 mmol) was added dropwise. The reaction mixture was stirred at 0° C. for 30 min, the layers were separated and the aqueous phase was extracted with ethyl acetate. The organic phases were combined, dried over MgSO₄, filtered and concentrated to dryness to give the title compound (1.1 g). HPLC retention time: 2.90 min; MS: 207 (M+H−100).

Step 2. Title compound: To a solution of potassium tert-butoxide (7.16 mL, 1M in THF, 7.16 mmol) in a mixture of THF:tert-butanol 2.3:1 (25 mL) heated at reflux, a solution of the crude product obtained in step 1 in THF (20 mL) was added dropwise over 1 h. The reaction mixture was cooled to r.t. and stirred overnight. The solvent was removed under vacuum, water was added to the residue and the mixture thus obtained was extracted with ethyl acetate. The organic phase was dried over MgSO₄, filtered and concentrated under vacuum to give the title compound (0.87 g, 74% yield for the 2 steps). HPLC retention time: 2.88 min; MS: 215 (M+H−56).

This method was used for the preparation of intermediates 3H-3K using suitable starting materials:

| INT | Structure | Chemical name | s.m. | Ret time (min) | MS (M + H) |
|---|---|---|---|---|---|
| 3H | 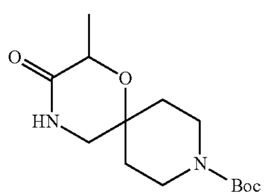 [SMILES: CC1OC2(CCN(C(=O)OC(C)(C)C)CC2)CNC1=O] | tert-butyl 2-methyl-3-oxo-1-oxa-4,9-diazaspiro[5.5]undecane-9-carboxylate | 2M | 3.16 | 229 |
| 3I | 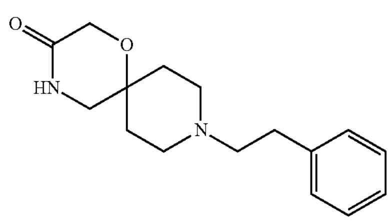 [SMILES: O=C1COC2(CCN(CCc3ccccc3)CC2)CN1] | 9-phenethyl-1-oxa-4,9-diazaspiro[5.5]undecan-3-one | 2N | 2.80 | 275 |
| 3J | 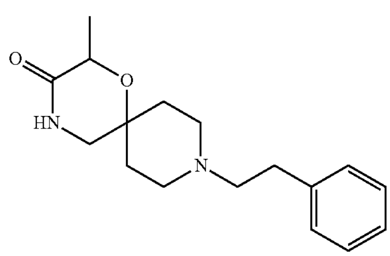 [SMILES: CC1OC2(CCN(CCc3ccccc3)CC2)CNC1=O] | 2-methyl-9-phenethyl-1-oxa-4,9-diazaspiro[5.5]undecan-3-one | 2N | 3.13 | 289 |

| INT | Structure | Chemical name | s.m. | Ret time (min) | MS (M + H) |
|---|---|---|---|---|---|
| 3K | 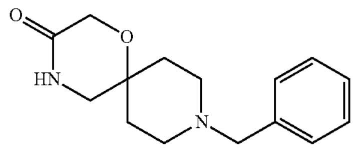 [SMILES: O=C1COC2(CCN(Cc3ccccc3)CC2)CN1] | 9-benzyl-1-oxa-4,9-diazaspiro[5.5]undecane-3-one | 2O | 2.58 | 261 |

Intermediate 3L: tert-butyl 3-oxo-4-(pyridin-2-ylmethyl)-1-oxa-4,9-diazaspiro[5.5]undecane-9-carboxylate

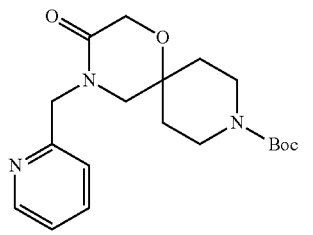

To a solution of intermediate 2Q (0.5 g, 1.56 mmol) and triethylamine (0.65 mL, 4.67 mmol) in dichloromethane (44 mL), a solution of chloroacetyl chloride (0.19 g, 1.71 mmol) in dichloromethane (9 mL) was added dropwise at 0° C. and the reaction mixture was stirred at that temperature for 2 h. NaHCO$_3$ sat solution was added and the aqueous phase was extracted twice with dichloromethane. The organic phases were combined, washed with brine, dried over MgSO$_4$, filtered and concentrated to dryness. The residue was dissolved in tert-butanol (24 mL) and heated to 50° C. Powdered KOH (3.02 g, 34.7 mmol) was added and the mixture was stirred at 50° C. overnight. The solvent was evaporated and the residue was taken into water and ethyl acetate. The aqueous phase was back extracted with ethyl acetate. The organic phases were combined, dried over MgSO$_4$, filtered and concentrated under vacuum. The residue was purified by flash chromatography, silica gel, gradient dichloromethane to methanol:dichloromethane (1:4) to give the title compound (306 mg, 52% yield). HPLC retention time: 3.43 min; MS: 362 (M+H).

Intermediate 3M: tert-butyl 3-oxo-4-(((5-(trifluoromethyl)pyridin-2-yl)methyl)-1-oxa-4,9-diazaspiro[5.5]undecane-9-carboxylate

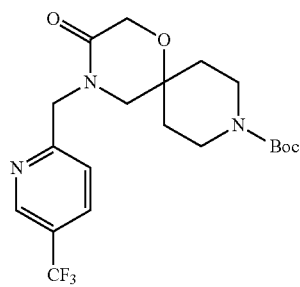 [SMILES: CC(C)(C)OC(=O)N1CCC2(CC1)CN(Cc1ccc(C(F)(F)F)cn1)C(=O)CO2]

To a solution of intermediate 3G (0.97 g, 3.59 mmol) in dry DMF (5 mL), NaH (362 mg, 60 wt % in mineral oil, 8.98 mmol) was added. The mixture was stirred at r.t. for 30 min, then a solution of 2-(chloromethyl)-5-(trifluoromethyl)pyridine hydrochloride (0.92 g, 3.95 mmol) in DMF (5 mL) was added and the resulting mixture was stirred at r.t. overnight. Water was then added to the reaction mixture and it was extracted with ethyl acetate. The organic phases were combined, washed with brine, dried over MgSO$_4$, filtered and concentrated to dryness. The residue was purified by flash chromatography, silica gel, gradient dichloromethane to methanol:dichloromethane (1:4) to give the title compound (561 mg, 36% yield). HPLC retention time: 4.22 min; MS: 374 (M+H−56).

This method was used for the preparation of intermediates 3N-3Q using suitable starting materials:

| INT | Structure | Chemical name | s.m. | Ret time (min) | MS (M + H) |
|---|---|---|---|---|---|
| 3N | 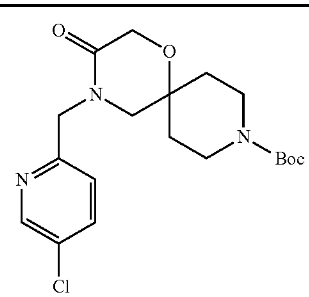 | tert-butyl 4-((5-chloropyridin-2-yl)methyl)-3-oxo-1-oxa-4,9-diazaspiro[5.5]undecane-9-carboxylate | 3G | 3.91 | 396 |

-continued

| INT | Structure | Chemical name | s.m. | Ret time (min) | MS (M + H) |
|---|---|---|---|---|---|
| 3O | 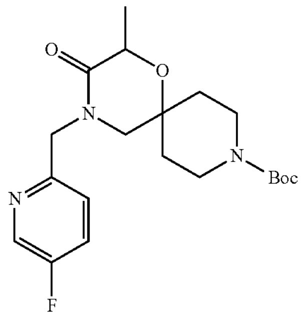 [SMILES: CC1OC2(CCN(C(=O)OC(C)(C)C)CC2)CN(Cc2ccc(F)cn2)C1=O] | tert-butyl 4-((5-fluoropyridin-2-yl)methyl)-2-methyl-3-oxo-1-oxa-4,9-diazaspiro[5.5]undecane-9-carboxylate | 3H | 3.98 | 394 |
| 3P | 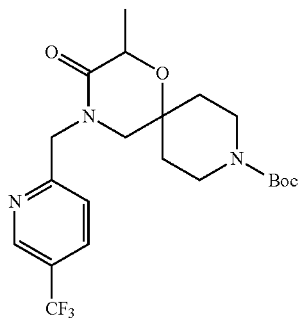 [SMILES: CC1OC2(CCN(C(=O)OC(C)(C)C)CC2)CN(Cc2ccc(C(F)(F)F)cn2)C1=O] | tert-butyl 2-methyl-3-oxo-4-((5-(trifluoromethyl)pyridin-2-yl)methyl)-1-oxa-4,9-diazaspiro[5.5]undecane-9-carboxylate | 3H | 4.41 | 388 (M + H − 56) |
| 3Q | 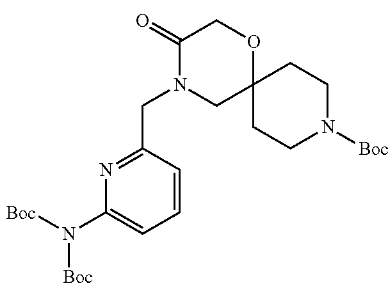 [SMILES: CC(C)(C)OC(=O)N1CCC2(CC1)CN(Cc1cccc(N(C(=O)OC(C)(C)C)C(=O)OC(C)(C)C)n1)C(=O)CO2] | tert-butyl 4-((6-(di(tert-butoxycarbonyl)amino)pyridin-2-yl)methyl)-3-oxo-1-oxa-4,9-diazaspiro[5.5]undecane-9-carboxylate | 3G | 4.90 | 477 (M + H − 100) |

Intermediate 3R: tert-butyl 2-methyl-3-oxo-4-(thiazol-4-yl)-1-oxa-4,9-diazaspiro[5.5]undecane-9-carboxylate

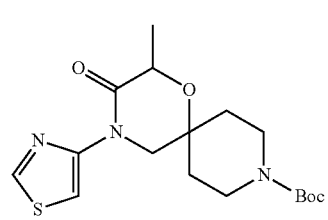 [SMILES: CC1OC2(CCN(C(=O)OC(C)(C)C)CC2)CN(c2cscn2)C1=O]

A mixture of intermediate 3H (500 mg, 1.76 mmol), K₃PO₄ (747 mg, 3.52 mmol), CuI (33 mg, 0.176 mmol), trans-1,2-cyclohexanediamine (0.042 mL, 0.352 mmol) and 4-bromothiazole (0.19 mL, 2.11 mmol) in dry 1,4-dioxane (5 mL) was heated under an argon atmosphere at 110° C. overnight. The reaction crude was cooled and ethyl acetate and water were added. The phases were separated and the aqueous phase was back extracted with ethyl acetate. The combined organic phases were dried over MgSO₄ and concentrated under vacuum. The residue was purified by flash chromatography, silica gel, gradient dichloromethane to methanol:dichloromethane (1:4) to give the title compound (270 mg, 41% yield). HPLC retention time: 4.16 min; MS: 312 (M+H−56).

Intermediate 3S: tert-butyl 2-methyl-3-oxo-4-(4-(trifluoromethyl)pyridin-3-yl)-1-oxa-4,9-diazaspiro[5.5]undecane-9-carboxylate

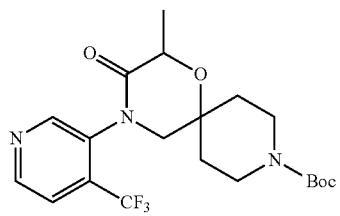

A mixture of intermediate 3H (1.00 g, 3.52 mmol), Cs₂CO₃ (1.49 g, 7.74 mmol), tris(dibenzylideneacetone)dipalladium(0) (161 mg, 0.176 mmol), 4,5-bis(diphenylphosphino)-9,9-dimethylxanthene (173 mg, 0.299 mmol) and 3-bromo-4-(trifluoromethyl)pyridine (0.954 g, 4.22 mmol) in dry 1,4-dioxane (28 mL) was heated under an argon atmosphere at 110° C. overnight. After cooling the solids were filtered off and the reaction mixture was concentrated to dryness. Additional Cs$_2$CO$_3$ (1.49 g, 7.74 mmol), tris(dibenzylideneacetone)dipalladium(0) (161 mg, 0.176 mmol), 4,5-bis(diphenylphosphino)-9,9-dimethylxanthene (173 mg, 0.299 mmol), 3-bromo-4-(trifluoromethyl) pyridine (0.397 g, 1.76 mmol) and dry 1,4-dioxane (28 mL) were added. After stirring an additional day at 110° C. under an argon atmosphere, the solids were filtered off and the solvent evaporated to dryness. Again, additional Cs$_2$CO$_3$ (1.49 g, 7.74 mmol), tris(dibenzylideneacetone)dipalladium (0) (161 mg, 0.176 mmol), 4,5-bis(diphenylphosphino)-9,9-dimethylxanthene (173 mg, 0.299 mmol), 3-bromo-4-(trifluoromethyl)pyridine (0.410 g, 1.81 mmol) and dry 1,4-dioxane (28 mL) were added. The mixture was stirred at 110° C. overnight. The solids were filtered off, and the reaction mixture concentrated under vacuum. The residue was purified by flash chromatography, silica gel, gradient dichloromethane to methanol:dichloromethane (1:4) to give the title compound (627 mg, 41% yield). HPLC retention time: 4.25 min; MS: 374 (M+H−56).

This method was used for the preparation of intermediate 3T using suitable starting materials:

bined, dried over MgSO$_4$, filtered and concentrated to dryness. The residue was purified by flash chromatography, silica gel, gradient dichloromethane to methanol:dichloromethane (1:4) to give the title compound (513 mg, 60% yield). HPLC retention time: 3.22 min; MS: 307 (M+H).

Intermediate 4: tert-butyl 4-(2-fluorophenyl)-2,3-dioxo-1-oxa-4,9-diazaspiro[5.5]undecane-9-carboxylate

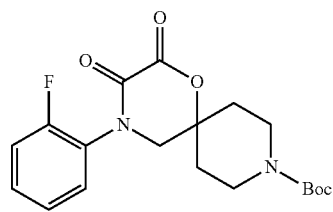

| INT | Structure | Chemical name | s.m. | Ret time (min) | MS (M + H) |
|---|---|---|---|---|---|
| 3T | 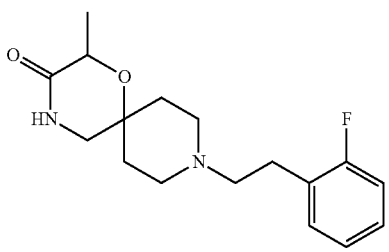 | tert-butyl 2-methyl-3-oxo-4-(2-(trifluoromethyl)pyridin-3-yl)-1-oxa-4,9-diazaspiro[5.5]undecane-9-carboxylate | 3H | 4.3 | 374 (M + H − 56) |

Intermediate 3U: 9-(2-fluorophenethyl)-2-methyl-1-oxa-4,9-diazaspiro[5.5]undecan-3-one

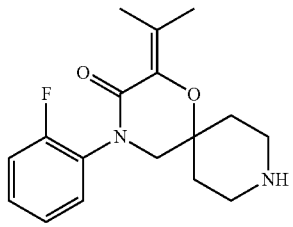 [SMILES: CC(C)=C1OC2(CCNCC2)CN(c2ccccc2F)C1=O]

Step 1: 2-methyl-1-oxa-4,9-diazaspiro[5.5]undecan-3-one trifluoroacetate. To a solution of intermediate 3H (0.80 g, 2.8 mmol) in dichloromethane (8 mL), trifluoroacetic acid (2.2 mL, 28.0 mmol) was added, and the reaction mixture was stirred at r.t. for 3 h. The solvent was evaporated to dryness to give the title compound as a crude product (1.54 g, 54 wt %, quant yield), that was used in the following step without further purification. HPLC retention time: 0.30 min; MS: 185 (M+H).

Step 2: A mixture of the crude product obtained in step 1 (1.54 g, 54 wt %, 2.78 mmol), 2-fluorophenethyl methanesulfonate (prepared as described in WO2008105497 Ex88-step1) (1.03 g, 4.74 mmol) and K$_2$CO$_3$ (1.93 g, 13.9 mmol) in acetonitrile (23 mL) was heated at 80° C. in a sealed tube overnight. Water was added, and the reaction mixture was extracted with ethyl acetate. The organic phases were com- To a solution of intermediate 2G (2.0 g, 6.16 mmol) and 4-dimethylaminopyridine (0.038 g, 0.308 mmol) in dichloromethane (200 mL) at 0° C., triethylamine (3.18 mL, 22.8 mmol) was added. After stirring for 10 min at 0° C., a solution of oxalyl chloride (0.783 mL, 9.25 mmol) in dichloromethane (100 mL) was added dropwise over 3 h. The reaction mixture was stirred at 0° C. for 2 hours, and then ice was added. The organic layer was separated and washed with water, dried over MgSO$_4$, filtered and concentrated to dryness, to give the title compound as a crude product (2.5 g, quant. yield), that was used in the following step without further purification. HPLC retention time: 3.94 min; MS: 323 (M+H−56).

Intermediate 5A: 4-(2-fluorophenyl)-2-(propan-2-ylidene)-1-oxa-4,9-diazaspiro[5.5]undecan-3-one Step 1. 4-(2-fluorophenyl)-2-hydroxy-2-isopropyl-1-oxa-4,9-diazaspiro[5.5]undecan-3-one: To a solution of intermediate 4 (1.0 g, 2.64 mmol) in dry tetrahydrofuran (10 mL), isopropylmagnesium chloride solution (2.1 mL, 2M in THF, 4.2 mmol) was added dropwise. The reaction mixture was stirred at r.t. for 40 min, then NH₄Cl sat solution was added and the aqueous phase was extracted with ethyl acetate. The organic phases were combined, washed with brine, dried over MgSO₄, filtered and concentrated to dryness to give the title compound (0.918 g, 82% yield), that was used in the next step without further purification. HPLC retention time: 4.62 min; MS: 405 (M+H−OH).

Step 2. Title compound: To a solution of the crude product obtained in step 1 in DCM (18 mL), boron trifluoride diethyl etherate (2.40 mL, 22.7 mmol) was added at 0° C. The reaction mixture was stirred at r.t. overnight. Ice was added, and the resulting mixture was basified to pH 9 with 1 M NaOH aqueous solution and extracted with dichloromethane. The combined organic phases were washed with brine, dried over MgSO₄, filtered and concentrated to dryness to give the title compound as a crude product (0.666 g, quant. yield), that was used in the next step without further purification. HPLC retention time: 2.69 min; MS: 305 (M+H).

This method was used for the preparation of intermediates 5B-5C using suitable starting materials:

Intermediate 6: 4-(2-fluorophenyl)-2-isopropyl-1-oxa-4,9-diazaspiro[5.5]undecan-3-one acetate

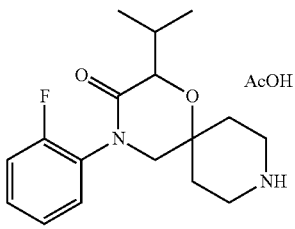

A mixture of intermediate 5A (0.350 g, 1.15 mmol), AcOH (0.13 mL, 2.30 mmol) and palladium (55 mg, 10% wt on charcoal) in methanol (11.5 mL) was heated at 50° C. under 4 bars of H₂ for 3 days. Then, additional palladium (100 mg, 10% wt on charcoal) was added, and the reaction mixture was heated at 60° C. under 4.5 bars of H₂. After 2 days, the solids were filtered off and the solvent was removed under vacuum, to give the title compound as a crude product (0.438 g, quant. yield), that was used in the next step without further purification. HPLC retention time: 2.79 min; MS: 307 (M+H).

| INT | Structure | Chemical name | s.m. | Ret time (min) | MS (M + H) |
|---|---|---|---|---|---|
| 5B | 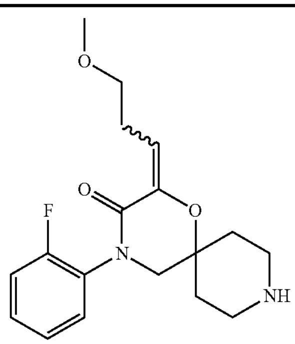 | 4-(2-fluorophenyl)-2-(3-methoxypropylidene)-1-oxa-4,9-diazaspiro[5.5]undecane-3-one | 4 | 2.48 | 335 |
| 5C | 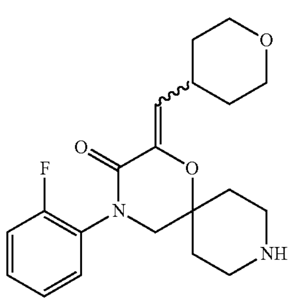 [SMILES: O=C1C(=CC2CCOCC2)OC2(CCNCC2)CN1c1ccccc1F] | 4-(2-fluorophenyl)-2-((tetrahydro-2H-pyran-4-yl)methylene)-1-oxa-4,9-diazaspiro[5.5]undecane-3-one | 4 | 2.61 | 361 |

Intermediate 7: tert-butyl 2-methylene-3-oxo-4-phenyl-1-oxa-4,9-diazaspiro[5.5]undecane-9-carboxylate

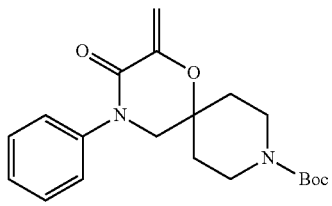

A solution of intermediate 3C (1.278 g, 2.74 mmol) in THF (46 mL) was cooled to −78° C. using a dry ice/acetone bath. After addition of potassium tert-butoxide solution (3.0 mL, 1M in THF, 3.0 mmol), the reaction mixture was stirred at −30° C. for 30 min. NH$_4$Cl sat solution was added and the aqueous phase was extracted with ethyl acetate. The organic phase was dried over MgSO$_4$, filtered and concentrated under vacuum. The residue was purified by flash chromatography, silica gel, gradient dichloromethane to methanol:dichloromethane (1:4) to give the title compound (0.577 g, 59% yield). HPLC retention time: 4.41 min; MS: 359 (M+H).

Intermediate 8A: tert-butyl 13-oxo-12-phenyl-4-oxa-8,12-diazadispiro[2.1.5.3]tridecane-8-carboxylate

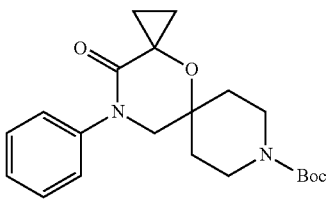 [SMILES: CC(C)(C)OC(=O)N1CCC2(CC1)CN(c1ccccc1)C(=O)C1(CC1)O2]

To a suspension of trimethylsulfoxonium iodide (0.645 g, 2.93 mmol) and NaH (0.117 g, 60 wt % in mineral oil, 2.93 mmol) in DMSO (3 mL), a solution of intermediate 7 (0.700 g, 1.95 mmol) in DMSO (3 mL) was added dropwise. The reaction mixture was stirred at r.t. for 30 min, then heated at 50° C. for 2 h. After cooling to r.t., ice was slowly added, and the reaction mixture was extracted three times with ethyl acetate. The organic phases were combined, washed with water, dried over MgSO$_4$ and concentrated under vacuum. The residue was purified by flash chromatography, silica gel, gradient dichloromethane to methanol:dichloromethane (1:4) to give the title compound (0.191 g, 26% yield). HPLC retention time: 4.39 min; MS: 373 (M+H).

Alternative method for the preparation of Intermediate 8A:

A mixture of intermediate 8E (200 mg, 0.67 mmol), K$_3$PO$_4$ (286 mg, 1.35 mmol), CuI (33 mg, 0.67 mmol), trans-1,2-cyclohexanediamine (0.081 mL, 0.67 mmol) and iodobenzene (0.09 mL, 0.81 mmol) in dry 1,4-dioxane (4 mL) was heated under an argon atmosphere at 110° C. overnight. The reaction crude was cooled and ethyl acetate and water were added. The phases were separated and the aqueous phase was back extracted with ethyl acetate. The combined organic phases were dried over MgSO$_4$ and concentrated under vacuum. The residue was purified by flash chromatography, silica gel, gradient dichloromethane to methanol:dichloromethane (1:4) to give the title compound (185 mg, 73% yield). HPLC retention time: 4.42 min; MS: 373 (M+H).

Intermediate 8B: tert-butyl 12-(4-methoxybenzyl)-13-oxo-4-oxa-8,12-diazadispiro[2.1.5.3]tridecane-8-carboxylate

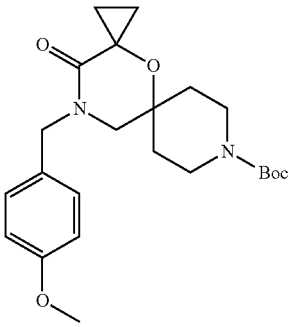 [SMILES: COc1ccc(CN2CC3(CCN(C(=O)OC(C)(C)C)CC3)OC3(CC3)C2=O)cc1]

Step 1. tert-butyl 4-((2-bromo-4-chloro-N-(4-methoxybenzyl)butanamido)methyl)-4-hydroxypiperidine-1-carboxylate: To a solution of intermediate 2P (9.94 g, 28.4 mmol) and triethylamine (9.5 mL, 68.1 mmol) in dichloromethane (500 mL), a solution of 2-bromo-4-chlorobutanoyl chloride (prepared as described in U.S. Pat. No. 6,114,541A1 (2000) Ex1) (9.35 g, 20.2 mmol) in dichloromethane (200 mL) was added dropwise at 0° C. The reaction mixture was stirred at 0° C. for 3 h. Dichloromethane and NaHCO$_3$ aqueous sat solution were added and the phases were separated. The aqueous phase was back extracted with dichloromethane. The organic phases were combined, dried over MgSO$_4$, filtered and concentrated to dryness to give the title compound (17.6 g, crude product). HPLC retention time: 4.82 min; MS: 435 (M+H−100).

Step 2. Title compound: A solution of the crude product obtained in step 1 (14.8 g, 27.7 mmol) in THF (185 mL) was cooled under nitrogen to 0° C. After addition of potassium tert-butoxide solution (111 mL, 1M in THF, 111 mmol), the reaction mixture was stirred at 0° C. for 2 h. NH$_4$Cl sat solution was then added, and the aqueous phase was extracted with ethyl acetate. The organic phases were combined, dried over MgSO$_4$, filtered and concentrated under vacuum. The residue was purified by flash chromatography, silica gel, gradient dichloromethane to methanol:dichloromethane (1:4) to give the title compound (5.51 g, 48% yield for the 2 steps). HPLC retention time: 4.46 min; MS: 417 (M+H).

Intermediate 8C: 8-phenethyl-4-oxa-8,12-diazadispiro[2.1.5.3]tridecan-13-one

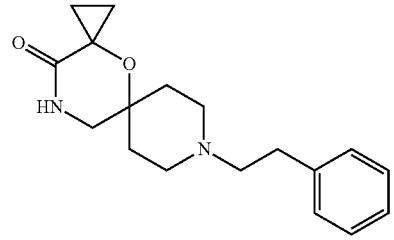 [SMILES: O=C1NCC2(CCN(CCc3ccccc3)CC2)OC12CC2]

A mixture of example 109 (free base) (0.170 g, 0.404 mmol) and CAN (0.568 g, 1.21 mmol) in a mixture of acetonitrile-water 1:1 (5 mL) was stirred at r.t. for 7 h. Na$_2$CO$_3$ sat solution was added to the reaction mixture and it was extracted with ethyl acetate. The organic phases were combined, washed with brine, dried over MgSO$_4$, filtered and concentrated to dryness. The residue was purified by eluting through an acidic ion exchange resin cartridge (SCX), to give the title compound (106 mg, 88% yield). HPLC retention time: 3.31 min; MS: 301 (M+H).

This method was used for the preparation of intermediate 8D using suitable starting materials:

| INT | Structure | Chemical name | s.m. | Ret time (min) | MS (M + H) |
|---|---|---|---|---|---|
| 8D | 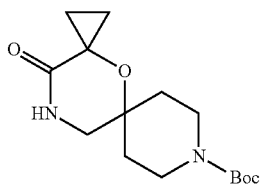 [SMILES: CC(C)(C)OC(=O)N1CCC2(CC1)CNC(=O)C1(CC1)O2] | 8-(2-fluorophenethyl)-4-oxa-8,12-diazadispiro[2.1.5.3]tridecan-13-one | Ex 149 | 3.41 | 319 |

Intermediate 8E: tert-butyl 13-oxo-4-oxa-8,12-diazadispiro[2.1.5.3]tridecane-8-carboxylate

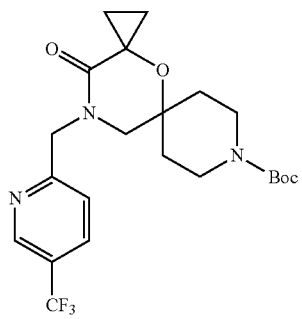 [SMILES: CC(C)(C)OC(=O)N1CCC2(CC1)CN(Cc1ccc(C(F)(F)F)cn1)C(=O)C1(CC1)O2]

Step 1. 4-oxa-8,12-diazadispiro[2.1.5.3]tridecan-13-one trifluoroacetate: A solution of intermediate 8B (1.78 g, 4.26 mmol) in TFA (20 mL) was stirred in a sealed tube at 80° C. for 4 days. The reaction mixture was concentrated to dryness and water was added to the residue. The acidic aqueous phase was washed with ethyl ether, which was discarded. The aqueous layer was evaporated to dryness to give the title compound (1.17 g, 88% yield). HPLC retention time: 0.33 min; MS: 197 (M+H).

Step 2. Title compound: A solution of the crude product obtained in step 1 and di-tert-butyl dicarbonate (1.40 g, 6.40 mmol) in a mixture of 1,4-dioxane (40 mL) and 1M NaOH aqueous solution (10 mL) was stirred at r.t. overnight. Water was added and the resulting mixture was extracted with ethyl acetate. The organic phases were combined, dried over MgSO₄, filtered and concentrated to dryness. The residue was purified by flash chromatography, silica gel, gradient dichloromethane to methanol:dichloromethane (1:4) to give the title compound (0.872 g, 78% yield). HPLC retention time: 3.29 min; MS: 297 (M+H).

Intermediate 8F: tert-butyl 13-oxo-12-((5-(trifluoromethyl)pyridin-2-yl)methyl)-4-oxa-8,12-diazadispiro[2.1.5.3]tridecane-8-carboxylate

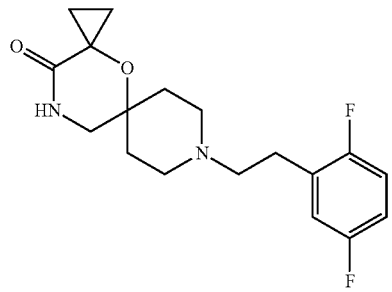 [SMILES: O=C1NCC2(CCN(CCc3cc(F)ccc3F)CC2)OC12CC2]

To a solution of intermediate 8E (0.400 g, 1.35 mmol) in dry DMF (3 mL), NaH (135 mg, 60 wt % in mineral oil, 3.37 mmol) was added at r.t. The reaction mixture was stirred at r.t. for 30 min, then a solution of 2-(chloromethyl)-5-(trifluoromethyl)pyridine hydrochloride (0.344 g, 1.485 mmol) in DMF (3 mL) was dropwise added and the resulting mixture was stirred at r.t. overnight. Additional NaH and alkylating agent were added and the reaction was stirred at r.t. overnight to get the reaction to completion. Water was added to the reaction mixture and it was extracted with ethyl acetate. The organic phases were combined, washed with brine, dried over MgSO₄, filtered and concentrated to dryness. The residue was purified by flash chromatography, silica gel, gradient cyclohexane to ethyl acetate:cyclohexane (1:1) to give the title compound (290 mg, 47% yield). HPLC retention time: 4.66 min; MS: 456 (M+H).

Intermediate 8G: 8-(2,5-difluorophenethyl)-4-oxa-8,12-diazadispiro[2.1.5.3]tridecan-13-one

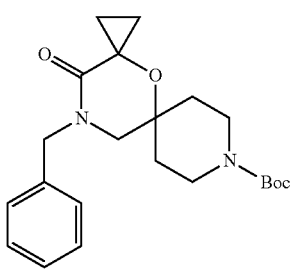 [SMILES: CC(C)(C)OC(=O)N1CCC2(CC1)CN(Cc1ccccc1)C(=O)C1(CC1)O2]

Intermediate 8G was prepared according to the procedure described for Intermediate 3U, using Intermediate 8E as starting material. HPLC retention time: 4.51 min; MS: 337 (M+H).

Intermediate 8H: tert-butyl 12-(benzyl)-13-oxo-4-oxa-8,12-diazadispiro[2.1.5.3]tridecane-8-carboxylate Intermediate 8H was prepared according to the procedure described for Intermediate 8B, using Intermediate 2R as starting material. HPLC retention time: 4.69 min; MS: 387 (M+H).

Intermediate 9A: tert-butyl 1-oxa-4,9-diazaspiro[5.5]undecane-9-carboxylate

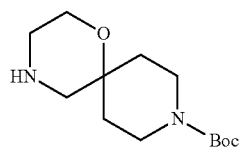

To a solution of intermediate 3I (1.25 g, 4.56 mmol) in THF (25 mL), lithium aluminium hydride solution (18.2 mL, 1M in THF, 18.2 mmol) was added dropwise and the reaction mixture was stirred at 50° C. overnight. Then, 1M NaOH aqueous solution was added, and the aqueous phase was extracted with dichloromethane. The organic phases were combined, dried over MgSO$_4$, filtered and concentrated under vacuum to give the title compound (1.10 g, 84% yield). HPLC retention time: 2.67 min; MS: 261 (M+H).

This method was used for the preparation of intermediate 9C using suitable starting materials:

| INT | Structure | Chemical name | s.m. | Ret time (min) | MS (M + H) |
|---|---|---|---|---|---|
| 9C | 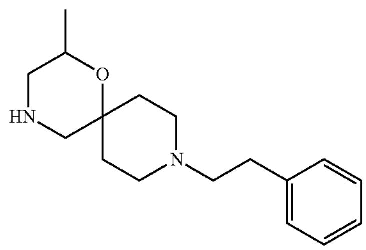 | 2-methyl-9-phenethyl-1-oxa-4,9-diazaspiro[5.5]undecane | 3J | 3.00 | 275 |

To a solution of intermediate 3G (1.50 g, 5.55 mmol) in THF (19 mL), borane-dimethyl sulfide complex (1.67 mL, 16.6 mmol) was added dropwise at r.t. The reaction mixture was stirred at 55° C. for 2 h, then it was cooled to r.t. MeOH was added dropwise and the solvent was concentrated under vacuum. The obtained residue was dissolved in methanol (20 mL), N,N'-dimethylethylenediamine (3.0 mL, 28.3 mmol) was added and the mixture was stirred under reflux overnight. After cooling to r.t., the volatiles were removed under vacuum, and the residue was purified by flash chromatography, silica gel, gradient dichloromethane to methanol:dichloromethane (1:4) to give the title compound (0.928 g, 65% yield). HPLC retention time: 2.91 min; MS: 257 (M+H).

Intermediate 9B: 9-phenethyl-1-oxa-4,9-diazaspiro[5.5]undecane

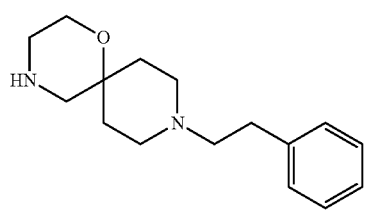 [SMILES: c1ccc(CCN2CCC3(CC2)CNCCO3)cc1]

Intermediate 9D: tert-butyl 12-benzyl-4-oxa-8,12-diazadispiro[2.1.5.3]tridecane-8-carboxylate

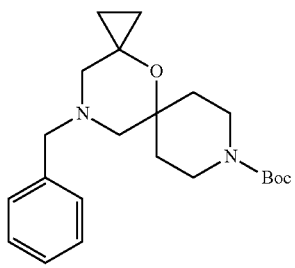 [SMILES: CC(C)(C)OC(=O)N1CCC2(CC1)CN(Cc1ccccc1)CC1(CC1)O2]

Intermediate 9D was prepared according to the procedure described for Intermediate 9A, using Intermediate 8H as starting material. HPLC retention time: 5.80 min; MS: 373 (M+H).

Intermediate 10: tert-butyl 4-benzyl-1-oxa-4,9-diazaspiro[5.5]undecane-9-carboxylate

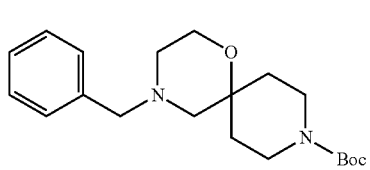 [SMILES: CC(C)(C)OC(=O)N1CCC2(CC1)CN(Cc1ccccc1)CCO2]

To a solution of intermediate 9A (0.311 g, 1.21 mmol) and benzaldehyde (0.15 mL, 1.45 mmol) in THF (8 mL), acetic acid (0.15 mL, 2.67 mmol) was added. The reaction mixture was stirred at r.t. for 15 min. and sodium triacetoxyborohydride (0.77 g, 3.63 mmol) was added in 3 portions during a period of 30 min. The resulting mixture was stirred at r.t. overnight. Water was added, the pH of the mixture was adjusted to 9 by addition of concentrated NH$_3$ and it was extracted with ethyl acetate. The organic phases were combined, dried over MgSO$_4$, filtered and concentrated to dryness. The residue was purified by flash chromatography, silica gel, gradient dichloromethane to methanol/dichloromethane (1:4) to give the title compound (350 mg, 83% yield). HPLC retention time: 5.36 min; MS: 347 (M+H).

Intermediate 11: tert-butyl 3-methyl-4-phenyl-1-oxa-4,9-diazaspiro[5.5]undecane-9-carboxylate

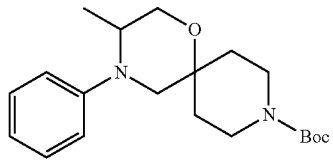 [SMILES: CC1COC2(CCN(C(=O)OC(C)(C)C)CC2)CN1c1ccccc1]

Step 1. tert-butyl 3-methyl-4-phenyl-1-oxa-4,9-diazaspiro[5.5]undec-2-ene-9-carboxylate: To a solution of intermediate 3B (0.150 g, 0.43 mmol) in dry tetrahydrofuran (2.5 mL) cooled at −10° C., zirconium tetrachloride (0.100 g, 0.43 mmol) was added. The mixture was stirred at −10° C. for 30 min under a N$_2$ atmosphere. Then, methylmagnesium bromide solution (0.72 mL, 3M in diethyl ether, 2.16 mmol) was added dropwise. The reaction mixture was stirred at r.t. for 6 h, then 2M NaOH aqueous solution was added and the mixture was filtered through a pad of celite. The aqueous phase was extracted with ethyl acetate. The organic phases were combined, washed with brine, dried over MgSO$_4$, filtered and concentrated to dryness to give the title compound (0.107 g, 72% yield), used in the next step without further purification. HPLC retention time: 5.58 min; MS: 345 (M+H).

Step 2. Title compound: A mixture of the crude product obtained in step 1 (0.107 g, 0.31 mmol) and palladium (11 mg, 10% wt on charcoal) in ethanol (2 mL) was stirred at r.t. under 3 bars of H$_2$ overnight. Additional palladium (11 mg, 10% wt on charcoal) was added and the reaction mixture was again stirred at r.t. under 3 bars of H$_2$ overnight. The solids were filtered off and the solvent was removed under vacuum, to give the title compound as a crude product (78 mg, 72% yield), that was used in the next step without further purification. HPLC retention time: 5.30 min; MS: 347 (M+H).

Synthesis of Examples

Example 1: 4-(4-methoxyphenyl)-2-methyl-9-phenethyl-1-oxa-4,9-diazaspiro[5.5]undecan-3-one hydrochloride

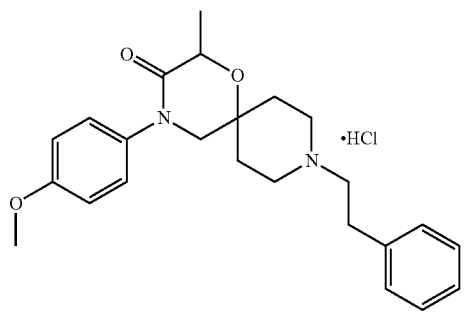 [SMILES: COc1ccc(N2CC3(CCN(CCc4ccccc4)CC3)OC(C)C2=O)cc1 ; Cl]

Step 1. 2-chloro-N-((4-hydroxy-1-phenethylpiperidin-4-yl)methyl)-N-(4-methoxyphenyl) propanamide: To a solution of intermediate 2E (0.266 g, 0.78 mmol) and triethylamine (0.26 mL, 1.88 mmol) in dichloromethane (10 mL), 2-chloropropionyl chloride (0.11 mL, 1.17 mmol) was added dropwise at 0° C. Then, the reaction mixture was stirred at 0° C. for 2 h. NaHCO$_3$ sat solution was then added and the aqueous phase extracted with dichlorometane. The organic phases were combined, washed with brine, dried over MgSO$_4$, filtered and concentrated to dryness to give the title compound (0.296 g, 88% yield). HPLC retention time: 4.05 min; MS: 431.1 (M+H).

Step 2. Title compound: A solution of the crude product obtained in step 1 (296 mg, 0.69 mmol) in THF (12 mL) was cooled to −78° C. using a dry ice/acetone bath. After addition of potassium tert-butoxide solution (1.03 mL, 1M in THF, 1.03 mmol), the reaction mixture was stirred at −30° C. for 2 h. Water was then added, and the aqueous phase was extracted with ethyl acetate. The organic phases were combined, dried over MgSO$_4$, filtered and concentrated under vacuum to give the title compound (251 mg, 93% yield). HPLC retention time: 4.10 min; MS: 395.2 (M+H).

Step 3. Preparation of the hydrochloride salt: To a solution of the free base (50 mg, 0.13 mmol) in anhydrous diethyl ether (1 mL), HCl (2M solution in diethyl ether, 0.063 mL, 0.13 mmol) was added and the mixture was stirred at r.t. for 1 h. The solids were filtered and dried under vacuum to give the corresponding HCl salt (37 mg, 68% yield). HPLC retention time: 4.08 min; MS: 395.2 (M+H).

This method was used for the preparation of examples 2-22 using suitable starting materials:

| EX | Structure | Chemical name | Ret time (min) | MS (M + H) |
|---|---|---|---|---|
| 2 | 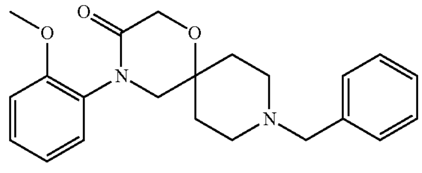 [SMILES: COc1ccccc1N1CC2(CCN(Cc3ccccc3)CC2)OCC1=O] | 9-benzyl-4-(2-methoxyphenyl)-1-oxa-4,9-diazaspiro[5.5]undecan-3-one | 3.90 (methodB) | 367.1 |

-continued

| EX | Structure | Chemical name | Ret time (min) | MS (M + H) |
|---|---|---|---|---|
| 3 | 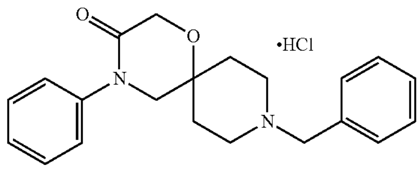 [SMILES: O=C1COC2(CCN(Cc3ccccc3)CC2)CN1c1ccccc1 ; Cl] | 9-benzyl-4-phenyl-1-oxa-4,9-diazaspiro[5.5]undecan-3-one hydrochloride | 3.86 (methodB) | 337.1 |
| 4 | 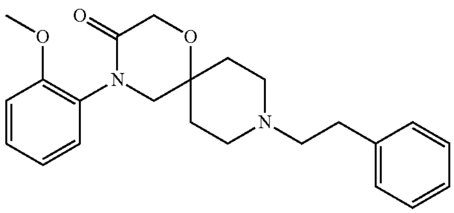 [SMILES: COc1ccccc1N1CC2(CCN(CCc3ccccc3)CC2)OCC1=O] | 4-(2-methoxyphenyl)-9-phenethyl-1-oxa-4,9-diazaspiro[5.5]undecan-3-one | 3.91 (methodB) | 381.2 |
| 5 | 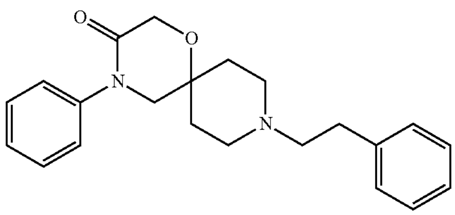 [SMILES: O=C1COC2(CCN(CCc3ccccc3)CC2)CN1c1ccccc1] | 9-phenethyl-4-phenyl-1-oxa-4,9-diazaspiro[5.5]undecan-3-one | 3.88 (methodB) | 351.2 |
| 6 | 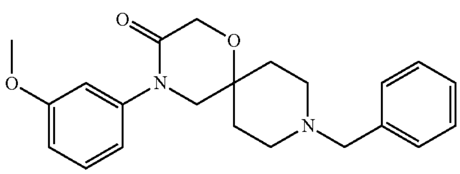 [SMILES: COc1cccc(N2CC3(CCN(Cc4ccccc4)CC3)OCC2=O)c1] | 9-benzyl-4-(3-methoxyphenyl)-1-oxa-4,9-diazaspiro[5.5]undecan-3-one | 4.01 (methodB) | 367.2 |
| 7 | 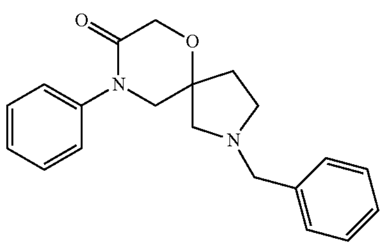 [SMILES: O=C1COC2(CCN(Cc3ccccc3)C2)CN1c1ccccc1] | 2-benzyl-9-phenyl-6-oxa-2,9-diazaspiro[4.5]decan-8-one | 3.77 | 323.1 |
| 8 | 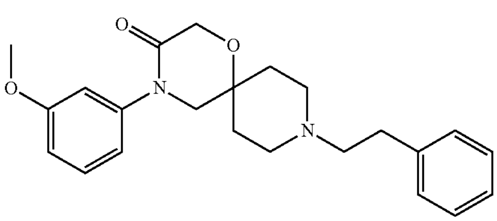 [SMILES: COc1cccc(N2CC3(CCN(CCc4ccccc4)CC3)OCC2=O)c1] | 4-(3-methoxyphenyl)-9-phenethyl-1-oxa-4,9-diazaspiro[5.5]undecan-3-one | 3.86 | 381.2 |
| 9 | 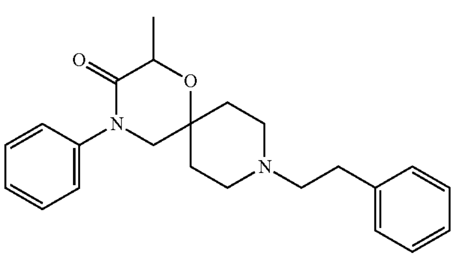 [SMILES: CC1OC2(CCN(CCc3ccccc3)CC2)CN(c2ccccc2)C1=O] | 2-methyl-9-phenethyl-4-phenyl-1-oxa-4,9-diazaspiro[5.5]undecan-3-one | 4.10 | 365.2 |

-continued

| EX | Structure | Chemical name | Ret time (min) | MS (M + H) |
|---|---|---|---|---|
| 10a | 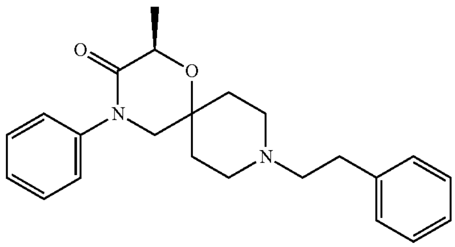 [SMILES: C[C@H]1OC2(CCN(CCc3ccccc3)CC2)CN(c2ccccc2)C1=O] | (R)-2-methyl-9-phenethyl-4-phenyl-1-oxa-4,9-diazaspiro[5.5]undecan-3-one (1*) | 4.10 | 365.2 |
| 10b | 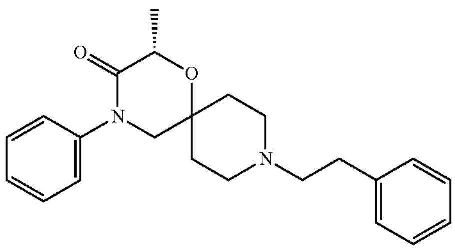 | (S)-2-methyl-9-phenethyl-4-phenyl-1-oxa-4,9-diazaspiro[5.5]undecan-3-one (1*) | 4.10 | 365.2 |
| 11 | 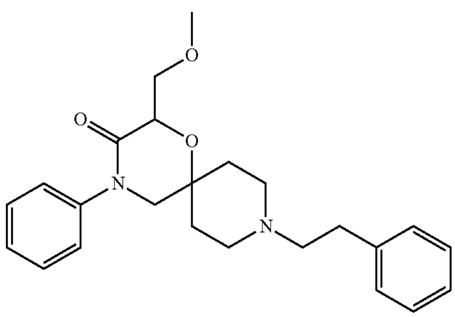 [SMILES: COCC1OC2(CCN(CCc3ccccc3)CC2)CN(c2ccccc2)C1=O] | 2-(methoxymethyl)-9-phenethyl-4-phenyl-1-oxa-4,9-diazaspiro[5.5]undecan-3-one | 3.85 | 395.2 |
| 12a | 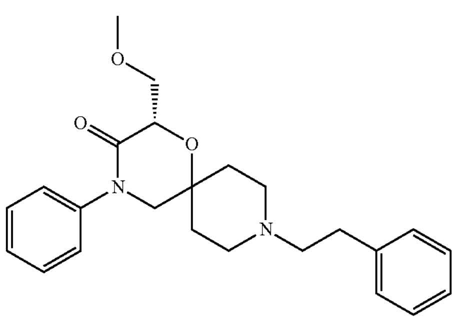 [SMILES: COC[C@@H]1OC2(CCN(CCc3ccccc3)CC2)CN(c2ccccc2)C1=O] | (S)-2-(methoxymethyl)-9-phenethyl-4-phenyl-1-oxa-4,9-diazaspiro[5.5]undecan-3-one (2*) | 3.85 | 395.2 |
| 12b | 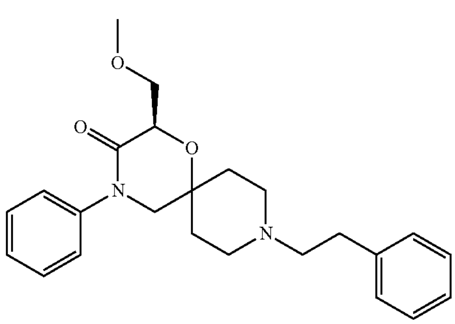 [SMILES: COC[C@H]1OC2(CCN(CCc3ccccc3)CC2)CN(c2ccccc2)C1=O] | (R)-2-(methoxymethyl)-9-phenethyl-4-phenyl-1-oxa-4,9-diazaspiro[5.5]undecan-3-one (2*) | 3.85 | 395.2 |

-continued

| EX | Structure | Chemical name | Ret time (min) | MS (M + H) |
|---|---|---|---|---|
| 13 | 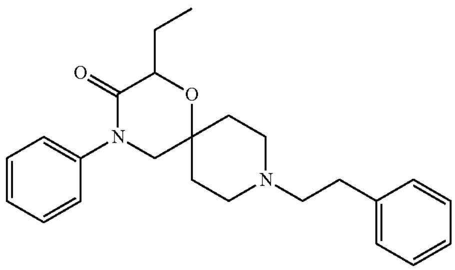 [SMILES: CCC1OC2(CCN(CCc3ccccc3)CC2)CN(c2ccccc2)C1=O] | 2-ethyl-9-phenethyl-4-phenyl-1-oxa-4,9-diazaspiro[5.5]undecan-3-one | 4.45 | 379.2 |
| 14 | 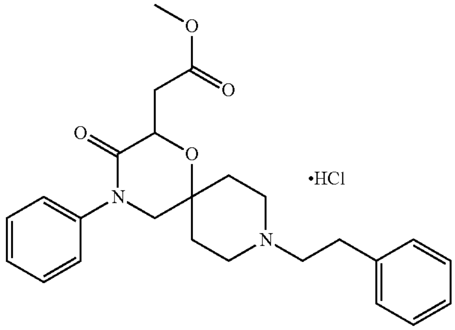 [SMILES: COC(=O)CC1OC2(CCN(CCc3ccccc3)CC2)CN(c2ccccc2)C1=O ; Cl] | methyl 2-(3-oxo-9-phenethyl-4-phenyl-1-oxa-4,9-diazaspiro[5.5]undecan-2-yl)acetate hydrochloride | 4.08 | 423.2 |
| 15 | 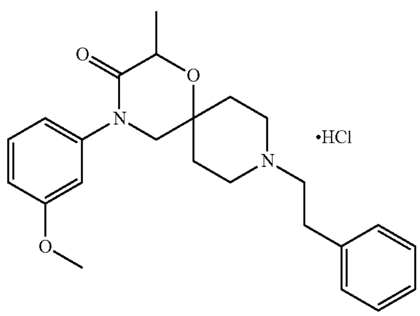 [SMILES: COc1cccc(N2CC3(CCN(CCc4ccccc4)CC3)OC(C)C2=O)c1 ; Cl] | 4-(3-methoxyphenyl)-2-methyl-9-phenethyl-1-oxa-4,9-diazaspiro[5.5]undecan-3-one hydrochloride | 4.16 | 395.2 |
| 16 | 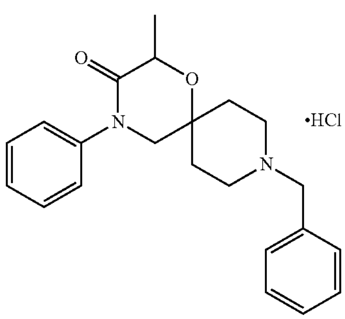 [SMILES: CC1OC2(CCN(Cc3ccccc3)CC2)CN(c2ccccc2)C1=O ; Cl] | 9-benzyl-2-methyl-4-phenyl-1-oxa-4,9-diazaspiro[5.5]undecan-3-one hydrochloride | 4.09 | 351.2 |
| 17 | 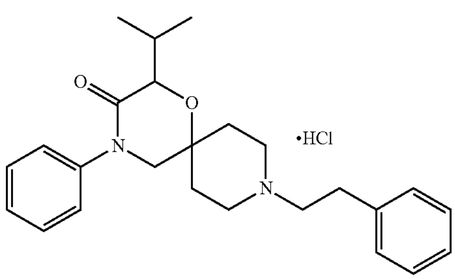 [SMILES: CC(C)C1OC2(CCN(CCc3ccccc3)CC2)CN(c2ccccc2)C1=O ; Cl] | 2-isopropyl-9-phenethyl-4-phenyl-1-oxa-4,9-diazaspiro[5.5]undecan-3-one hydrochloride | 4.96 | 393.2 |

-continued

| EX | Structure | Chemical name | Ret time (min) | MS (M + H) |
|---|---|---|---|---|
| 18 | 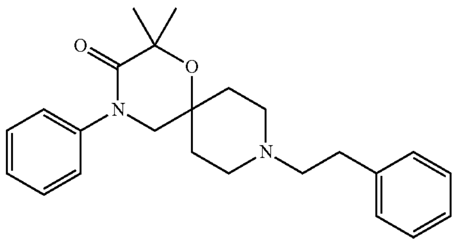 [SMILES: CC1(C)OC2(CCN(CCc3ccccc3)CC2)CN(c2ccccc2)C1=O] | 2,2-dimethyl-9-phenethyl-4-phenyl-1-oxa-4,9-diazaspiro[5.5]undecan-3-one | 5.03 | 379.2 |
| 19 | 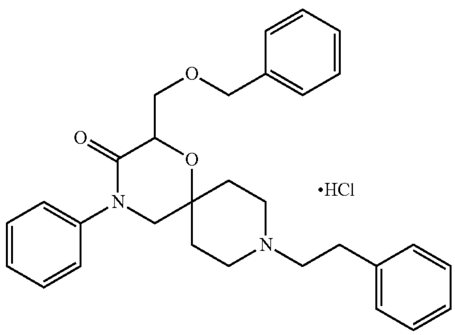 [SMILES: O=C1C(COCc2ccccc2)OC2(CCN(CCc3ccccc3)CC2)CN1c1ccccc1 ; Cl] | 2-((benzyloxy)methyl)-9-phenethyl-4-phenyl-1-oxa-4,9-diazaspiro[5.5]undecan-3-one hydrochloride | 4.95 | 471.2 |
| 20 | 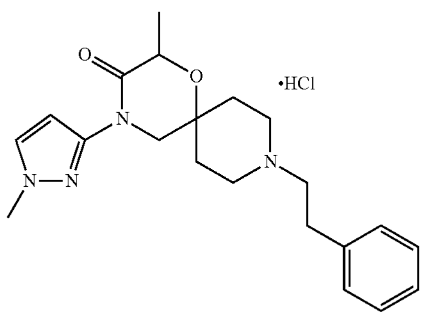 [SMILES: CC1OC2(CCN(CCc3ccccc3)CC2)CN(c2ccn(C)n2)C1=O ; Cl] | 2-methyl-4-(1-methyl-1H-pyrazol-3-yl)-9-phenethyl-1-oxa-4,9-diazaspiro[5.5]undecan-3-one hydrochloride | 3.74 | 369.2 |
| 21 | 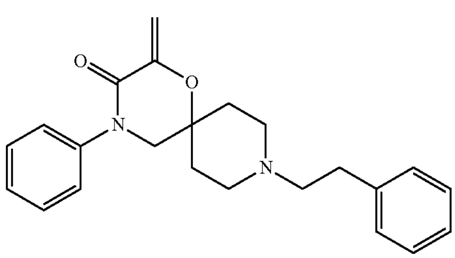 [SMILES: C=C1OC2(CCN(CCc3ccccc3)CC2)CN(c2ccccc2)C1=O] | 2-methylene-9-phenethyl-4-phenyl-1-oxa-4,9-diazaspiro[5.5]undecan-3-one (3*) | 4.46 | 363.1 |
| 22 | 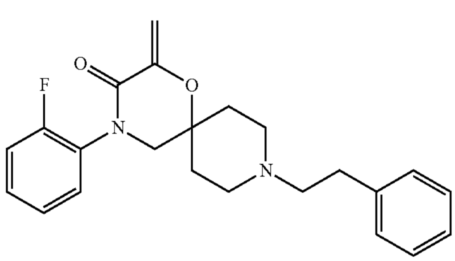 [SMILES: C=C1OC2(CCN(CCc3ccccc3)CC2)CN(c2ccccc2F)C1=O] | 4-(2-fluorophenyl)-2-methylene-9-phenethyl-1-oxa-4,9-diazaspiro[5.5]undecan-3-one (3*) | 4.53 | 381.1 |

Where indicated, the hydrochloride salts were prepared as described in example 1.
1*. Obtained by chiral preparative HPLC from previous example: Column: Chiralpak IA; Temperature: ambient; Flow: 0.9 mL/min; Mobile phase: n-Heptane/(IPA + 2% DEA) 95/5 v/v
2*. Obtained by chiral preparative HPLC from previous example: Column: Chiralpak ASH; Temperature: ambient; Flow: 0.8 mL/min; Mobile phase: n-Heptane/EtOH 90/10 v/v
3*. Obtained as by-product under the reaction conditions when preparing the corresponding 2-methoxymethyl derivatives

Example 23: 2-methyl-9-(2-(5-nitropyridin-2-yl)ethyl)-4-phenyl-1-oxa-4,9-diazaspiro[5.5]undecan-3-one

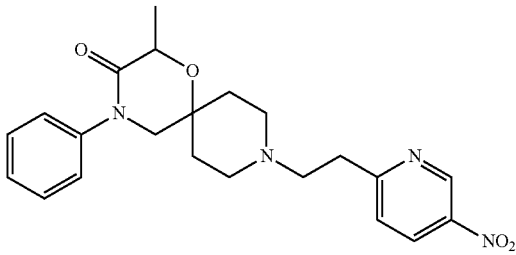

Step 1: 2-methyl-4-phenyl-1-oxa-4,9-diazaspiro[5.5]undecan-3-one trifluoroacetate. To a solution of intermediate 3A (3.57 g, 9.90 mmol) in dichloromethane (35 mL), trifluoroacetic acid (7.8 mL, 99.0 mmol) was added, and the reaction mixture was refluxed for 5 h. The solvent was evaporated to dryness to give the title compound as a crude product (7.1 g, 53 wt %, quant yield), that was used in the following step without further purification. HPLC retention time: 1.94 min; MS: 261 (M+H).

Step 2: 2-methyl-4-phenyl-1-oxa-4,9-diazaspiro[5.5]undecan-3-one. The crude product obtained in step 1 (0.519 g, 53 wt %, 0.72 mmol) was dissolved in dichloromethane and it was washed three times with 1M NaOH aqueous solution. The combined aqueous phases were back extracted with dichloromethane. The organic phases were combined, washed with water, dried over MgSO$_4$, filtered and concentrated under vacuum to give the title compound as a crude product (0.207 g, quant yield). HPLC retention time: 1.91 min; MS: 261 (M+H).

Step 3: Title compound: A solution of the compound obtained in step 2 (0.095 g, 0.365 mmol) and 3-nitro-6-vinylpyridine (prepared similarly as described in WO2009/32667 Ex 40.C) (0.071 g, 0.474 mmol) in isopropanol (1 mL) was heated at 140° C. under microwave irradiation for 15 min. The reaction mixture was allowed to cool to r.t. and the solvent was evaporated to dryness. The residue was purified by flash chromatography, silica gel, gradient dichloromethane to methanol:dichloromethane (1:4) to give the title compound (90 mg, 60% yield). HPLC retention time: 3.51 min; MS: 411.2 (M+H).

This method was used for the preparation of examples 24-32 using suitable starting materials:

| EX | Structure | Chemical name | Ret time (min) | MS (M + H) |
|---|---|---|---|---|
| 24 | 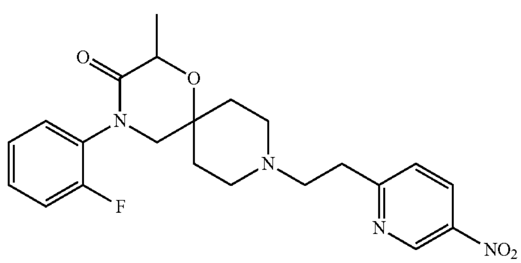 | 4-(2-fluorophenyl)-2-methyl-9-(2-(5-nitropyridin-2-yl)ethyl)-1-oxa-4,9-diazaspiro[5.5]undecan-3-one | 3.61 | 429.2 |
| 25 | 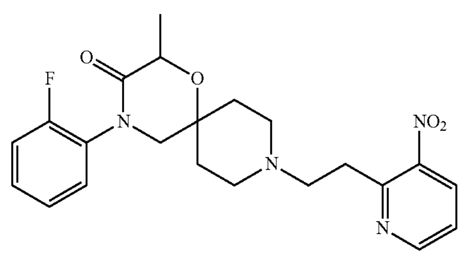 | 4-(2-fluorophenyl)-2-methyl-9-(2-(3-nitropyridin-2-yl)ethyl)-1-oxa-4,9-diazaspiro[5.5]undecan-3-one | 3.62 | 429.2 |
| 26 | 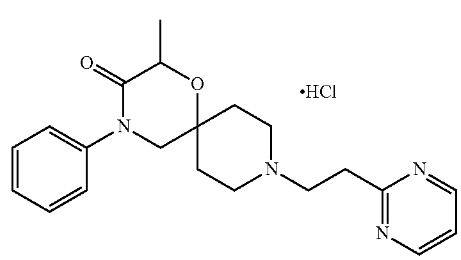 [SMILES: CC1OC2(CCN(CCc3ncccn3)CC2)CN(c2ccccc2)C1=O ; Cl] | 2-methyl-4-phenyl-9-(2-(pyrimidin-2-yl)ethyl)-1-oxa-4,9-diazaspiro[5.5]undecan-3-one hydrochloride | 3.75 | 367.1 |

-continued

| EX | Structure | Chemical name | Ret time (min) | MS (M + H) |
|----|-----------|---------------|----------------|------------|
| 27 | 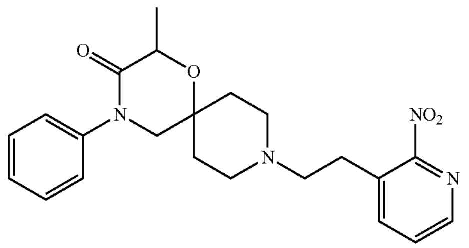 [SMILES: CC1OC2(CCN(CCc3cccnc3[N+](=O)[O-])CC2)CN(c2ccccc2)C1=O] | 2-methyl-9-(2-(2-nitropyridin-3-yl)ethyl)-4-phenyl-1-oxa-4,9-diazaspiro[5.5]undecan-3-one | 3.59 | 411.2 |
| 28 | 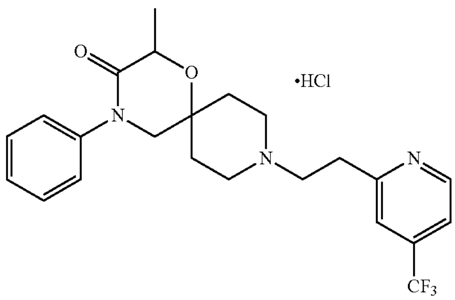 [SMILES: CC1OC2(CCN(CCc3cc(C(F)(F)F)ccn3)CC2)CN(c2ccccc2)C1=O ; Cl] | 2-methyl-4-phenyl-9-(2-(4-(trifluoromethyl)pyridin-2-yl)ethyl)-1-oxa-4,9-diazaspiro[5.5]undecan-3-one hydrochloride | 3.99 | 434.1 |
| 29 | 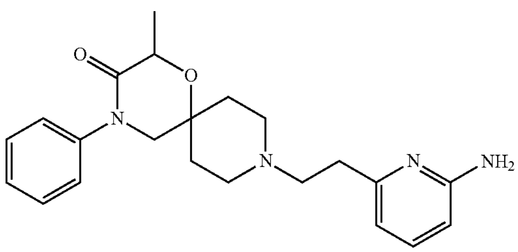 [SMILES: CC1OC2(CCN(CCc3cccc(N)n3)CC2)CN(c2ccccc2)C1=O] | 9-(2-(6-aminopyridin-2-yl)ethyl)-2-methyl-4-phenyl-1-oxa-4,9-diazaspiro[5.5]undecan-3-one | 3.04 | 381.2 |
| 30 | 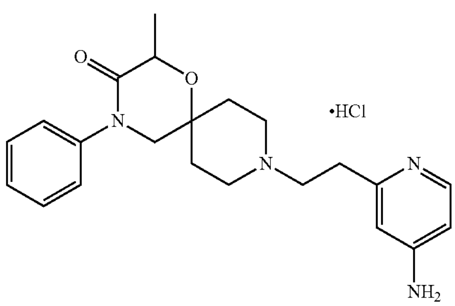 [SMILES: CC1OC2(CCN(CCc3cc(N)ccn3)CC2)CN(c2ccccc2)C1=O ; Cl] | 9-(2-(4-aminopyridin-2-yl)ethyl)-2-methyl-4-phenyl-1-oxa-4,9-diazaspiro[5.5]undecan-3-one hydrochloride | 2.57 | 381.2 |
| 31 | 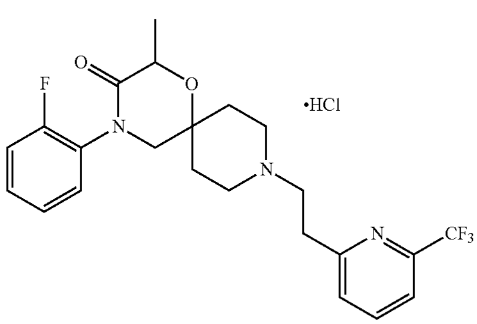 [SMILES: CC1OC2(CCN(CCc3cccc(C(F)(F)F)n3)CC2)CN(c2ccccc2F)C1=O ; Cl] | 4-(2-fluorophenyl)-2-methyl-9-(2-(6-(trifluoromethyl)pyridin-2-yl)ethyl)-1-oxa-4,9-diazaspiro[5.5]undecan-3-one hydrochloride (*1) | 4.22 | 452.2 |

| EX | Structure | Chemical name | Ret time (min) | MS (M + H) |
|---|---|---|---|---|
| 32 | 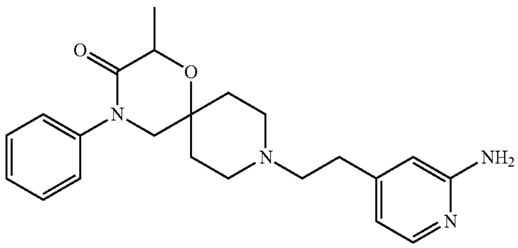 [SMILES: CC1OC2(CCN(CCc3ccnc(N)c3)CC2)CN(c2ccccc2)C1=O] | 9-(2-(2-aminopyridin-4-yl)ethyl)-2-methyl-4-phenyl-1-oxa-4,9-diazaspiro[5.5]undecan-3-one (*1) | 2.92 | 381.1 |

Where indicated, the hydrochloride salts were prepared as described in example 1.
*1. The reaction was carried out in butanol at 180° C.

Example 33: 2-methyl-4-phenyl-9-(2-(3-(trifluoromethyl)pyridin-2-yl)ethyl)-1-oxa-4,9-diazaspiro[5.5]undecan-3-one hydrochloride

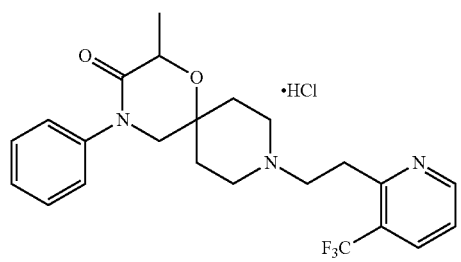 [SMILES: CC1OC2(CCN(CCc3ncccc3C(F)(F)F)CC2)CN(c2ccccc2)C1=O ; Cl]

A solution of the crude product obtained in step 2 of example 23 (0.060 g, 0.231 mmol) and 3-trifluoromethyl-2-vinylpyridine (prepared similarly as described in Angewandte Chemie—International Edition, 2013, vol. 52, nb 37 p. 9755) (0.068 g, 0.393 mmol) in 2-methoxyethanol (1.1 mL) was heated at 120° C. in a sealed tube under argon for 1 day. The reaction mixture was allowed to cool to r.t. and the solvent was evaporated. The residue was purified by flash chromatography, silica gel, gradient dichloromethane to methanol:dichloromethane (1:4) to give the title compound as its free base (41 mg, 41% yield).

The previous compound was converted to its hydrochloride salt as described in example 1.

HPLC retention time: 3.92 min; MS: 434.0 (M+H).

This method was used for the preparation of examples 34-50 using suitable starting materials:

| EX | Structure | Chemical name | Ret time (min) | MS (M + H) |
|---|---|---|---|---|
| 34 | 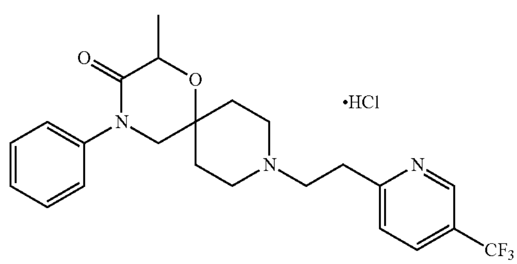 [SMILES: CC1OC2(CCN(CCc3ccc(C(F)(F)F)cn3)CC2)CN(c2ccccc2)C1=O ; Cl] | 2-methyl-4-phenyl-9-(2-(5-(trifluoromethyl)pyridin-2-yl)ethyl)-1-oxa-4,9-diazaspiro[5.5]undecan-3-one hydrochloride | 3.98 | 434.0 |
| 35 | 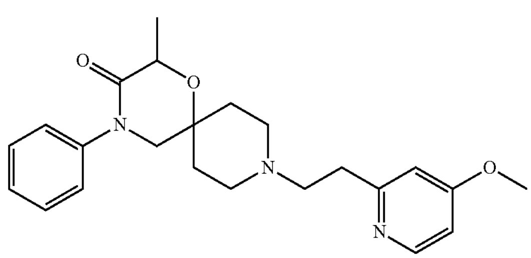 [SMILES: COc1ccnc(CCN2CCC3(CC2)CN(c2ccccc2)C(=O)C(C)O3)c1] | 9-(2-(4-methoxypyridin-2-yl)ethyl)-2-methyl-4-phenyl-1-oxa-4,9-diazaspiro[5.5]undecan-3-one | 3.27 | 396.1 |

-continued

| EX | Structure | Chemical name | Ret time (min) | MS (M + H) |
|---|---|---|---|---|
| 36 | 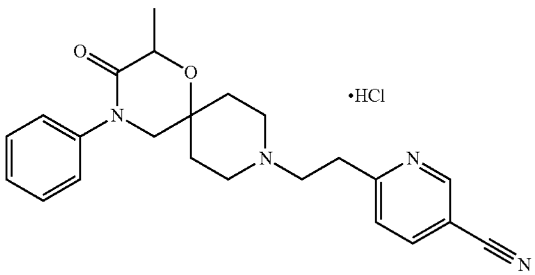 [SMILES: CC1OC2(CCN(CCc3ccc(C#N)cn3)CC2)CN(c2ccccc2)C1=O ; Cl] | 6-(2-(2-methyl-3-oxo-4-phenyl-1-oxa-4,9-diazaspiro[5.5]undecan-9-yl)ethyl)nicotinonitrile hydrochloride | 3.30 | 391.0 |
| 37 | 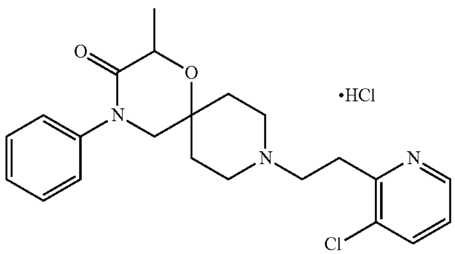 [SMILES: CC1OC2(CCN(CCc3ncccc3Cl)CC2)CN(c2ccccc2)C1=O ; Cl] | 9-(2-(3-chloropyridin-2-yl)ethyl)-2-methyl-4-phenyl-1-oxa-4,9-diazaspiro[5.5]undecan-3-one hydrochloride | 3.68 | 400.1 |
| 38 | 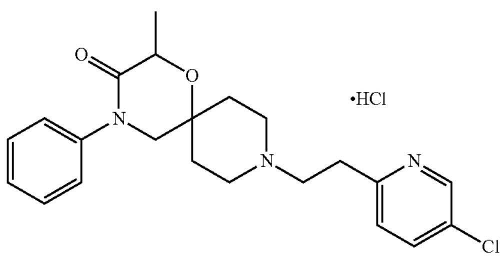 [SMILES: CC1OC2(CCN(CCc3ccc(Cl)cn3)CC2)CN(c2ccccc2)C1=O ; Cl] | 9-(2-(5-chloropyridin-2-yl)ethyl)-2-methyl-4-phenyl-1-oxa-4,9-diazaspiro[5.5]undecan-3-one hydrochloride | 3.72 | 400.1 |
| 39 | 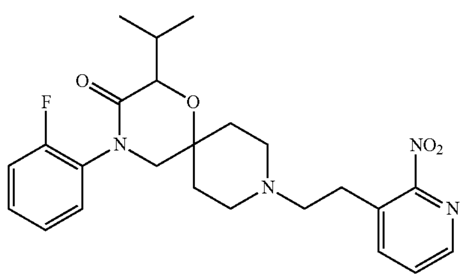 [SMILES: CC(C)C1OC2(CCN(CCc3cccnc3[N+](=O)[O-])CC2)CN(c2ccccc2F)C1=O] | 4-(2-fluorophenyl)-2-isopropyl-9-(2-(2-nitropyridin-3-yl)ethyl)-1-oxa-4,9-diazaspiro[5.5]undecan-3-one | 4.49 | 457.2 |
| 40 | 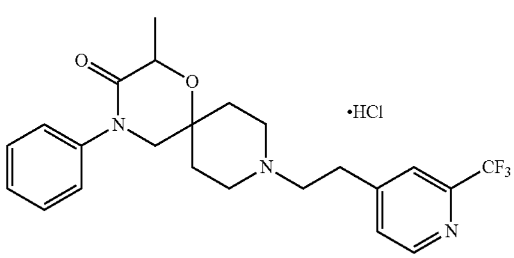 [SMILES: CC1OC2(CCN(CCc3ccnc(C(F)(F)F)c3)CC2)CN(c2ccccc2)C1=O ; Cl] | 2-methyl-4-phenyl-9-(2-(2-(trifluoromethyl)pyridin-4-yl)ethyl)-1-oxa-4,9-diazaspiro[5.5]undecan-3-one hydrochloride | 4.05 | 434.2 |

| EX | Structure | Chemical name | Ret time (min) | MS (M + H) |
|---|---|---|---|---|
| 41 | 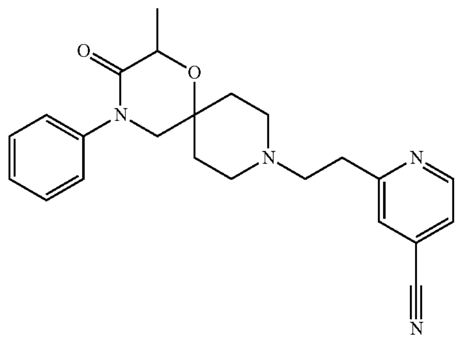 [SMILES: CC1OC2(CCN(CCc3cc(C#N)ccn3)CC2)CN(c2ccccc2)C1=O] | 2-(2-(2-methyl-3-oxo-4-phenyl-1-oxa-4,9-diazaspiro[5.5]undecan-9-yl)ethyl)isonicotinonitrile | 3.25 | 391.2 |
| 42 | ·HCl | 9-(2-(6-aminopyridin-2-yl)ethyl)-2-methyl-4-(4-(trifluoromethyl)pyridin-3-yl)-1-oxa-4,9-diazaspiro[5.5]undecan-3-one hydrochloride | 3.05 | 450.2 |
| 43 | 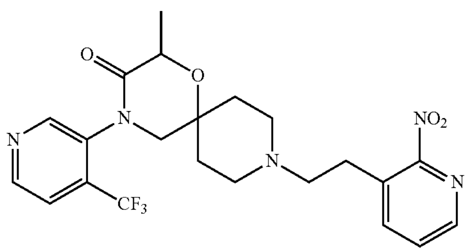 [SMILES: CC1OC2(CCN(CCc3cccnc3[N+](=O)[O-])CC2)CN(c2cnccc2C(F)(F)F)C1=O] | 2-methyl-9-(2-(2-nitropyridin-3-yl)ethyl)-4-(4-(trifluoromethyl)pyridin-3-yl)-1-oxa-4,9-diazasprio[5.5]undecan-3-one | 3.69 | 480.2 |
| 44 | ·HCl | 9-(2-(3-chloropyridin-2-yl)ethyl)-2-methyl-4-(4-(trifluoromethyl)pyridin-3-yl)-1-oxa-4,9-diazaspiro[5.5]undecan-3-one hydrochloride | 3.76 | 469.1 |
| 45 | ·HCl | 9-(2-(3-chloropyridin-2-yl)ethyl)-2-methyl-4-((5-(trifluoromethyl)pyridin-2-yl)methyl)-1-oxa-4,9-diazaspiro[5.5]undecan-3-one hydrochloride | 3.99 | 483.2 |

-continued

| EX | Structure | Chemical name | Ret time (min) | MS (M + H) |
|---|---|---|---|---|
| 46 | 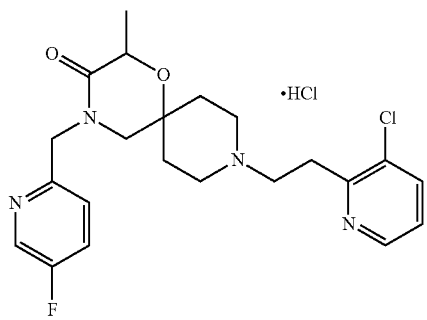 [SMILES: CC1OC2(CCN(CCc3ncccc3Cl)CC2)CN(Cc2ccc(F)cn2)C1=O ; Cl] | 9-(2-(3-chloropyridin-2-yl)ethyl)-4-((5-fluoropyridin-2-yl)methyl)-2-methyl-1-oxa-4,9-diazaspiro[5.5]undecan-3-one hydrochloride | 3.46 | 433.1 |
| 47 | 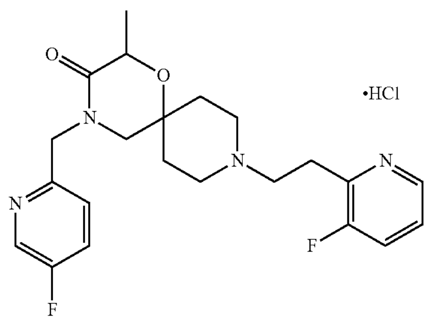 [SMILES: CC1OC2(CCN(CCc3ncccc3F)CC2)CN(Cc2ccc(F)cn2)C1=O ; Cl] | 9-(2-(3-fluoropyridin-2-yl)ethyl)-4-((5-fluoropyridin-2-yl)methyl)-2-methyl-1-oxa-4,9-diazaspiro[5.5]undecan-3-one hydrochloride | 3.24 | 417.2 |
| 48 | 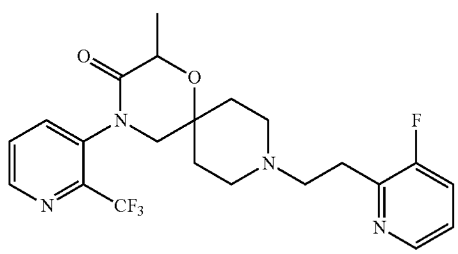 [SMILES: CC1OC2(CCN(CCc3ncccc3F)CC2)CN(c2cccnc2C(F)(F)F)C1=O] | 9-(2-(3-fluoropyridin-2-yl)ethyl)-2-methyl-4-(2-(trifluoromethyl)pyridin-3-yl)-1-oxa-4,9-diazaspiro[5.5]undecan-3-one | 3.53 | 453.2 |
| 49 | 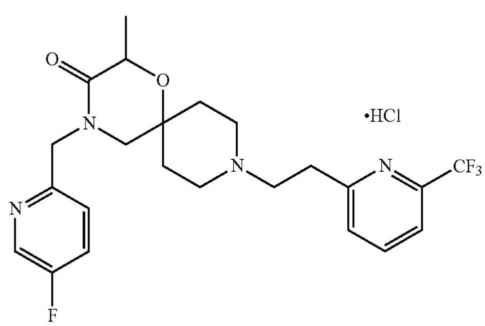 [SMILES: CC1OC2(CCN(CCc3cccc(C(F)(F)F)n3)CC2)CN(Cc2ccc(F)cn2)C1=O ; Cl] | 4-((5-fluoropyridin-2-yl)methyl)-2-methyl-9-(2-(6-(trifluoromethyl)pyridin-2-yl)ethyl)-1-oxa-4,9-diazaspiro[5.5]undecan-3-one hydrochloride | 3.92 | 467.2 |
| 50 | 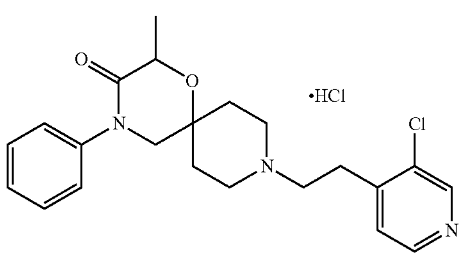 [SMILES: CC1OC2(CCN(CCc3ccncc3Cl)CC2)CN(c2ccccc2)C1=O ; Cl] | 9-(2-(3-chloropyridin-4-yl)ethyl)-2-methyl-4-phenyl-1-oxa-4,9-diazaspiro[5.5]undecan-3-one hydrochloride | 3.58 | 400.1 |

Where indicated, the hydrochloride salts were prepared as described in example 1.

Example 51: 9-(2-fluorophenethyl)-2-methyl-4-phenyl-1-oxa-4,9-diazaspiro[5.5]undecan-3-one hydrochloride

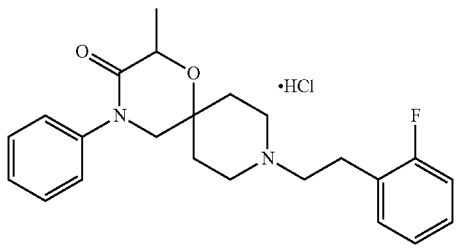 [SMILES: CC1OC2(CCN(CCc3ccccc3F)CC2)CN(c2ccccc2)C1=O ; Cl]

A mixture of the crude product obtained in step 1 of example 23 (0.326 g, 61 wt %, 0.534 mmol), 1-(2-bromoethyl)-2-fluorobenzene (0.075 mL, 0.534 mmol), sodium iodide (0.048 g, 0.321 mmol) and $K_2CO_3$ (0.369 g, 2.671 mmol) in acetonitrile (4 mL) was heated at 80° C. in a sealed tube overnight. Water was added, and the reaction mixture was extracted with ethyl acetate. The organic phases were combined, washed with brine, dried over $MgSO_4$, filtered and concentrated to dryness. The residue was purified by flash chromatography, silica gel, gradient dichloromethane to methanol:dichloromethane (1:9) to give the title compound as its free base (148 mg, 72% yield).

The previous compound was converted to its hydrochloride salt as described in example 1.

HPLC retention time: 4.32 min; MS: 383.2 (M+H).

This method was used for the preparation of examples 52-148 using suitable starting materials:

| EX | Structure | Chemical name | Ret time (min) | MS (M + H) |
|---|---|---|---|---|
| 52 | 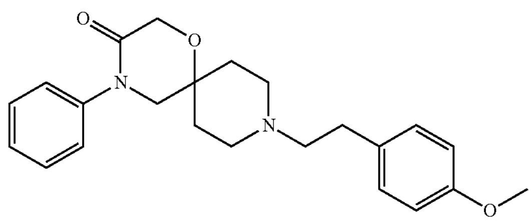 [SMILES: COc1ccc(CCN2CCC3(CC2)CN(c2ccccc2)C(=O)CO3)cc1] | 9-(4-methoxyphenethyl)-4-phenyl-1-oxa-4,9-diazaspiro[5.5]undecan-3-one | 3.65 | 381.2 |
| 53 | 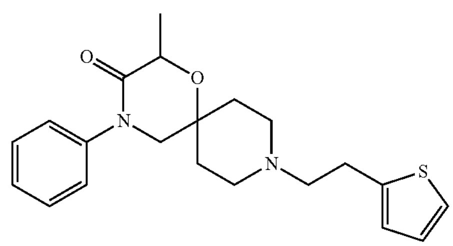 [SMILES: CC1OC2(CCN(CCc3cccs3)CC2)CN(c2ccccc2)C1=O] | 2-methyl-4-phenyl-9-(2-(thiophen-2-yl)ethyl)-1-oxa-4,9-diazaspiro[5.5]undecan-3-one | 4.19 | 371.1 |
| 54 | 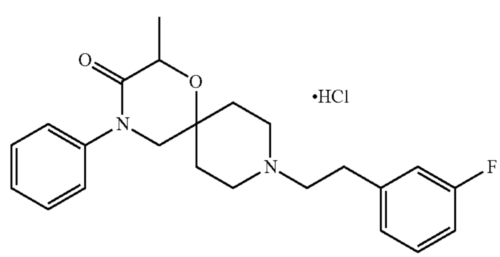 [SMILES: CC1OC2(CCN(CCc3cccc(F)c3)CC2)CN(c2ccccc2)C1=O ; Cl] | 9-(3-fluorophenethyl)-2-methyl-4-phenyl-1-oxa-4,9-diazaspiro[5.5]undecan-3-one hydrochloride | 4.31 | 383.2 |
| 55 | 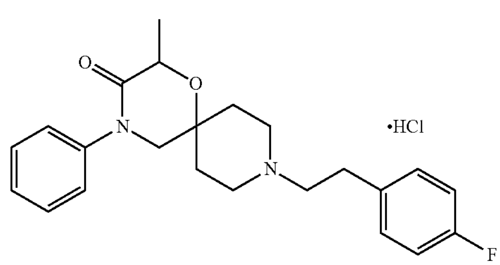 [SMILES: CC1OC2(CCN(CCc3ccc(F)cc3)CC2)CN(c2ccccc2)C1=O ; Cl] | 9-(4-fluorophenethyl)-2-methyl-4-phenyl-1-oxa-4,9-diazaspiro[5.5]undecan-3-one hydrochloride | 4.26 | 383.1 |

| EX | Structure | Chemical name | Ret time (min) | MS (M + H) |
|---|---|---|---|---|
| 56 | 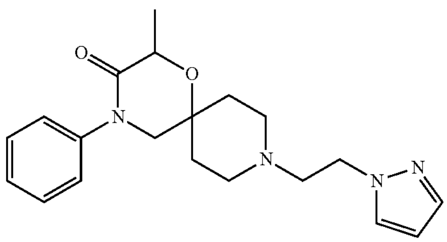 [SMILES: CC1OC2(CCN(CCn3cccn3)CC2)CN(c2ccccc2)C1=O] | 9-(2-(1H-pyrazol-1-yl)ethyl-2-methyl-4-phenyl-1-oxa-4,9-diazaspiro[5.5]undecan-3-one | 3.06 | 355.2 |
| 57 | 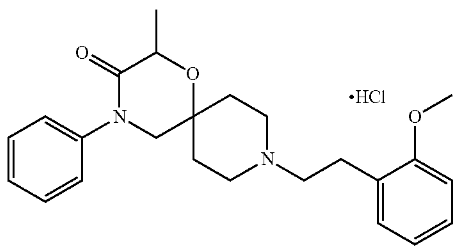 [SMILES: COc1ccccc1CCN1CCC2(CC1)CN(c1ccccc1)C(=O)C(C)O2 ; Cl] | 9-(2-methoxyphenethyl)-2-methyl-4-phenyl-1-oxa-4,9-diazaspiro[5.5]undecan-3-one hydrochloride | 4.18 | 395.2 |
| 58 | 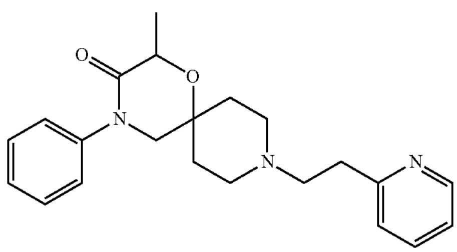 [SMILES: CC1OC2(CCN(CCc3ccccn3)CC2)CN(c2ccccc2)C1=O] | 2-methyl-4-phenyl-9-(2-(pyridin-2-yl)ethyl)-1-oxa-4,9-diazaspiro[5.5]undecan-3-one | 3.12 | 366.2 |
| 59 | 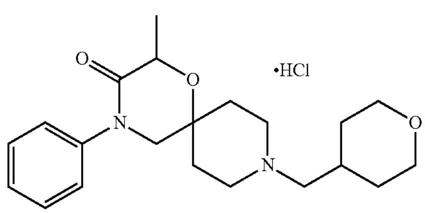 [SMILES: CC1OC2(CCN(CC3CCOCC3)CC2)CN(c2ccccc2)C1=O ; Cl] | 2-methyl-4-phenyl-9-((tetrahydro-2H-pyran-4-yl)methyl)-1-oxa-4,9-diazaspiro[5.5]undecan-3-one hydrchloride | 3.21 | 359.2 |
| 60 | 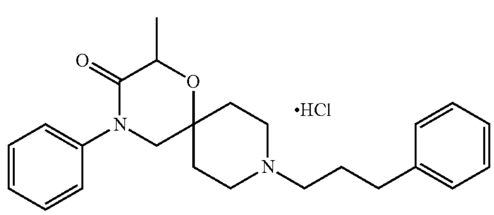 [SMILES: CC1OC2(CCN(CCCc3ccccc3)CC2)CN(c2ccccc2)C1=O ; Cl] | 2-methyl-4-phenyl-9-(3-phenylpropyl)-1-oxa-4,9-diazaspiro[5.5]undecan-3-one hydrochloride | 4.29 | 379.2 |
| 61 | 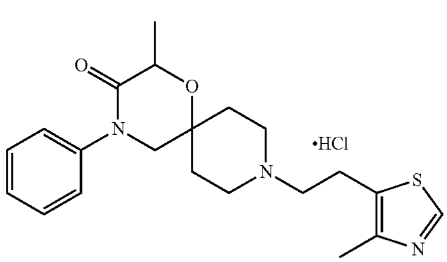 [SMILES: Cc1ncsc1CCN1CCC2(CC1)CN(c1ccccc1)C(=O)C(C)O2 ; Cl] | 2-methyl-9-(2-(4-methylthiazol-5-yl)ethyl)-4-phenyl-1-oxa-4,9-diazaspiro[5.5]undecan-3-one hydrochloride | 3.41 | 386.1 |

| EX | Structure | Chemical name | Ret time (min) | MS (M + H) |
|---|---|---|---|---|
| 62 | 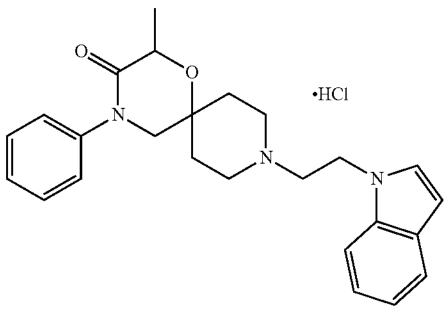 [SMILES: CC1OC2(CCN(CCn3ccc4ccccc43)CC2)CN(c2ccccc2)C1=O ; Cl] | 9-(2-(1H-indol-1-yl)ethyl)-2-methyl-4-phenyl-1-oxa-4,9-diazaspiro[5.5]undecan-3-one hydrochloride | 4.54 | 404.2 |
| 63 | 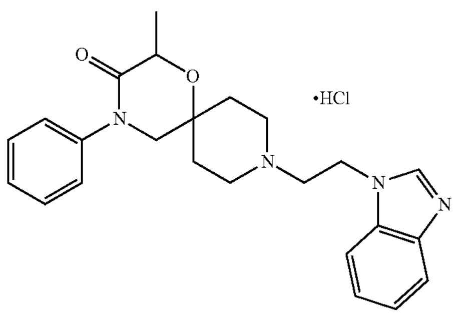 [SMILES: CC1OC2(CCN(CCn3cnc4ccccc43)CC2)CN(c2ccccc2)C1=O ; Cl] | 9-(2-(1H-benzo[d]imidazol-1-yl)ethyl)-2-methyl-4-phenyl-1-oxa-4,9-diazaspiro[5.5]undecan-3-one hydrochloride | 3.48 | 405.2 |
| 64 | 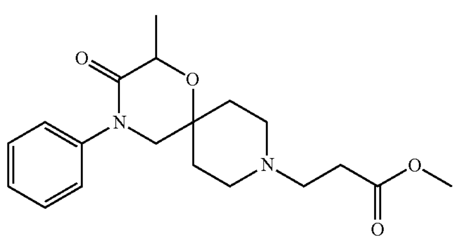 [SMILES: COC(=O)CCN1CCC2(CC1)CN(c1ccccc1)C(=O)C(C)O2] | methyl 3-(2-methyl-3-oxo-4-phenyl-1-oxa-4,9-diazaspiro[5.5]undecan-9-yl)propanoate | 3.11 | 347.1 |
| 65 | 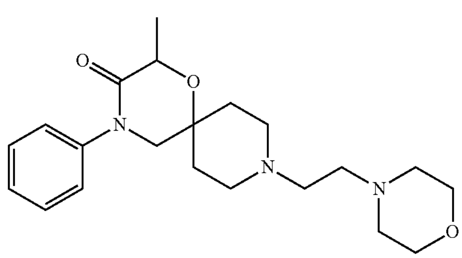 [SMILES: CC1OC2(CCN(CCN3CCOCC3)CC2)CN(c2ccccc2)C1=O] | 2-methyl-9-(2-morpholinoethyl)-4-phenyl-1-oxa-4,9-diazaspiro[5.5]undecan-3-one | 2.74 | 374.2 |
| 66 | 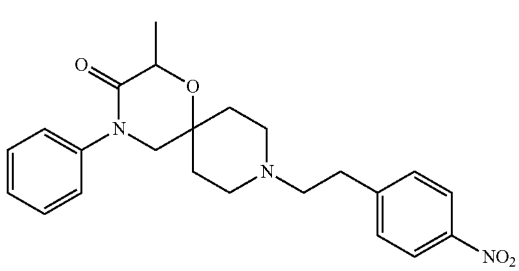 | 2-methyl-9-(4-nitrophenethyl)-4-phenyl-1-oxa-4,9-diazaspiro[5.5]undecan-3-one | 4.26 | 410.2 |

-continued

| EX | Structure | Chemical name | Ret time (min) | MS (M + H) |
|---|---|---|---|---|
| 67 | 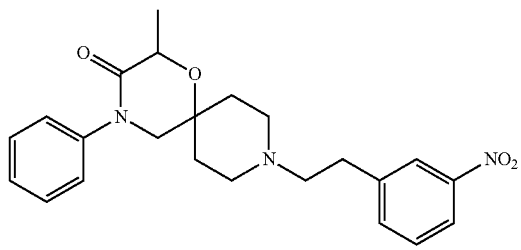 [SMILES: CC1OC2(CCN(CCc3cccc([N+](=O)[O-])c3)CC2)CN(c2ccccc2)C1=O] | 2-methyl-9-(3-nitrophenethyl)-4-phenyl-1-oxa-4,9-diazaspiro[5.5]undecan-3-one | 4.20 | 410.2 |
| 68 | 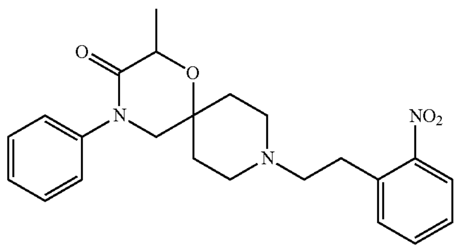 | 2-methyl-9-(2-nitrophenethyl)-4-phenyl-1-oxa-4,9-diazapspiro[5.5]undecan-3-one | 4.18 | 410.1 |
| 69 | 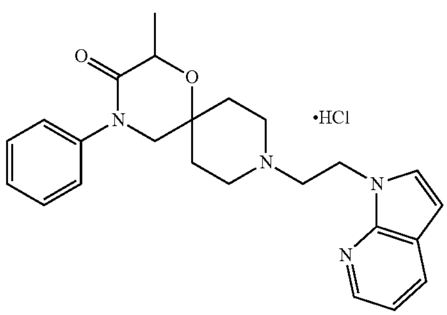 [SMILES: CC1OC2(CCN(CCn3ccc4cccnc43)CC2)CN(c2ccccc2)C1=O ; Cl] | 9-(2-(1H-pyrrolo[2,3-b]pyridin-1-yl)ethyl)-2-methyl-4-phenyl-1-oxa-4,9-diazaspiro[5.5]undecan-3-one hydrochloride | 3.89 | 405.2 |
| 70 | 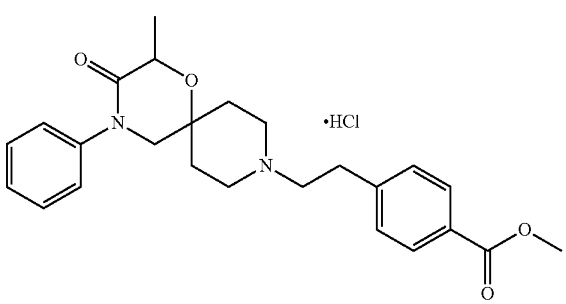 [SMILES: COC(=O)c1ccc(CCN2CCC3(CC2)CN(c2ccccc2)C(=O)C(C)O3)cc1 ; Cl] | methyl 4-(2-(2-methyl-3-oxo-4-phenyl-1-oxa-4,9-diazaspiro[5.5]undecan-9-yl)ethyl)benzoate hydrochloride | 4.12 | 423.2 |
| 71 | 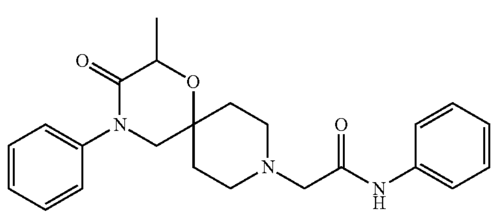 [SMILES: CC1OC2(CCN(CC(=O)Nc3ccccc3)CC2)CN(c2ccccc2)C1=O] | 2-(2-methyl-3-oxo-4-phenyl-1-oxa-4,9-diazaspiro[5.5]undecan-9-yl)-N-phenylacetamide | 3.88 | 394.2 |
| 72 | 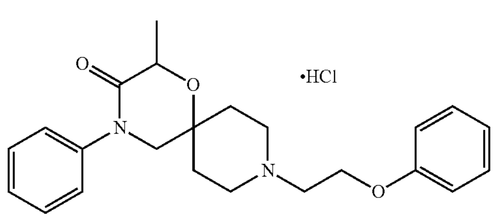 [SMILES: CC1OC2(CCN(CCOc3ccccc3)CC2)CN(c2ccccc2)C1=O ; Cl] | 2-methyl-9-(2-phenoxyethyl)-4-phenyl-1-oxa-4,9-diazaspiro[5.5]undecan-3-one hydrochloride | 4.15 | 381.2 |

-continued

| EX | Structure | Chemical name | Ret time (min) | MS (M + H) |
|---|---|---|---|---|
| 73 | 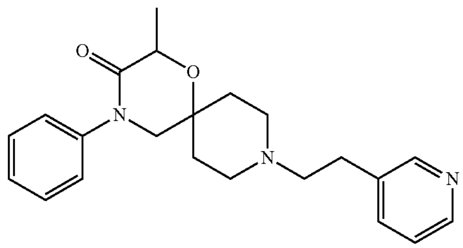 [SMILES: CC1OC2(CCN(CCc3cccnc3)CC2)CN(c2ccccc2)C1=O] | 2-methyl-4-phenyl-9-(2-(pyridin-3-yl)ethyl)-1-oxa-4,9-diazaspiro[5.5]undecan-3-one | 3.13 | 366.2 |
| 74 | 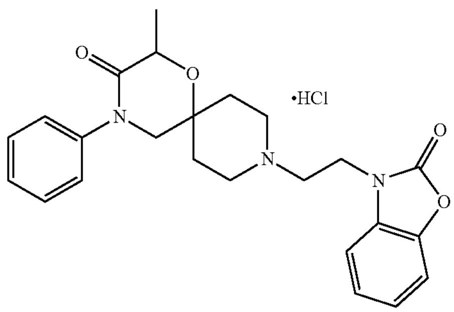 [SMILES: CC1OC2(CCN(CCn3c(=O)oc4ccccc43)CC2)CN(c2ccccc2)C1=O ; Cl] | 3-(2-(2-methyl-3-oxo-4-phenyl-1-oxa-4,9-diazaspiro[5.5]undecan-9-yl)ethyl)benzo[d]oxazol-2(3H)-one hydrochloride | 3.88 | 422.1 |
| 75 | 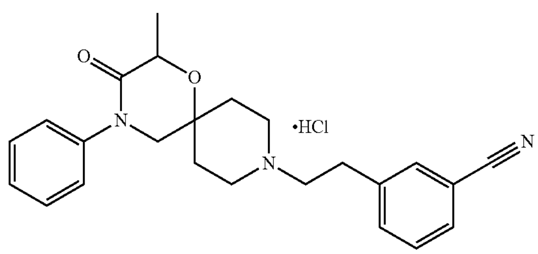 [SMILES: CC1OC2(CCN(CCc3cccc(C#N)c3)CC2)CN(c2ccccc2)C1=O ; Cl] | 3-(2-(2-methyl-3-oxo-4-phenyl-1-oxa-4,9-diazaspiro[5.5]undecan-9-yl)ethyl)benzonitrile hydrochloride | 3.95 | 390.2 |
| 76 | 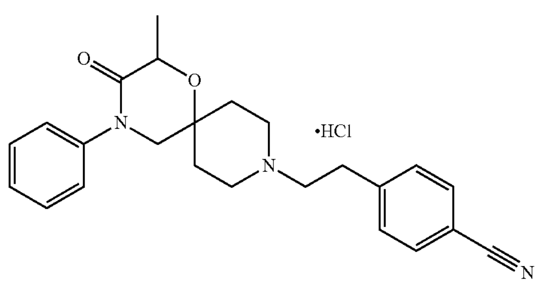 [SMILES: CC1OC2(CCN(CCc3ccc(C#N)cc3)CC2)CN(c2ccccc2)C1=O ; Cl] | 4-(2-(2-methyl-3-oxo-4-phenyl-1-oxa-4,9-diazaspiro[5.5]undecan-9-yl)ethyl)benzonitrile hydrochloride | 3.91 | 390.2 |
| 77 | 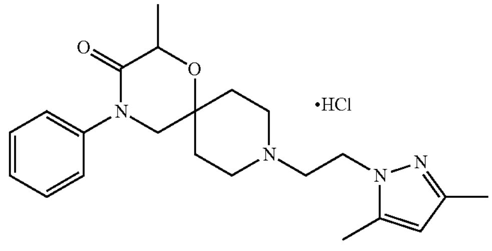 [SMILES: Cc1cc(C)n(CCN2CCC3(CC2)CN(c2ccccc2)C(=O)C(C)O3)n1 ; Cl] | 9-(2-(3,5-dimethyl-1H-pyrazol-1-yl)ethyl)-2-methyl-4-phenyl-1-oxa-4,9-diazaspiro[5.5]undecan-3-one hydrochloride | 3.47 | 383.2 |

-continued

| EX | Structure | Chemical name | Ret time (min) | MS (M + H) |
|---|---|---|---|---|
| 78 | 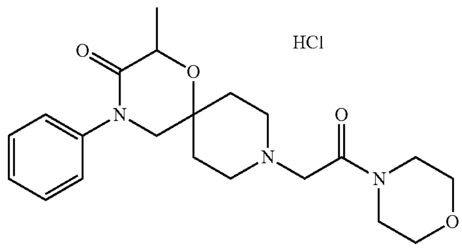 [SMILES: CC1OC2(CCN(CC(=O)N3CCOCC3)CC2)CN(c2ccccc2)C1=O ; Cl] | 2-methyl-9-(2-morpholino-2-oxoethyl)-4-phenyl-1-oxa-4,9-diazaspiro[5.5]undecan-3-one hydrochloride | 2.8 | 388.2 |
| 79 | 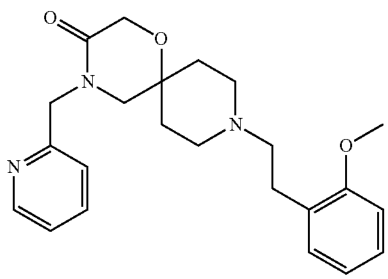 [SMILES: COc1ccccc1CCN1CCC2(CC1)CN(Cc1ccccn1)C(=O)CO2] | 9-(2-methoxyphenethyl)-4-(pyridin-2-ylmethyl)-1-oxa-4,9-diazaspiro[5.5]undecan-3-one | 3.43 | 396.2 |
| 80 | 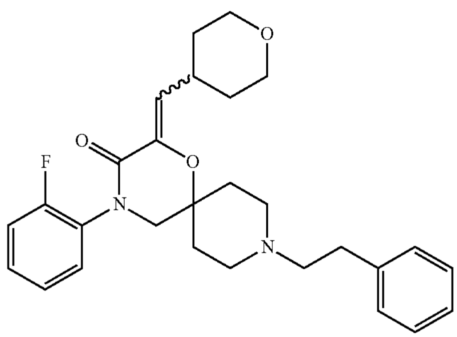 [SMILES: O=C1C(=CC2CCOCC2)OC2(CCN(CCc3ccccc3)CC2)CN1c1ccccc1F] | 4-(2-fluorophenyl)-9-phenethyl-2-((tetrahydro-2H-pyran-4-yl)methylene)-1-oxa-4,9-diazaspiro[5.5]undecan-3-one | 4.62 | 465.2 |
| 81 | 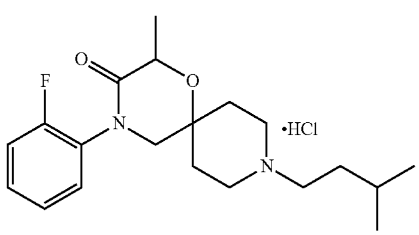 [SMILES: CC(C)CCN1CCC2(CC1)CN(c1ccccc1F)C(=O)C(C)O2 ; Cl] | 4-(2-fluorophenyl)-9-isopentyl-2-methyl-1-oxa-4,9-diazaspiro[5.5]undecan-3-one hydrochloride | 4.00 | 349.2 |
| 82 | 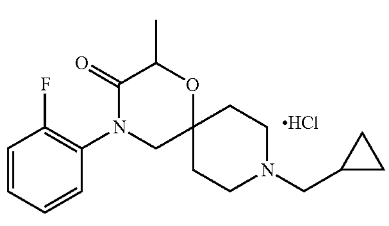 [SMILES: CC1OC2(CCN(CC3CC3)CC2)CN(c2ccccc2F)C1=O ; Cl] | 9-(cyclopropylmethyl)-4-(2-fluorophenyl)-2-methyl-1-oxa-4,9-diazaspiro[5.5]undecan-3-one hydrochloride | 3.18 | 333.2 |

-continued

| EX | Structure | Chemical name | Ret time (min) | MS (M + H) |
|---|---|---|---|---|
| 83 | 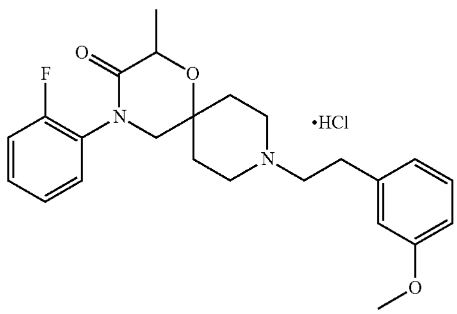 [SMILES: COc1cccc(CCN2CCC3(CC2)CN(c2ccccc2F)C(=O)C(C)O3)c1 ; Cl] | 4-(2-fluorophenyl)-9-(3-methoxyphenethyl)-2-methyl-1-oxa-4,9-diazaspiro[5.5]undecan-3-one hydrochloride | 4.21 | 413.2 |
| 84 | 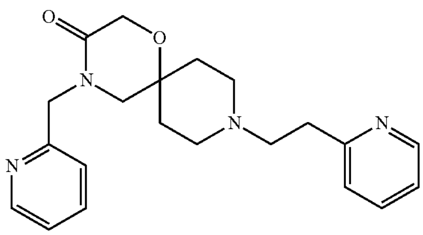 [SMILES: O=C1COC2(CCN(CCc3ccccn3)CC2)CN1Cc1ccccn1] | 9-(2-(pyridin-2-yl)ethyl)-4-(pyridin-2-ylmethyl)-1-oxa-4,9-diazaspiro[5.5]undecan-3-one | 2.54 | 367.2 |
| 85 | 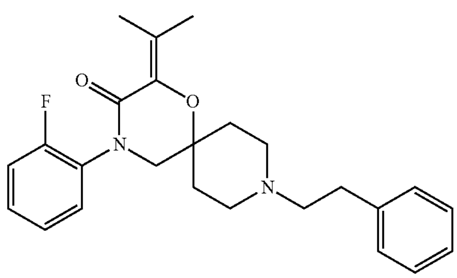 [SMILES: CC(C)=C1OC2(CCN(CCc3ccccc3)CC2)CN(c2ccccc2F)C1=O] | 4-(2-fluorophenyl)-9-phenethyl-2-(propan-2-ylidene)-1-oxa-4,9-diazaspiro[5.5]undecan-3-one | 5.11 | 409.2 |
| 86 | 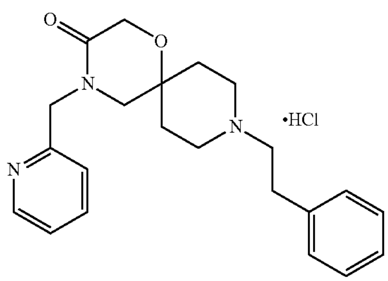 [SMILES: O=C1COC2(CCN(CCc3ccccc3)CC2)CN1Cc1ccccn1 ; Cl] | 9-phenethyl-4-(pyridin-2-ylmethyl)-1-oxa-4,9-diazaspiro[5.5]undecan-3-one hydrochloride | 3.37 | 366.2 |
| 87 | 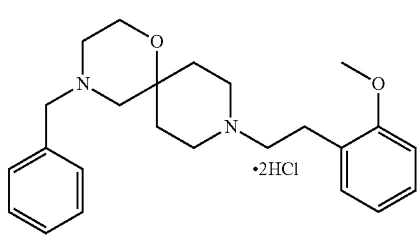 [SMILES: COc1ccccc1CCN1CCC2(CC1)CN(Cc1ccccc1)CCO2] | 4-benzyl-9-(2-methoxyphenethyl)-1-oxa-4,9-diazaspiro[5.5]undecane dihydrochloride | 4.80 | 381.2 |

-continued

| EX | Structure | Chemical name | Ret time (min) | MS (M + H) |
|----|-----------|---------------|----------------|------------|
| 88 | 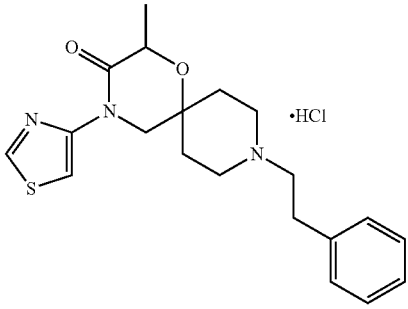 [SMILES: CC1OC2(CCN(CCc3ccccc3)CC2)CN(c2cscn2)C1=O ; Cl] | 2-methyl-9-phenethyl-4-(thiazol-4-yl)-1-oxa-4,9-diazaspiro[5.5]undecan-3-one hydrochloride | 4.04 | 372.1 |
| 89 | 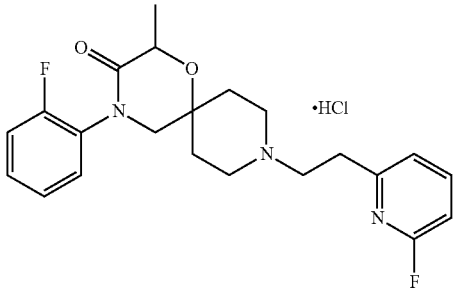 [SMILES: CC1OC2(CCN(CCc3cccc(F)n3)CC2)CN(c2ccccc2F)C1=O ; Cl] | 4-(2-fluorophenyl)-9-(2-(6-fluoropyridin-2-yl)ethyl)-2-methyl-1-oxa-4,9-diazaspiro[5.5]undecan-3-one hydrochloride | 3.60 | 402.2 |
| 90 | 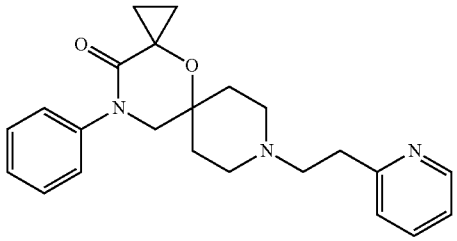 [SMILES: O=C1N(c2ccccc2)CC2(CCN(CCc3ccccn3)CC2)OC12CC2] | 12-phenyl-8-[2-(pyridin-2-yl)ethyl]-4-oxa-8,12-diazaspiro[2.1.5.3]tridecan-13-one | 3.29 | 378.2 |
| 91 | 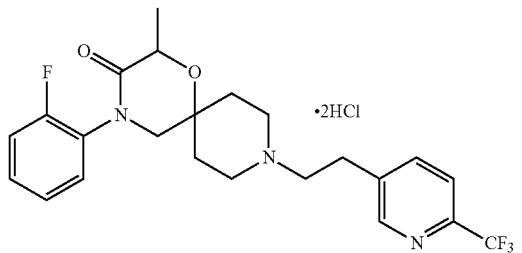 [SMILES: CC1OC2(CCN(CCc3ccc(C(F)(F)F)nc3)CC2)CN(c2ccccc2F)C1=O ; "·2HCl"] | 4-(2-fluorophenyl)-2-methyl-9-(2-(6-(trifluoromethyl)pyridin-3-yl)ethyl)-1-oxa-4,9-diazaspiro[5.5]undecan-3-one dihydrochloride | 4.18 | 452.2 |
| 92 | 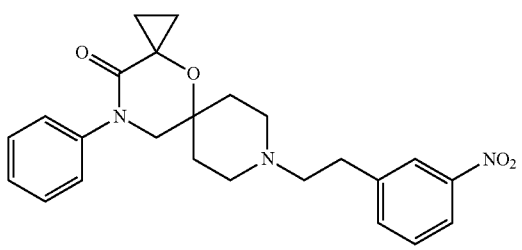 [SMILES: O=C1N(c2ccccc2)CC2(CCN(CCc3cccc([N+](=O)[O-])c3)CC2)OC12CC2] | 8-(3-nitrophenethyl)-12-phenyl-4-oxa-8,12-diazaspiro[2.1.5.3]tridecan-13-one | 4.36 | 422.2 |

-continued

| EX | Structure | Chemical name | Ret time (min) | MS (M + H) |
|---|---|---|---|---|
| 93 | 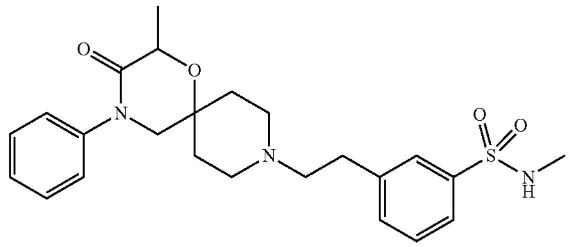 [SMILES: CNS(=O)(=O)c1cccc(CCN2CCC3(CC2)CN(c2ccccc2)C(=O)C(C)O3)c1] | N-methyl-3-(2-(2-methyl-3-oxo-4-phenyl-1-oxa-4,9-diazaspiro[5.5]undecan-9-yl)ethyl)benzenesulfonamide | 3.46 | 458.2 |
| 94 | 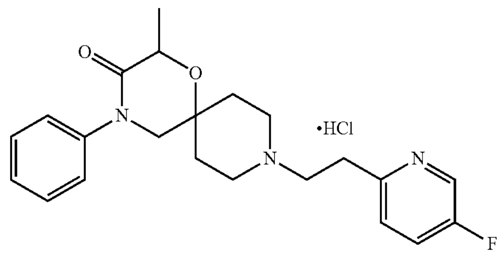 [SMILES: CC1OC2(CCN(CCc3ccc(F)cn3)CC2)CN(c2ccccc2)C1=O ; Cl] | 9-(2-(5-fluoropyridin-2-yl)ethyl)-2-methyl-4-phenyl-1-oxa-4,9-diazaspiro[5.5]undecan-3-one hydrochloride | 3.29 | 384.1 |
| 95 | 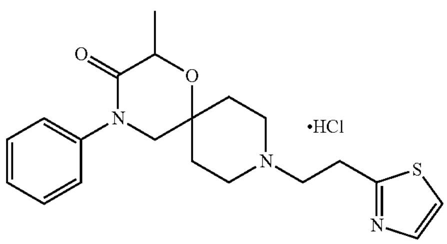 [SMILES: CC1OC2(CCN(CCc3nccs3)CC2)CN(c2ccccc2)C1=O ; Cl] | 2-methyl-4-phenyl-9-(2-(thiazol-2-yl)ethyl)-1-oxa-4,9-diazaspiro[5.5]undecan-3-one hydrochloride | 3.32 | 372.1 |
| 96 | 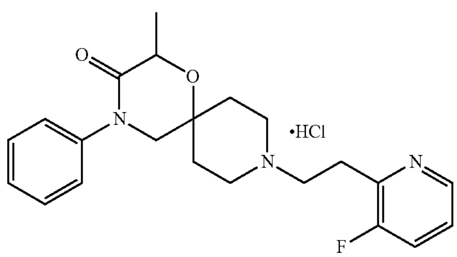 [SMILES: CC1OC2(CCN(CCc3ncccc3F)CC2)CN(c2ccccc2)C1=O ; Cl] | 9-(2-(3-fluoropyridin-2-yl)ethyl)-2-methyl-4-phenyl-1-oxa-4,9-diazaspiro[5.5]undecan-3-one hydrochloride | 3.42 | 384.2 |
| 97 | 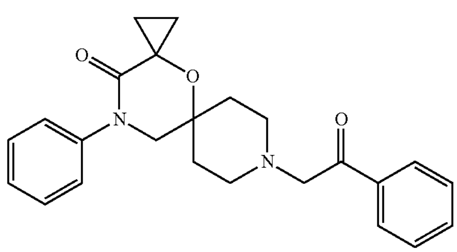 [SMILES: O=C(CN1CCC2(CC1)CN(c1ccccc1)C(=O)C1(CC1)O2)c1ccccc1] | 8-(2-oxo-2-phenylethyl)-12-phenyl-4-oxa-8,12-diazadispiro[2.1.5.3]tridecan-13-one | 3.91 | 391.1 |
| 98 | 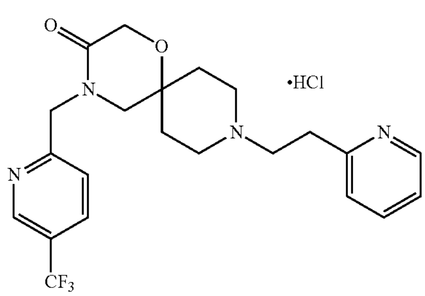 [SMILES: O=C1COC2(CCN(CCc3ccccn3)CC2)CN1Cc1ccc(C(F)(F)F)cn1 ; Cl] | 9-(2-(pyridin-2-yl)ethyl)-4-((5-(trifluoromethyl)pyridin-2-yl)methyl)-1-oxa-4,9-diazaspiro[5.5]undecan-3-one hydrochloride | 3.19 | 435.1 |

-continued

| EX | Structure | Chemical name | Ret time (min) | MS (M + H) |
|---|---|---|---|---|
| 99 | 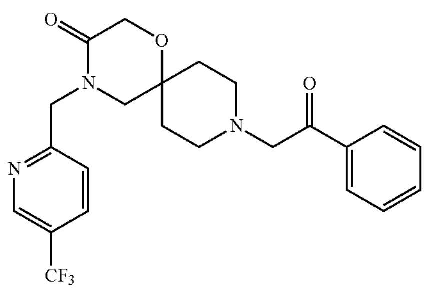 [SMILES: O=C(CN1CCC2(CC1)CN(Cc1ccc(C(F)(F)F)cn1)C(=O)CO2)c1ccccc1] | 9-(2-oxo-2-phenylethyl)-4-((5-(trifluoromethyl)pyridin-2-yl)methyl)-1-oxa-4,9-diazaspiro[5.5]undecan-3-one | 3.87 | 448.1 |
| 100 | •HCl | N-methyl-3-(2-methyl-3-oxo-4-phenyl-1-oxa-4,9-diazaspiro[5.5]undecan-9-yl)-N-phenylpropanamide hydrochloride | 3.47 | 422.2 |
| 101 | •HCl | 2-methyl-9-(2-(pyridin-2-yl)ethyl)-4-(4-(trifluoromethyl)pyridin-3-yl)-1-oxa-4,9-diazaspiro[5.5]undecan-3-one hydrochloride | 3.22 | 435.2 |
| 102 | •HCl | 9-(2-(6-methoxypyridin-2-yl)ethyl)-2-methyl-4-phenyl-1-oxa-4,9-diazaspiro[5.5]undecan-3-one hydrochloride | 3.77 | 396.2 |
| 103 | 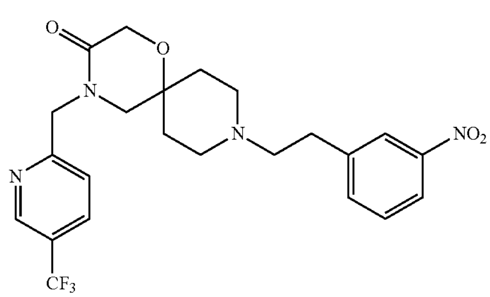 [SMILES: O=C1COC2(CCN(CCc3cccc([N+](=O)[O-])c3)CC2)CN1Cc1ccc(C(F)(F)F)cn1] | 9-(3-nitrophenethyl)-4-((5-(trifluoromethyl)pyridin-2-yl)methyl)-1-oxa-4,9-diazaspiro[5.5]undecan-3-one | 4.19 | 479.1 |

| EX | Structure | Chemical name | Ret time (min) | MS (M + H) |
|---|---|---|---|---|
| 104 | 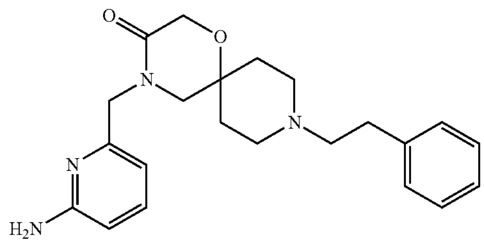 [SMILES: Nc1cccc(CN2CC3(CCN(CCc4ccccc4)CC3)OCC2=O)n1] | 4-((6-aminopyridin-2-yl)methyl)-9-phenethyl-1-oxa-4,9-diazaspiro[5.5]undecan-3-one | 3.27 | 381.2 |
| 105 | 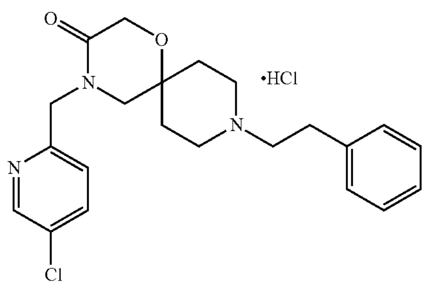 [SMILES: O=C1COC2(CCN(CCc3ccccc3)CC2)CN1Cc1ccc(Cl)cn1 ; Cl] | 4-((5-chloropyridin-2-yl)methyl)-9-phenethyl-1-oxa-4,9-diazaspiro[5.5]undecan-3-one hydrochloride | 3.93 | 400.1 |
| 106 | 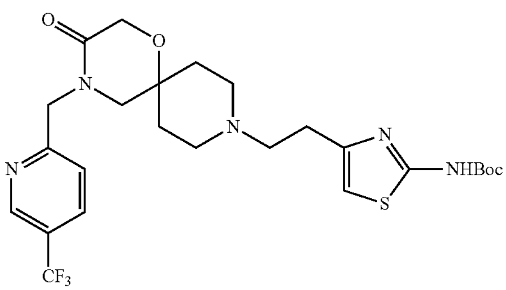 [SMILES: CC(C)(C)OC(=O)Nc1nc(CCN2CCC3(CC2)CN(Cc2ccc(C(F)(F)F)cn2)C(=O)CO3)cs1] | tert-butyl (4-(2-(3-oxo-4-((5-(trifluoromethyl)pyridin-2-yl)methyl)-1-oxa-4,9-diazaspiro[5.5]undecan-9-yl)ethyl)thiazol-2-yl)carbamate | 4.100 | 556.2 |
| 107 | 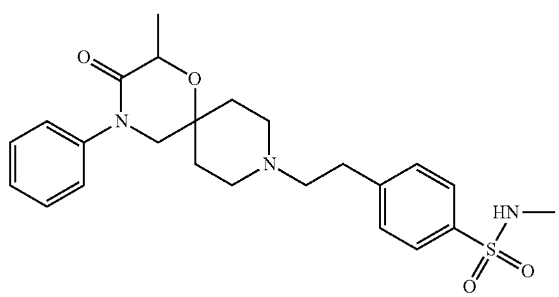 [SMILES: CNS(=O)(=O)c1ccc(CCN2CCC3(CC2)CN(c2ccccc2)C(=O)C(C)O3)cc1] | N-methyl-4-(2-(2-methyl-3-oxo-4-phenyl-1-oxa-4,9-diazaspiro[5.5]undecan-9-yl)ethyl)benzenesulfonamide | 3.39 | 458.0 |
| 108 | 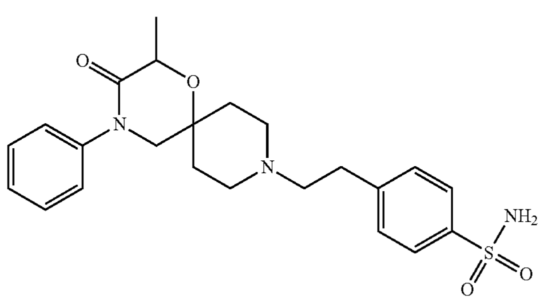 [SMILES: CC1OC2(CCN(CCc3ccc(S(N)(=O)=O)cc3)CC2)CN(c2ccccc2)C1=O] | 4-(2-(2-methyl-3-oxo-4-phenyl-1-oxa-4,9-diazaspiro[5.5]undecan-9-yl)ethyl)benzenesulfonamide | 3.17 | 444 |

| EX | Structure | Chemical name | Ret time (min) | MS (M + H) |
|----|-----------|---------------|----------------|------------|
| 109 | 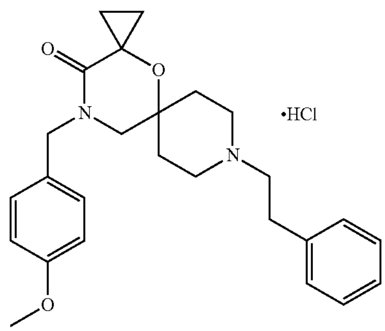 [SMILES: COc1ccc(CN2CC3(CCN(CCc4ccccc4)CC3)OC3(CC3)C2=O)cc1 ; Cl] | 12-(4-methoxybenzyl)-8-phenethyl-4-oxa-8,12-diazadispiro[2.1.5.3]tridecan-13-one hydrochloride | 4.55 | 421.1 |
| 110 | 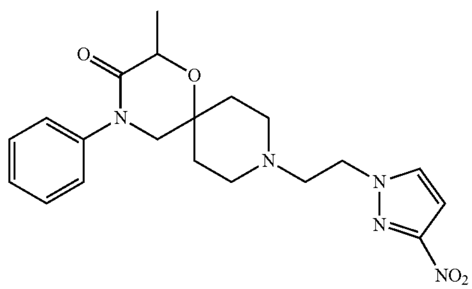 [SMILES: CC1OC2(CCN(CCn3ccc([N+](=O)[O-])n3)CC2)CN(c2ccccc2)C1=O] | 2-methyl-9-(2-(3-nitro-1H-pyrazol-1-yl)ethyl)-4-phenyl-1-oxa-4,9-diazaspiro[5.5]undecan-3-one | 3.49 | 400 |
| 111 | 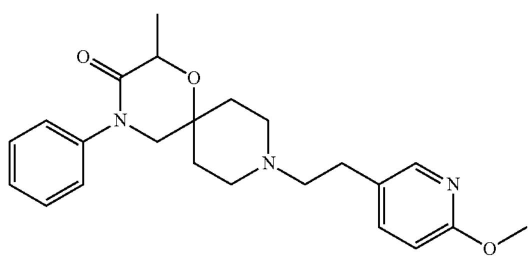 [SMILES: COc1ccc(CCN2CCC3(CC2)CN(c2ccccc2)C(=O)C(C)O3)cn1] | 9-(2-(6-methoxypyridin-3-yl)ethyl)-2-methyl-4-phenyl-1-oxa-4,9-diazaspiro[5.5]undecan-3-one | 3.64 | 396.2 |
| 112 | 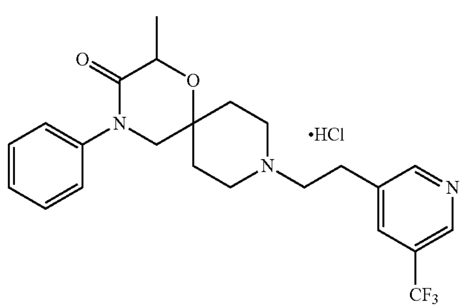 [SMILES: CC1OC2(CCN(CCc3cncc(C(F)(F)F)c3)CC2)CN(c2ccccc2)C1=O ; Cl] | 2-methyl-4-phenyl-9-(2-(5-(trifluoromethyl)pyridin-3-yl)ethyl)-1-oxa-4,9-diazaspiro[5.5]undecan-3-one hydrochloride | 4.01 | 434.2 |
| 113 | 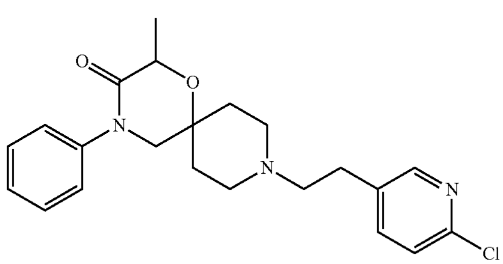 [SMILES: CC1OC2(CCN(CCc3ccc(Cl)nc3)CC2)CN(c2ccccc2)C1=O] | 9-(2-(6-chloropyridin-3-yl)ethyl)-2-methyl-4-phenyl-1-oxa-4,9-diazaspiro[5.5]undecan-3-one | 3.72 | 400.1 |

| EX | Structure | Chemical name | Ret time (min) | MS (M + H) |
|---|---|---|---|---|
| 114 | 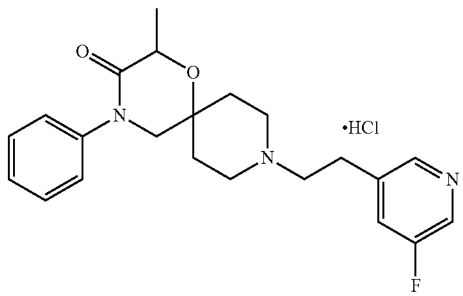 [SMILES: CC1OC2(CCN(CCc3cncc(F)c3)CC2)CN(c2ccccc2)C1=O ; Cl] | 9-(2-(5-fluoropyridin-3-yl)ethyl)-2-methyl-4-phenyl-1-oxa-4,9-diazaspiro[5.5]undecan-3-one hydrochloride | 3.42 | 384.2 |
| 115 | 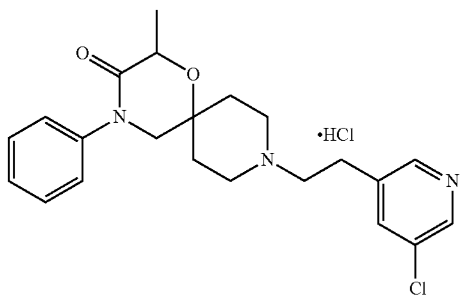 [SMILES: CC1OC2(CCN(CCc3cncc(Cl)c3)CC2)CN(c2ccccc2)C1=O ; Cl] | 9-(2-(5-chloropyridin-3-yl)ethyl)-2-methyl-4-phenyl-1-oxa-4,9-diazaspiro[5.5]undecan-3-one hydrochloride | 3.27 | 400.2 |
| 116 | 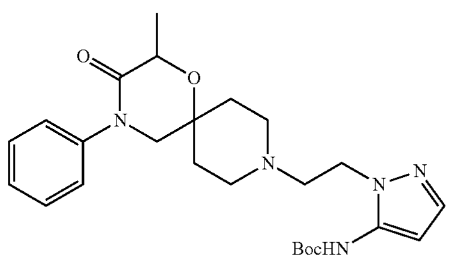 [SMILES: CC1OC2(CCN(CCn3nccc3NC(=O)OC(C)(C)C)CC2)CN(c2ccccc2)C1=O] | tert-butyl (1-(2-(2-methyl-3-oxo-4-phenyl-1-oxa-4,9-diazaspiro[5.5]undecan-9-yl)ethyl)-1H-pyrazol-5-yl)carbamate | 4.63 | 470.1 |
| 117 | 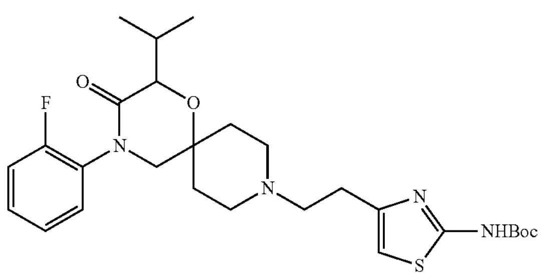 [SMILES: CC(C)C1OC2(CCN(CCc3csc(NC(=O)OC(C)(C)C)n3)CC2)CN(c2ccccc2F)C1=O] | tert-butyl (4-(2-(4-(2-fluorophenyl)-2-isopropyl-3-oxo-1-oxa-4,9-diazaspiro[5.5]undecan-9-yl)ethyl)thiazol-2-yl)carbamate | 4.86 | 533.3 |
| 118 | 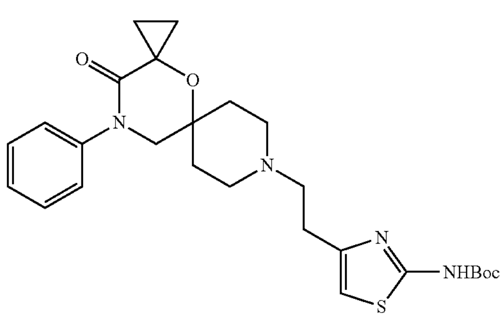 [SMILES: CC(C)(C)OC(=O)Nc1nc(CCN2CCC3(CC2)CN(c2ccccc2)C(=O)C2(CC2)O3)cs1] | tert-butyl (4-(2-(13-oxo-12-phenyl-4-oxa-8,12-diazadispiro[2.1.5.3]tridecan-8-yl)ethyl)thiazol-2-yl)carbamate | 4.30 | 499.2 |

| EX | Structure | Chemical name | Ret time (min) | MS (M + H) |
|---|---|---|---|---|
| 119 | 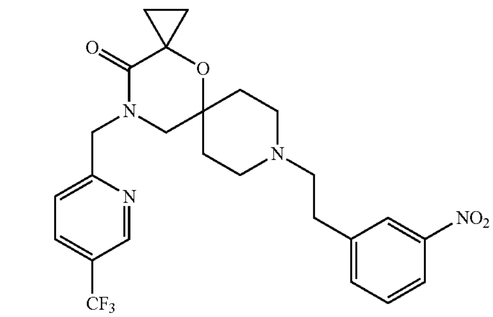 | 8-(3-nitrophenethyl)-12-{[5-(trifluoromethyl)pyridin-2-yl]methyl}-4-oxa-8,12-diazadispiro[2.1.5.3]tridecan-13-one | 4.59 | 505.2 |
| 120 | 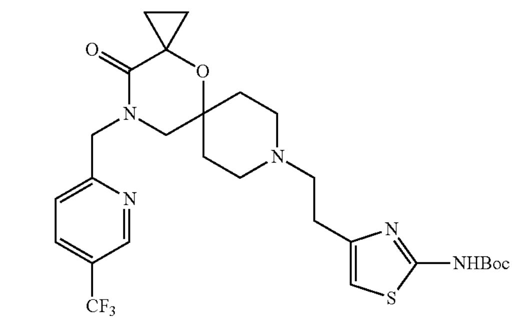 [SMILES: CC(C)(C)OC(=O)Nc1nc(CCN2CCC3(CC2)CN(Cc2ccc(C(F)(F)F)cn2)C(=O)C2(CC2)O3)cs1] | tert-butyl (4-(2-(13-oxo-12-{[5-(trifluoromethyl)pyridin-2-yl]methyl}-4-oxa-8,12-diazadispiro[2.1.5.3]tridecan-8-yl)ethyl)thiazol-2-yl)carbamate | 4.51 | 582.2 |
| 121 | 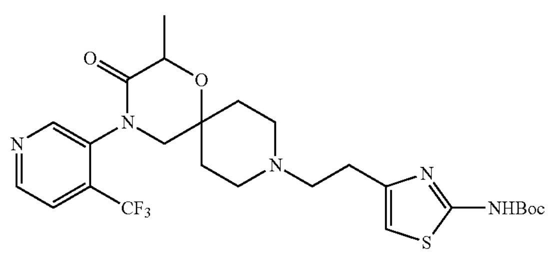 [SMILES: CC1OC2(CCN(CCc3csc(NC(=O)OC(C)(C)C)n3)CC2)CN(c2cnccc2C(F)(F)F)C1=O] | tert-butyl (4-(2-(2-methyl-3-oxo-4-(4-(trifluoromethyl)pyridin-3-yl)-1-oxa-4,9-diazaspiro[5.5]undecan-9-yl)ethyl)thiazol-2-yl)carbamate | 4.19 | 556.2 |
| 122 | 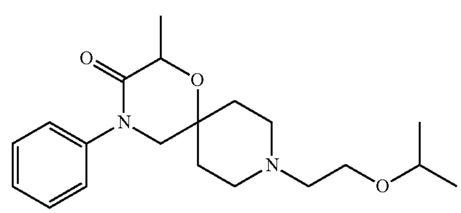 [SMILES: CC(C)OCCN1CCC2(CC1)CN(c1ccccc1)C(=O)C(C)O2] | 9-(2-isopropoxyethyl)-2-methyl-4-phenyl-1-oxa-4,9-diazaspiro[5.5]undecan-3-one | 3.47 | 347.2 |
| 123 | 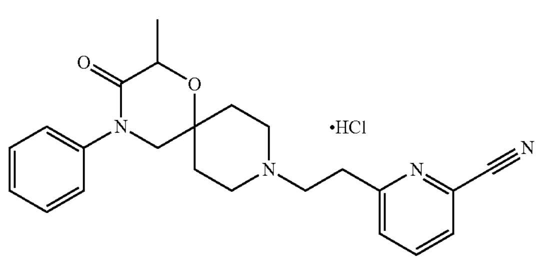 [SMILES: CC1OC2(CCN(CCc3cccc(C#N)n3)CC2)CN(c2ccccc2)C1=O ; Cl] | 6-(2-(2-methyl-3-oxo-4-phenyl-1-oxa-4,9-diazaspiro[5.5]undecan-9-yl)ethyl)picolinonitrile hydrochloride | 3.47 | 391.1 |

-continued

| EX | Structure | Chemical name | Ret time (min) | MS (M + H) |
|---|---|---|---|---|
| 124 | 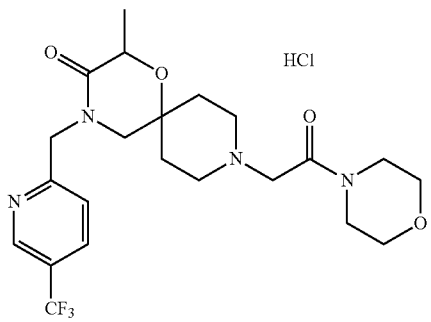 [SMILES: CC1OC2(CCN(CC(=O)N3CCOCC3)CC2)CN(Cc2ccc(C(F)(F)F)cn2)C1=O ; Cl] | 2-methyl-9-(2-morpholino-2-oxoethyl)-4-((5-(trifluoromethyl)pyridin-2-yl)methyl)-1-oxa-4,9-diazaspiro[5.5]undecan-3-one hydrochloride | 3.17 | 471.2 |
| 125 | 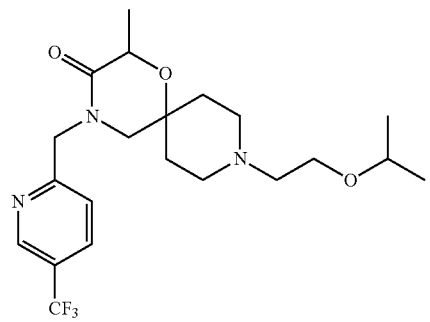 [SMILES: CC(C)OCCN1CCC2(CC1)CN(Cc1ccc(C(F)(F)F)cn1)C(=O)C(C)O2] | 9-(2-isopropoxyethyl)-2-methyl-4-((5-(trifluoromethyl)pyridin-2-yl)methyl)-1-oxa-4,9-diazaspiro[5.5]undecan-3-one | 3.81 | 430.2 |
| 126 | 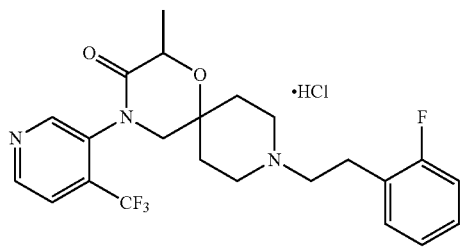 [SMILES: CC1OC2(CCN(CCc3ccccc3F)CC2)CN(c2cnccc2C(F)(F)F)C1=O ; Cl] | 9-(2-fluorophenethyl)-2-methyl-4-(4-(trifluoromethyl)pyridin-3-yl)-1-oxa-4,9-diazaspiro[5.5]undecan-3-one hydrochloride (5*) | 4.35 | 452.2 |
| 127a | 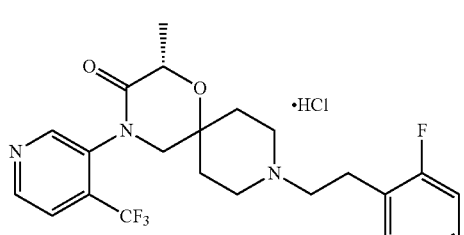 | (S)-9-(2-fluorophenethyl)-2-methyl-4-(4-(trifluoromethyl)pyridin-3-yl)-1-oxa-4,9-diazaspiro[5.5]undecan-3-one hydrochloride (6*) | 4.22 | 452.2 |
| 127b | 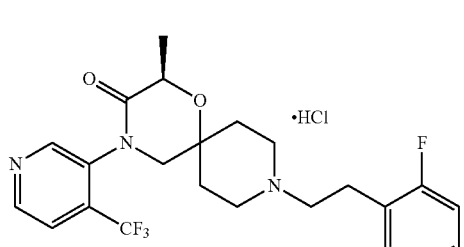 | (R)-9-(2-fluorophenethyl)-2-methyl-4-(4-(trifluoromethyl)pyridin-3-yl)-1-oxa-4,9-diazaspiro[5.5]undecan-3-one hydrochloride (6*) | 4.22 | 452.2 |

-continued

| EX | Structure | Chemical name | Ret time (min) | MS (M + H) |
|---|---|---|---|---|
| 128 | 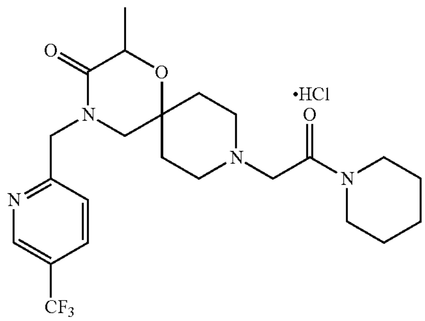 [SMILES: CC1OC2(CCN(CC(=O)N3CCCCC3)CC2)CN(Cc2ccc(C(F)(F)F)cn2)C1=O ; Cl] | 2-methyl-9-(2-oxo-2-(piperidin-1-yl)ethyl)-4-((5-(trifluoromethyl)pyridin-2-yl)methyl)-1-oxa-4,9-diazaspiro[5.5]undecan-3-one hydrochloride | 3.79 | 469.2 |
| 129 | 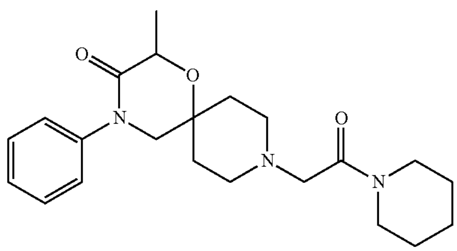 [SMILES: CC1OC2(CCN(CC(=O)N3CCCCC3)CC2)CN(c2ccccc2)C1=O] | 2-methyl-9-(2-oxo-2-(piperidin-1-yl)ethyl)-4-phenyl-1-oxa-4,9-diazaspiro[5.5]undecan-3-one | 3.49 | 386.2 |
| 130 | 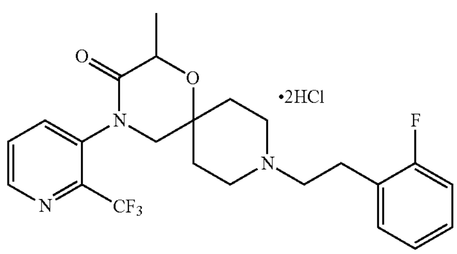 [SMILES: CC1OC2(CCN(CCc3ccccc3F)CC2)CN(c2cccnc2C(F)(F)F)C1=O] | 9-(2-fluorophenethyl)-2-methyl-4-(2-(trifluoromethyl)pyridin-3-yl)-1-oxa-4,9-diazaspiro[5.5]undecan-3-one dihydrochloride | 4.41 | 452.2 |
| 131 | 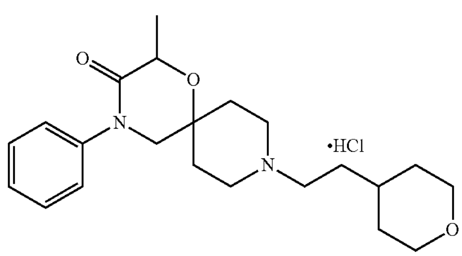 [SMILES: CC1OC2(CCN(CCC3CCOCC3)CC2)CN(c2ccccc2)C1=O ; Cl] | 2-methyl-4-phenyl-9-(2-(tetrahydro-2H-pyran-4-yl)ethyl)-1-oxa-4,9-dizaspiro[5.5]undecan-3-one hydrochloride (1*) | 3.17 | 373.2 |
| 132 | 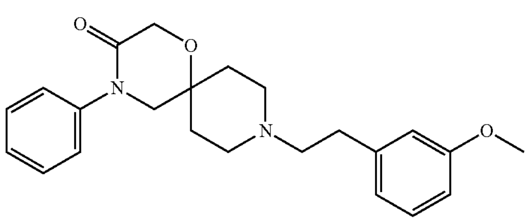 [SMILES: COc1cccc(CCN2CCC3(CC2)CN(c2ccccc2)C(=O)CO3)c1] | 9-(3-methoxyphenethyl)-4-phenyl-1-oxa-4,9-diazaspiro[5.5]undecan-3-one (2*) | 3.75 | 381.2 |
| 133 | 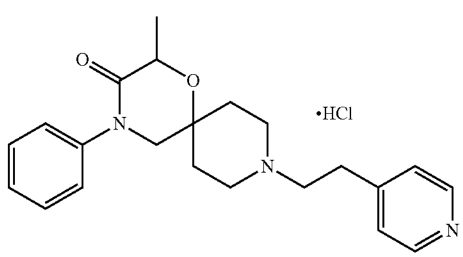 [SMILES: CC1OC2(CCN(CCc3ccncc3)CC2)CN(c2ccccc2)C1=O ; Cl] | 2-methyl-4-phenyl-9-(2-(pyridin-4-yl)ethyl)-1-oxa-4,9-diazaspiro[5.5]undecan-3-one hydrochloride (2*) | 3.10 | 366.1 |

-continued

| EX | Structure | Chemical name | Ret time (min) | MS (M + H) |
|---|---|---|---|---|
| 134 | 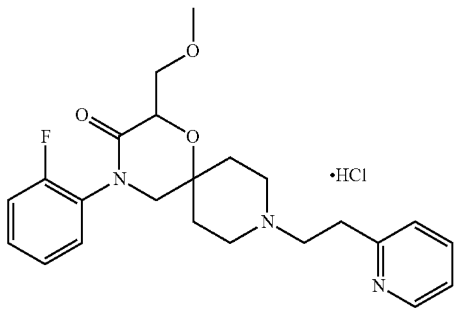 [SMILES: COCC1OC2(CCN(CCc3ccccn3)CC2)CN(c2ccccc2F)C1=O ; Cl] | 4-(2-fluorophenyl)-2-(methoxymethyl)-9-(2-(pyridin-2-yl)ethyl)-1-oxa-4,9-diazaspiro[5.5]undecan-3-one hydrochloride (3*) | 3.09 | 414.2 |
| 135 | 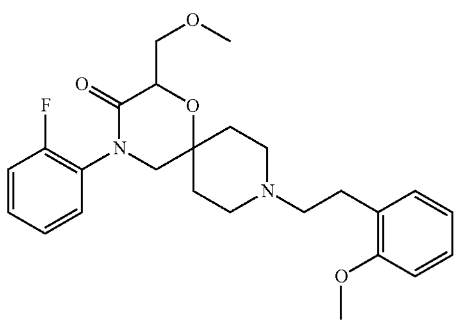 [SMILES: COCC1OC2(CCN(CCc3ccccc3OC)CC2)CN(c2ccccc2F)C1=O] | 4-(2-fluorophenyl)-2-(methoxymethyl)-9-(2-methoxyphenethyl)-1-oxa-4,9-diazaspiro[5.5]undecan-3-one (3*) | 4.09 | 443.2 |
| 136 | 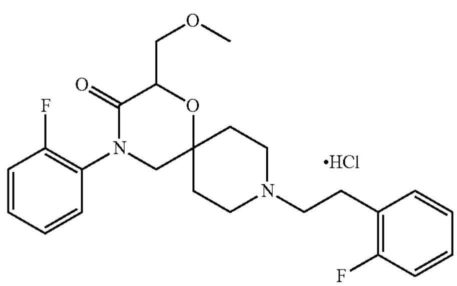 [SMILES: COCC1OC2(CCN(CCc3ccccc3F)CC2)CN(c2ccccc2F)C1=O ; Cl] | 9-(2-fluorophenethyl)-4-(2-fluorophenyl)-2-(methoxymethyl)-1-oxa-4,9-diazaspiro[5.5]undecan-3-one hydrochloride (3*) | 4.17 | 431.2 |
| 137 | 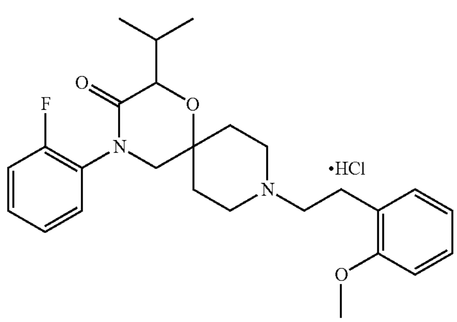 [SMILES: COc1ccccc1CCN1CCC2(CC1)CN(c1ccccc1F)C(=O)C(C(C)C)O2 ; Cl] | 4-(2-fluorophenyl)-2-isopropyl-9-(2-methoxyphenethyl)-1-oxa-4,9-diazaspiro[5.5]undecan-3-one hydrochloride (3*) | 5.04 | 441.2 |
| 138 | 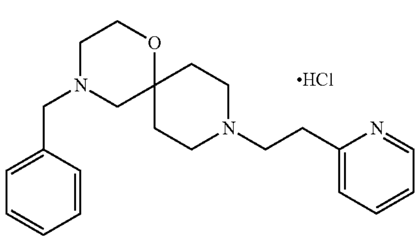 [SMILES: c1ccc(CN2CCOC3(CCN(CCc4ccccn4)CC3)C2)cc1 ; Cl] | 4-benzyl-9-(2-(pyridin-2-yl)ethyl)-1-oxa-4,9-diazaspiro[5.5]undecane hydrochloride (3*) | 3.78 | 352.2 |

| EX | Structure | Chemical name | Ret time (min) | MS (M + H) |
|---|---|---|---|---|
| 139 | 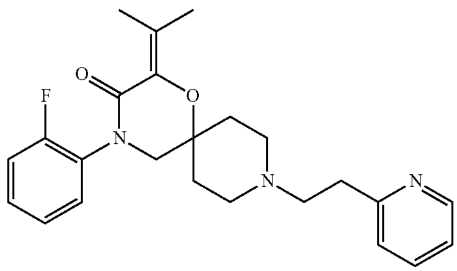 [SMILES: CC(C)=C1OC2(CCN(CCc3ccccn3)CC2)CN(c2ccccc2F)C1=O] | 4-(2-fluorophenyl)-2-(propan-2-ylidene)-9-(2-(pyridin-2-yl)ethyl-1-oxa-4,9-diazaspiro[5.5]undecan-3-one (3*) | 3.99 | 410.1 |
| 140 | 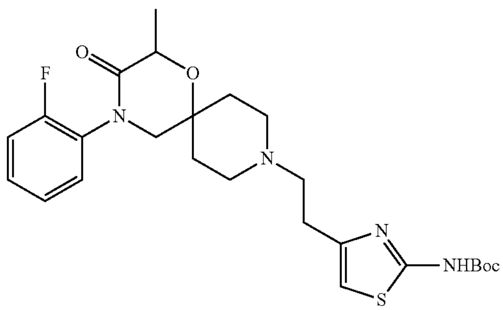 [SMILES: CC1OC2(CCN(CCc3csc(NC(=O)OC(C)(C)C)n3)CC2)CN(c2ccccc2F)C1=O] | tert-butyl (4-(2-(4-(2-fluorophenyl)-2-methyl-3-oxo-1-oxa-4,9-diazaspiro[5.5]undecan-9-yl)ethyl)thiazol-2-yl)carbamate (3*) | 4.22 | 505.2 |
| 141 | 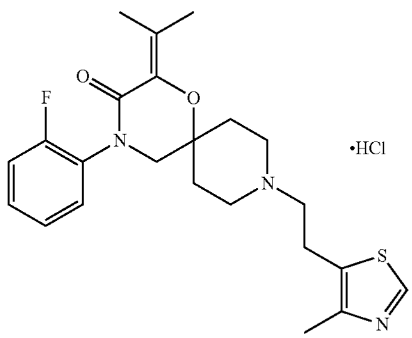 [SMILES: CC(C)=C1OC2(CCN(CCc3scnc3C)CC2)CN(c2ccccc2F)C1=O ; Cl] | 4-(2-fluorophenyl)-9-(2-(4-methylthiazol-5-yl)ethyl)-2-(propan-2-ylidene)-1-oxa-4,9-diazaspiro[5.5]undecan-3-one hydrochloride (3*) | 4.30 | 430.2 |
| 142 | 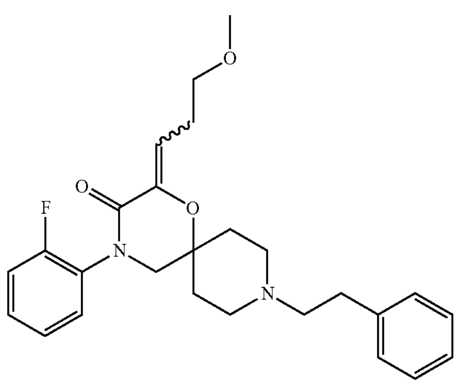 [SMILES: COCCC=C1OC2(CCN(CCc3ccccc3)CC2)CN(c2ccccc2F)C1=O] | 4-(2-fluorophenyl)-2-(3-methoxypropylidene)-9-phenethyl-1-oxa-4,9-diazaspiro[5.5]undecan-3-one (3*) | 4.53 | 439.2 |
| 143 | 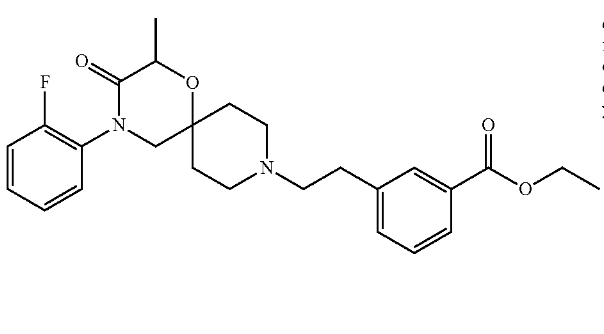 [SMILES: CCOC(=O)c1cccc(CCN2CCC3(CC2)CN(c2ccccc2F)C(=O)C(C)O3)c1] | ethyl 3-(2-(4-(2-fluorophenyl)-2-methyl-3-oxo-1-oxa-4,9-diazaspiro[5.5]undecan-9-yl)ethyl)benzoate (3*) | 4.53 | 455.2 |

| EX | Structure | Chemical name | Ret time (min) | MS (M + H) |
|---|---|---|---|---|
| 144 | 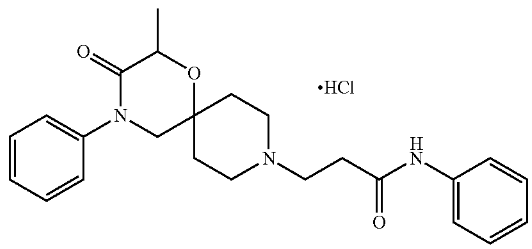 [SMILES: CC1OC2(CCN(CCC(=O)Nc3ccccc3)CC2)CN(c2ccccc2)C1=O ; Cl] | 3-(2-methyl-3-oxo-4-phenyl-1-oxa-4,9-diazaspiro[5.5]undecan-9-yl)-N-phenylpropanamide hydrochloride (3*) (4*) | 3.57 | 408.2 |
| 145 | 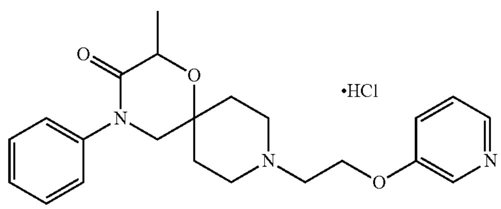 [SMILES: CC1OC2(CCN(CCOc3cccnc3)CC2)CN(c2ccccc2)C1=O ; Cl] | 2-methyl-4-phenyl-9-(2-(pyridin-3-yloxy)ethyl)-1-oxa-4,9-diazaspiro[5.5]undecan-3-one hydrochloride (3*) (4*) | 3.18 | 382.2 |
| 146 | 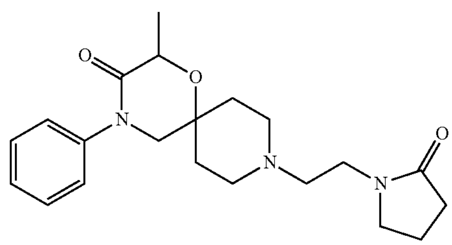 [SMILES: CC1OC2(CCN(CCN3CCCC3=O)CC2)CN(c2ccccc2)C1=O] | 2-methyl-9-(2-(2-oxopyrrolidin-1-yl)ethyl)-4-phenyl-1-oxa-4,9-diazaspiro[5.5]undecan-3-one (3*) (4*) | 2.79 | 372.2 |
| 147 | 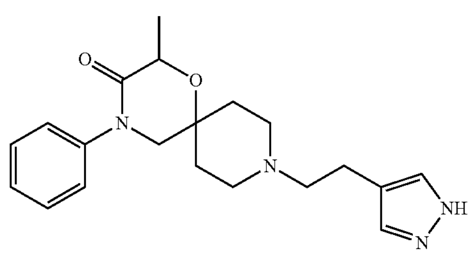 [SMILES: CC1OC2(CCN(CCc3cn[nH]c3)CC2)CN(c2ccccc2)C1=O] | 9-(2-(1H-pyrazol-4-yl)ethyl)-2-methyl-4-phenyl-1-oxa-4,9-diazaspiro[5.5]undecan-3-one (3*) (4*) | 2.74 | 355.2 |
| 148 | 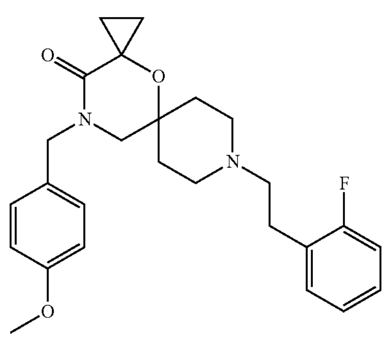 [SMILES: COc1ccc(CN2CC3(CCN(CCc4ccccc4F)CC3)OC3(CC3)C2=O)cc1] | 8-(2-fluorophenethyl)-12-(4-methoxybenzyl)-4-oxa-8,12-diazadispiro[2.1.5.3]tridecan-13-one | 4.64 | 439.2 |

Where indicated, the hydrochloride salts were prepared as described in example 1.

1*. Dioxane was used instead of ACN.
2*. DMF was used instead of ACN.
3*. DIPEA was used instead of triethylamine.
4*. Dichloromethane was used instead of ACN.
5* Alternatively obtained following the method described in Example 218
6* Obtained by chiral preparative HPLC from previous example: Column: Chiralpak ASH; Temperature: ambient; Flow: 0.8 mL/min; Mobile phase: n-Heptane/(EtOH + 0.33% DEA) 85/15 v/v

Example 149: 2-phenethyl-9-phenyl-6-oxa-2,9-diazaspiro[4.5]decan-8-one hydrochloride

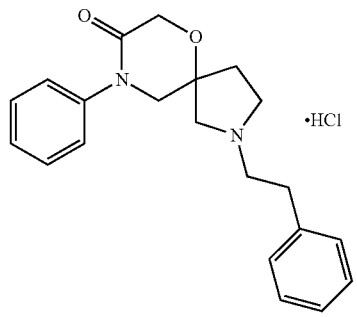 [SMILES: O=C1COC2(CCN(CCc3ccccc3)C2)CN1c1ccccc1 ; Cl]

Step 1: 9-phenyl-6-oxa-2,9-diazaspiro[4.5]decan-8-one: A mixture of example 7 (0.124 g, 0.385 mmol) and palladium (12 mg, 10% wt on charcoal) in methanol (10 mL) was stirred at r.t. under 3 bars of $H_2$ for 3 days. The solids were filtered off and the solvent was removed under vacuum. The residue was submitted to a second hydrogenation cycle, using fresh catalyst and a drop of AcOH, stirring the mixture at r.t. under 3 bars of $H_2$ overnight. The solids were filtered off and the solvent was removed under vacuum, to give the title compound as a crude product that was used without further purification (96 mg). HPLC retention time: 1.16 min; MS: 233.2 (M+H).

Step 2: Title compound: A mixture of the crude product obtained in step 1 (95 mg, 0.385 mmol), (2-bromoethyl)benzene (0.056 mL, 0.41 mmol), and DIPEA (0.184 mL, 1.06 mmol) in 1,4-dioxane (3 mL) was heated at 95° C. in a sealed tube overnight. Water was added, and the reaction mixture was extracted with ethyl acetate. The organic phases were combined, washed with brine, dried over $MgSO_4$, filtered and concentrated to dryness. The residue was purified by flash chromatography, silica gel, gradient dichloromethane to methanol:dichloromethane (1:4) to give the title compound as its free base (23 mg, 18% yield for the 2 steps).

The previous compound was converted to its hydrochloride salt as described in example 1.

HPLC retention time: 3.90 min; MS: 337.1 (M+H).

Example 150: 9-(2-hydroxy-2-phenylethyl)-2-methyl-4-phenyl-1-oxa-4,9-diazaspiro[5.5]undecan-3-one

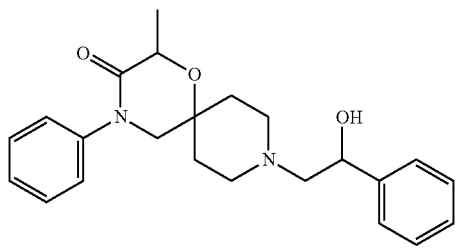 [SMILES: CC1OC2(CCN(CC(O)c3ccccc3)CC2)CN(c2ccccc2)C1=O]

A mixture of the crude product obtained in step 2 of example 23 (0.200 g, 0.768 mmol), 2-phenyloxirane (0.088 mL, 0.768 mmol) and montmorillonite K (0.020 g) was stirred at r.t. for 1 h. Ethyl ether (0.4 mL) was added and the mixture was stirred at r.t. overnight. Additional diethyl ether was added, and the solids were filtered off and washed with dichloromethane. The filtrate was dried over $MgSO_4$, filtered and concentrated to dryness. The residue was purified by flash chromatography, silica gel, gradient dichloromethane to methanol:dichloromethane (1:4) to give the title compound (75 mg, 25% yield) as a mixture of 4 diastereomers. HPLC retention time: 3.73 min; MS: 381.2 (M+H).

Examples 151a, 151b, 151c, 151d

Ex 151a

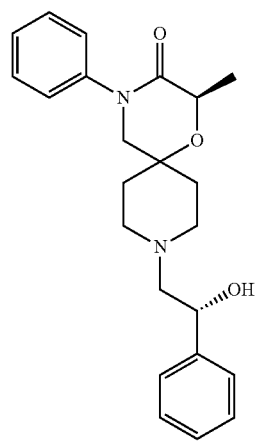

Ex 151b

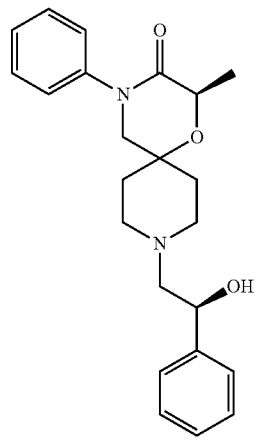

Ex 151c

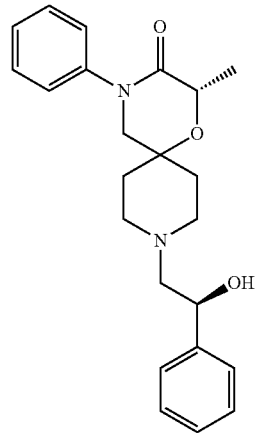

205

-continued

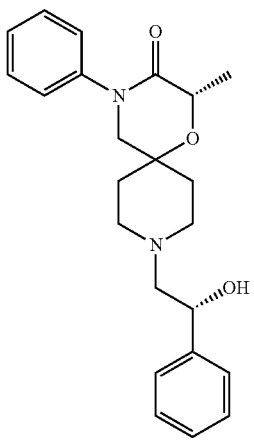

Ex 151d

Example 150 was purified by chiral preparative HPLC and the four diastereomers were separated, yielding (R)-9-((R)-2-hydroxy-2-phenylethyl)-2-methyl-4-phenyl-1-oxa-4,9-diazaspiro[5.5]undecan-3-one (Example 151a), (R)-9-((S)-2-hydroxy-2-phenylethyl)-2-methyl-4-phenyl-1-oxa-4,9-diazaspiro[5.5]undecan-3-one (Example 151 b), (S)-9-((S)-2-hydroxy-2-phenylethyl)-2-methyl-4-phenyl-1-oxa-4,9-diazaspiro[5.5]undecan-3-one (Example 151c) and (S)-9-((R)-2-hydroxy-2-phenylethyl)-2-methyl-4-phenyl-1-oxa-4,9-diazaspiro[5.5]undecan-3-one (Example 151d).
  Conditions of Chiral HPLC:
  Column: Chiralcel ODH
  Temperature: ambient
  Flow: 0.4 mL/min
  Mobile phase: n-Heptane/IPA 50/50 v/v

206

Example 152: 4-benzyl-2-methyl-9-phenethyl-1-oxa-4,9-diazaspiro[5.5]undecan-3-one hydrochloride

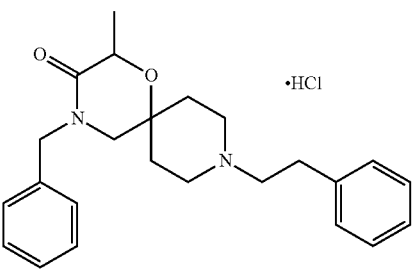 [SMILES: CC1OC2(CCN(CCc3ccccc3)CC2)CN(Cc2ccccc2)C1=O ; Cl]

To a solution of intermediate 3J (0.250 g, 0.867 mmol) in dry DMF (6 mL), NaH (69 mg, 60 wt % in mineral oil, 1.734 mmol) was added. The reaction mixture was stirred at r.t. for 30 min, then benzyl bromide (0.103 mL, 0.867 mmol) was added and the resulting mixture was stirred at r.t. for 4 h, and finally 5 h at 50° C. Water was added to the reaction mixture and it was extracted with ethyl acetate. The organic phases were combined, washed with brine, dried over MgSO$_4$, filtered and concentrated to dryness. The residue was purified by flash chromatography, silica gel, gradient dichloromethane to methanol:dichloromethane (1:9) to give the title compound as its free base (186 mg, 56% yield).
  The previous compound was converted to its hydrochloride salt as described in example 1.
  HPLC retention time: 4.33 min; MS: 379.2 (M+H).
  This method was used for the preparation of examples 153-187 using suitable starting materials:

| EX | Structure | Chemical name | Ret time (min) | MS (M + H) |
|---|---|---|---|---|
| 153 | ![structure] | 4-benzyl-9-phenethyl-1-oxa-4,9-diazaspiro[5.5]undecan-3-one hydrochloride | 3.99 | 365.2 |
| 154 | ![structure] | 4-(2-fluorobenzyl)-2-methyl-9-phenethyl-1-oxa-4,9-diazaspiro[5.5]undecan-3-one hydrochloride | 4.43 | 397.2 |

| EX | Structure | Chemical name | Ret time (min) | MS (M + H) |
|---|---|---|---|---|
| 155 | 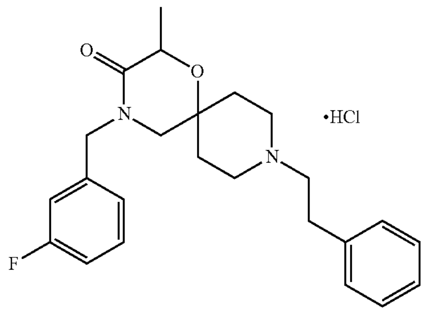 [SMILES: CC1OC2(CCN(CCc3ccccc3)CC2)CN(Cc2cccc(F)c2)C1=O ; Cl] | 4-(3-fluorobenzyl)-2-methyl-9-phenethyl-1-oxa-4,9-diazaspiro[5.5]undecan-3-one hydrochloride | 4.45 | 397.2 |
| 156 | 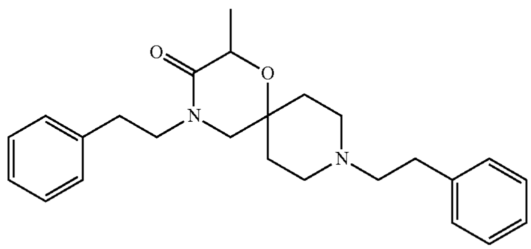 [SMILES: CC1OC2(CCN(CCc3ccccc3)CC2)CN(CCc2ccccc2)C1=O] | 2-methyl-4,9-diphenethyl-1-oxa-4,9-diazaspiro[5.5]undecan-3-one | 4.41 | 393.2 |
| 157 | 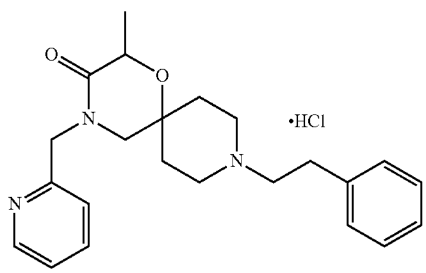 [SMILES: CC1OC2(CCN(CCc3ccccc3)CC2)CN(Cc2ccccn2)C1=O ; Cl] | 2-methyl-9-phenethyl-4-(pyridin-2-ylmethyl)-1-oxa-4,9-diazaspiro[5.5]undecan-3-one hydrochloride | 3.58 | 380.2 |
| 158 | 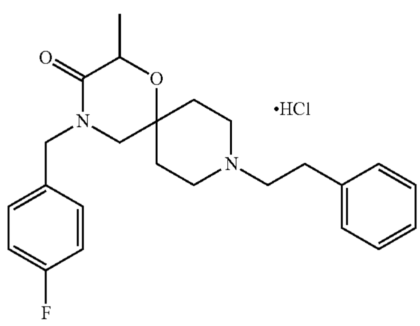 [SMILES: CC1OC2(CCN(CCc3ccccc3)CC2)CN(Cc2ccc(F)cc2)C1=O ; Cl] | 4-(4-fluorobenzyl)-2-methyl-9-phenethyl-1-oxa-4,9-diazaspiro[5.5]undecan-3-one hydrochloride | 4.39 | 397.2 |
| 159 | 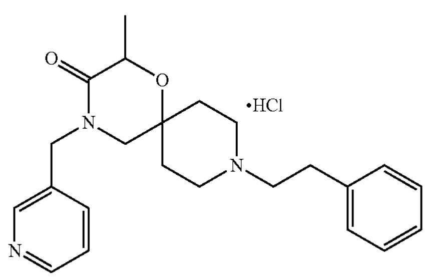 [SMILES: CC1OC2(CCN(CCc3ccccc3)CC2)CN(Cc2cccnc2)C1=O ; Cl] | 2-methyl-9-phenethyl-4-(pyridin-3-ylmethyl)-1-oxa-4,9-diazaspiro[5.5]undecan-3-one hydrochloride | 3.48 | 380.2 |

| EX | Structure | Chemical name | Ret time (min) | MS (M + H) |
|---|---|---|---|---|
| 160 | 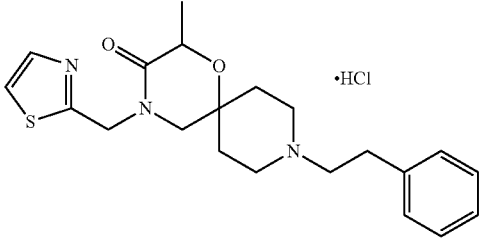 [SMILES: CC1OC2(CCN(CCc3ccccc3)CC2)CN(Cc2nccs2)C1=O ; Cl] | 2-methyl-9-phenethyl-4-(thiazol-2-ylmethyl)-1-oxa-4,9-diazaspiro[5.5]undecan-3-one hydrochloride | 3.76 | 386.2 |
| 161 | 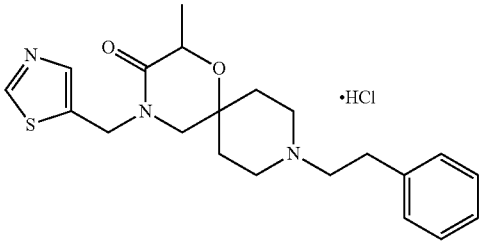 [SMILES: CC1OC2(CCN(CCc3ccccc3)CC2)CN(Cc2cncs2)C1=O ; Cl] | 2-methyl-9-phenethyl-4-(thiazol-5-ylmethyl)-1-oxa-4,9-diazaspiro[5.5]undecan-3-one hydrochloride | 3.62 | 386.1 |
| 162 | 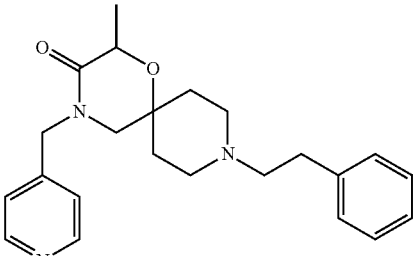 | 2-methyl-9-phenethyl-4-(pyridin-4-ylmethyl)-1-oxa-4,9-diazaspiro[5.5]undecan-3-one | 3.51 | 380.2 |
| 163 | 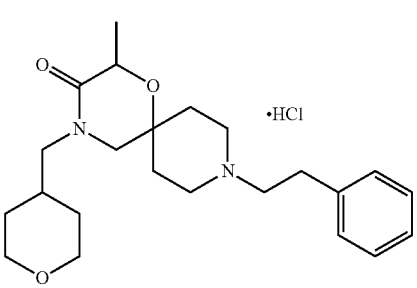 [SMILES: CC1OC2(CCN(CCc3ccccc3)CC2)CN(CC2CCOCC2)C1=O ; Cl] | 2-methyl-9-phenethyl-4-((tetrahydro-2H-pyran-4-yl)methyl)-1-oxa-4,9-diazaspiro[5.5]undecan-3-one hydrochloride | 3.64 | 387.2 |
| 164 | 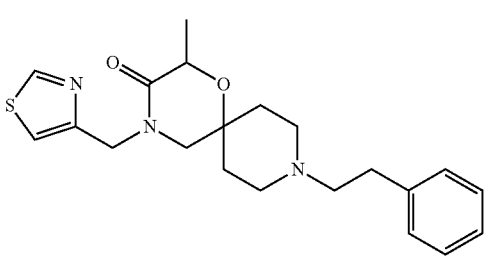 [SMILES: CC1OC2(CCN(CCc3ccccc3)CC2)CN(Cc2cscn2)C1=O] | 2-methyl-9-phenethyl-4-(thiazol-4-ylmethyl)-1-oxa-4,9-diazaspiro[5.5]undecan-3-one | 3.57 | 386.1 |
| 165 | 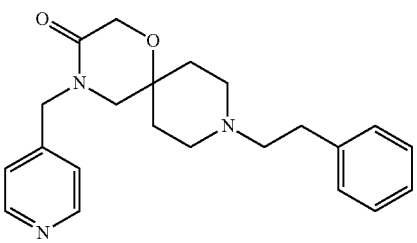 [SMILES: O=C1COC2(CCN(CCc3ccccc3)CC2)CN1Cc1ccncc1] | 9-phenethyl-4-(pyridin-4-ylmethyl)-1-oxa-4,9-diazaspiro[5.5]undecan-3-one | 3.23 | 366.2 |

-continued

| EX | Structure | Chemical name | Ret time (min) | MS (M + H) |
|---|---|---|---|---|
| 166 | 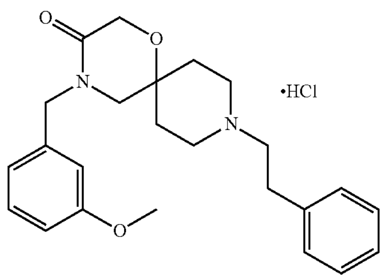 [SMILES: COc1cccc(CN2CC3(CCN(CCc4ccccc4)CC3)OCC2=O)c1 ; Cl] | 4-(3-methoxybenzyl)-9-phenethyl-1-oxa-4,9-diazaspiro[5.5]undecan-3-one hydrochloride | 4.09 | 395.2 |
| 167 | 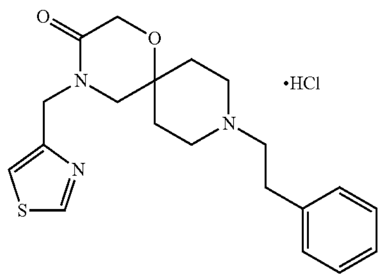 [SMILES: O=C1COC2(CCN(CCc3ccccc3)CC2)CN1Cc1cscn1 ; Cl] | 9-phenethyl-4-(thiazol-4-ylmethyl)-1-oxa-4,9-diazaspiro[5.5]undecan-3-one hydrochloride | 3.35 | 372.1 |
| 168 | 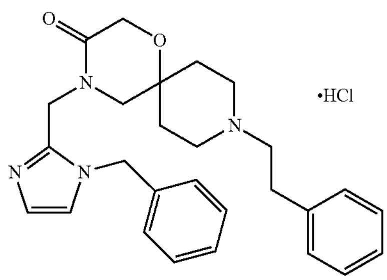 [SMILES: O=C1COC2(CCN(CCc3ccccc3)CC2)CN1Cc1nccn1Cc1ccccc1 ; Cl] | 4-((1-benzyl-1H-imidazol-2-yl)methyl)-9-phenethyl-1-oxa-4,9-diazaspiro[5.5]undecan-3-one hydrochloride | 3.91 | 445.2 |
| 169 | 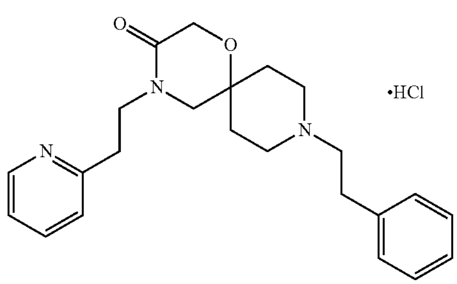 [SMILES: O=C1COC2(CCN(CCc3ccccc3)CC2)CN1CCc1ccccn1 ; Cl] | 9-phenethyl-4-(2-(pyridin-2-yl)ethyl)-1-oxa-4,9-diazaspiro[5.5]undecan-3-one hydrochloride | 3.37 | 380.2 |
| 170 | 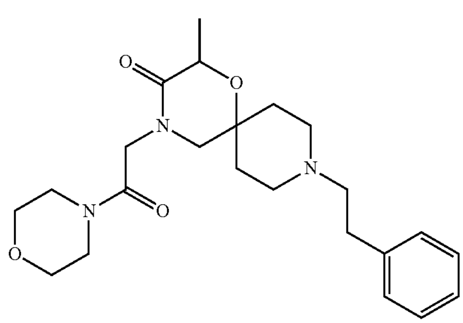 [SMILES: CC1OC2(CCN(CCc3ccccc3)CC2)CN(CC(=O)N2CCOCC2)C1=O] | 2-methyl-4-(2-morpholino-2-oxoethyl)-9-phenethyl-1-oxa-4,9-diazaspiro[5.5]undecan-3-one hydrochloride | 3.21 | 416.2 |

-continued

| EX | Structure | Chemical name | Ret time (min) | MS (M + H) |
|---|---|---|---|---|
| 171 | 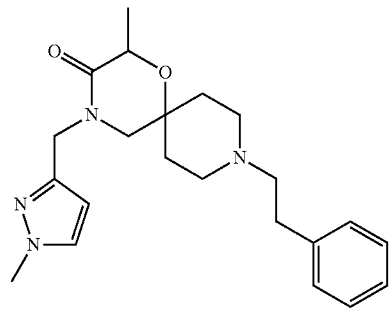 [SMILES: CC1OC2(CCN(CCc3ccccc3)CC2)CN(Cc2ccn(C)n2)C1=O] | 2-methyl-4-((1-methyl-1H-pyrazol-3-yl)methyl)-9-phenethyl-1-oxa-4,9-diazaspiro[5.5]undecan-3-one | 3.51 | 383.2 |
| 172 | 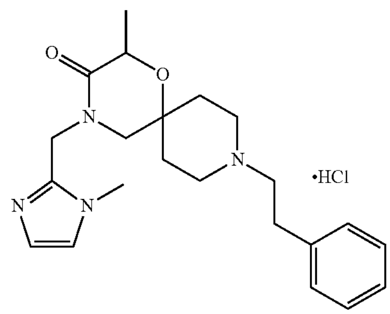 [SMILES: CC1OC2(CCN(CCc3ccccc3)CC2)CN(Cc2nccn2C)C1=O ; Cl] | 2-methyl-4-((1-methyl-1H-imidazol-2-yl)methyl)-9-phenethyl-1-oxa-4,9-diazaspiro[5.5]undecan-3-one hydrochloride | 3.39 | 383.2 |
| 173 | 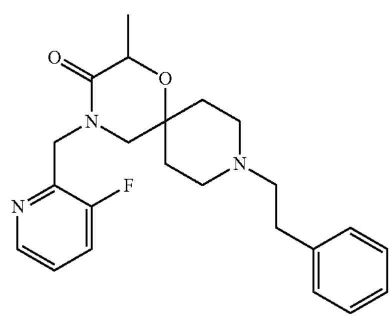 [SMILES: CC1OC2(CCN(CCc3ccccc3)CC2)CN(Cc2ncccc2F)C1=O] | 4-((3-fluoropyridin-2-yl)methyl)-2-methyl-9-phenethyl-1-oxa-4,9-diazaspiro[5.5]undecan-3-one | 3.82 | 398.2 |
| 174 | 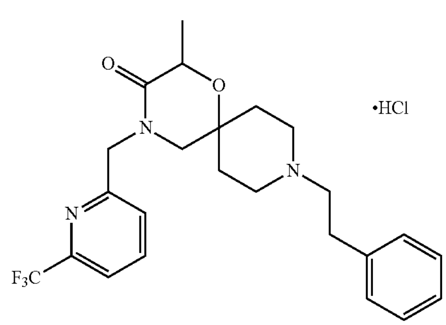 [SMILES: CC1OC2(CCN(CCc3ccccc3)CC2)CN(Cc2cccc(C(F)(F)F)n2)C1=O ; Cl] | 2-methyl-9-phenethyl-4-((6-(trifluoromethyl)pyridin-2-yl)methyl)-1-oxa-4,9-diazaspiro[5.5]undecan-3-one hydrochloride | 4.53 | 448.2 |

| EX | Structure | Chemical name | Ret time (min) | MS (M + H) |
|---|---|---|---|---|
| 175 | 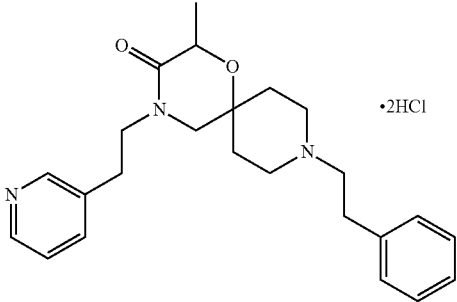 [SMILES: CC1OC2(CCN(CCc3ccccc3)CC2)CN(CCc2cccnc2)C1=O ; "·2HCl"] | 2-methyl-9-phenethyl-4-(2-(pyridin-3-yl)ethyl)-1-oxa-4,9-diazaspiro[5.5]undecan-3-one dihydrochloride | 3.58 | 394.2 |
| 176 | 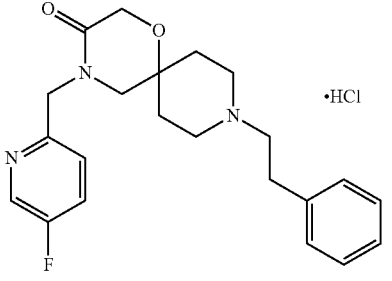 [SMILES: O=C1COC2(CCN(CCc3ccccc3)CC2)CN1Cc1ccc(F)cn1 ; Cl] | 4-((5-fluoropyridin-2-yl)methyl)-9-phenethyl-1-oxa-4,9-diazaspiro[5.5]undecan-3-one hydrochloride | 3.61 | 384.2 |
| 177 | 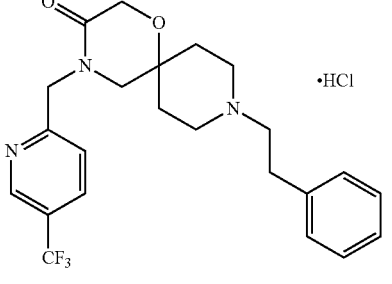 | 9-phenethyl-4-((5-(trifluoromethyl)pyridin-2-yl)methyl)-1-oxa-4,9-diazaspiro[5.5]undecan-3-one hydrochloride | 4.18 | 434.2 |
| 178 | 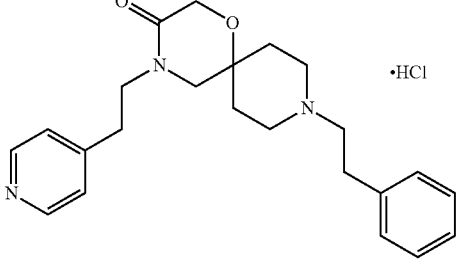 | 9-phenethyl-4-(2-(pyridin-4-yl)ethyl)-1-oxa-4,9-diazaspiro[5.5]undecan-3-one hydrochloride | 3.30 | 380.2 |
| 179 | 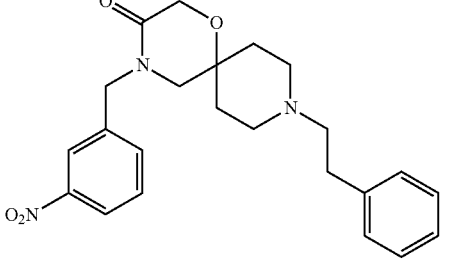 | 4-(3-nitrobenzyl)-9-phenethyl-1-oxa-4,9-diazaspiro[5.5]undecan-3-one | 4.02 | 410.1 |

| EX | Structure | Chemical name | Ret time (min) | MS (M + H) |
|---|---|---|---|---|
| 180 | 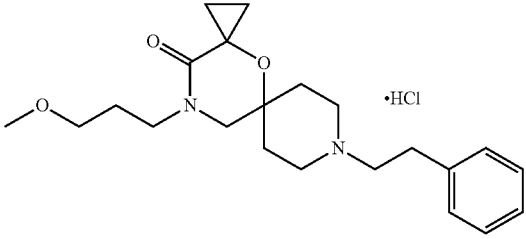 [SMILES: COCCCN1CC2(CCN(CCc3ccccc3)CC2)OC2(CC2)C1=O ; Cl] | 12-(3-methoxypropyl)-8-phenethyl-4-oxa-8,12-diazadispiro[2.1.5.3]tridecan-13-one hydrochloride | 3.82 | 373.2 |
| 181 | 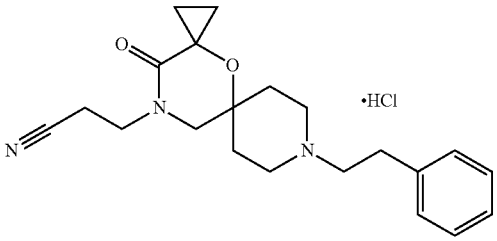 [SMILES: N#CCCN1CC2(CCN(CCc3ccccc3)CC2)OC2(CC2)C1=O ; Cl] | 3-[13-oxo-8-phenethyl-4-oxa-8,12-diazadispiro[2.1.5.3]tridecan-12-yl]propanenitrile hydrochloride | 3.68 | 354.2 |
| 182 | 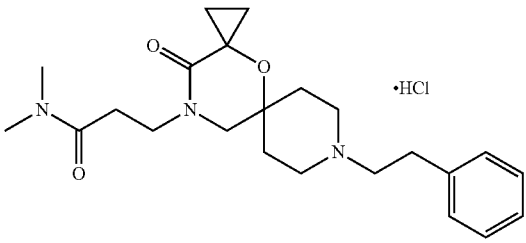 [SMILES: CN(C)C(=O)CCN1CC2(CCN(CCc3ccccc3)CC2)OC2(CC2)C1=O ; Cl] | N,N-dimethyl-3-[13-oxo-8-phenethyl-4-oxa-8,12-diazadispiro[2.1.5.3]tridecan-12-yl]propanamide hydrochloride | 3.50 | 400.2 |
| 183 | 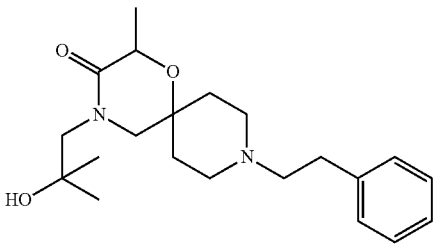 [SMILES: CC1OC2(CCN(CCc3ccccc3)CC2)CN(CC(C)(C)O)C1=O] | 4-(2-hydroxy-2-methylpropyl)-2-methyl-9-phenethyl-1-oxa-4,9-diazaspiro[5.5]undecan-3-one | 3.43 | 361.2 |
| 184 | 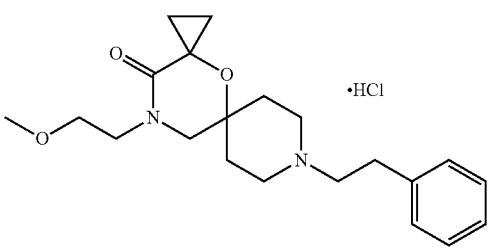 [SMILES: COCCN1CC2(CCN(CCc3ccccc3)CC2)OC2(CC2)C1=O ; Cl] | 12-(2-methoxyethyl)-8-phenethyl-4-oxa-8,12-diazadispiro[2.1.5.3]tridecan-13-one hydrochloride | 3.72 | 359.1 |
| 185 | 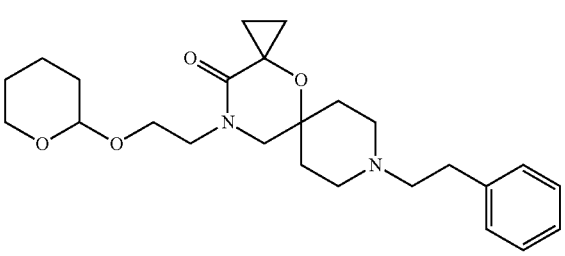 [SMILES: O=C1N(CCOC2CCCCO2)CC2(CCN(CCc3ccccc3)CC2)OC12CC2] | 12-(2-((tetrahydro-2H-pyran-2-yl)oxy)ethyl)-8-phenethyl-4-oxa-8,12-diazadispiro[2.1.5.3]tridecan-13-one | 4.28 | 429.2 |

| EX | Structure | Chemical name | Ret time (min) | MS (M + H) |
|---|---|---|---|---|
| 186 | 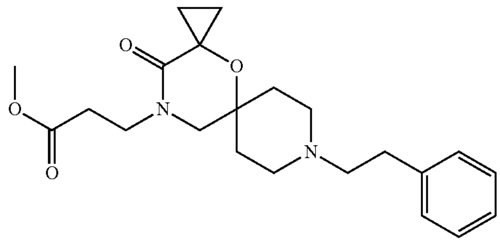 [SMILES: COC(=O)CCN1CC2(CCN(CCc3ccccc3)CC2)OC2(CC2)C1=O] | methyl 3-(13-oxo-8-phenethyl-4-oxa-8,12-diazadispiro[2.1.5.3]tridecan-12-yl)propanoate | 3.84 | 387.2 |
| 187 | 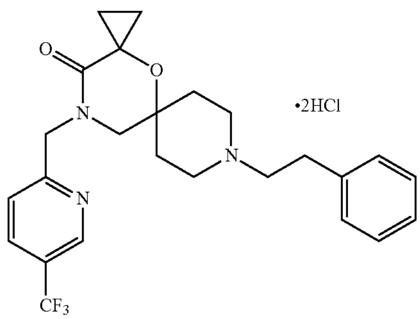 [SMILES: O=C1N(Cc2ccc(C(F)(F)F)cn2)CC2(CCN(CCc3ccccc3)CC2)OC12CC2 ; "·2HCl"] | 8-phenethyl-12-{[5-(trifluoromethyl)pyridin-2-yl]methyl}-4-oxa-8,12-diazadispiro[2.1.5.3]tridecan-13-one dihydrochloride | 4.56 | 460.2 |

Where indicated, the hydrochloride salts were prepared as described in example 1.

Example 188: 9-benzyl-4-(4-fluorophenyl)-1-oxa-4,9-diazaspiro[5.5]undecan-3-one hydrochloride

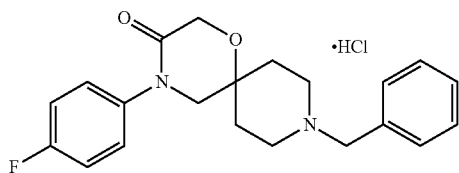 [SMILES: O=C1COC2(CCN(Cc3ccccc3)CC2)CN1c1ccc(F)cc1 ; Cl]

A mixture of intermediate 3K (112 mg, 0.430 mmol), K$_3$PO$_4$ (152 mg, 0.717 mmol), CuI (0.7 mg, 0.004 mmol), trans-1,2-cyclohexanediamine (0.004 mL, 0.036 mmol) and 1-fluoro-4-iodobenzene (0.41 mL, 0.359 mmol) in dry 1,4-dioxane (1 mL) was heated under an argon atmosphere at 110° C. overnight. The reaction mixture was allowed to cool to r.t., and dichloromethane and 1M NaOH aqueous solution were added. The phases were separated and the aqueous phase was back extracted with ethyl acetate. The combined organic phases were washed with brine, dried over MgSO$_4$ and concentrated under vacuum. The residue was purified by flash chromatography, silica gel, gradient dichloromethane to methanol:dichloromethane (1:4) to give the title compound as its free base (68 mg, 53% yield).

The previous compound was converted to its hydrochloride salt as described in example 1.

HPLC retention time: 3.82 min; MS: 355.1 (M+H).

This method was used for the preparation of examples 189-217 using suitable starting materials:

| EX | Structure | Chemical name | Ret time (min) | MS (M + H) |
|---|---|---|---|---|
| 189 | 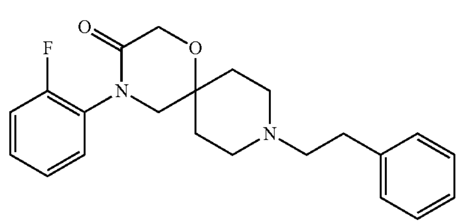 [SMILES: O=C1COC2(CCN(CCc3ccccc3)CC2)CN1c1ccccc1F] | 4-(2-fluorophenyl)-9-phenethyl-1-oxa-4,9-diazaspiro[5.5]undecan-3-one | 3.88 | 369.1 |

| EX | Structure | Chemical name | Ret time (min) | MS (M + H) |
|---|---|---|---|---|
| 190 | 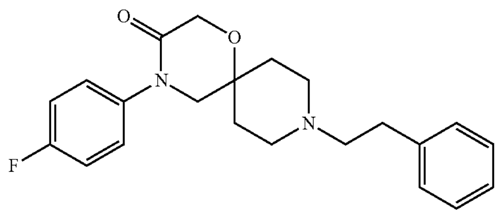 [SMILES: O=C1COC2(CCN(CCc3ccccc3)CC2)CN1c1ccc(F)cc1] | 4-(4-fluorophenyl)-9-phenethyl-1-oxa-4,9-diazaspiro[5.5]undecan-3-one | 3.85 | 369.1 |
| 191 | 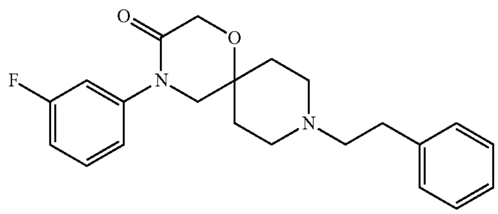 [SMILES: O=C1COC2(CCN(CCc3ccccc3)CC2)CN1c1cccc(F)c1] | 4-(3-fluorophenyl)-9-phenethyl-1-oxa-4,9-diazaspiro[5.5]undecan-3-one | 3.95 | 369.1 |
| 192 | 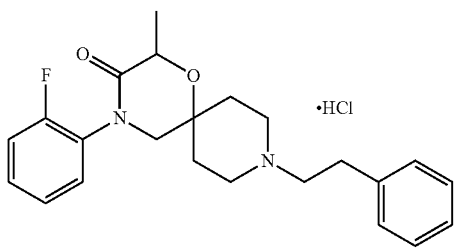 [SMILES: CC1OC2(CCN(CCc3ccccc3)CC2)CN(c2ccccc2F)C1=O ; Cl] | 4-(2-fluorophenyl)-2-methyl-9-phenethyl-1-oxa-4,9-diazaspiro[5.5]undecan-3-one hydrochloride | 4.28 | 383.2 |
| 193 | 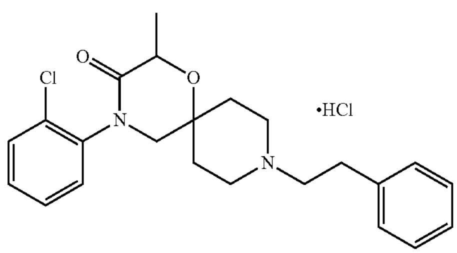 | 4-(2-chlorophenyl)-2-methyl-9-phenethyl-1-oxa-4,9-diazaspiro[5.5]undecan-3-one hydrochloride | 4.43 | 399.1 |
| 194 | 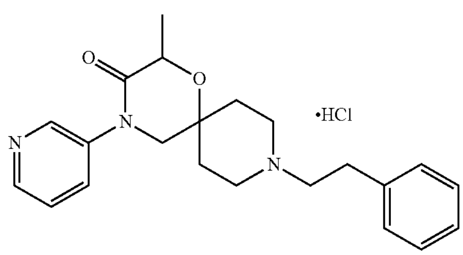 [SMILES: CC1OC2(CCN(CCc3ccccc3)CC2)CN(c2cccnc2)C1=O ; Cl] | 2-methyl-9-phenethyl-4-(pyridin-3-yl)-1-oxa-4,9-diazaspiro[5.5]undecan-3-one hydrochloride | 3.52 | 366.2 |
| 195 | 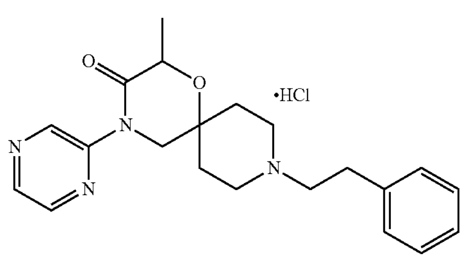 [SMILES: CC1OC2(CCN(CCc3ccccc3)CC2)CN(c2cnccn2)C1=O ; Cl] | 2-methyl-9-phenethyl-4-(pyrazin-2-yl)-1-oxa-4,9-diazaspiro[5.5]undecan-3-one hydrochloride | 3.86 | 367.1 |

-continued

| EX | Structure | Chemical name | Ret time (min) | MS (M + H) |
|---|---|---|---|---|
| 196 | 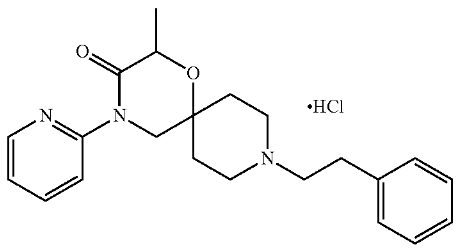 [SMILES: CC1OC2(CCN(CCc3ccccc3)CC2)CN(c2ccccn2)C1=O ; Cl] | 2-methyl-9-phenethyl-4-(pyridin-2-yl)-1-oxa-4,9-diazaspiro[5.5]undecan-3-one hydrochloride | 3.96 | 366.2 |
| 197 | 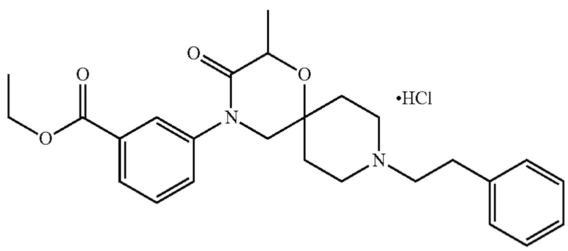 [SMILES: CCOC(=O)c1cccc(N2CC3(CCN(CCc4ccccc4)CC3)OC(C)C2=O)c1 ; Cl] | ethyl 3-(2-methyl-3-oxo-9-phenethyl-1-oxa-4,9-diazaspiro[5.5]undecan-4-yl)benzoate hydrochloride | 4.56 | 437.2 |
| 198 | 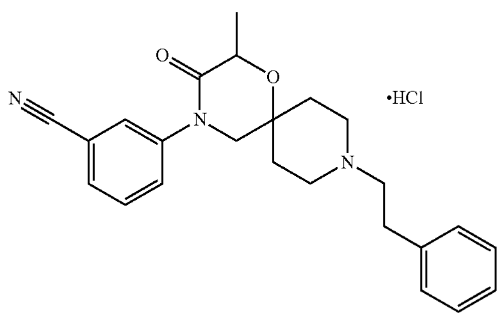 [SMILES: CC1OC2(CCN(CCc3ccccc3)CC2)CN(c2cccc(C#N)c2)C1=O ; Cl] | 3-(2-methyl-3-oxo-9-phenethyl-1-oxa-4,9-diazaspiro[5.5]undecan-4-yl)benzonitrile hydrochloride | 4.18 | 390.2 |
| 199 | 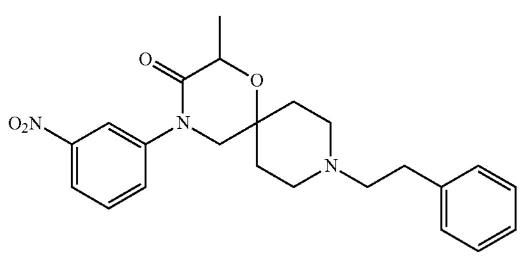 [SMILES: CC1OC2(CCN(CCc3ccccc3)CC2)CN(c2cccc([N+](=O)[O-])c2)C1=O] | 2-methyl-4-(3-nitrophenyl)-9-phenethyl-1-oxa-4,9-diazaspiro[5.5]undecan-3-one | 4.39 | 410.2 |
| 200 | 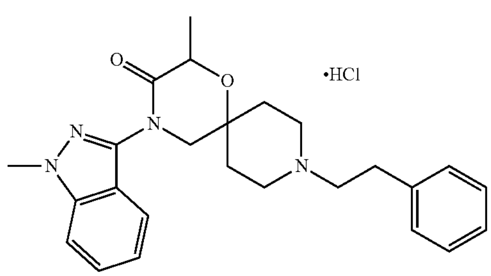 [SMILES: CC1OC2(CCN(CCc3ccccc3)CC2)CN(c2nn(C)c3ccccc23)C1=O ; Cl] | 2-methyl-4-(1-methyl-1H-indazol-3-yl)-9-phenethyl-1-oxa-4,9-diazaspiro[5.5]undecan-3-one hydrochloride | 4.40 | 419.2 |

-continued

| EX | Structure | Chemical name | Ret time (min) | MS (M + H) |
|---|---|---|---|---|
| 201 | 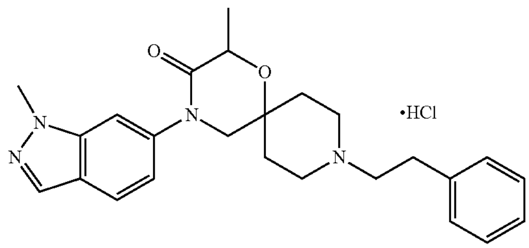 [SMILES: CC1OC2(CCN(CCc3ccccc3)CC2)CN(c2ccc3cnn(C)c3c2)C1=O ; Cl] | 2-methyl-4-(1-methyl-1H-indazol-6-yl)-9-phenethyl-1-oxa-4,9-diazaspiro[5.5]undecan-3-one hydrochloride | 4.00 | 419.2 |
| 202 | 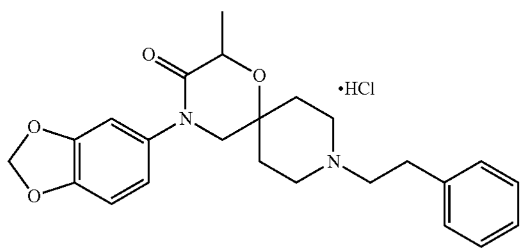 [SMILES: CC1OC2(CCN(CCc3ccccc3)CC2)CN(c2ccc3c(c2)OCO3)C1=O ; Cl] | 4-(benzo[d][1,3]dioxol-5-yl)-2-methyl-9-phenethyl-1-oxa-4,9-diazaspiro[5.5]undecan-3-one hydrochloride | 4.18 | 409.2 |
| 203 | 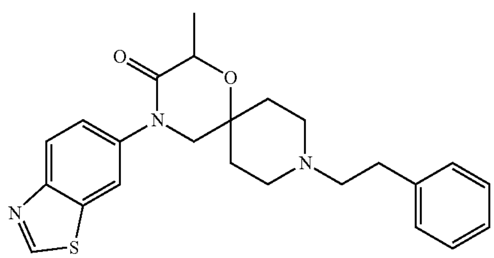 [SMILES: CC1OC2(CCN(CCc3ccccc3)CC2)CN(c2ccc3ncsc3c2)C1=O] | 4-(benzo[d]thiazol-6-yl)-2-methyl-9-phenethyl-1-oxa-4,9-diazaspiro[5.5]undecan-3-one | 4.05 | 422.2 |
| 204 | 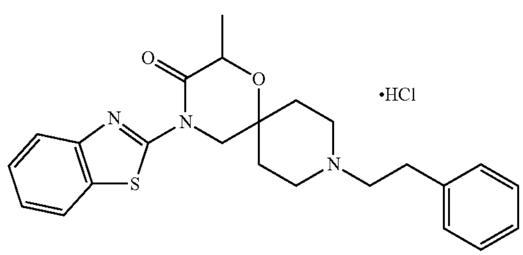 [SMILES: CC1OC2(CCN(CCc3ccccc3)CC2)CN(c2nc3ccccc3s2)C1=O ; Cl] | 4-(benzo[d]thiazol-2-yl)-2-methyl-9-phenethyl-1-oxa-4,9-diazaspiro[5.5]undecan-3-one hydrochloride | 5.27 | 422.1 |
| 205 | 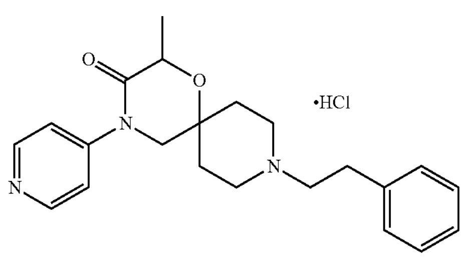 [SMILES: CC1OC2(CCN(CCc3ccccc3)CC2)CN(c2ccncc2)C1=O ; Cl] | 2-methyl-9-phenethyl-4-(pyridin-4-yl)-1-oxa-4,9-diazaspiro[5.5]undecan-3-one hydrochloride | 3.69 | 366.2 |
| 206 | 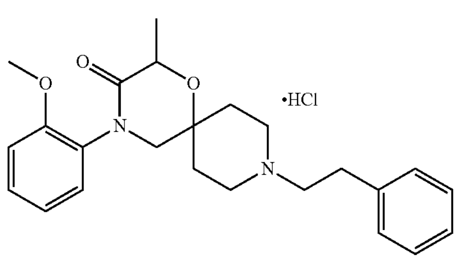 [SMILES: COc1ccccc1N1CC2(CCN(CCc3ccccc3)CC2)OC(C)C1=O ; Cl] | 4-(2-methoxyphenyl)-2-methyl-9-phenethyl-1-oxa-4,9-diazaspiro[5.5]undecan-3-one hydrochloride | 4.17 | 395.2 |

-continued

| EX | Structure | Chemical name | Ret time (min) | MS (M + H) |
|---|---|---|---|---|
| 207 | 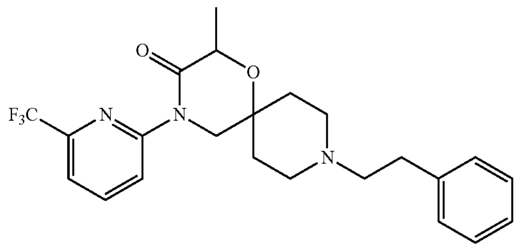 [SMILES: CC1OC2(CCN(CCc3ccccc3)CC2)CN(c2cccc(C(F)(F)F)n2)C1=O] | 2-methyl-9-phenethyl-4-(6-(trifluoromethyl)pyridin-2-yl)-1-oxa-4,9-diazaspiro[5.5]undecan-3-one | 5.10 | 434.2 |
| 208 | 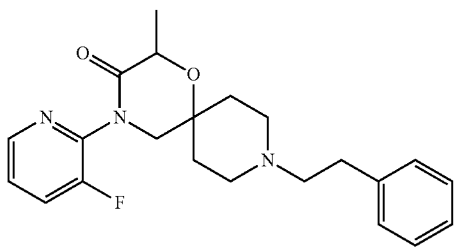 [SMILES: CC1OC2(CCN(CCc3ccccc3)CC2)CN(c2ncccc2F)C1=O] | 4-(3-fluoropyridin-2-yl)-2-methyl-9-phenethyl-1-oxa-4,9-diazaspiro[5.5]undecan-3-one | 3.92 | 384.2 |
| 209 | ·HCl | 2-methyl-9-phenethyl-4-(thiazol-2-yl)-1-oxa-4,9-diazaspiro[5.5]undecan-3-one hydrochloride | 4.43 | 372.1 |
| 210 | 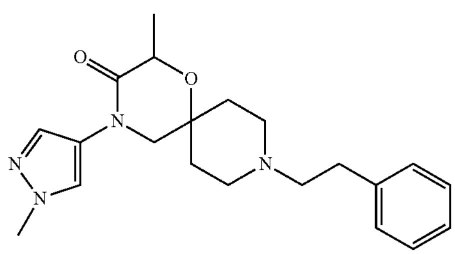 [SMILES: CC1OC2(CCN(CCc3ccccc3)CC2)CN(c2cnn(C)c2)C1=O] | 2-methyl-4-(1-methyl-1H-pyrazol-4-yl)-9-phenethyl-1-oxa-4,9-diazaspiro[5.5]undecan-3-one | 3.61 | 369.2 |
| 211 | ·HCl | 4-(6-methoxypyridin-2-yl)-2-methyl-9-phenethyl-1-oxa-4,9-diazaspiro[5.5]undecan-3-one hydrochloride | 4.62 | 396.2 |
| 212 | ·HCl | 2-methyl-9-phenethyl-4-(6-(trifluoromethyl)pyridin-3-yl)-1-oxa-4,9-diazaspiro[5.5]undecan-3-one hydrochloride | 4.52 | 434.2 |

-continued

| EX | Structure | Chemical name | Ret time (min) | MS (M + H) |
|---|---|---|---|---|
| 213 | 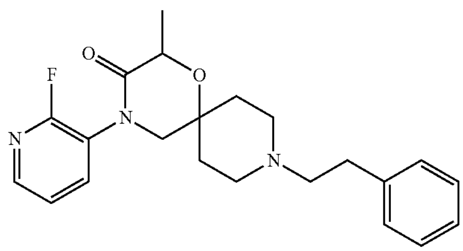 [SMILES: CC1OC2(CCN(CCc3ccccc3)CC2)CN(c2cccnc2F)C1=O] | 4-(2-fluoropyridin-3-yl)-2-methyl-9-phenethyl-1-oxa-4,9-diazaspiro[5.5]undecan-3-one | 3.90 | 384.2 |
| 214 | ·HCl | 2-methyl-9-phenethyl-4-(4-(trifluoromethyl)pyridin-3-yl)-1-oxa-4,9-diazaspiro[5.5]undecan-3-one hydrochloride | 4.23 | 434.2 |
| 215 | ·HCl | 2-methyl-9-phenethyl-4-(2-(trifluoromethyl)pyridin-3-yl)-1-oxa-4,9-diazaspiro[5.5]undecan-3-one hydrochloride | 4.27 | 434.2 |
| 216 | ·HCl | 4-(5-fluoropyridin-3-yl)-2-methyl-9-phenethyl-1-oxa-4,9-diazaspiro[5.5]undecan-3-one hydrochloride | 3.85 | 384.2 |
| 217 | ·HCl | 2-methyl-9-phenethyl-4-(5-(trifluoromethyl)pyridin-3-yl)-1-oxa-4,9-diazaspiro[5.5]undecan-3-one hydrochloride | 4.38 | 434.2 |

Where indicated, the hydrochloride salts were prepared as described in example 1.

Example 218: 2-methyl-9-phenethyl-4-(3-(trifluoromethyl)pyridin-2-yl)-1-oxa-4,9-diazaspiro[5.5]undecan-3-one

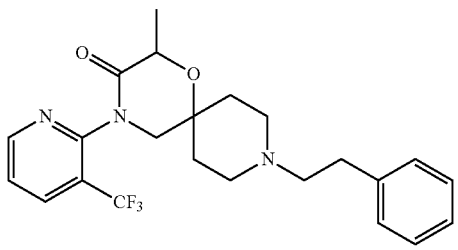 [SMILES: CC1OC2(CCN(CCc3ccccc3)CC2)CN(c2ncccc2C(F)(F)F)C1=O]

A mixture of intermediate 3J (0.070 g, 0.243 mmol), Cs$_2$CO$_3$ (0.103 g, 0.534 mmol), tris(dibenzylideneacetone)dipalladium(0) (11 mg, 0.012 mmol), 4,5-bis(diphenylphosphino)-9,9-dimethylxanthene (12 mg, 0.021 mmol) and 2-bromo-3-(trifluoromethyl)pyridine (0.066 g, 0.291 mmol) in dry 1,4-dioxane (4 mL) was heated under an argon atmosphere at 110° C. overnight. The reaction mixture was allowed to cool to r.t., the solids were filtered off and it was concentrated to dryness. Additional reagents and solvent were added and the reaction cycle was repeated to get the reaction to completion. The residue was purified by flash chromatography, silica gel, gradient dichloromethane to methanol:dichloromethane (1:4) to give the title compound (33 mg, 33% yield). HPLC retention time: 4.19 min; MS: 434.2 (M+H).

This method was used for the preparation of examples 219-223 using suitable starting materials:

| EX | Structure | Chemical name | Ret time (min) | MS (M + H) |
|---|---|---|---|---|
| 219 | 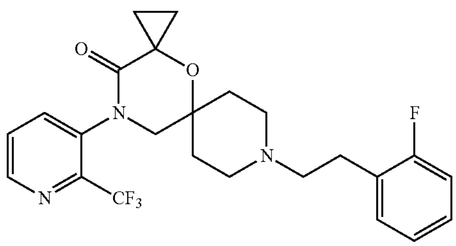 [SMILES: O=C1N(c2cccnc2C(F)(F)F)CC2(CCN(CCc3ccccc3F)CC2)OC12CC2] | 8-(2-fluorophenethyl)-12-(2-(trifluoromethyl)pyridin-3-yl)-4-oxa-8,12-diazadispiro[2.1.5.3]tridecan-13-one | 4.46 | 464.2 |
| 220 | 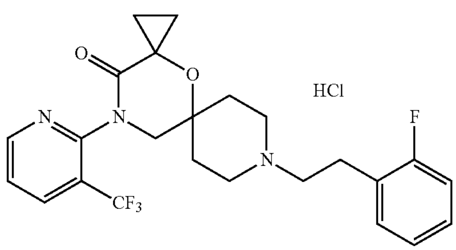 [SMILES: O=C1N(c2ncccc2C(F)(F)F)CC2(CCN(CCc3ccccc3F)CC2)OC12CC2 ; Cl] | 8-(2-fluorophenethyl)-12-(3-(trifluoromethyl)pyridin-2-yl)-4-oxa-8,12-diazadispiro[2.1.5.3]tridecan-13-one hydrochloride | 4.49 | 464.2 |
| 221 | 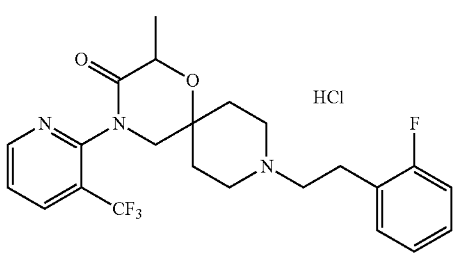 [SMILES: CC1OC2(CCN(CCc3ccccc3F)CC2)CN(c2ncccc2C(F)(F)F)C1=O ; Cl] | 9-(2-fluorophenethyl)-2-methyl-4-(3-(trifluoromethyl)pyridin-2-yl)-1-oxa-4,9-diazaspiro[5.5]undecan-3-one | 4.36 | 452.2 |
| 222a | 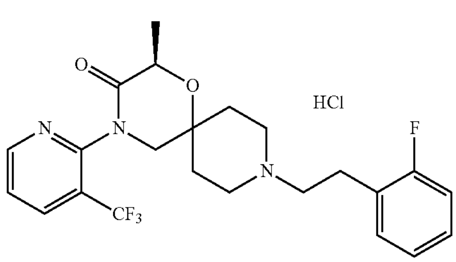 [SMILES: C[C@H]1OC2(CCN(CCc3ccccc3F)CC2)CN(c2ncccc2C(F)(F)F)C1=O ; Cl] | (R)-9-(2-fluorophenethyl)-2-methyl-4-(3-(trifluoromethyl)pyridin-2-yl)-1-oxa-4,9-diazaspiro[5.5]undecan-3-one (1*) | 4.33 | 452.2 |

| EX | Structure | Chemical name | Ret time (min) | MS (M + H) |
|---|---|---|---|---|
| 222b | 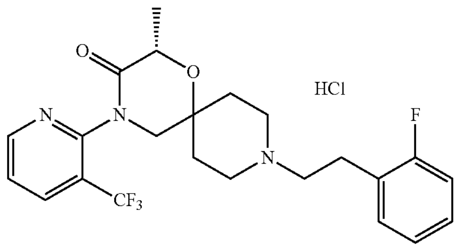 [SMILES: C[C@@H]1OC2(CCN(CCc3ccccc3F)CC2)CN(c2ncccc2C(F)(F)F)C1=O ; Cl] | (S)-9-(2-fluorophenethyl)-2-methyl-4-(3-(trifluoromethyl)pyridin-2-yl)-1-oxa-4,9-diazaspiro[5.5]undecan-3-one (1*) | 4.33 | 452.2 |
| 223 | 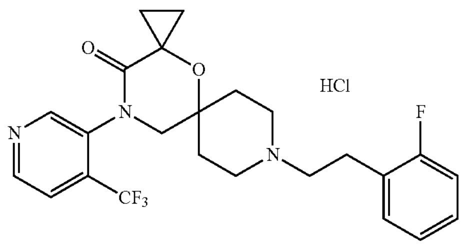 [SMILES: O=C1N(c2cnccc2C(F)(F)F)CC2(CCN(CCc3ccccc3F)CC2)OC12CC2 ; Cl] | 8-(2-fluorophenethyl)-12-(4-(trifluoromethyl)pyridin-3-yl)-4-oxa-8,12-diazadispiro[2.1.5.3]tridecan-13-one hydrochloride | 4.43 | 464.2 |

Where indicated, the hydrochloride salts were prepared as described in example 1.
1* Obtained by chiral preparative HPLC from previous example: Column: Chiralpak ASH; Temperature: ambient; Flow: 0.8 mL/min; Mobile phase: n-Heptane/(EtOH + 0.33% DEA) 85/15 v/v Example 224: 12-(2-fluorophenyl)-8-phenethyl-4-oxa-8,12-diazadispiro[2.1.5.3]tridecan-13-one

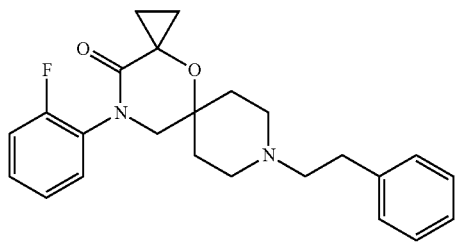 [SMILES: O=C1N(c2ccccc2F)CC2(CCN(CCc3ccccc3)CC2)OC12CC2]

To a suspension of trimethylsulfoxonium iodide (0.054 g, 0.426 mmol) and NaH (0.017 g, 60 wt % in mineral oil, 0.426 mmol) in DMSO (1 mL), a solution of example 22 (0.054 g, 0.142 mmol) in DMSO (1 mL) was added dropwise. The reaction mixture was stirred at r.t. for 30 min and heated at 50° C. for 2 h. After cooling to r.t., ice was slowly added, and the reaction mixture was extracted three times with ethyl acetate. The organic phases were combined, washed with water, dried over MgSO$_4$ and concentrated under vacuum. The residue was purified by flash chromatography, silica gel, gradient dichloromethane to methanol:dichloromethane (1:4) to give the title compound (0.021 g, 37% yield). HPLC retention time: 4.47 min; MS: 395.2 (M+H).

This method was used for the preparation of example 225 using suitable starting materials:

| EX | Structure | Chemical name | Ret time (min) | MS (M + H) |
|---|---|---|---|---|
| 225 | 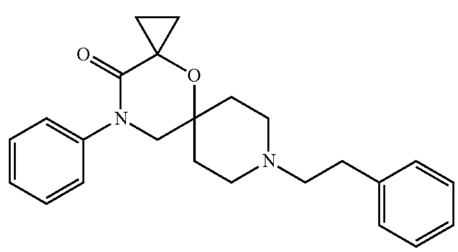 | 8-phenethyl-12-phenyl-4-oxa-8,12-diazadispiro[2.1.5.3]tridecan-13-one | 4.35 | 377.2 |

Example 226: 9-(3-aminophenethyl)-2-methyl-4-phenyl-1-oxa-4,9-diazaspiro[5.5]undecan-3-one

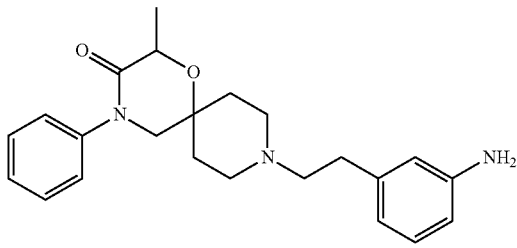 [SMILES: CC1OC2(CCN(CCc3cccc(N)c3)CC2)CN(c2ccccc2)C1=O]

A mixture of example 67 (0.248 g, 0.606 mmol) and palladium (26 mg, 10% wt on charcoal) in methanol (5 mL) was stirred at r.t. under 4 bars of $H_2$ overnight. Then, the solids were filtered off, and the solvent was removed under vacuum. The residue was purified by flash chromatography, silica gel, gradient dichloromethane to methanol:dichloromethane (1:4) to give the title compound (0.160 g, 70% yield). HPLC retention time: 3.33 min; MS: 380.2 (M+H).

This method was used for the preparation of examples 227-240 starting from the corresponding examples described above:

| EX | Structure | Chemical name | Ret time (min) | MS (M + H) |
|----|-----------|---------------|----------------|------------|
| 227 | 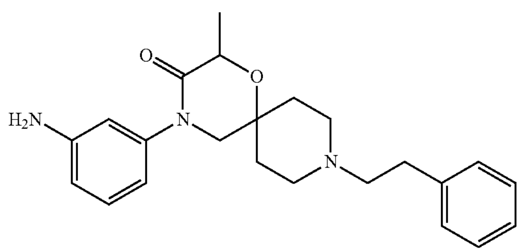 | 4-(3-aminophenyl)-2-methyl-9-phenethyl-1-oxa-4,9-diazaspiro[5.5]undecan-3-one | 3.66 | 380.2 |
| 228 | 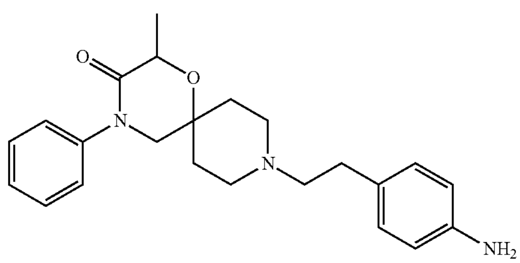 [SMILES: CC1OC2(CCN(CCc3ccc(N)cc3)CC2)CN(c2ccccc2)C1=O] | 9-(4-aminophenethyl)-2-methyl-4-phenyl-1-oxa-4,9-diazaspiro[5.5]undecan-3-one | 3.18 | 380.2 |
| 229 | 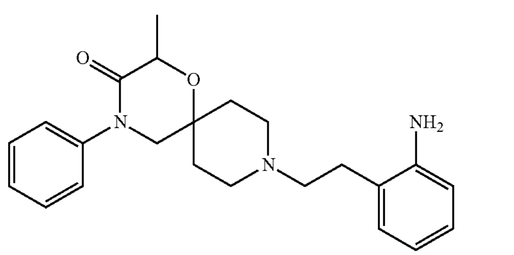 | 9-(2-aminophenethyl)-2-methyl-4-phenyl-1-oxa-4,9-diazaspiro[5.5]undecan-3-one | 3.60 | 380.2 |
| 230 | 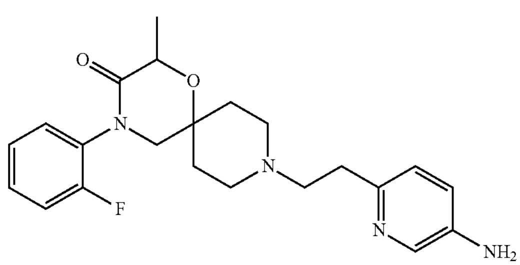 [SMILES: CC1OC2(CCN(CCc3ccc(N)cn3)CC2)CN(c2ccccc2F)C1=O] | 9-(2-(5-aminopyridin-2-yl)ethyl)-4-(2-fluorophenyl)-2-methyl-1-oxa-4,9-diazaspiro[5.5]undecan-3-one | 2.83 | 399.2 |

-continued

| EX | Structure | Chemical name | Ret time (min) | MS (M + H) |
|----|-----------|---------------|----------------|------------|
| 231 | 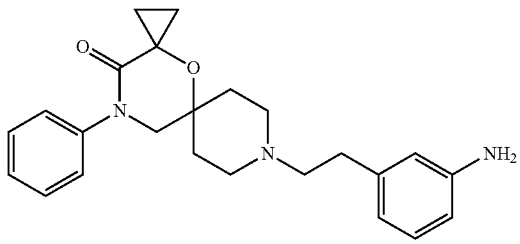 [SMILES: Nc1cccc(CCN2CCC3(CC2)CN(c2ccccc2)C(=O)C2(CC2)O3)c1] | 8-(3-aminophenethyl)-12-phenyl-4-oxa-8,12-diazadispiro[2.1.5.3]tridecan-13-one | 3.51 | 392.2 |
| 232 | 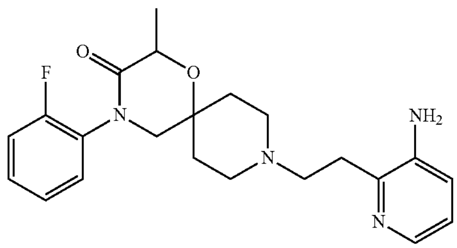 [SMILES: CC1OC2(CCN(CCc3ncccc3N)CC2)CN(c2ccccc2F)C1=O] | 9-(2-(3-aminopyridin-2-yl)ethyl)-4-(2-fluorophenyl)-2-methyl-1-oxa-4,9-diazaspiro[5.5]undecan-3-one | 2.82 | 399.2 |
| 233 | 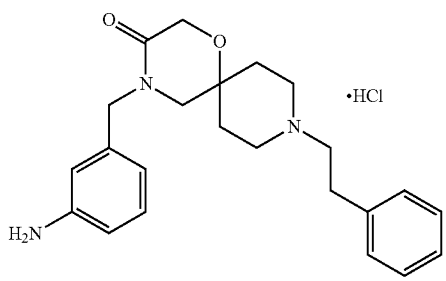 [SMILES: Nc1cccc(CN2CC3(CCN(CCc4ccccc4)CC3)OCC2=O)c1 ; Cl] | 4-(3-aminobenzyl)-9-phenethyl-1-oxa-4,9-diazaspiro[5.5]undecan-3-one hydrochloride | 3.42 | 380.2 |
| 234 | 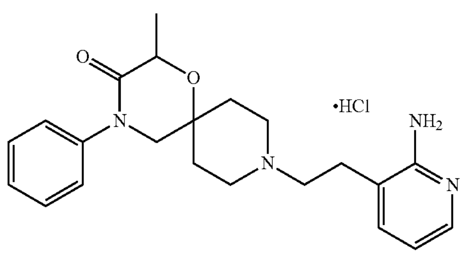 [SMILES: CC1OC2(CCN(CCc3cccnc3N)CC2)CN(c2ccccc2)C1=O ; Cl] | 9-(2-(2-aminopyridin-3-yl)ethyl)-2-methyl-4-phenyl-1-oxa-4,9-diazaspiro[5.5]undecan-3-one hydrochloride | 3.19 | 381.2 |
| 235 | 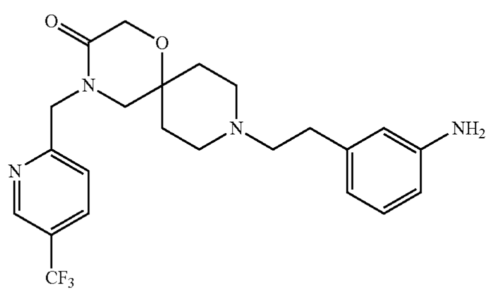 | 9-(3-aminophenethyl)-4-((5-(trifluoromethyl)pyridin-2-yl)methyl)-1-oxa-4,9-diazaspiro[5.5]undecan-3-one | 3.37 | 449.2 |

-continued

| EX | Structure | Chemical name | Ret time (min) | MS (M + H) |
|---|---|---|---|---|
| 236 | 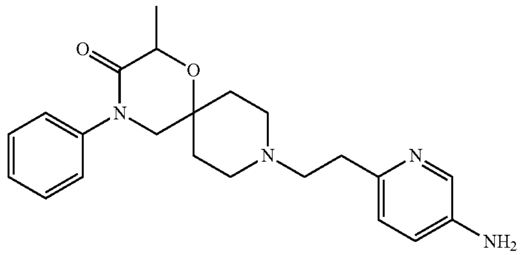 [SMILES: CC1OC2(CCN(CCc3ccc(N)cn3)CC2)CN(c2ccccc2)C1=O] | 9-(2-(5-aminopyridin-2-yl)ethyl)-2-methyl-4-phenyl-1-oxa-4,9-diazaspiro[5.5]undecan-3-one | 2.73 | 381.2 |
| 237 | ·HCl | 9-(2-(3-amino-1H-pyrazol-1-yl)ethyl)-2-methyl-4-phenyl-1-oxa-4,9-diazaspiro[5.5]undecan-3-one hydrochloride | 2.64 | 370.2 |
| 238 | ·2HCl | 9-(2-(2-aminopyridin-3-yl)ethyl)-4-(2-fluorophenyl)-2-isopropyl-1-oxa-4,9-diazaspiro[5.5]undecan-3-one dihydrochloride | 4.00 | 427.2 |
| 239 | 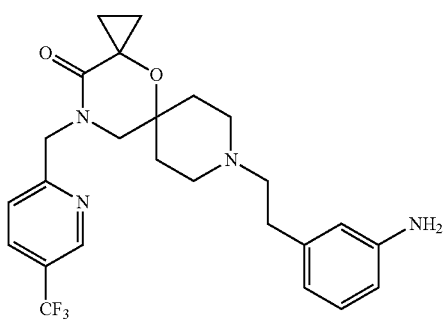 [SMILES: Nc1cccc(CCN2CCC3(CC2)CN(Cc2ccc(C(F)(F)F)cn2)C(=O)C2(CC2)O3)c1] | 8-(3-aminophenethyl)-12-{[5-(trifluoromethyl)pyridin-2-yl]methyl}-4-oxa-8,12-diazadispiro[2.1.5.3]tridecan-13-one | 3.83 | 475.2 |
| 240 | ·HCl | 9-(2-(2-aminopyridin-3-yl)ethyl)-2-methyl-4-(4-(trifluoromethyl)pyridin-3-yl)-1-oxa-4,9-diazaspiro[5.5]undecan-3-one hydrochloride | 3.15 | 450.2 |

Where indicated, the HCl salts were prepared as described in example 1

241

Example 241: N-(4-(2-(2-methyl-3-oxo-4-phenyl-1-oxa-4,9-diazaspiro[5.5]undecan-9-yl)ethyl)phenyl) acetamide hydrochloride

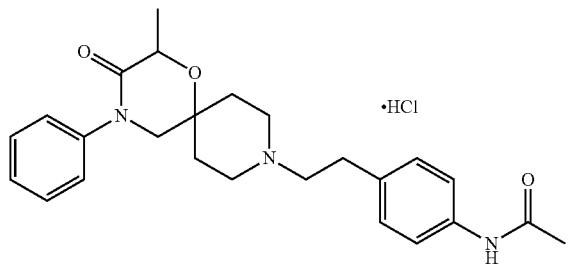 [SMILES: CC(=O)Nc1ccc(CCN2CCC3(CC2)CN(c2ccccc2)C(=O)C(C)O3)cc1 ; Cl]

242

To a solution of example 228 (0.070 g, 0.184 mmol) and triethylamine (0.039 mL, 0.277 mmol) in dichloromethane (1.5 mL), acetyl chloride (0.014 mL, 0.203 mmol) was added dropwise at r.t. The reaction mixture was stirred at r.t. overnight. NaHCO$_3$ sat solution was added and the aqueous phase was extracted with dichlorometane. The organic phases were combined, dried over MgSO$_4$, filtered and concentrated to dryness. The residue was purified by flash chromatography, silica gel, gradient dichloromethane to methanol:dichloromethane (1:4) to give the title compound as its free base (27 mg, 35% yield). HPLC retention time: 3.20 min; MS: 422.2 (M+H).

The previous compound was converted to its hydrochloride salt as described in example 1.

HPLC retention time: 3.82 min; MS: 355.1 (M+H).

This method was used for the preparation of examples 242-255 starting from the corresponding examples described above:

| EX | Structure | Chemical name | Ret time (min) | MS (M + H) |
|---|---|---|---|---|
| 242 | 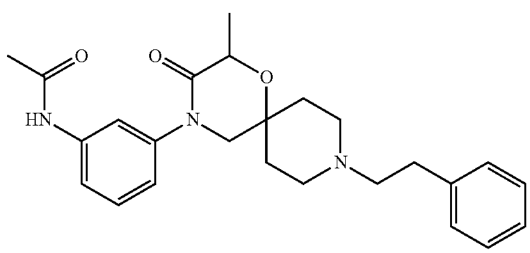 [SMILES: CC(=O)Nc1cccc(N2CC3(CCN(CCc4ccccc4)CC3)OC(C)C2=O)c1] | N-(3-(2-methyl-3-oxo-9-phenethyl-1-oxa-4,9-diazaspiro[5.5]undecan-4-yl)phenyl)acetamide | 3.61 | 422.2 |
| 243 | 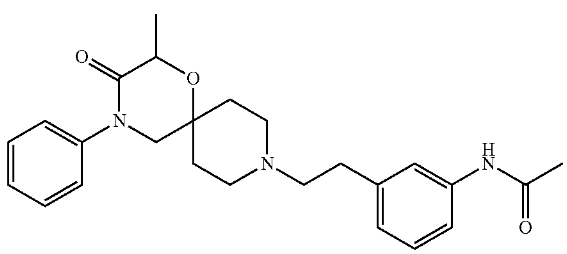 [SMILES: CC(=O)Nc1cccc(CCN2CCC3(CC2)CN(c2ccccc2)C(=O)C(C)O3)c1] | N-(3-(2-(2-methyl-3-oxo-4-phenyl-1-oxa-4,9-diazaspiro[5.5]undecan-9-yl)ethyl)phenyl)acetamide | 3.30 | 422.2 |
| 244a | 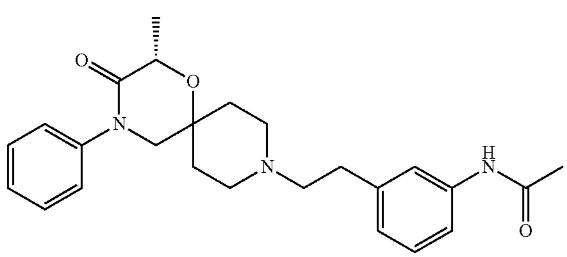 [SMILES: CC(=O)Nc1cccc(CCN2CCC3(CC2)CN(c2ccccc2)C(=O)[C@H](C)O3)c1] | (S)-N-(3-(2-(2-methyl-3-oxo-4-phenyl-1-oxa-4,9-diazaspiro[5.5]undecan-9-yl)ethyl)phenyl)acetamide hydrochloride (1*) | 3.27 | 422.2 |
| 244b | 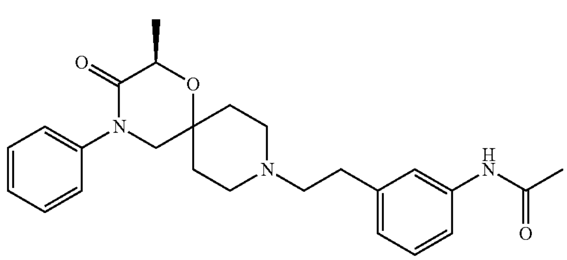 [SMILES: CC(=O)Nc1cccc(CCN2CCC3(CC2)CN(c2ccccc2)C(=O)[C@@H](C)O3)c1] | (R)-N-(3-(2-(2-methyl-3-oxo-4-phenyl-1-oxa-4,9-diazaspiro[5.5]undecan-9-yl)ethyl)phenyl)acetamide hydrochloride (1*) | 3.29 | 422.2 |

-continued

| EX | Structure | Chemical name | Ret time (min) | MS (M + H) |
|---|---|---|---|---|
| 245 | 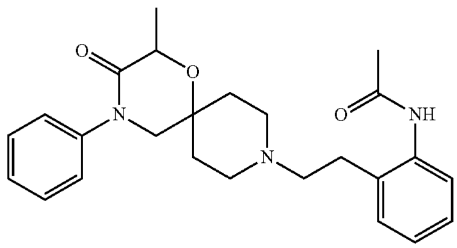 [SMILES: CC(=O)Nc1ccccc1CCN1CCC2(CC1)CN(c1ccccc1)C(=O)C(C)O2] | N-(2-(2-(2-methyl-3-oxo-4-phenyl-1-oxa-4,9-diazaspiro[5.5]undecan-9-yl)ethyl)phenyl)acetamide | 3.27 | 422.2 |
| 246 | 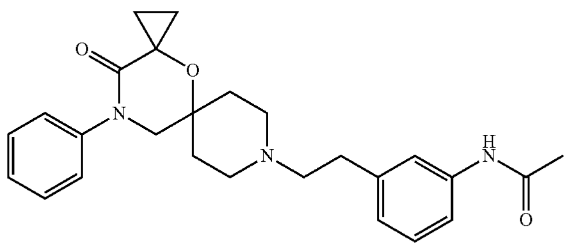 [SMILES: CC(=O)Nc1cccc(CCN2CCC3(CC2)CN(c2ccccc2)C(=O)C2(CC2)O3)c1] | N-[3-(2-{13-oxo-12-phenyl-4-oxa-8,12-diazadispiro[2.1.5.3]tridecan-8-yl}ethyl)phenyl]acetamide | 3.46 | 434.2 |
| 247 | 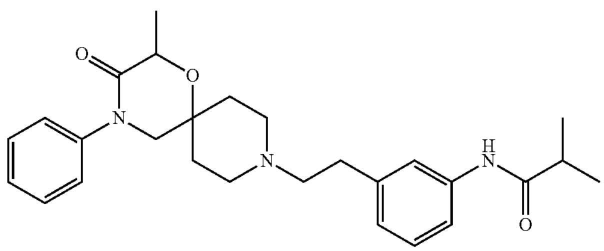 [SMILES: CC(C)C(=O)Nc1cccc(CCN2CCC3(CC2)CN(c2ccccc2)C(=O)C(C)O3)c1] | N-(3-(2-(2-methyl-3-oxo-4-phenyl-1-oxa-4,9-diazaspiro[5.5]undecan-9-yl)ethyl)phenyl)isobutyramide | 3.81 | 450.2 |
| 248 | 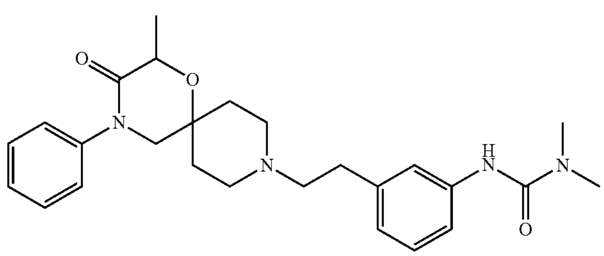 | 1,1-dimethyl-3-(3-(2-(2-methyl-3-oxo-4-phenyl-1-oxa-4,9-diazaspiro[5.5]undecan-9-yl)ethyl)phenyl)urea (2*) | 3.29 | 451.2 |
| 249 | 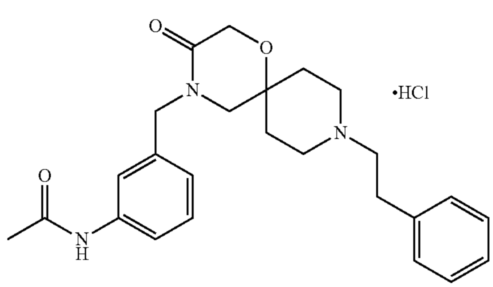 [SMILES: CC(=O)Nc1cccc(CN2CC3(CCN(CCc4ccccc4)CC3)OCC2=O)c1 ; Cl] | N-(3-((3-oxo-9-phenethyl-1-oxa-4,9-diazaspiro[5.5]undecan-4-yl)methyl)phenyl)acetamide hydrochloride | 3.48 | 422.2 |
| 250 | 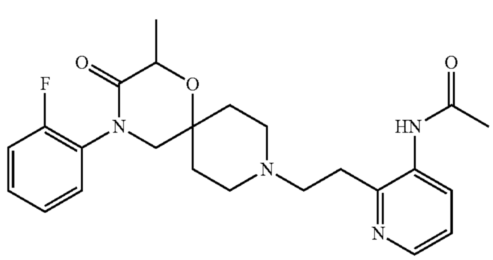 [SMILES: CC(=O)Nc1cccnc1CCN1CCC2(CC1)CN(c1ccccc1F)C(=O)C(C)O2] | N-(2-(2-(4-(2-fluorophenyl)-2-methyl-3-oxo-1-oxa-4,9-diazaspiro[5.5]undecan-9-yl)ethyl)pyridin-3-yl)acetamide | 2.70 | 441.2 |

-continued

| EX | Structure | Chemical name | Ret time (min) | MS (M + H) |
|---|---|---|---|---|
| 251 | 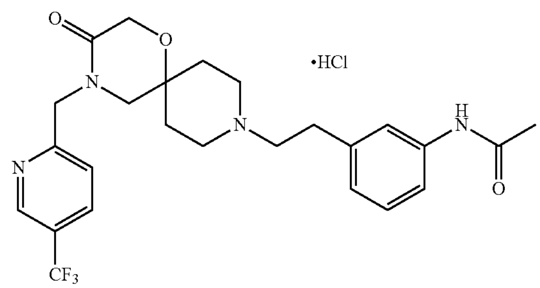 [SMILES: CC(=O)Nc1cccc(CCN2CCC3(CC2)CN(Cc2ccc(C(F)(F)F)cn2)C(=O)CO3)c1 ; Cl] | N-(3-(2-(3-oxo-4-((5-(trifluoromethyl)pyridin-2-yl)methyl)-1-oxa-4,9-diazaspiro[5.5]undecan-9-yl)ethyl)phenyl)acetamide hydrochloride | 3.34 | 491.2 |
| 252 | 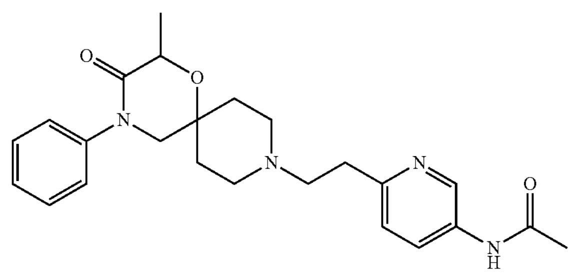 [SMILES: CC(=O)Nc1ccc(CCN2CCC3(CC2)CN(c2ccccc2)C(=O)C(C)O3)nc1] | N-(6-(2-(2-methyl-3-oxo-4-phenyl-1-oxa-4,9-diazaspiro[5.5]undecan-9-yl)ethyl)pyridin-3-yl)acetamide | 2.86 | 423.2 |
| 253 | 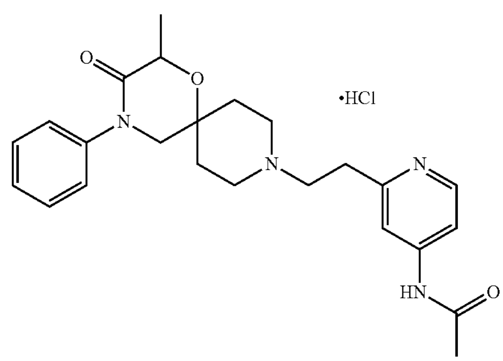 [SMILES: CC(=O)Nc1ccnc(CCN2CCC3(CC2)CN(c2ccccc2)C(=O)C(C)O3)c1 ; Cl] | N-(2-(2-(2-methyl-3-oxo-4-phenyl-1-oxa-4,9-diazaspiro[5.5]undecan-9-yl)ethyl)pyridin-4-yl)acetamide hydrochloride | 2.83 | 423.1 |
| 254 | 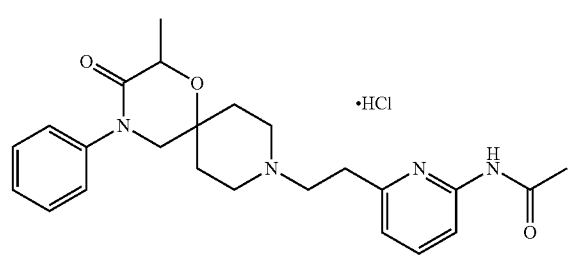 [SMILES: CC(=O)Nc1cccc(CCN2CCC3(CC2)CN(c2ccccc2)C(=O)C(C)O3)n1 ; Cl] | N-(6-(2-(2-methyl-3-oxo-4-phenyl-1-oxa-4,9-diazaspiro[5.5]undecan-9-yl)ethyl)pyridin-2-yl)acetamide hydrochloride | 3.11 | 423 |
| 255 | 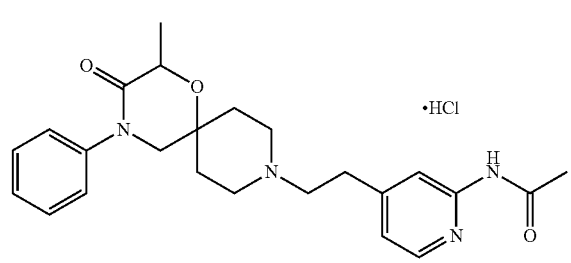 [SMILES: CC(=O)Nc1cc(CCN2CCC3(CC2)CN(c2ccccc2)C(=O)C(C)O3)ccn1 ; Cl] | N-(4-(2-(2-methyl-3-oxo-4-phenyl-1-oxa-4,9-diazaspiro[5.5]undecan-9-yl)ethyl)pyridin-2-yl)acetamide hydrochloride | 3.07 | 423 |

Where indicated, the HCl salts were prepared as described in example 1
1*. Obtained by chiral preparative HPLC from previous example: Column: Chiralpak ASH; Temperature: ambient; Flow: 0.6 mL/min; Mobile phase: n-Heptane/EtOH 80/20 v/v
2* Dimethylcarbamic chloride was used instead of acetyl chloride Example 256: N-(3-(2-(2-methyl-3-oxo-4-phenyl-1-oxa-4,9-diazaspiro[5.5]undecan-9-yl)ethyl)phenyl)methanesulfonamide

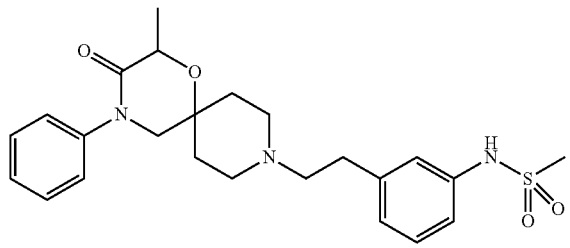 [SMILES: CC1OC2(CCN(CCc3cccc(NS(C)(=O)=O)c3)CC2)CN(c2ccccc2)C1=O]

To a solution of example 226 (0.091 g, 0.240 mmol) and triethylamine (0.050 mL, 0.360 mmol) in dichloromethane (2 mL), methanesulfonyl chloride (0.020 mL, 0.264 mmol) was added dropwise at r.t. The reaction mixture was stirred at r.t. overnight. NaHCO$_3$ aqueous sat. solution was added and the aqueous phase was extracted with dichlorometane. The organic phases were combined, dried over MgSO$_4$, filtered and concentrated to dryness. The residue was purified by flash chromatography, silica gel, gradient dichloromethane to methanol:dichloromethane (1:4) to give the title compound (18 mg, 16% yield). HPLC retention time: 3.47 min; MS: 458.2 (M+H).

This method was used for the preparation of examples 257-260 starting from the corresponding examples described above:

| EX | Structure | Chemical name | Ret time (min) | MS (M + H) |
|---|---|---|---|---|
| 257 | 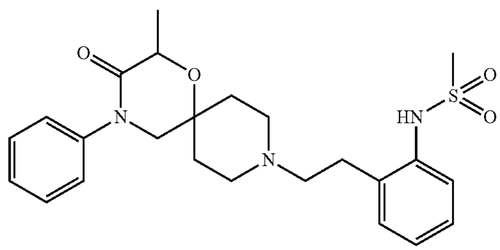 [SMILES: CC1OC2(CCN(CCc3ccccc3NS(C)(=O)=O)CC2)CN(c2ccccc2)C1=O] | N-(2-(2-(2-methyl-3-oxo-4-phenyl-1-oxa-4,9-diazaspiro[5.5]undecan-9-yl)ethyl)phenyl)methanesulfonamide | 4.05 | 458.2 |
| 258 | 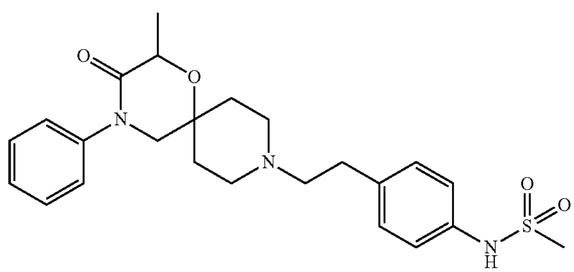 [SMILES: CC1OC2(CCN(CCc3ccc(NS(C)(=O)=O)cc3)CC2)CN(c2ccccc2)C1=O] | N-(4-(2-(2-methyl-3-oxo-4-phenyl-1-oxa-4,9-diazaspiro[5.5]undecan-9-yl)ethyl)phenyl)methanesulfonamide | 3.39 | 458.2 |
| 259 | 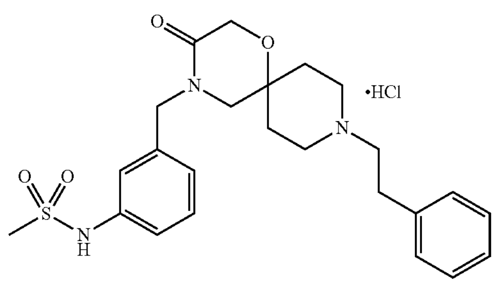 [SMILES: CS(=O)(=O)Nc1cccc(CN2CC3(CCN(CCc4ccccc4)CC3)OCC2=O)c1 ; Cl] | N-(3-((3-oxo-9-phenethyl-1-oxa-4,9-diazaspiro[5.5]undecan-4-yl)methyl)phenyl)methanesulfonamide hydrochloride | 3.60 | 458.1 |
| 260 | 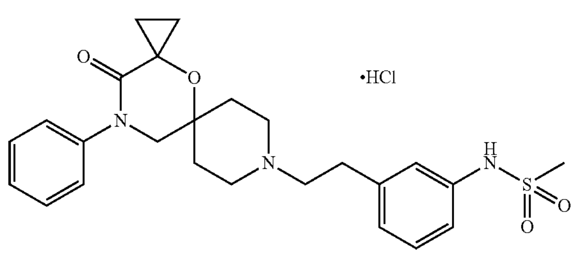 [SMILES: CS(=O)(=O)Nc1cccc(CCN2CCC3(CC2)CN(c2ccccc2)C(=O)C2(CC2)O3)c1 ; Cl] | N-[3-(2-{13-oxo-12-phenyl-4-oxa-8,12-diazadispiro[2.1.5.3]tridecan-8-yl}ethyl)phenyl]methanesulfonamide hydrochloride | 3.56 | 470.1 |

Where indicated, the hydrochloride salts were prepared as described in example 1

Example 261: N-(3-(2-(2-methyl-3-oxo-4-phenyl-1-oxa-4,9-diazaspiro[5.5]undecan-9-yl)ethyl)phenyl)propane-2-sulfonamide hydrochloride

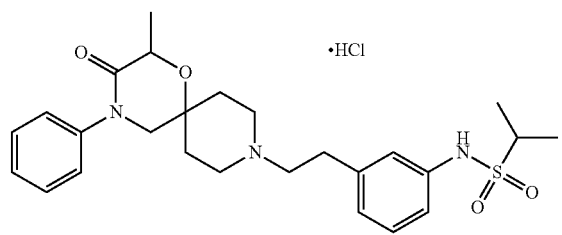 [SMILES: CC1OC2(CCN(CCc3cccc(NS(=O)(=O)C(C)C)c3)CC2)CN(c2ccccc2)C1=O ; Cl]

Example 262: 1-(3-(2-(2-methyl-3-oxo-4-phenyl-1-oxa-4,9-diazaspiro[5.5]undecan-9-yl)ethyl)phenyl)urea

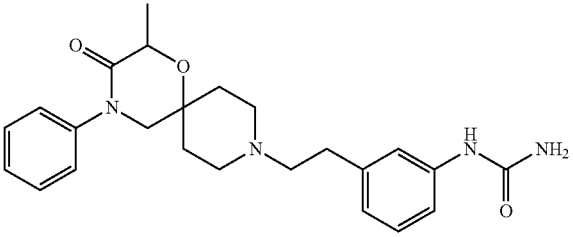 [SMILES: CC1OC2(CCN(CCc3cccc(NC(N)=O)c3)CC2)CN(c2ccccc2)C1=O]

To a solution of 2-propanesulfonyl chloride (0.024 mL, 0.217 mmol) in dichloromethane (0.15 mL), LiBr (19 mg, 0.217 mmol), pyridine (0.088 mL, 1.09 mmol) and example 226 (0.075 g, 0.198 mmol) were sequentially added and the reaction mixture was stirred at r.t. overnight. An additional load of reagents was added and the reaction mixture was again stirred at r.t. overnight to get the reaction to completion. It was then evaporated to dryness, water was added to the residue and it was extracted with dichloromethane. The organic phases were combined, dried over MgSO$_4$, filtered and concentrated to dryness. The residue was purified by flash chromatography, silica gel, gradient dichloromethane to methanol:dichloromethane (1:4) to give the title compound as its free base (21 mg, 22% yield).

The previous compound was converted to its hydrochloride salt as described in example 1.

HPLC retention time: 3.81 min; MS: 486.2 (M+H).

To a solution of example 226 (0.100 g, 0.263 mmol) in a mixture of acetic acid:water 1:1.5 (3 mL), potassium cyanate (0.032 g, 0.395 mmol) was added, and the reaction mixture was stirred at r.t. overnight. NaHCO$_3$ aqueous sat solution was added, and the aqueous phase was extracted with ethyl acetate. The organic phases were combined, washed with water, dried over MgSO$_4$, filtered and concentrated under vacuum. The residue was purified by flash chromatography, silica gel, gradient dichloromethane to methanol:dichloromethane (1:4) to give the title compound (0.046 g, 53% yield). HPLC retention time: 3.08 min; MS: 423.2 (M+H).

This method was used for the preparation of example 263 starting from the corresponding example described above:

| EX | Structure | Chemical name | Ret time (min) | MS (M + H) |
|---|---|---|---|---|
| 263 | ![structure] | {3-[2-(13-oxo-12-{[5-(trifluoromethyl)pyridin-2-yl]methyl}-4-oxa-8,12-diazadispiro[2.1.5.3]tridecan-8-yl)ethyl]phenyl}urea dihydrochloride | 3.42 | 518.2 |

Where indicated, the hydrochloride salts were prepared as described in example 1.

Example 264: 1-(6-(2-(2-methyl-3-oxo-4-phenyl-1-oxa-4,9-diazaspiro[5.5]undecan-9-yl)ethyl)pyridin-2-yl)urea

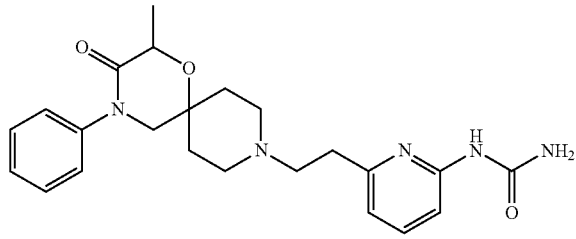 [SMILES: CC1OC2(CCN(CCc3cccc(NC(N)=O)n3)CC2)CN(c2ccccc2)C1=O]

To a solution of example 29 (0.050 g, 0.131 mmol) in dichloromethane (1.1 mL), benzoyl isocyanate (0.290 g, 0.197 mmol) was added under nitrogen atmosphere and the reaction mixture was heated to reflux overnight. The mixture was concentrated to dryness and the residue was dissolved in ethanol (8.3 mL). $K_2CO_3$ (0.027 g, 0.197 mmol) was added and after stirring at 80° C. for 1 h the solvent was evaporated. Water was added to the residue, and the mixture was extracted with ethyl acetate. The organic phases were combined, dried over $MgSO_4$, filtered and concentrated to dryness. The residue was purified by flash chromatography, $C_{18}$, gradient aqueous $NH_4HCO_3$ pH 8 to acetonitrile, to give the title compound (22 mg, 40% yield). HPLC retention time: 2.96 min; MS: 424.1 (M+H).

Example 265: N-[3-(2-{2-methyl-3-oxo-4-phenyl-1-oxa-4,9-diazaspiro[5.5]undecan-9-yl}ethyl)phenyl]aminosulfonamide

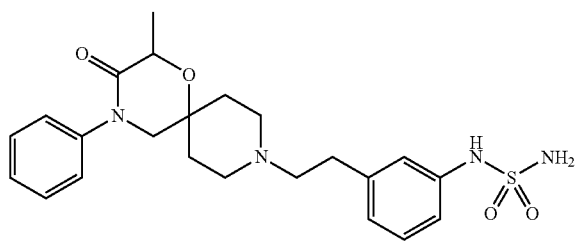 [SMILES: CC1OC2(CCN(CCc3cccc(NS(N)(=O)=O)c3)CC2)CN(c2ccccc2)C1=O]

To a solution of chlorosulfonyl isocyanate (0.22 mL, 1.48 mmol) in acetonitrile (15 mL) cooled at 0° C., water (0.042 mL, 2.32 mmol) was added and the mixture was stirred at r.t. for 3 h. 1.9 mL of the resulting solution were cooled to 0° C., then pyridine (0.034 mL, 0.422 mmol) and a solution of example 226 (0.080 g, 0.211 mmol) in acetonitrile (1.5 mL) were added. The reaction mixture was stirred at r.t. overnight. Water was then added and the mixture was extracted with ethyl acetate. The organic phases were combined, dried over $MgSO_4$, filtered and concentrated to dryness. The residue was purified by flash chromatography, silica gel, gradient dichloromethane to methanol:dichloromethane (1:4) to give the title compound (9 mg, 9% yield). HPLC retention time: 3.23 min; MS: 459.0 (M+H).

Example 266: 3-(2-(2-methyl-3-oxo-4-phenyl-1-oxa-4,9-diazaspiro[5.5]undecan-9-yl)ethyl)benzamide

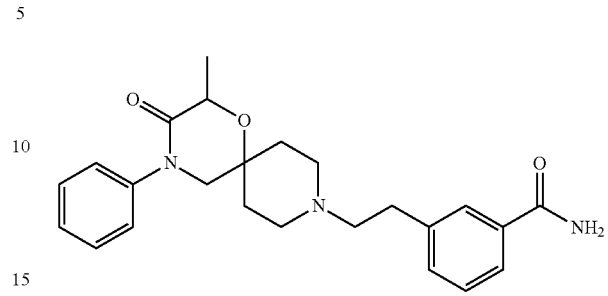

To a solution of example 75 (0.149 g, 0.383 mmol) in dichloromethane (0.5 mL) cooled with an ice/water bath, concentrated sulfuric acid (0.28 mL, 5.28 mmol) was added dropwise, maintaining the temperature below 20° C. The reaction mixture was then stirred at r.t. overnight, after which it was cooled to 0° C. Water was added dropwise, the mixture was diluted with dichloromethane and the phases were separated. The aqueous phase was washed with dichloromethane, basified with aqueous ammonia to pH 10 and extracted with dichloromethane. The organic phases were combined, washed with brine, dried over $MgSO_4$, filtered and concentrated to dryness. The residue was purified by flash chromatography, silica gel, gradient dichloromethane to methanol:dichloromethane (1:4) to give the title compound (0.034 g, 22% yield). HPLC retention time: 3.07 min; MS: 408.2 (M+H).

Example 267: 4-(2-(2-methyl-3-oxo-4-phenyl-1-oxa-4,9-diazaspiro[5.5]undecan-9-yl)ethyl)benzoic acid

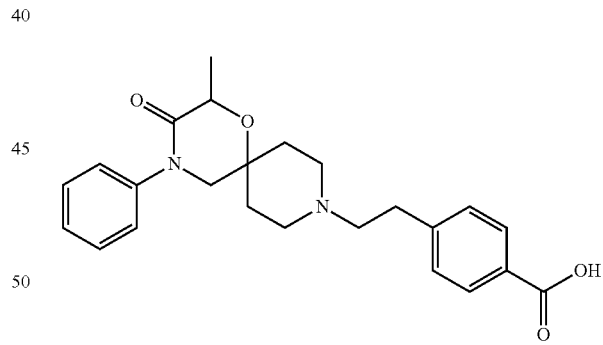

To a solution of example 70 (0.066 g, 0.151 mmol) in a mixture of THF/methanol 1:1 (3.4 mL), 1M NaOH aqueous solution (0.33 mL, 0.33 mmol) was added. The reaction mixture was stirred at r.t. overnight. The solvent was removed under vacuum, the pH was adjusted to 5 by addition of 1M HCl aqueous solution and the mixture was extracted with dichloromethane. The organic phases were combined, dried over $MgSO_4$, filtered and concentrated to dryness to give the title compound (0.048 g, 77% yield). HPLC retention time: 2.42 min; MS: 409.2 (M+H).

This method was used for the preparation of examples 268-270 starting from the corresponding examples described above:

| EX | Structure | Chemical name | Ret time (min) | MS (M + H) |
|---|---|---|---|---|
| 268 | 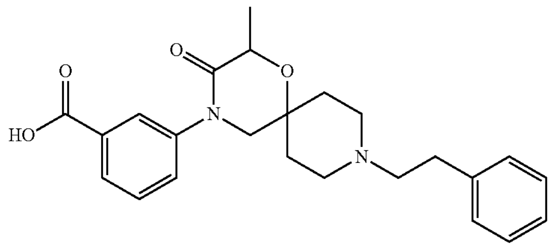 [SMILES: CC1OC2(CCN(CCc3ccccc3)CC2)CN(c2cccc(C(=O)O)c2)C1=O] | 3-(2-methyl-3-oxo-9-phenethyl-1-oxa-4,9-diazaspiro[5.5]undecan-4-yl)benzoic acid | 2.91 | 409.2 |
| 269 | 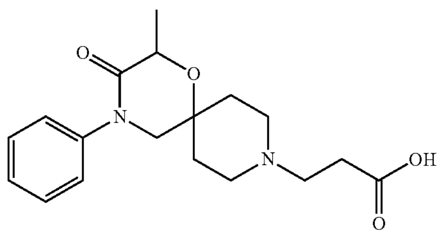 [SMILES: CC1OC2(CCN(CCC(=O)O)CC2)CN(c2ccccc2)C1=O] | 3-(2-methyl-3-oxo-4-phenyl-1-oxa-4,9-diazaspiro[5.5]undecan-9-yl)propanoic acid (*1) | 1.81 | 333.1 |
| 270 | 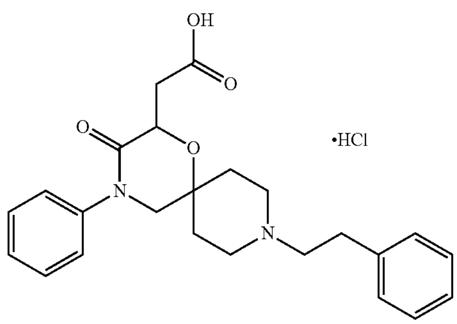 [SMILES: O=C(O)CC1OC2(CCN(CCc3ccccc3)CC2)CN(c2ccccc2)C1=O ; Cl] | 2-(3-oxo-9-phenethyl-4-phenyl-1-oxa-4,9-diazaspiro[5.5]undecan-2-yl)acetic acid hydrochloride (*2) | 2.72 | 409.2 |

Where indicated, the hydrochloride salts were prepared as described in example 1.
(*1) LiOH was used instead of NaOH
(*2) Potassium carbonate was used instead of NaOH Example 271: N,N-dimethyl-3-(2-methyl-3-oxo-9-phenethyl-1-oxa-4,9-diazaspiro[5.5]undecan-4-yl) benzamide hydrochloride

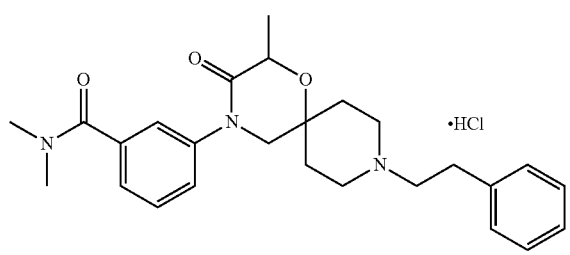 [SMILES: CC1OC2(CCN(CCc3ccccc3)CC2)CN(c2cccc(C(=O)N(C)C)c2)C1=O ; Cl]

To a solution of example 268 (0.047 g, 0.115 mmol) in dichloromethane (4 mL), dimethylamine solution (0.173 mL, 2M in THF, 0.345 mmol), 1-hydroxybenzotriazole (0.017 g, 0.127 mmol), N-(3-dimethylaminopropyl)-N-ethylcarbodiimide hydrochloride (0.022 g, 0.115 mmol) and triethylamine (0.053, 0.380 mmol) were added. The reaction mixture was stirred at r.t. overnight, then additional dimethylamine solution (0.173 mL, 2M in THF, 0.345 mmol), 1-hydroxybenzotriazole (0.017 g, 0.127 mmol), N-(3-dimethylaminopropyl)-N-ethylcarbodiimide hydrochloride (0.022 g, 0.115 mmol) and triethylamine (0.053, 0.380 mmol) were added. The reaction mixture was stirred at r.t. for an additional day. Water was added to the reaction mixture and it was extracted with dichloromethane. The organic phases were combined, washed with brine, dried over MgSO$_4$, filtered and concentrated to dryness. The residue was purified by flash chromatography, silica gel, gradient dichloromethane to methanol:dichloromethane (1:9) to give the title compound as its free base (25 mg, 46% yield).

The previous compound was converted to its hydrochloride salt as described in example 1.

HPLC retention time: 3.73 min; MS: 436.2 (M+H).

This method was used for the preparation of examples 272-274 starting from the corresponding examples described above:

| EX | Structure | Chemical name | Ret time (min) | MS (M + H) |
|---|---|---|---|---|
| 272 | 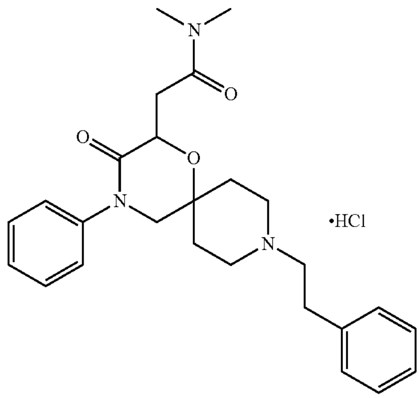 [SMILES: CN(C)C(=O)CC1OC2(CCN(CCc3ccccc3)CC2)CN(c2ccccc2)C1=O ; Cl] | N,N-dimethyl-2-(3-oxo-9-phenethyl-4-phenyl-1-oxa-4,9-diazaspiro[5.5]undecan-2-yl)acetamide hydrochloride | 3.68 | 436.2 |
| 273 | 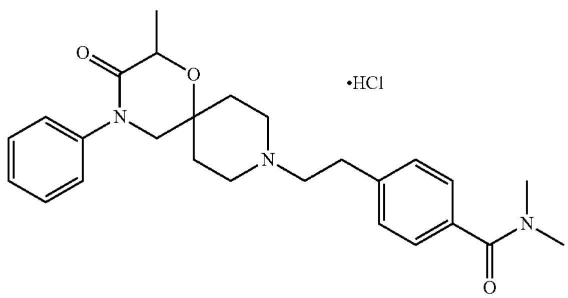 [SMILES: CC1OC2(CCN(CCc3ccc(C(=O)N(C)C)cc3)CC2)CN(c2ccccc2)C1=O ; Cl] | N,N-dimethyl-4-(2-(2-methyl-3-oxo-4-phenyl-1-oxa-4,9-diazaspiro[5.5]undecan-9-yl)ethyl)benzamide hydrochloride | 3.35 | 436.2 |
| 274 | 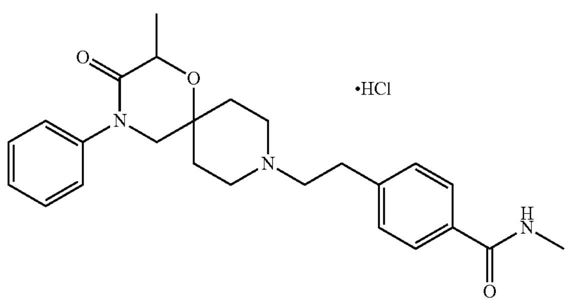 [SMILES: CNC(=O)c1ccc(CCN2CCC3(CC2)CN(c2ccccc2)C(=O)C(C)O3)cc1 ; Cl] | N-methyl-4-(2-(2-methyl-3-oxo-4-phenyl-1-oxa-4,9-diazaspiro[5.5]undecan-9-yl)ethyl)benzamide hydrochloride | 3.12 | 422.2 |

Example 275: N-methyl-3-[13-oxo-8-phenethyl-4-oxa-8,12-diazadispiro[2.1.5.3]tridecan-12-yl]propanamide hydrochloride

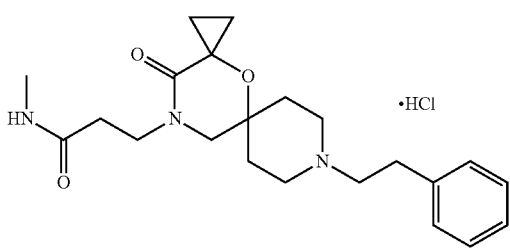 [SMILES: CNC(=O)CCN1CC2(CCN(CCc3ccccc3)CC2)OC2(CC2)C1=O ; Cl]

To a solution of example 186 (0.052 g, 0.135 mmol) in methanol (1.3 mL), methylamine solution (0.33 mL, 33% in ethanol, 2.69 mmol) was added. The reaction mixture was stirred at 100° C. in a sealed tube overnight. The residue obtained after concentration to dryness, was purified by flash chromatography, silica gel, gradient dichloromethane to methanol:dichloromethane (1:4) to give the title compound as its free base (0.040 g, 77% yield).

The previous compound was converted to its hydrochloride salt as described in example 1.

HPLC retention time: 3.31 min; MS: 386.2 (M+H).

This method was used for the preparation of example 276 starting from the corresponding example described above:

| EX | Structure | Chemical name | Ret time (min) | MS (M + H) |
|---|---|---|---|---|
| 276 | 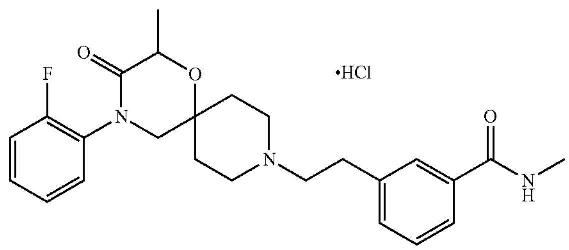 [SMILES: CNC(=O)c1cccc(CCN2CCC3(CC2)CN(c2ccccc2F)C(=O)C(C)O3)c1 ; Cl] | 3-(2-(4-(2-fluorophenyl)-2-methyl-3-oxo-1-oxa-4,9-diazaspiro[5.5]undecan-9-yl)ethyl)-N-methylbenzamide hydrochloride | 3.25 | 440.2 |

Example 277: 8-(2-hydroxy-2-phenylethyl)-12-phenyl-4-oxa-8,12-diazadispiro[2.1.5.3]tridecan-13-one

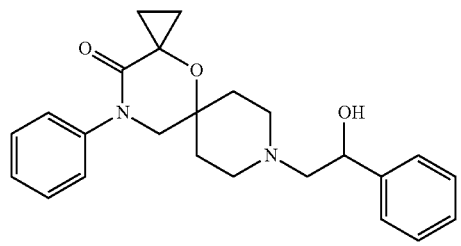 [SMILES: O=C1N(c2ccccc2)CC2(CCN(CC(O)c3ccccc3)CC2)OC12CC2]

To a solution of example 97 (0.050 g, 0.128 mmol) in methanol (0.2 mL) cooled at 0° C., NaBH₄ (10 mg, 0.256 mmol) was added. The reaction mixture was stirred at r.t. for 2 h, and then the solvent was evaporated. NaHCO₃ sat solution was added and it was extracted with ethyl acetate. The organic phases were combined, dried over MgSO₄, filtered and concentrated to dryness. The residue was purified by flash chromatography, silica gel, gradient dichloromethane to methanol:dichloromethane (1:4) and then the product was purified again by flash chromatography, C₁₈, gradient aqueous NH₄HCO₃ (pH 8) to acetonitrile, to give the title compound (0.014 g, 28% yield). HPLC retention time: 3.94 min; MS: 393.2 (M+H).

This method was used for the preparation of example 278 starting from the corresponding example described above:

Example 279: 12-(3-hydroxypropyl)-8-phenethyl-4-oxa-8,12-diazadispiro[2.1.5.3]tridecan-13-one hydrochloride

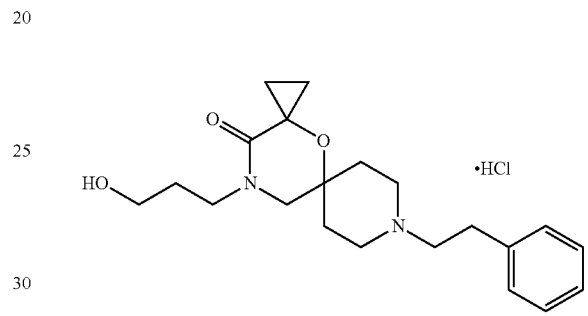

To a solution of example 186 (0.052 g, 0.128 mmol) in methanol (0.2 mL) cooled at 0° C., LiBH₄ (10 mg, 0.256 mmol) was added. The reaction mixture was stirred at r.t. overnight, and then the solvent was evaporated. NaHCO₃ aqueous sat. solution was added and the mixture was extracted with ethyl acetate. The organic phases were combined, dried over MgSO₄, filtered and concentrated to dryness. The residue was purified by flash chromatography, silica gel, gradient dichloromethane to methanol:dichloromethane (1:4) to give the title compound as its free base (0.023 g, 48% yield).

The previous compound was converted to its hydrochloride salt as described in example 1.

HPLC retention time: 3.43 min; MS: 359.2 (M+H).

| EX | Structure | Chemical name | Ret time (min) | MS (M + H) |
|---|---|---|---|---|
| 278 | 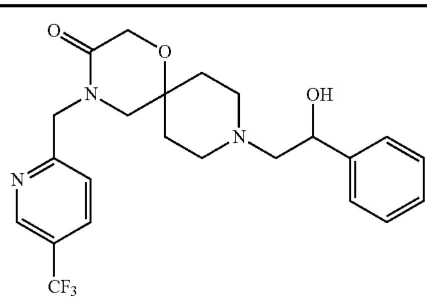 | 9-(2-hydroxy-2-phenylethyl)-4-((5-(trifluoromethyl)pyridin-2-yl)methyl)-1-oxa-4,9-diazaspiro[5.5]undecan-3-one | 3.72 | 450.2 |

Example 280: 9-(2-(6-aminopyridin-3-yl)ethyl)-2-methyl-4-phenyl-1-oxa-4,9-diazaspiro[5.5]undecan-3-one

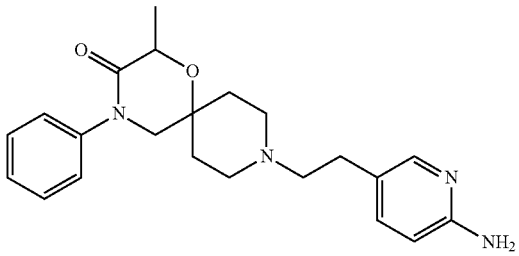

Step 1: 9-(2-(6-((diphenylmethylene)amino)pyridin-3-yl)ethyl)-2-methyl-4-phenyl-1-oxa-4,9-diazaspiro[5.5]undecan-3-one. A mixture of example 113 (0.117 g, 0.284 mmol), sodium tert-butoxide (0.038 g, 0.398 mmol), tris(dibenzylideneacetone)dipalladium(0) (3 mg, 0.011 mmol), 2,2'-bis(diphenylphosphino)-1,1'-binaphthalene (14 mg, 0.023 mmol) and benzophenone imine (0.062 g, 0.341 mmol) in dry toluene (3 mL) was heated in a sealed tube under an argon atmosphere at 100° C. for 2 days. The reaction mixture was cooled to r.t., NaHCO$_3$ aqueous sat. solution was added and it was extracted with ethyl acetate. The organic phases were combined, dried over MgSO$_4$ and concentrated under vacuum to give the title compound as a crude product, that was used in the following step without further purification. HPLC retention time: 4.74 min; MS: 545 (M+H).

Step 2: Title compound. A solution of the crude product obtained in step 1 in a 2:1 mixture of THF/10% HCl aqueous solution (6 mL) was stirred at r.t. overnight. 1M NaOH aqueous solution was added until pH >10 and the reaction mixture was extracted with ethyl acetate. The organic phases were combined, dried over MgSO$_4$, filtered and concentrated to dryness. The residue was purified by flash chromatography, silica gel, gradient dichloromethane to methanol:dichloromethane (1:9) to give the title compound (0.049 g, 45% yield for the two steps). HPLC retention time: 2.89 min; MS: 381.2 (M+H).

Example 281: 4-(2-fluorophenyl)-9-(2-(2-hydroxyethoxy)phenethyl)-2-isopropyl-1-oxa-4,9-diazaspiro[5.5]undecan-3-one

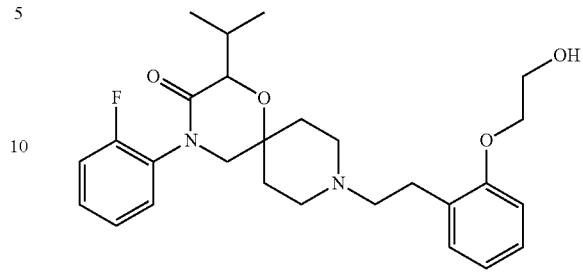

A solution of example 297 (0.065 g, 0.152 mmol), ethylene carbonate (0.015 mL, 0.229 mmol) and K$_2$CO$_3$ (0.042 g, 0.305 mmol) in DMF (0.8 mL) was stirred at 110° C. in a sealed tube overnight. Water was added and the reaction mixture was extracted with ethyl acetate. The organic phases were combined, washed with brine, dried over MgSO$_4$, filtered and concentrated to dryness. The residue was purified by flash chromatography, silica gel, gradient dichloromethane to methanol:dichloromethane (1:4) to give the title compound (39 mg, 55% yield). HPLC retention time: 4.45 min; MS: 471.3 (M+H).

This method was used for the preparation of example 282 starting from the corresponding example described above:

| EX | | Chemical name | Ret time (min) | MS (M + H) |
|---|---|---|---|---|
| 282 | | 4-(2-fluorophenyl)-9-(3-(2-hydroxyethoxy)phenethyl)-2-methyl-1-oxa-4,9-diazaspiro[5.5]undecan-3-one hydrochloride | 3.54 | 443.2 |

The hydrochloride salt was prepared as described in example 1.

Example 283: 2-(hydroxymethyl)-9-phenethyl-4-phenyl-1-oxa-4,9-diazaspiro[5.5]undecan-3-one

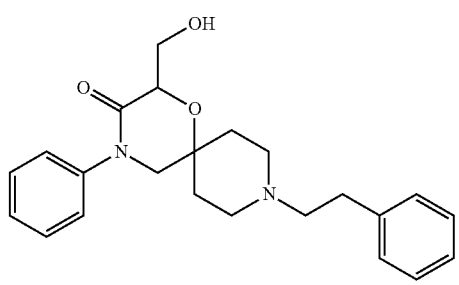 [SMILES: O=C1C(CO)OC2(CCN(CCc3ccccc3)CC2)CN1c1ccccc1]

A mixture of example 19 (free base) (1.53 g, 3.26 mmol) and palladium hydroxide (306 mg, 20% wt on charcoal) in a mixture of THF/AcOH 9:1 (15 mL) was heated at 50° C. under 3 bars of H$_2$ overnight. The solids were filtered off and the solvent was evaporated to dryness. This hydrogenation cycle was repeated 3 times adding fresh catalyst each time until reaction completion. Finally, the solids were filtered off and the solvent was removed under vacuum. The residue was purified by flash chromatography, silica gel, gradient dichloromethane to methanol:dichloromethane (1:9) to give the title compound (0.657 g, 53% yield). HPLC retention time: 3.44 min; MS: 381.2 (M+H).

Example 284: 4-((1H-imidazol-2-yl)methyl)-9-phenethyl-1-oxa-4,9-diazaspiro[5.5]undecan-3-one hydrochloride

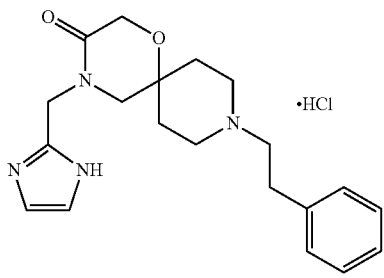 [SMILES: O=C1COC2(CCN(CCc3ccccc3)CC2)CN1Cc1ncc[nH]1 ; Cl]

A mixture of example 168 (free base) (0.051 g, 0.115 mmol), palladium (10 mg, 10% wt on charcoal) and some drops of AcOH in MeOH (2 mL) was heated at 65° C. under 5 bars of $H_2$ overnight. This hydrogenation cycle was repeated 3 times adding fresh catalyst and some drops of AcOH each time and heating at 65° C. under 3 bars of $H_2$ until reaction completion. Finally, the solids were filtered off and the solvent was removed under vacuum. The residue was purified by flash chromatography, silica gel, gradient dichloromethane to methanol:dichloromethane (1:4) to give the title compound as its free base (0.012 g, 30% yield).

The previous compound was converted to its hydrochloride salt as described in example 1.
HPLC retention time: 2.90 min; MS: 355.2 (M+H).

Example 285: 9-benzyl-4-(2-hydroxyphenyl)-1-oxa-4,9-diazaspiro[5.5]undecan-3-one

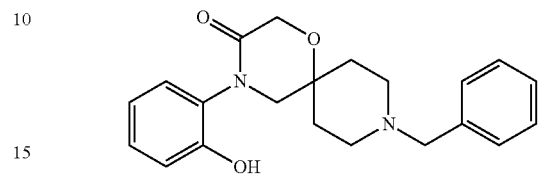

To a solution of example 2 (0.119 g, 0.325 mmol) in dichloromethane (5 mL), boron tribromide solution (0.97 mL, 1M in dichloromethane, 0.97 mmol) was added dropwise at −78° C. The reaction mixture was allowed to warm to −40° C. over 2 h. Then, 8M NaOH aqueous solution was added until pH 12 and the reaction mixture was extracted with dichloromethane. The organic phases were combined, washed with brine, dried over $MgSO_4$, filtered and concentrated to dryness. The residue was purified by flash chromatography, silica gel, gradient dichloromethane to methanol:dichloromethane (1:9) to give the title compound (0.040 g, 35% yield). HPLC retention time (method B): 3.43 min; MS: 353.1 (M+H).

This method was used for the preparation of examples 286-302 starting from the corresponding examples described above:

| EX | Structure | Chemical name | Ret time (min) | MS (M + H) |
|---|---|---|---|---|
| 286 | 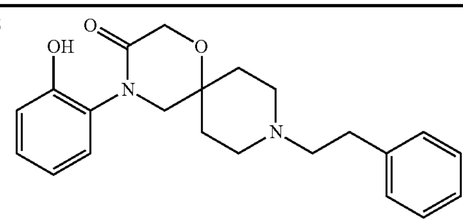 | 4-(2-hydroxyphenyl)-9-phenethyl-1-oxa-4,9-diazaspiro[5.5]undecan-3-one | 3.50 (method B) | 367.2 |
| 287 | 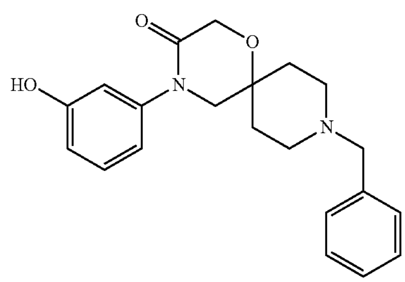 [SMILES: O=C1COC2(CCN(Cc3ccccc3)CC2)CN1c1cccc(O)c1] | 9-benzyl-4-(3-hydroxyphenyl)-1-oxa-4,9-diazaspiro[5.5]undecan-3-one | 3.39 (method B) | 353.1 |
| 288 | 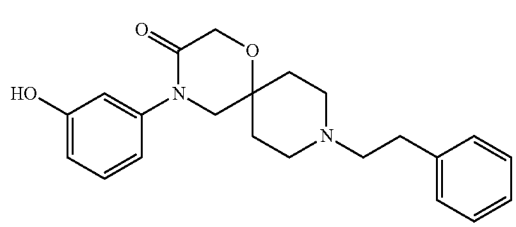 [SMILES: O=C1COC2(CCN(CCc3ccccc3)CC2)CN1c1cccc(O)c1] | 4-(3-hydroxyphenyl)-9-phenethyl-1-oxa-4,9-diazaspiro[5.5]undecan-3-one | 3.37 | 367.2 |

| EX | Structure | Chemical name | Ret time (min) | MS (M + H) |
|---|---|---|---|---|
| 289 | 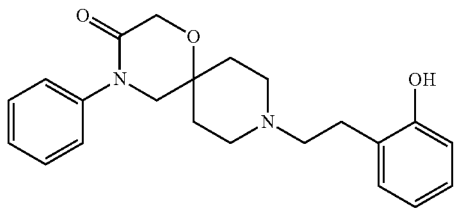 [SMILES: O=C1COC2(CCN(CCc3ccccc3O)CC2)CN1c1ccccc1] | 9-(2-hydroxyphenethyl)-4-phenyl-1-oxa-4,9-diazaspiro[5.5]undecan-3-one | 3.69 | 367.1 |
| 290 | 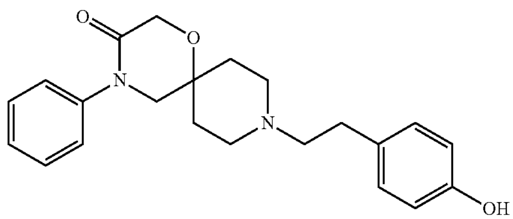 [SMILES: O=C1COC2(CCN(CCc3ccc(O)cc3)CC2)CN1c1ccccc1] | 9-(4-hydroxyphenethyl)-4-phenyl-1-oxa-4,9-diazaspiro[5.5]undecan-3-one | 2.91 | 367.1 |
| 291 | 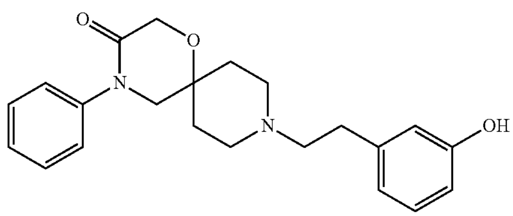 [SMILES: O=C1COC2(CCN(CCc3cccc(O)c3)CC2)CN1c1ccccc1] | 9-(3-hydroxyphenethyl)-4-phenyl-1-oxa-4,9-diazaspiro[5.5]undecan-3-one | 3.04 | 367.1 |
| 292 | 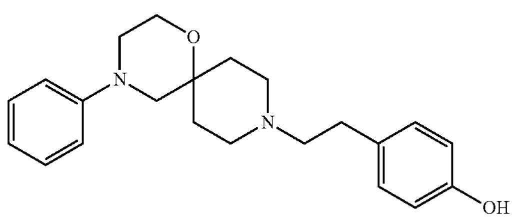 [SMILES: Oc1ccc(CCN2CCC3(CC2)CN(c2ccccc2)CCO3)cc1] | 4-(2-(4-phenyl-1-oxa-4,9-diazaspiro[5.5]undecan-9-yl)ethyl)phenol | 3.75 | 353.2 |
| 293 | 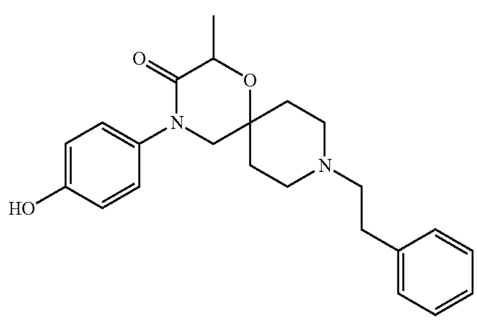 [SMILES: CC1OC2(CCN(CCc3ccccc3)CC2)CN(c2ccc(O)cc2)C1=O] | 4-(4-hydroxyphenyl)-2-methyl-9-phenethyl-1-oxa-4,9-diazaspiro[5.5]undecan-3-one | 3.59 | 381.2 |
| 294 | 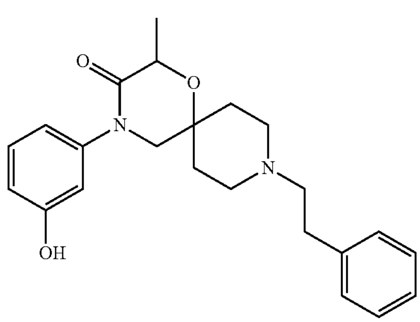 [SMILES: CC1OC2(CCN(CCc3ccccc3)CC2)CN(c2cccc(O)c2)C1=O] | 4-(3-hydroxyphenyl)-2-methyl-9-phenethyl-1-oxa-4,9-diazaspiro[5.5]undecan-3-one | 3.67 | 381.2 |

| EX | Structure | Chemical name | Ret time (min) | MS (M + H) |
|---|---|---|---|---|
| 295 | 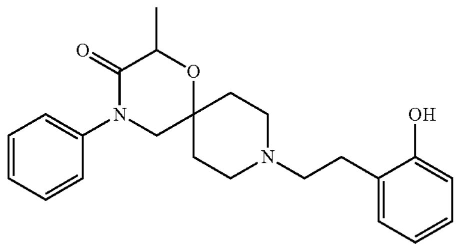 [SMILES: CC1OC2(CCN(CCc3ccccc3O)CC2)CN(c2ccccc2)C1=O] | 9-(2-hydroxyphenethyl)-2-methyl-4-phenyl-1-oxa-4,9-diazaspiro[5.5]undecan-3-one | 4.09 | 381.2 |
| 296 | 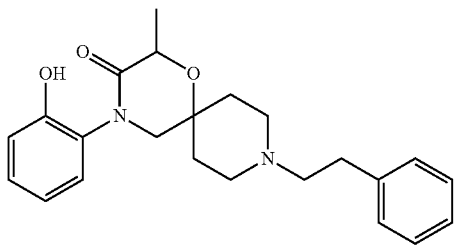 [SMILES: CC1OC2(CCN(CCc3ccccc3)CC2)CN(c2ccccc2O)C1=O] | 4-(2-hydroxyphenyl)-2-methyl-9-phenethyl-1-oxa-4,9-diazaspiro[5.5]undecan-3-one | 3.78 | 381.2 |
| 297 | 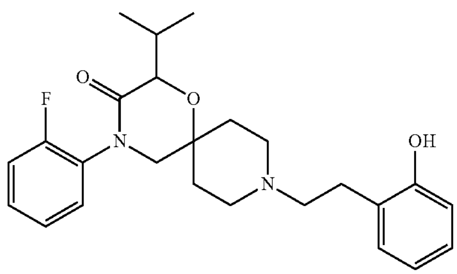 [SMILES: CC(C)C1OC2(CCN(CCc3ccccc3O)CC2)CN(c2ccccc2F)C1=O] | 4-(2-fluorophenyl)-9-(2-hydroxyphenethyl)-2-isopropyl-1-oxa-4,9-diazaspiro[5.5]undecan-3-one | 4.95 | 427.2 |
| 298 | 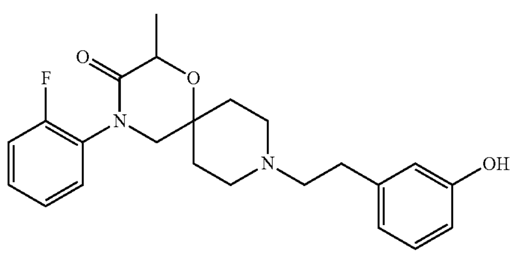 [SMILES: CC1OC2(CCN(CCc3cccc(O)c3)CC2)CN(c2ccccc2F)C1=O] | 4-(2-fluorophenyl)-9-(3-hydroxyphenethyl)-2-methyl-1-oxa-4,9-diazaspiro[5.5]undecan-3-one | 3.49 | 399.2 |
| 299 | 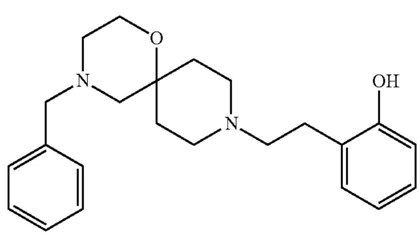 [SMILES: Oc1ccccc1CCN1CCC2(CC1)CN(Cc1ccccc1)CCO2] | 2-(2-(4-benzyl-1-oxa-4,9-diazaspiro[5.5]undecan-9-yl)ethyl)phenol | 5.01 | 367.2 |
| 300 | 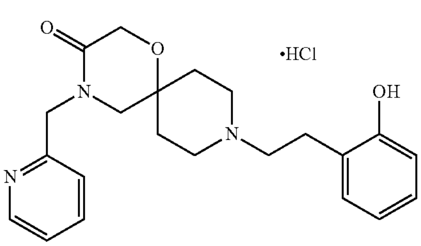 [SMILES: O=C1COC2(CCN(CCc3ccccc3O)CC2)CN1Cc1ccccn1 ; Cl] | 9-(2-hydroxyphenethyl)-4-(pyridin-2-ylmethyl)-1-oxa-4,9-diazaspiro[5.5]undecan-3-one hydrochloride | 3.31 | 382.2 |

| EX | Structure | Chemical name | Ret time (min) | MS (M + H) |
|---|---|---|---|---|
| 301 | 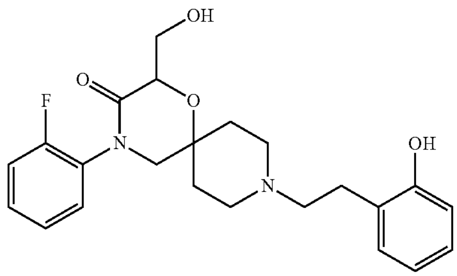 [SMILES: O=C1C(CO)OC2(CCN(CCc3ccccc3O)CC2)CN1c1ccccc1F] | 4-(2-fluorophenyl)-2-(hydroxymethyl)-9-(2-hydroxyphenethyl)-1-oxa-4,9-diazaspiro[5.5]undecan-3-one | 3.51 | 415.2 |
| 302 | 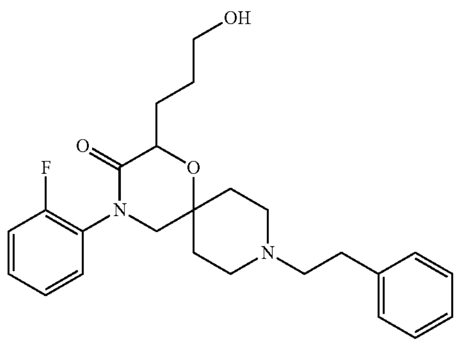 [SMILES: O=C1C(CCCO)OC2(CCN(CCc3ccccc3)CC2)CN1c1ccccc1F] | 4-(2-fluorophenyl)-2-(3-hydroxypropyl)-9-phenethyl-1-oxa-4,9-diazaspiro[5.5]undecan-3-one | 3.82 | 427.2 |

Where indicated, the hydrochloride salts were prepared as described in example 1.

Example 303: 9-(2-(2-aminothiazol-4-yl)ethyl)-4-(2-fluorophenyl)-2-methyl-1-oxa-4,9-diazaspiro[5.5]undecan-3-one

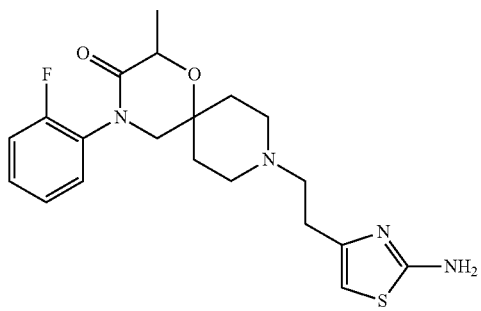 [SMILES: CC1OC2(CCN(CCc3csc(N)n3)CC2)CN(c2ccccc2F)C1=O]

To a solution of example 140 (0.067 g, 0.13 mmol) in dichloromethane (0.5 mL), trifluoroacetic acid (0.1 mL, 1.32 mmol) was added. The reaction mixture was stirred at r.t. overnight and then it was concentrated to dryness. The residue was taken into water and dichloromethane, and the pH was adjusted to basic with 1N NaOH aqueous solution. The organic phase was separated and the aqueous phase was back extracted with dichloromethane. The organic phases were combined, dried over $MgSO_4$, filtered and concentrated to dryness. The residue was purified by flash chromatography, silica gel, gradient dichloromethane to methanol:dichloromethane (1:4) to give the title compound (0.028 g, 54% yield). HPLC retention time: 3.03 min; MS: 405.1 (M+H).

This method was used for the preparation of examples 304-309 starting from the corresponding examples described above:

| EX | Structure | Chemical name | Ret time (min) | MS (M + H) |
|---|---|---|---|---|
| 304 | 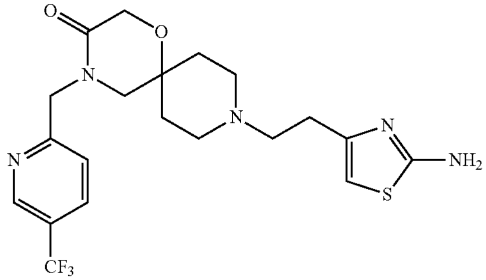 [SMILES: Nc1nc(CCN2CCC3(CC2)CN(Cc2ccc(C(F)(F)F)cn2)C(=O)CO3)cs1] | 9-(2-(2-aminothiazol-4-yl)ethyl)-4-((5-(trifluoromethyl)pyridin-2-yl)methyl)-1-oxa-4,9-diazaspiro[5.5]undecan-3-one | 3.08 | 456.1 |

-continued

| EX | Structure | Chemical name | Ret time (min) | MS (M + H) |
|---|---|---|---|---|
| 305 | ·HCl | 9-(2-(5-amino-1H-pyrazol-1-yl)ethyl)-2-methyl-4-phenyl-1-oxa-4,9-diazaspiro[5.5]undecan-3-one hydrochloride | 2.68 | 370.2 |
| 306 | ·2HCl | 9-(2-(2-aminothiazol-4-yl)ethyl)-4-(2-fluorophenyl)-2-isopropyl-1-oxa-4,9-diazaspiro[5.5]undecan-3-one dihydrochloride | 3.76 | 433.2 |
| 307 | ·2HCl | 8-[2-(2-aminothiazol-4-yl)ethyl]-12-phenyl-4-oxa-8,12-diazadispiro[2.1.5.3]tridecan-13-one dihydrochloride | 3.11 | 399.2 |
| 308 | ·3HCl | 8-[2-(2-aminothiazol-4-yl)ethyl]-12-{[5-(trifluoromethyl)pyridin-2-yl]methyl}-4-oxa-8,12-diazadispiro[2.1.5.3]tridecan-13-one trihydrochloride | 3.43 | 482.2 |
| 309 | 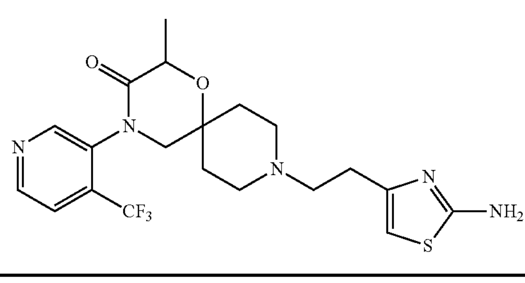 | 9-(2-(2-aminothiazol-4-yl)ethyl)-2-methyl-4-(4-(trifluoromethyl)pyridin-3-yl)-1-oxa-4,9-diazaspiro[5.5]undecan-3-one | 2.98 | 456.1 |

Where indicated, the hydrochloride salts were prepared as described in example 1.

Example 310: 12-(2-hydroxyethyl)-8-phenethyl-4-oxa-8,12-diazadispiro[2.1.5.3]tridecan-13-one hydrochloride

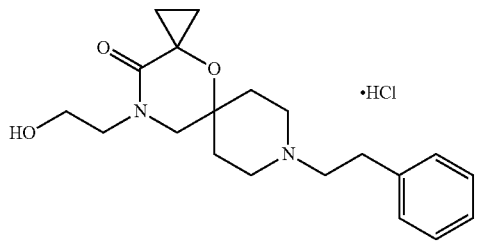 [SMILES: O=C1N(CCO)CC2(CCN(CCc3ccccc3)CC2)OC12CC2 ; Cl]

A solution of example 185 (0.105 g, 0.155 mmol) in a mixture of THF/1M HCl aqueous solution 1:1 (2 mL) was stirred at r.t. for 2 h. Then, NaHCO₃ sat solution was added until pH 8. The aqueous phase was extracted with dichloromethane and the organic phases were combined, dried over MgSO₄, filtered and concentrated to dryness. The residue was purified by flash chromatography, silica gel, gradient dichloromethane to methanol:dichloromethane (1:4) to give the title compound as its free base (0.036 g, 100% yield).

The previous compound was converted to its hydrochloride salt as described in example 1.

HPLC retention time: 3.30 min; MS: 345.2 (M+H).

Example 311: 4-(2-fluorophenyl)-9-phenethyl-2-((tetrahydro-2H-pyran-4-yl)methyl)-1-oxa-4,9-diazaspiro[5.5]undecan-3-one hydrochloride

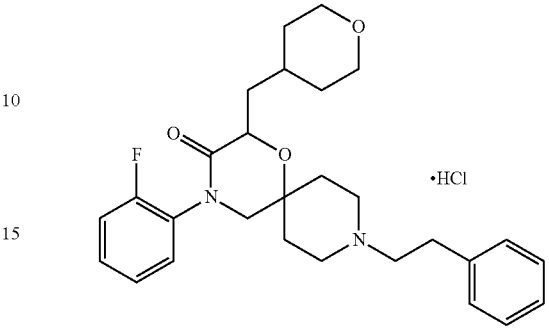

A mixture of example 80 (0.054 g, 0.116 mmol) and palladium (16 mg, 10% wt on charcoal) in ethyl acetate (2 mL) was heated at 30° C. under 3 bars of H₂ overnight. Then, the solids were filtered off, and the solvent was removed under vacuum to give the title compound as its free base (0.049 g, 91% yield).

The previous compound was converted to its hydrochloride salt as described in example 1.

HPLC retention time: 4.53 min; MS: 467.3 (M+H).

This method was used for the preparation of examples 312-314 starting from the corresponding examples described above:

| EX | Structure | Chemical name | Ret time (min) | MS (M + H) |
|---|---|---|---|---|
| 312 | 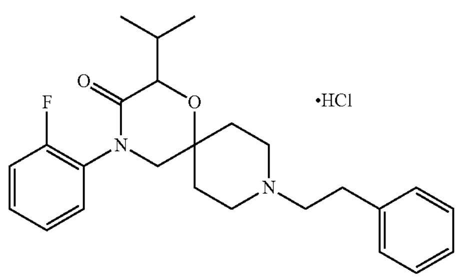 [SMILES: CC(C)C1OC2(CCN(CCc3ccccc3)CC2)CN(c2ccccc2F)C1=O ; Cl] | 4-(2-fluorophenyl)-2-isopropyl-9-phenethyl-1-oxa-4,9-diazaspiro[5.5]undecan-3-one hydrochloride | 5.07 | 411.2 |
| 313 | 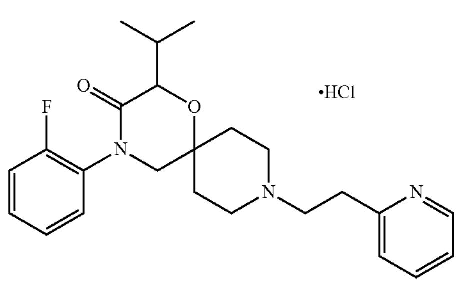 [SMILES: CC(C)C1OC2(CCN(CCc3ccccn3)CC2)CN(c2ccccc2F)C1=O ; Cl] | 4-(2-fluorophenyl)-2-isopropyl-9-(2-(pyridin-2-yl)ethyl)-1-oxa-4,9-diazaspiro[5.5]undecan-3-one hydrochloride | 4.00 | 412.2 |

| EX | Structure | Chemical name | Ret time (min) | MS (M + H) |
|---|---|---|---|---|
| 314 | 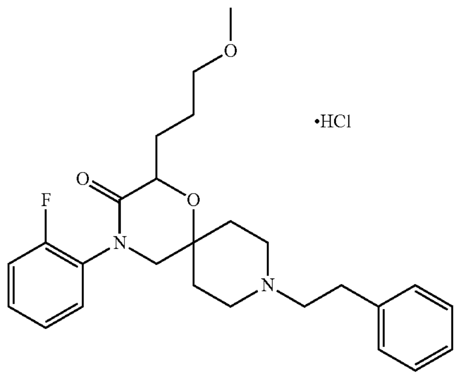 [SMILES: COCCCC1OC2(CCN(CCc3ccccc3)CC2)CN(c2ccccc2F)C1=O ; Cl] | 4-(2-fluorophenyl)-2-(3-methoxypropyl)-9-phenethyl-1-oxa-4,9-diazaspiro[5.5]undecan-3-one hydrochloride | 4.52 | 441.2 |

Example 315: N-methyl-2-(2-methyl-3-oxo-4-phenyl-1-oxa-4,9-diazaspiro[5.5]undecan-9-yl)-N-phenylacetamide hydrochloride To a solution of example 71 (24 mg, 0.170 mmol) in dry THF (2 mL), NaH (10 mg, 60 wt % in mineral oil, 0.069 mmol) was added. The reaction mixture was stirred at r.t. for 30 min, then iodomethane (0.067 mL, 0.170 mmol) was added and the resulting mixture was stirred at r.t. overnight. Dichloromethane was added to the reaction mixture and the organic phase was washed with $NaHCO_3$ sat solution and then with brine, dried over $MgSO_4$, filtered and concentrated to dryness. The residue was purified by flash chromatography, silica gel, gradient dichloromethane to methanol:dichloromethane (1:9) to give the title compound as its free base (32 mg, 46% yield).

The previous compound was converted to its hydrochloride salt as described in example 1.

HPLC retention time: 3.64 min; MS: 408.2 (M+H).

Example 316: 3-(9-phenethyl-1-oxa-4,9-diazaspiro[5.5]undecan-4-yl)phenol

To a solution of example 288 (0.055 g, 0.150 mmol) in THF (3.2 mL), $LiAlH_4$ solution (0.60 mL, 1M in THF, 0.60 mmol) was added dropwise. The reaction mixture was stirred at 70° C. for 2 h. Then, water and 1M NaOH aqueous solution were added. The resulting suspension was filtered through a pad of celite, dried over $MgSO_4$, filtered and concentrated to dryness. The residue was purified by flash chromatography, silica gel, gradient dichloromethane to methanol:dichloromethane (0.5:9.5) to give the title compound (0.037 g, 70% yield). HPLC retention time: 3.89 min; MS: 353.2 (M+H).

This method was used for the preparation of examples 317-331 starting from the corresponding examples described above:

| EX | Structure | Chemical name | Ret time (min) | MS (M + H) |
|---|---|---|---|---|
| 317 | 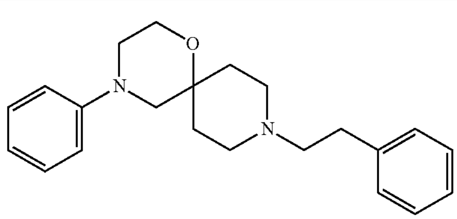 [SMILES: c1ccc(CCN2CCC3(CC2)CN(c2ccccc2)CCO3)cc1] | 9-phenethyl-4-phenyl-1-oxa-4,9-diazaspiro[5.5]undecane | 5.01 (method B) | 337.2 |

-continued

| EX | Structure | Chemical name | Ret time (min) | MS (M + H) |
|---|---|---|---|---|
| 318 | 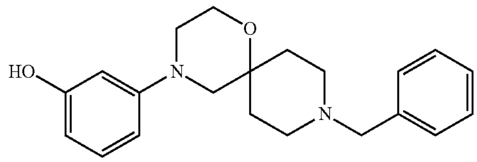 [SMILES: Oc1cccc(N2CCOC3(CCN(Cc4ccccc4)CC3)C2)c1] | 3-(9-benzyl-1-oxa-4,9-diazaspiro[5.5]undecan-4-yl)phenol | 3.88 | 339.2 |
| 319 | 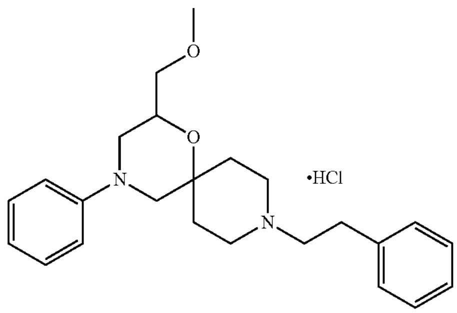 [SMILES: COCC1CN(c2ccccc2)CC2(CCN(CCc3ccccc3)CC2)O1 ; Cl] | 2-(methoxymethyl)-9-phenethyl-4-phenyl-1-oxa-4,9-diazaspiro[5.5]undecane hydrochloride | 4.77 | 381.2 |
| 320 | 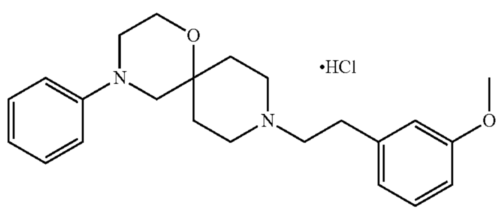 [SMILES: COc1cccc(CCN2CCC3(CC2)CN(c2ccccc2)CCO3)c1 ; Cl] | 9-(3-methoxyphenethyl)-4-phenyl-1-oxa-4,9-diazaspiro[5.5]undecane hydrochloride | 4.65 | 367.2 |
| 321 | 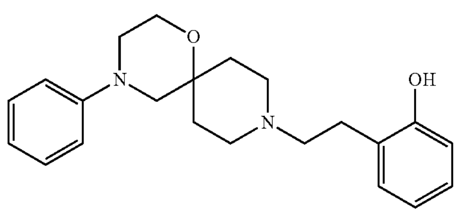 [SMILES: Oc1ccccc1CCN1CCC2(CC1)CN(c1ccccc1)CCO2] | 2-(2-(4-phenyl-1-oxa-4,9-diazaspiro[5.5]undecan-9-yl)ethyl)phenol | 4.72 | 353.1 |
| 322 | 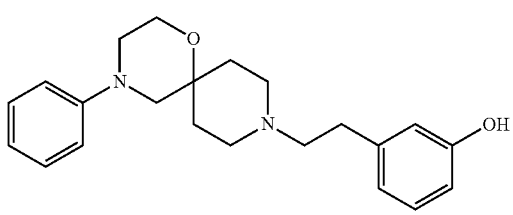 [SMILES: Oc1cccc(CCN2CCC3(CC2)CN(c2ccccc2)CCO3)c1] | 3-(2-(4-phenyl-1-oxa-4,9-diazaspiro[5.5]undecan-9-yl)ethyl)phenol | 3.90 | 353.2 |
| 323 | 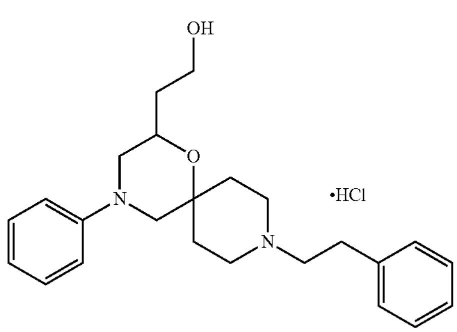 [SMILES: OCCC1CN(c2ccccc2)CC2(CCN(CCc3ccccc3)CC2)O1 ; Cl] | 2-(9-phenethyl-4-phenyl-1-oxa-4,9-diazaspiro[5.5]undecan-2-yl)ethanol hydrochloride | 4.09 | 381.2 |

| EX | Structure | Chemical name | Ret time (min) | MS (M + H) |
|---|---|---|---|---|
| 324 | 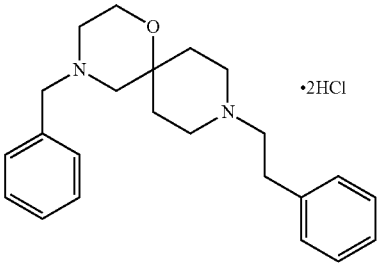 [SMILES: c1ccc(CCN2CCC3(CC2)CN(Cc2ccccc2)CCO3)cc1 ; "·2HCl"] | 4-benzyl-9-phenethyl-1-oxa-4,9-diazaspiro[5.5]undecane dihydrochloride | 4.93 | 351.2 |
| 325 | 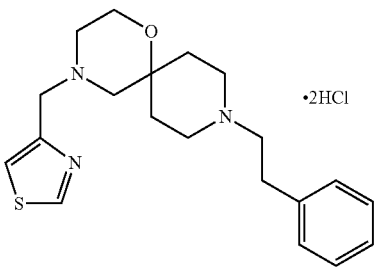 [SMILES: c1ccc(CCN2CCC3(CC2)CN(Cc2cscn2)CCO3)cc1 ; "·2HCl"] | 9-phenethyl-4-(thiazol-4-ylmethyl)-1-oxa-4,9-diazaspiro[5.5]undecane dihydrochloride | 3.48 | 358.2 |
| 326 | 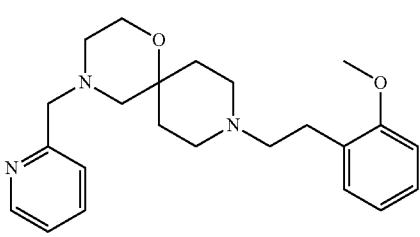 [SMILES: COc1ccccc1CCN1CCC2(CC1)CN(Cc1ccccn1)CCO2] | 9-(2-methoxyphenethyl)-4-(pyridin-2-ylmethyl)-1-oxa-4,9-diazaspiro[5.5]undecane | 3.62 | 382.2 |
| 327 | 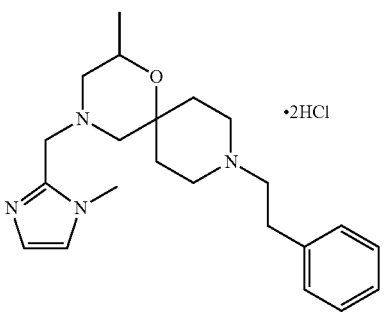 [SMILES: CC1CN(Cc2nccn2C)CC2(CCN(CCc3ccccc3)CC2)O1 ; "·2HCl"] | 2-methyl-4-((1-methyl-1H-imidazol-2-yl)methyl)-9-phenethyl-1-oxa-4,9-diazaspiro[5.5]undecane dihydrochloride | 3.60 | 369.2 |
| 328 | 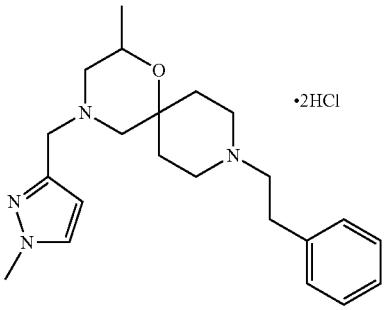 [SMILES: CC1CN(Cc2ccn(C)n2)CC2(CCN(CCc3ccccc3)CC2)O1 ; "·2HCl"] | 2-methyl-4-((1-methyl-1H-pyrazol-3-yl)methyl)-9-phenethyl-1-oxa-4,9-diazaspiro[5.5]undecane dihydrochloride | 3.64 | 369.2 |

-continued

| EX | Structure | Chemical name | Ret time (min) | MS (M + H) |
|---|---|---|---|---|
| 329 | 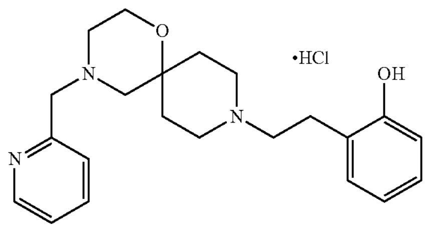 [SMILES: Oc1ccccc1CCN1CCC2(CC1)CN(Cc1ccccn1)CCO2 ; Cl] | 2-(2-(4-(pyridin-2-ylmethyl)-1-oxa-4,9-diazaspiro[5.5]undecan-9-yl)ethyl)phenol hydrochloride | 3.71 | 368.2 |
| 330 | 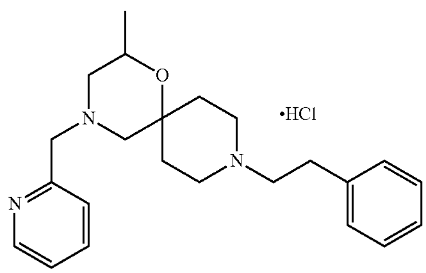 [SMILES: CC1CN(Cc2ccccn2)CC2(CCN(CCc3ccccc3)CC2)O1 ; Cl] | 2-methyl-9-phenethyl-4-(pyridin-2-ylmethyl)-1-oxa-4,9-diazaspiro[5.5]undecane hydrochloride | 4.03 | 366.2 |
| 331 | 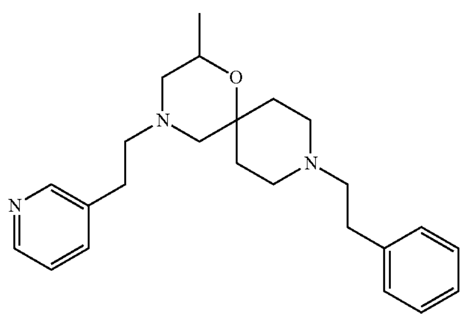 [SMILES: CC1CN(CCc2cccnc2)CC2(CCN(CCc3ccccc3)CC2)O1] | 2-methyl-9-phenethyl-4-(2-(pyridin-3-yl)ethyl)-1-oxa-4,9-diazaspiro[5.5]undecane hydrochloride | 4.02 | 380.2 |

Where indicated, the hydrochloride salts were prepared as described in example 1.

Example 332: 9-(4-methoxyphenethyl)-4-phenyl-1-oxa-4,9-diazaspiro[5.5]undecane

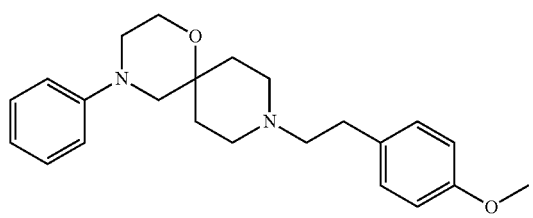 [SMILES: COc1ccc(CCN2CCC3(CC2)CN(c2ccccc2)CCO3)cc1]

To a solution of example 52 (0.150 g, 0.394 mmol) in THF (6.5 mL), LiAlH₄ solution (1.58 mL, 1M in THF, 1.58 mmol) was added dropwise. The reaction mixture was stirred at 70° C. for 2 h. Then, water and 1M NaOH aqueous solution were added. The resulting suspension was filtered through a pad of celite, dried over MgSO₄, filtered and concentrated to dryness. The residue was dissolved in ethanol (1.7 mL) and palladium (13 mg, 10% wt on charcoal) was added. The resulting mixture was stirred under 3 bars of H₂ at r.t. overnight. Then, the solids were filtered off, and the solvent was removed under vacuum. The residue was purified by flash chromatography, silica gel, gradient dichloromethane to methanol:dichloromethane (1:9) to give the title compound (0.079 g, 55% yield). HPLC retention time: 4.56 min; MS: 367.2 (M+H).

This method was used for the preparation of examples 333-334 starting from the corresponding examples described above:

| EX | Structure | Chemical name | Ret time (min) | MS (M + H) |
|---|---|---|---|---|
| 333 | 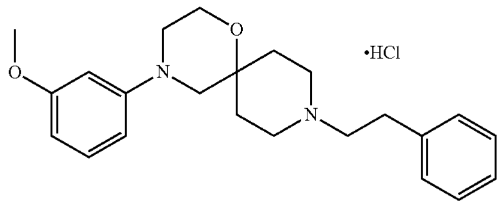 [SMILES: COc1cccc(N2CCOC3(CCN(CCc4ccccc4)CC3)C2)c1 ; Cl] | 4-(3-methoxyphenyl)-9-phenethyl-1-oxa-4,9-diazaspiro[5.5]undecane hydrochloride | 4.64 | 367.2 |
| 334 | 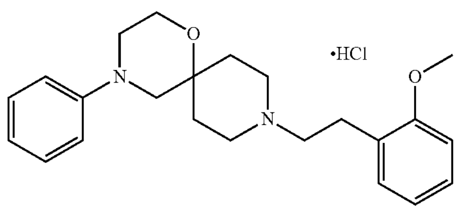 [SMILES: COc1ccccc1CCN1CCC2(CC1)CN(c1ccccc1)CCO2 ; Cl] | 9-(2-methoxyphenethyl)-4-phenyl-1-oxa-4,9-diazaspiro[5.5]undecane hydrochloride | 4.65 | 367.2 |

The hydrochloride salts were prepared as described in example 1.

Example 335: 4-benzyl-2-methyl-9-phenethyl-1-oxa-4,9-diazaspiro[5.5]undecane dihydrochloride

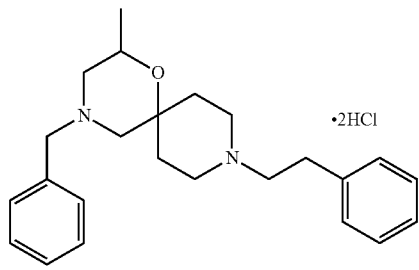 [SMILES: CC1CN(Cc2ccccc2)CC2(CCN(CCc3ccccc3)CC2)O1]

To a solution of intermediate 9C (0.142 g, 0.518 mmol) and benzaldehyde (0.105 mL, 1.035 mmol) in THF (5 mL), acetic acid (0.064 mL, 1.138 mmol) was added. The reaction mixture was stirred at r.t. for 15 min. and sodium triacetoxyborohydride (0.219 g, 1.035 mmol) was added portionwise. The resulting mixture was stirred at r.t. overnight. Water was added, the pH of the mixture was adjusted to 9 by addition of 1M NaOH aqueous solution and it was extracted with dichloromethane. The organic phases were combined, dried over MgSO$_4$, filtered and concentrated to dryness. The residue was purified by flash chromatography, silica gel, gradient dichloromethane to methanol:dichloromethane (1:9) to give the title compound as its free base (114 mg, 60% yield).

The previous compound was converted to its hydrochloride salt as described in example 1.

HPLC retention time: 5.36 min; MS: 365.2 (M+H).

This method was used for the preparation of examples 336-339 using suitable starting materials and protection, deprotection steps:

| EX | Structure | Chemical name | Ret time (min) | MS (M + H) |
|---|---|---|---|---|
| 336 | 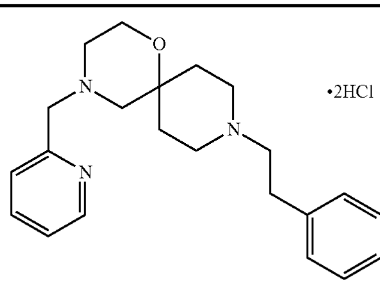 | 9-phenethyl-4-(pyridin-2-ylmethyl)-1-oxa-4,9-diazaspiro[5.5]undecane dihydrochloride | 3.65 | 352.2 |

| EX | Structure | Chemical name | Ret time (min) | MS (M + H) |
|---|---|---|---|---|
| 337 | 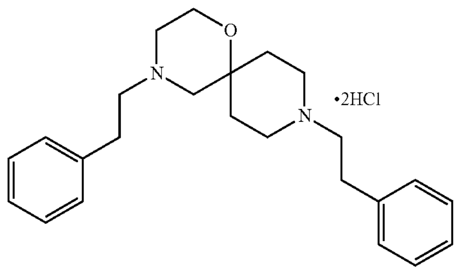 [SMILES: c1ccc(CCN2CCC3(CC2)CN(CCc2ccccc2)CCO3)cc1 ; "·2HCl"] | 4,9-diphenethyl-1-oxa-4,9-diazaspiro[5.5]undecane dihydrochloride | 4.84 | 365.2 |
| 338 | 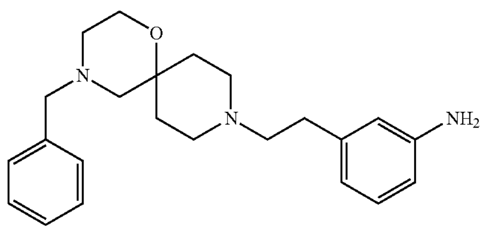 [SMILES: Nc1cccc(CCN2CCC3(CC2)CN(Cc2ccccc2)CCO3)c1] | 3-(2-(4-benzyl-1-oxa-4,9-diazaspiro[5.5]undecan-9-yl)ethyl)aniline | 3.87 | 366.2 |
| 339 | 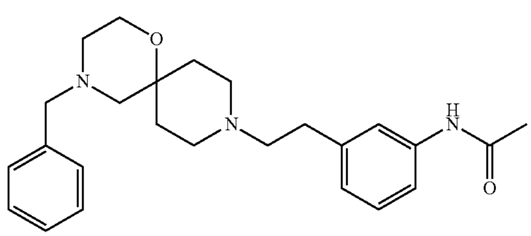 [SMILES: CC(=O)Nc1cccc(CCN2CCC3(CC2)CN(Cc2ccccc2)CCO3)c1] | N-(3-(2-(4-benzyl-1-oxa-4,9-diazaspiro[5.5]undecan-9-yl)ethyl)phenyl)acetamide | 3.90 | 408.2 |

Example 340: 3-methyl-9-phenethyl-4-phenyl-1-oxa-4,9-diazaspiro[5.5]undecane hydrochloride

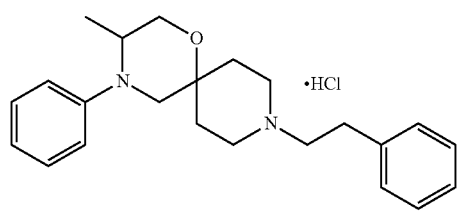 [SMILES: CC1COC2(CCN(CCc3ccccc3)CC2)CN1c1ccccc1 ; Cl]

Step 1: 3-methyl-4-phenyl-1-oxa-4,9-diazaspiro[5.5]undecane trifluoroacetate. To a solution of intermediate 11 (0.078 g, 0.225 mmol) in dichloromethane (0.8 mL), trifluoroacetic acid (0.16 mL, 9.1 mmol) was added, and the reaction mixture was heated at 40° C. for 2 h. The solvent was evaporated to dryness to give the title compound as a crude product (0.156 g, quant yield, 52 wt %), that was used in the following step without further purification. HPLC retention time: 2.79 min; MS: 247 (M+H).

Step 2: Title compound: To a solution of the crude product obtained in step 1 (0.156 g, 52 wt %, 0.22 mmol) and phenylacetaldehyde (0.054 g, 0.45 mmol) in THF (2 mL), acetic acid (0.028 mL, 0.48 mmol) was added. The reaction mixture was stirred at r.t. for 15 min., then sodium triacetoxyborohydride (0.095 g, 0.45 mmol) was added portionwise. The resulting mixture was stirred at r.t. overnight. Water was added, the pH of the mixture was adjusted to 9 by addition of 1M NaOH aqueous solution and it was extracted with dichloromethane. The organic phases were combined, dried over MgSO₄, filtered and concentrated to dryness. The residue was purified by flash chromatography, silica gel, gradient dichloromethane to methanol:dichloromethane (1:4) to give the title compound as its free base (10 mg, 13% yield).

The previous compound was converted to its hydrochloride salt as described in example 1.

HPLC retention time: 5.04 min; MS: 351.2 (M+H).

Examples 341 to 343 were prepared according to the procedure described in Example 218, using suitable starting materials:

| EX | EST | Structure | Chemical name | Ret time (min) | MS (M + H) |
|---|---|---|---|---|---|
| 341 | EST0073428.A | 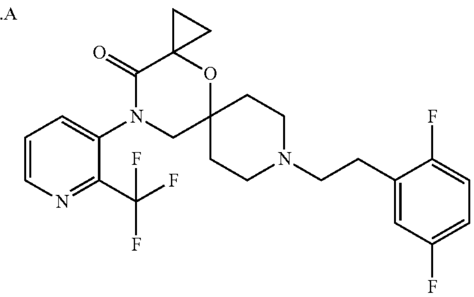 | 8-(2,5-difluorophenethyl)-12-(2-(trifluoromethyl)pyridin-3-yl)-4-oxa-8,12-diazadispiro[2.1.5.3]tridecan-13-one | 4.49 | 482.2 |
| 342 | EST0073447.A | 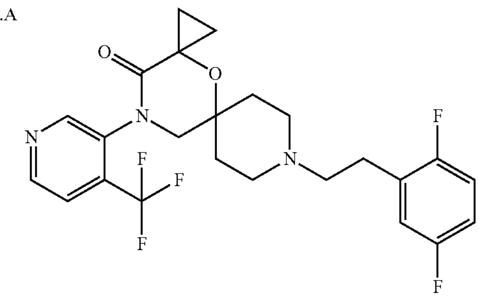 | 8-(2,5-difluorophenethyl)-12-(4-(trifluoromethyl)pyridin-3-yl)-4-oxa-8,12-diazadispiro[2.1.5.3]tridecan-13-one | 4.43 | 482.2 |
| 343 | EST0073472.A | 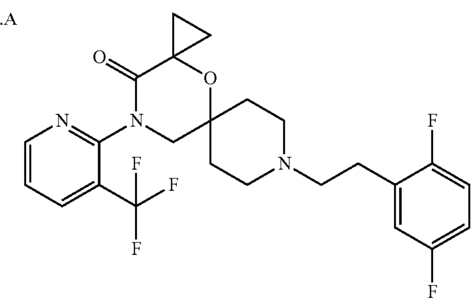 | 8-(2,5-difluorophenethyl)-12-(3-(trifluoromethyl)pyridin-2-yl)-4-oxa-8,12-diazadispiro[2.1.5.3]tridecan-13-one | 4.59 | 482.2 |

Example 344: 12-benzyl-8-(2-(3-fluoropyridin-2-yl)ethyl)-4-oxa-8,12-diazadispiro[2.1.5.3]tridecane (EST0073850)

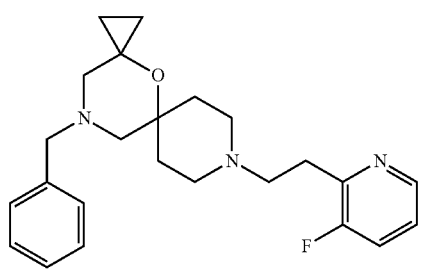 [SMILES: Fc1cccnc1CCN1CCC2(CC1)CN(Cc1ccccc1)CC1(CC1)O2]

Example 344 was prepared according to the procedure described in Example 33, using suitable starting materials and refluxing ethanol as the solvent. HPLC retention time (method C): 4.72 min; MS: 396.2 (M+H).

Example 345: 8-(2-(3-fluoropyridin-2-yl)ethyl)-12-(3-methylpyridin-2-yl)-4-oxa-8,12-diazadispiro[2.1.5.3]tridecane (EST0074067.A)

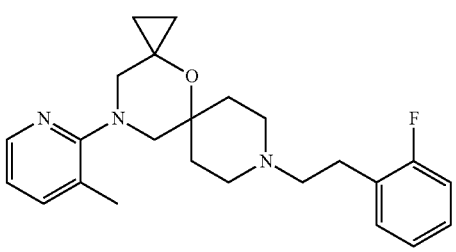 [SMILES: Cc1cccnc1N1CC2(CCN(CCc3ccccc3F)CC2)OC2(CC2)C1]

Example 345 was prepared according to the procedure described in Example 316, using Example 220 as starting material. HPLC retention time (method C): 5.00 min; MS: 396.2 (M+H).

Examples 346 to 348 were prepared according to the procedure described in Example 51, using suitable starting materials:

| EX | EST | Structure | Chemical name | Ret time (min) | MS (M + H) |
|---|---|---|---|---|---|
| 346 | EST0073425.A | 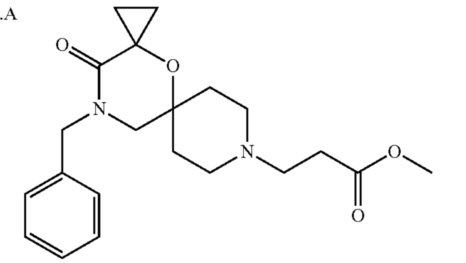 | methyl 3-(12-benzyl-13-oxo-4-oxa-8,12-diazadispiro[2.1.5.3]tridecan-8-yl)propanoate | 3.37 | 373.2 |
| 347 | EST0073445.A | 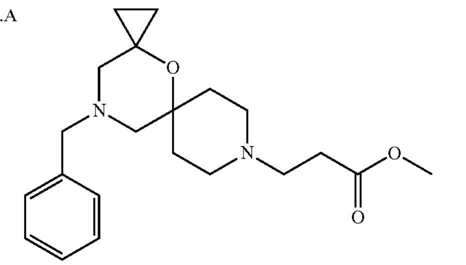 | methyl 3-(12-benzyl-4-oxa-8,12-diazadispiro[2.1.5.3]tridecan-8-yl)propanoate | 4.19 | 359.2 |
| 348 | EST0073446.A | 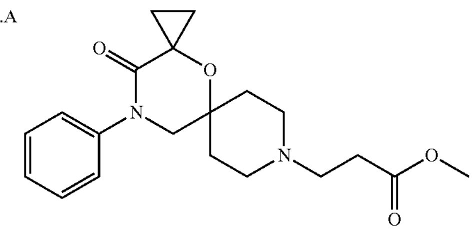 | methyl 3-(13-oxo-12-phenyl-4-oxa-8,12-diazadispiro[2.1.5.3]tridecan-8-yl)propanoate | 3.12 | 359.1 |

Examples 349 and 350: (R)-2-benzyl-9-phenyl-6-oxa-2,9-diazaspiro[4.5]decan-8-one (EST0074477.A) and (S)-2-benzyl-9-phenyl-6-oxa-2,9-diazaspiro[4.5]decan-8-one (EST0074478.A)

Starting from example 7, a chiral preparative HPLC separation (column: Chiralpak IA; temperature: ambient; flow: 55 mL/min; eluent: n-Heptane/EtOH 96/04 v/v+0.1% DEA) was carried out obtaining examples 349 and 350.

HPLC retention time (method C): 3.84 min; MS: 323.1 (M+H)

Table of Examples with Binding to the μ-Opioid Receptor and the σ$_1$-Receptor:

Biological Activity

Pharmacological Study

Human Sigma 1 Receptor Radioligand Assay

To investigate binding properties of test compounds to human σ$_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human μ-Opioid Receptor Radioligand Assay To investigate binding properties of test compounds to human μ-opioid receptor, transfected CHO-K1 cell membranes and [$^3$H]-DAMGO (Perkin Elmer, ES-542-C), as the radioligand, were used. The assay was carried out with 20 μg

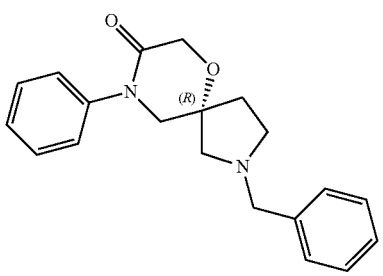

Ex 349

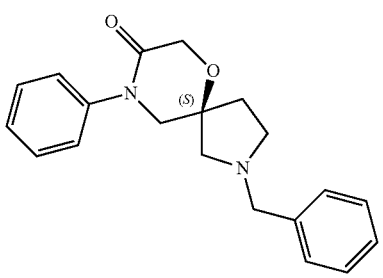

Ex 350 of membrane suspension, 1 nM of [³H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the μ-opiod receptor it is a very preferred embodiment in which the compounds are selected which act as dual ligands of the $\sigma_1$ receptor and the μ-opiod receptor and especially compounds which have a binding expressed as $K_i$ which is preferably <1000 nM for both receptors, more preferably <500 nM, even more preferably <100 nM.

The following scale as been adopted for representing the binding to the the $\sigma_1$ receptor and the μ-opiod receptor expressed as $K_i$:

+ Both $K_i$-μ and $K_i$-$\sigma_1$ >=500 nM
++ One $K_i$<500 nM while the other $K_i$ is >=500 nM
+++ Both $K_i$-μ and $K_i$-$\sigma_1$<500 nM
++++ Both $K_i$-μ and $K_i$-$\sigma_1$<100 nM All compounds prepared in the present application exhibit binding to the $\sigma_1$ receptor and the μ-opiod receptor, in particular the following binding results are shown:

| Ex | μ and $\sigma_1$ dual binding |
|---|---|
| 1 | ++ |
| 2 | ++ |
| 3 | ++ |
| 4 | ++ |
| 5 | +++ |
| 6 | ++ |
| 7 | ++ |
| 8 | ++ |
| 9 | ++++ |
| 10a | ++++ |
| 10b | ++++ |
| 11 | ++++ |
| 12a | +++ |
| 12b | ++++ |
| 13 | ++++ |
| 14 | ++++ |
| 15 | +++ |
| 16 | ++ |
| 17 | ++++ |
| 18 | ++++ |
| 19 | ++++ |
| 20 | ++ |
| 21 | + |
| 22 | + |
| 23 | + |
| 24 | + |
| 25 | + |
| 26 | + |
| 27 | + |
| 28 | ++++ |
| 29 | +++ |
| 30 | + |
| 31 | +++ |
| 32 | ++ |
| 33 | +++ |
| 34 | + |
| 35 | ++ |
| 36 | + |
| 37 | +++ |
| 38 | +++ |
| 39 | + |
| 40 | ++ |
| 41 | ++ |
| 42 | + |
| 43 | + |
| 44 | ++ |
| 45 | ++++ |
| 46 | +++ |
| 47 | +++ |
| 48 | + |
| 49 | ++ |
| 50 | +++ |
| 51 | ++++ |
| 52 | ++ |
| 53 | ++++ |
| 54 | ++++ |
| 55 | ++++ |
| 56 | ++ |
| 57 | ++++ |
| 58 | ++++ |
| 59 | ++ |
| 60 | +++ |
| 61 | +++ |
| 62 | ++++ |
| 63 | ++ |
| 64 | + |
| 65 | + |
| 66 | + |
| 67 | + |
| 68 | + |
| 69 | ++ |
| 70 | ++ |
| 71 | + |
| 72 | ++ |
| 73 | +++ |
| 74 | +++ |
| 75 | ++++ |
| 76 | ++ |
| 77 | ++ |
| 78 | + |
| 79 | +++ |
| 80 | +++ |
| 81 | ++ |
| 82 | + |
| 83 | ++++ |
| 84 | ++ |
| 85 | + |
| 86 | ++++ |
| 87 | + |
| 88 | +++ |
| 89 | +++ |
| 90 | ++++ |
| 91 | +++ |
| 92 | + |
| 93 | +++ |
| 94 | +++ |
| 95 | +++ |
| 96 | +++ |
| 97 | + |
| 98 | +++ |
| 99 | + |
| 100 | +++ |
| 101 | ++ |
| 102 | +++ |
| 103 | + |
| 104 | + |
| 105 | ++++ |
| 106 | + |
| 107 | + |
| 108 | + |
| 109 | ++++ |
| 110 | + |

| Ex | μ and σ₁ dual binding |
|---|---|
| 111 | ++ |
| 112 | +++ |
| 113 | + |
| 114 | +++ |
| 115 | +++ |
| 116 | + |
| 117 | + |
| 118 | + |
| 119 | + |
| 120 | + |
| 121 | + |
| 122 | + |
| 123 | ++ |
| 124 | + |
| 125 | ++ |
| 126 | ++++ |
| 127a | ++ |
| 127b | ++++ |
| 128 | + |
| 129 | + |
| 130 | +++ |
| 131 | ++ |
| 132 | +++ |
| 133 | ++ |
| 134 | ++ |
| 135 | ++ |
| 136 | +++ |
| 137 | ++++ |
| 138 | ++++ |
| 139 | + |
| 140 | + |
| 141 | +++ |
| 142 | +++ |
| 143 | + |
| 144 | +++ |
| 145 | + |
| 146 | + |
| 147 | + |
| 148 | + |
| 149 | ++ |
| 150 | + |
| 151a | +++ |
| 151b | +++ |
| 151c | +++ |
| 151d | +++ |
| 152 | ++++ |
| 153 | ++++ |
| 154 | ++++ |
| 155 | ++++ |
| 156 | ++++ |
| 157 | ++++ |
| 158 | ++++ |
| 159 | ++++ |
| 160 | ++++ |
| 161 | +++ |
| 162 | +++ |
| 163 | ++ |
| 164 | ++++ |
| 165 | ++ |
| 166 | +++ |
| 167 | ++++ |
| 168 | ++ |
| 169 | ++ |
| 170 | + |
| 171 | +++ |
| 172 | ++ |
| 173 | ++++ |
| 174 | ++++ |
| 175 | +++ |
| 176 | +++ |
| 177 | ++++ |
| 178 | ++ |
| 179 | + |
| 180 | +++ |
| 181 | + |
| 182 | + |
| 183 | + |
| 184 | ++ |
| 185 | + |
| 186 | + |
| 187 | ++++ |
| 188 | ++ |
| 189 | +++ |
| 190 | +++ |
| 191 | +++ |
| 192 | ++++ |
| 193 | ++++ |
| 194 | +++ |
| 195 | +++ |
| 196 | ++ |
| 197 | ++ |
| 198 | ++ |
| 199 | + |
| 200 | ++ |
| 201 | ++ |
| 202 | +++ |
| 203 | ++ |
| 204 | ++ |
| 205 | ++ |
| 206 | ++++ |
| 207 | ++++ |
| 208 | ++++ |
| 209 | +++ |
| 210 | ++ |
| 211 | +++ |
| 212 | + |
| 213 | ++++ |
| 214 | ++++ |
| 215 | +++ |
| 216 | +++ |
| 217 | +++ |
| 218 | +++ |
| 219 | +++ |
| 220 | +++ |
| 221 | +++ |
| 222a | +++ |
| 222b | + |
| 223 | ++++ |
| 224 | ++++ |
| 225 | ++++ |
| 226 | ++++ |
| 227 | + |
| 228 | +++ |
| 229 | ++++ |
| 230 | ++ |
| 231 | + |
| 232 | ++ |
| 233 | +++ |
| 234 | +++ |
| 235 | + |
| 236 | + |
| 237 | + |
| 238 | ++++ |
| 239 | + |
| 240 | + |
| 241 | ++ |
| 242 | ++ |
| 243 | +++ |
| 244a | +++ |
| 244b | ++++ |
| 245 | ++ |
| 246 | +++ |
| 247 | ++ |
| 248 | ++ |
| 249 | + |
| 250 | + |
| 251 | +++ |
| 252 | + |
| 253 | + |
| 254 | ++ |

| Ex | μ and σ₁ dual binding |
|---|---|
| 255 | + |
| 256 | +++ |
| 257 | +++ |
| 258 | ++ |
| 259 | + |
| 260 | +++ |
| 261 | +++ |
| 262 | +++ |
| 263 | +++ |
| 264 | +++ |
| 265 | ++ |
| 266 | +++ |
| 267 | + |
| 268 | + |
| 269 | + |
| 270 | + |
| 271 | ++ |
| 272 | ++ |
| 273 | + |
| 274 | +++ |
| 275 | + |
| 276 | +++ |
| 277 | ++++ |
| 278 | +++ |
| 279 | ++ |
| 280 | + |
| 281 | ++ |
| 282 | ++++ |
| 283 | +++ |
| 284 | + |
| 285 | ++ |
| 286 | ++ |
| 287 | ++ |
| 288 | +++ |
| 289 | +++ |
| 290 | ++ |
| 291 | +++ |
| 292 | ++ |
| 293 | ++ |
| 294 | ++ |
| 295 | ++++ |
| 296 | ++ |
| 297 | ++++ |
| 298 | ++++ |
| 299 | ++++ |
| 300 | ++ |
| 301 | ++ |
| 302 | +++ |
| 303 | +++ |
| 304 | +++ |
| 305 | + |
| 306 | ++ |
| 307 | +++ |
| 308 | ++ |
| 309 | + |
| 310 | + |
| 311 | +++ |
| 312 | ++++ |
| 313 | +++ |
| 314 | +++ |
| 315 | + |
| 316 | +++ |
| 317 | +++ |
| 318 | +++ |
| 319 | +++ |
| 320 | ++ |
| 321 | ++ |
| 322 | +++ |
| 323 | +++ |
| 324 | ++++ |
| 325 | +++ |
| 326 | +++ |
| 327 | +++ |
| 328 | ++ |
| 329 | ++++ |
| 330 | ++++ |
| 331 | ++ |
| 332 | ++ |
| 333 | ++ |
| 334 | ++ |
| 335 | ++++ |
| 336 | ++++ |
| 337 | ++ |
| 338 | + |
| 339 | ++++ |
| 340 | +++ |
| 341 | ++ |
| 342 | +++ |
| 343 | +++ |
| 344 | ++++ |
| 345 | +++ |
| 346 | ++ |
| 347 | +++ |
| 348 | + |
| 349 | + |
| 350 | + |

The invention claimed is:

1. A compound of Formula I wherein

Z is —C(O)—;
m is 1;
n is 1, 2 or 3;
$R_1$ is substituted or unsubstituted aryl, substituted or unsubstituted heterocyclyl, substituted or unsubstituted alkylaryl, or substituted or unsubstituted alkylheterocyclyl or —(CH2)$_r$-W—$R_{1'}$;
r is 0, 1 or 2;
W is —CH$_2$O—, —CH$_2$C(O)NR$_{5'}$—, —CH$_2$C(O)O—, —CH$_2$C(O)— or —C(CH$_3$)$_2$O—;
$R_{1'}$ is H, —CN, substituted or unsubstituted heterocyclyl, substituted or unsubstituted aryl, substituted or unsubstituted cycloalkyl or $R_5$;
wherein the aryl, heterocyclyl or cycloalkyl in $R_1$ or $R_{1'}$, if substituted, also in alkylaryl or alkylheterocyclyl, are substituted with substituents selected from the group consisting of —R$_5$, —OR$_5$, halogen, —NO$_2$, —NR$_5$R$_{5'''}$, —C(O)OR$_5$, NR$_5$C(O)R$_{5'}$, —C(O)NR$_5$R$_{5'}$, —NR$_5$S(O)$_2$R$_{5'}$, =O, —OCH$_2$CH$_2$OH, —NR$_5$C(O)

NR₅R₅‴, —S(O)₂NR₅R₅', —NR₅S(O)₂NR₅R₅‴, haloalkyl, haloalkoxy, —SR₅, and —S(O)R₅;

and wherein "aryl" is a monocyclic aryl and "heterocyclyl" is a heterocyclic ring system of one or two saturated or unsaturated rings of which at least one ring contains one or more heteroatoms from the group consisting of nitrogen, oxygen and/or sulfur in the ring;

X is a bond, —C(O)O—, —C(O)NR₅—, —C(O)—, —O— or —C(R₄R₄')—;

R₂ is H, substituted or unsubstituted aryl, substituted or unsubstituted heterocyclyl, substituted or unsubstituted cycloalkyl, substituted or unsubstituted C₁₋₆ alkyl, substituted or unsubstituted C₂₋₆ alkenyl or substituted or unsubstituted C₂₋₆ alkynyl, wherein the aryl, heterocyclyl or cycloalkyl in R₂, if substituted, also in alkylaryl, alkylcycloalkyl or alkylheterocyclyl, is substituted with substituents selected from the group consisting of —R₅, —OR₅, halogen, —CN, —NO₂, —NR₅R₅‴, —C(O)OR₅, —NR₅C(O)R₅', —C(O)NR₅R₅', —NR₅S(O)₂R₅', =O, —OCH₂CH₂OH, —NR₅C(O)NR₅R₅‴, —S(O)₂NR₅R₅', —NR₅S(O)₂NR₅R₅‴, haloalkyl, -haloalkoxy, —SR₅, —S(O)R₅ or —S(O)₂R₅;

and wherein "aryl" is a monocyclic aryl and "heterocyclyl" is a heterocyclic ring system of one or two saturated or unsaturated rings of which at least one ring contains one or more heteroatoms from the group consisting of nitrogen, oxygen and/or sulfur in the ring;

R₃ and R₃' are independently selected from the group consisting of H, substituted or unsubstituted C₁₋₆ alkyl, substituted or unsubstituted C₂₋₆ alkenyl, substituted or unsubstituted C₂₋₆ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, and substituted or unsubstituted alkylcycloalkyl;

wherein the aryl, cycloalkyl and heterocyclyl as defined in R₃, also in alkylaryl, alkylcycloalkyl or alkylheterocyclyl, if substituted, are substituted with substituents selected from the group consisting of —OR₅, halogen, —CN, haloalkyl, haloalkoxy, —SR₅, —S(O)R₅ or —S(O)₂R₅;

and wherein "aryl" is a monocyclic aryl and "heterocyclyl" is a heterocyclic ring system of one or two saturated or unsaturated rings of which at least one ring contains one or more heteroatoms from the group consisting of nitrogen, oxygen and/or sulfur in the ring;

R₄ is H, —OR₅, substituted or unsubstituted C₁₋₆ alkyl, substituted or unsubstituted C₂₋₆ alkenyl, substituted or unsubstituted C₂₋₆ alkynyl, —COOR₅, —CONR₅R₅', —NR₅COR₅', —NR₅R₅‴ or substituted or unsubstituted heterocyclyl, substituted or unsubstituted aryl, substituted or unsubstituted cycloalkyl, wherein the aryl, cycloalkyl and heterocyclyl as defined in R₄, if substituted, are substituted with substituents selected from the group consisting of —OR₅, halogen, —CN, haloalkyl, haloalkoxy, —SR₅, —S(O)R₅ and —S(O)₂R₅;

and wherein "aryl" is a monocyclic aryl and "heterocyclyl" is a heterocyclic ring system of one or two saturated or unsaturated rings of which at least one ring contains one or more heteroatoms from the group consisting of nitrogen, oxygen and/or sulfur in the ring;

R₄' is H, substituted or unsubstituted C₁₋₆ alkyl, substituted or unsubstituted C₂₋₆ alkenyl or substituted or unsubstituted C₂₋₆ alkynyl;

R₅, R₅' and R₅″ are independently selected from the group consisting of H, unsubstituted C₁₋₆ alkyl, unsubstituted C₂₋₆ alkenyl, unsubstituted C₂₋₆ alkynyl, unsubstituted aryl or unsubstituted alkylaryl;

wherein "aryl" is a monocyclic aryl;

R₅‴ is H, unsubstituted C₁₋₆ alkyl, unsubstituted C₂₋₆ alkenyl, unsubstituted C₂₋₆ alkynyl or -Boc;

R₈ and R₈' are independently selected from the group consisting of H, —OR₅, halogen, substituted or unsubstituted C₁₋₆ alkyl, substituted or unsubstituted C₂₋₆ alkenyl or substituted or unsubstituted C₂₋₆ alkynyl;

wherein the alkyl, alkenyl and alkynyl as defined in R₁, R₁', R₂, R₃, R₃', R₄, R₄', R₈, and R₈', if substituted, are substituted with substituents selected from the group consisting of —OR₅, halogen, —CN, haloalkyl, haloalkoxy, —SR₅, —S(O)R₅, —S(O)₂R₅, C(O)OR₅ and C(O)NR₅R₅';

optionally as a stereoisomer, including enantiomers and diastereomers, a racemate or in form of a mixture of at least two of stereoisomers, including enantiomers and/or diastereomers, in any mixing ratio, or a corresponding salt thereof, or a corresponding solvate thereof, with the proviso that the following compounds are excluded from formula I:

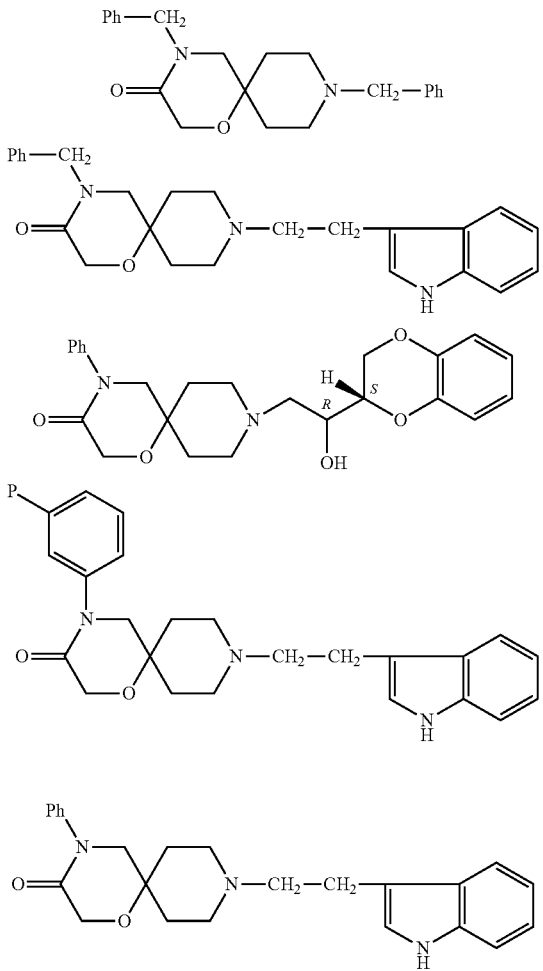

-continued

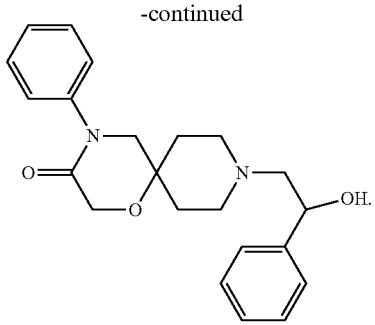

2. The compound according to claim 1, wherein $R_1$ is —(CH2)$_r$—W—$R_{1'}$ or $R_1$ is substituted or unsubstituted aryl, substituted or unsubstituted heterocyclyl, substituted or unsubstituted alkylaryl, or substituted or unsubstituted alkylheterocyclyl.

3. The compound according to claim 1, wherein X is a bond; —C($R_4R_{4'}$)—; —C(O)O—; —C(O)N$R_5$—; —C(O)—; or —O—.

4. The compound according to claim 1, wherein
m is 1 and
n is 2.

5. The compound according to claim 1, wherein
$R_1$ is substituted or unsubstituted aryl, substituted or unsubstituted heterocyclyl, substituted or unsubstituted alkylaryl, substituted or unsubstituted alkylheterocyclyl, or —(CH2)$_r$—W—$R_{1'}$, wherein
the aryl is phenyl;
and
the alkyl is $C_{1-6}$ alkyl.

6. The compound according to claim 5, wherein $R_1$ is substituted or unsubstituted phenyl; substituted or unsubstituted pyridine, pyrazine, indazole, benzodioxane, thiazole, benzothiazole, morpholine, tetrahydropyran, pyrazole, or imidazole; substituted or unsubstituted benzyl; or substituted or unsubstituted alkylheterocyclyl, wherein the heterocyclyl is pyridine, pyrazine, indazole, benzodioxane, thiazole, benzothiazole, morpholine, tetrahydropyrane, pyrazole, or imidazole and the alkyl is methyl.

7. The compound according to claim 1, wherein
$R_{1'}$ is H, —CN, substituted or unsubstituted heterocyclyl, substituted or unsubstituted aryl, substituted or unsubstituted cycloalkyl or $R_5$; wherein
the aryl is phenyl:
the heterocyclyl is a heterocyclic ring system of one or more saturated or unsaturated rings of which at least one ring contains one or more heteroatoms selected from the group consisting of nitrogen, oxygen and sulfur;
and
the cycloalkyl is $C_{3-8}$ cycloalkyl.

8. The compound according to claim 7, wherein $R_{1'}$ is substituted or unsubstituted phenyl; substituted or unsubstituted morpholine or tetrahydropyran; or substituted or unsubstituted cyclopropyl, cyclobutyl, cyclopentyl or cyclohexyl.

9. The compound according to claim 1, wherein
$R_2$ is H, substituted or unsubstituted aryl, substituted or unsubstituted heterocyclyl, substituted or unsubstituted cycloalkyl, substituted or unsubstituted $C_{1-6}$ alkyl, substituted or unsubstituted $C_{2-6}$ alkenyl or substituted or unsubstituted $C_{2-6}$ alkynyl; wherein
the aryl is phenyl;
and
the cycloalkyl is Cm cycloalkyl.

10. The compound according to claim 9, wherein $R_2$ is substituted or unsubstituted phenyl; substituted or unsubstituted pyridine, piperidine, thiazole, morpholine, tetrahydropyran, pyrazole, thiophene, indole, benzimidazole, pyrrolo[2,3b]pyridine, benzoxazole, oxopyrrolidine, or pyrimidine; substituted or unsubstituted cyclopropyl; substituted or unsubstituted methyl or isopropyl; substituted or unsubstituted ethenyl, propenyl, butenyl, pentenyl, or hexenyl; or substituted or unsubstituted ethynyl, propynyl, butynyl, pentynyl, or hexynyl.

11. The compound according to claim 1, wherein
$R_3$ and $R_{3'}$ are independently selected from the group consisting of H, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, and substituted or unsubstituted alkylcycloalkyl, wherein
the alkyl is $C_{1-6}$ alkyl;
the cycloalkyl is $C_{3-8}$ cycloalkyl; and
the aryl is phenyl.

12. The compound according to claim 11, wherein the $C_{1-6}$ alkyl is methyl or ethyl; the $C_{2-6}$ alkenyl is ethenyl, propenyl, butenyl, pentenyl, or hexenyl; the $C_{2-6}$ alkynyl is ethynyl, propynyl, butynyl, pentynyl, or hexynyl; the cycloalkyl is cyclopropyl, cyclobutyl, cyclopentyl, or cyclohexyl; the aryl is phenyl; and the heterocyclyl is imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, or quinazoline.

13. The compound according to claim 1, wherein
$R_4$ is H, —O$R_5$, substituted or unsubstituted $C_{1-6}$ alkyl, substituted or unsubstituted $C_{2-6}$ alkenyl, substituted or unsubstituted $C_{2-6}$ alkynyl, —COO$R_5$, —CON$R_5R_{5'}$, —N$R_5$CO$R_{5'}$, —NR5R5''', substituted or unsubstituted heterocyclyl, substituted or unsubstituted aryl, substituted or unsubstituted cycloalkyl,
and
$R_{4'}$ is H or substituted or unsubstituted $C_{1-6}$ alkyl, substituted or unsubstituted $C_{2-6}$ alkenyl or substituted or unsubstituted $C_{2-6}$ alkynyl), wherein
the cycloalkyl is $C_{3-8}$ cycloalkyl; and
the aryl is phenyl.

14. The compound according to claim 13, wherein the $C_{1-6}$ alkyl is methyl; the $C_{2-6}$ alkenyl is ethenyl, propenyl, butenyl, pentenyl, or hexenyl; the $C_{2-6}$ alkynyl is ethynyl, propynyl, butynyl, pentynyl, or hexynyl; the heterocyclyl is tetrahydropyran; the aryl is phenyl; and the cycloalkyl is cyclopropyl, cyclobutyl, cyclopentyl, or cyclohexyl.

15. The compound according to claim 1, wherein
$R_5$, $R_{5'}$ and $R_{5''}$ are independently H, unsubstituted $C_{1-6}$ alkyl, unsubstituted $C_{2-6}$ alkenyl, unsubstituted $C_{2-6}$ alkynyl, unsubstituted aryl or unsubstituted alkylaryl;
$R_{5'''}$ is H, unsubstituted $C_{1-6}$ alkyl, unsubstituted $C_{2-6}$ alkenyl, unsubstituted $C_{2-6}$ alkynyl or -Boc, wherein
the alkyl is $C_{1-6}$ alkyl;
and
the aryl is phenyl.

16. The compound according to claim 15, wherein the $C_{1-6}$ alkyl is methyl, ethyl, or isopropyl; the $C_{2-6}$ alkenyl is ethenyl, propenyl, butenyl, pentenyl, or hexenyl; the $C_{2-6}$ alkynyl is ethynyl, propynyl, butynyl, pentynyl, or hexynyl; and the aryl is phenyl.

17. The compound according to claim 1, wherein
$R_8$ and $R_{8'}$ are independently selected from the group consisting of H, —$OR_5$, halogen, substituted or unsubstituted $C_{1-6}$ alkyl, substituted or unsubstituted $C_{2-6}$ alkenyl or substituted or unsubstituted $C_{2-6}$ alkynyl.

18. The compound according to claim 17, wherein $R_8$ and $R_{8'}$ are independently selected from the group consisting of substituted or unsubstituted methyl, ethyl, propyl, butyl, pentyl, hexyl, isopropyl, or 2-methylpropyl; substituted or unsubstituted ethenyl, propenyl, butenyl, pentenyl, or hexenyl; or substituted or unsubstituted ethynyl, propynyl, butynyl, pentynyl, or hexynyl.

19. The compound according to claim 1, which is selected from the group consisting of:
- 4-(4-methoxyphenyl)-2-methyl-9-phenethyl-1-oxa-4,9-diazaspiro[5.5]undecan-3-one
- 9-benzyl-4-(2-methoxyphenyl)-1-oxa-4,9-diazaspiro[5.5]undecan-3-one
- 9-benzyl-4-phenyl-1-oxa-4,9-diazaspiro[5.5]undecan-3-one
- 4-(2-methoxyphenyl)-9-phenethyl-1-oxa-4,9-diazaspiro[5.5]undecan-3-one
- 9-phenethyl-4-phenyl-1-oxa-4,9-diazaspiro[5.5]undecan-3-one
- 9-benzyl-4-(3-methoxyphenyl)-1-oxa-4,9-diazaspiro[5.5]undecan-3-one
- 2-benzyl-9-phenyl-6-oxa-2,9-diazaspiro[4.5]decan-8-one
- 4-(3-methoxyphenyl)-9-phenethyl-1-oxa-4,9-diazaspiro[5.5]undecan-3-one
- 2-methyl-9-phenethyl-4-phenyl-1-oxa-4,9-diazaspiro[5.5]undecan-3-one
- (R)-2-methyl-9-phenethyl-4-phenyl-1-oxa-4,9-diazaspiro[5.5]undecan-3-one
- (S)-2-methyl-9-phenethyl-4-phenyl-1-oxa-4,9-diazaspiro[5.5]undecan-3-one
- 2-(methoxymethyl)-9-phenethyl-4-phenyl-1-oxa-4,9-diazaspiro[5.5]undecan-3-one
- (S)-2-(methoxymethyl)-9-phenethyl-4-phenyl-1-oxa-4,9-diazaspiro[5.5]undecan-3-one
- (R)-2-(methoxymethyl)-9-phenethyl-4-phenyl-1-oxa-4,9-diazaspiro[5.5]undecan-3-one
- 2-ethyl-9-phenethyl-4-phenyl-1-oxa-4,9-diazaspiro[5.5]undecan-3-one
- methyl 2-(3-oxo-9-phenethyl-4-phenyl-1-oxa-4,9-diazaspiro[5.5]undecan-2-yl)acetate
- 4-(3-methoxyphenyl)-2-methyl-9-phenethyl-1-oxa-4,9-diazaspiro[5.5]undecan-3-one
- 9-benzyl-2-methyl-4-phenyl-1-oxa-4,9-diazaspiro[5.5]undecan-3-one
- 2-isopropyl-9-phenethyl-4-phenyl-1-oxa-4,9-diazaspiro[5.5]undecan-3-one
- 2,2-dimethyl-9-phenethyl-4-phenyl-1-oxa-4,9-diazaspiro[5.5]undecan-3-one
- 2-(benzyloxymethyl)-9-phenethyl-4-phenyl-1-oxa-4,9-diazaspiro[5.5]undecan-3-one
- 2-methyl-4-(1-methyl-1H-pyrazol-3-yl)-9-phenethyl-1-oxa-4,9-diazaspiro[5.5]undecan-3-one
- 2-methyl-9-(2-(5-nitropyridin-2-yl)ethyl)-4-phenyl-1-oxa-4,9-diazaspiro[5.5]undecan-3-one
- 4-(2-fluorophenyl)-2-methyl-9-(2-(5-nitropyridin-2-yl)ethyl)-1-oxa-4,9-diazaspiro[5.5]undecan-3-one
- 4-(2-fluorophenyl)-2-methyl-9-(2-(3-nitropyridin-2-yl)ethyl)-1-oxa-4,9-diazaspiro[5.5]undecan-3-one
- 2-methyl-4-phenyl-9-(2-(pyrimidin-2-yl)ethyl)-1-oxa-4,9-diazaspiro[5.5]undecan-3-one
- 2-methyl-9-(2-(2-nitropyridin-3-yl)ethyl)-4-phenyl-1-oxa-4,9-diazaspiro[5.5]undecan-3-one
- 2-methyl-4-phenyl-9-(2-(4-(trifluoromethyl)pyridin-2-yl)ethyl)-1-oxa-4,9-diazaspiro[5.5]undecan-3-one
- 9-(2-(6-aminopyridin-2-yl)ethyl)-2-methyl-4-phenyl-1-oxa-4,9-diazaspiro[5.5]undecan-3-one
- 9-(2-(4-aminopyridin-2-yl)ethyl)-2-methyl-4-phenyl-1-oxa-4,9-diazaspiro[5.5]undecan-3-one
- 4-(2-fluorophenyl)-2-methyl-9-(2-(6-(trifluoromethyl)pyridin-2-yl)ethyl)-1-oxa-4,9-diazaspiro[5.5]undecan-3-one
- 9-(2-(2-aminopyridin-4-yl)ethyl)-2-methyl-4-phenyl-1-oxa-4,9-diazaspiro[5.5]undecan-3-one
- 2-methyl-4-phenyl-9-(2-(3-(trifluoromethyl)pyridin-2-yl)ethyl)-1-oxa-4,9-diazaspiro[5.5]undecan-3-one
- 2-methyl-4-phenyl-9-(2-(5-(trifluoromethyl)pyridin-2-yl)ethyl)-1-oxa-4,9-diazaspiro[5.5]undecan-3-one
- 9-(2-(4-methoxypyridin-2-yl)ethyl)-2-methyl-4-phenyl-1-oxa-4,9-diazaspiro[5.5]undecan-3-one
- 6-(2-(2-methyl-3-oxo-4-phenyl-1-oxa-4,9-diazaspiro[5.5]undecan-9-yl)ethyl)nicotinonitrile
- 9-(2-(3-chloropyridin-2-yl)ethyl)-2-methyl-4-phenyl-1-oxa-4,9-diazaspiro[5.5]undecan-3-one
- 9-(2-(5-chloropyridin-2-yl)ethyl)-2-methyl-4-phenyl-1-oxa-4,9-diazaspiro[5.5]undecan-3-one
- 4-(2-fluorophenyl)-2-isopropyl-9-(2-(2-nitropyridin-3-yl)ethyl)-1-oxa-4,9-diazaspiro[5.5]undecan-3-one
- 2-methyl-4-phenyl-9-(2-(2-(trifluoromethyl)pyridin-4-yl)ethyl)-1-oxa-4,9-diazaspiro[5.5]undecan-3-one
- 2-(2-(2-methyl-3-oxo-4-phenyl-1-oxa-4,9-diazaspiro[5.5]undecan-9-yl)ethyl)isonicotinonitrile
- 9-(2-(6-aminopyridin-2-yl)ethyl)-2-methyl-4-(4-(trifluoromethyl)pyridin-3-yl)-1-oxa-4,9-diazaspiro[5.5]undecan-3-one
- 2-methyl-9-(2-(2-nitropyridin-3-yl)ethyl)-4-(4-(trifluoromethyl)pyridin-3-yl)-1-oxa-4,9-diazaspiro[5.5]undecan-3-one
- 9-(2-(3-chloropyridin-2-yl)ethyl)-2-methyl-4-(4-(trifluoromethyl)pyridin-3-yl)-1-oxa-4,9-diazaspiro[5.5]undecan-3-one
- 9-(2-(3-chloropyridin-2-yl)ethyl)-2-methyl-4-((5-(trifluoromethyl)pyridin-2-yl)methyl)-1-oxa-4,9-diazaspiro[5.5]undecan-3-one
- 9-(2-(3-chloropyridin-2-yl)ethyl)-4-((5-fluoropyridin-2-yl)methyl)-2-methyl-1-oxa-4,9-diazaspiro[5.5]undecan-3-one
- 9-(2-(3-fluoropyridin-2-yl)ethyl)-4-((5-fluoropyridin-2-yl)methyl)-2-methyl-1-oxa-4,9-diazaspiro[5.5]undecan-3-one
- 9-(2-(3-fluoropyridin-2-yl)ethyl)-2-methyl-4-(2-(trifluormethyl)pyridin-3-yl)-1-oxa-4,9-diazaspiro[5.5]undecan-3-one
- 4-((5-fluoropyridin-2-yl)methyl)-2-methyl-9-(2-(6-(trifluoromethyl)pyridin-2-yl)ethyl)-1-oxa-4,9-diazaspiro[5.5]undecan-3-one
- 9-(2-(3-chloropyridin-4-yl)ethyl)-2-methyl-4-phenyl-1-oxa-4,9-diazaspiro[5.5]undecan-3-one
- 9-(2-fluorophenethyl)-2-methyl-4-phenyl-1-oxa-4,9-diazaspiro[5.5]undecan-3-one
- 9-(4-methoxyphenethyl)-4-phenyl-1-oxa-4,9-diazaspiro[5.5]undecan-3-one
- 2-methyl-4-phenyl-9-(2-(thiophen-2-yl)ethyl)-1-oxa-4,9-diazaspiro[5.5]undecan-3-one 9-(3-fluorophenethyl)-2-methyl-4-phenyl-1-oxa-4,9-diazaspiro[5.5]undecan-3-one
9-(4-fluorophenethyl)-2-methyl-4-phenyl-1-oxa-4,9-diazaspiro[5.5]undecan-3-one
9-(2-(1H-pyrazol-1-yl)ethyl)-2-methyl-4-phenyl-1-oxa-4,9-diazaspiro[5.5]undecan-3-one
9-(2-methoxyphenethyl)-2-methyl-4-phenyl-1-oxa-4,9-diazaspiro[5.5]undecan-3-one
2-methyl-4-phenyl-9-(2-(pyridin-2-yl)ethyl)-1-oxa-4,9-diazaspiro[5.5]undecan-3-one
2-methyl-4-phenyl-9-((tetrahydro-2H-pyran-4-yl)methyl)-1-oxa-4,9-diazaspiro[5.5]undecan-3-one
2-methyl-4-phenyl-9-(3-phenylpropyl)-1-oxa-4,9-diazaspiro[5.5]undecan-3-one
2-methyl-9-(2-(4-methylthiazol-5-yl)ethyl)-4-phenyl-1-oxa-4,9-diazaspiro[5.5]undecan-3-one
9-(2-(1H-indol-1-yl)ethyl)-2-methyl-4-phenyl-1-oxa-4,9-diazaspiro[5.5]undecan-3-one
9-(2-(1H-benzo[d]imidazol-1-yl)ethyl)-2-methyl-4-phenyl-1-oxa-4,9-diazaspiro[5.5]undecan-3-one
methyl 3-(2-methyl-3-oxo-4-phenyl-1-oxa-4,9-diazaspiro[5.5]undecan-9-yl)propanoate
2-methyl-9-(2-morpholinoethyl)-4-phenyl-1-oxa-4,9-diazaspiro[5.5]undecan-3-one
2-methyl-9-(4-nitrophenethyl)-4-phenyl-1-oxa-4,9-diazaspiro[5.5]undecan-3-one
2-methyl-9-(3-nitrophenethyl)-4-phenyl-1-oxa-4,9-diazaspiro[5.5]undecan-3-one
2-methyl-9-(2-nitrophenethyl)-4-phenyl-1-oxa-4,9-diazaspiro[5.5]undecan-3-one
9-(2-(1H-pyrrolo[2,3-b]pyridin-1-yl)ethyl)-2-methyl-4-phenyl-1-oxa-4,9-diazaspiro[5.5]undecan-3-one
methyl 4-(2-(2-methyl-3-oxo-4-phenyl-1-oxa-4,9-diazaspiro[5.5]undecan-9-yl)ethyl)benzoate
2-(2-methyl-3-oxo-4-phenyl-1-oxa-4,9-diazaspiro[5.5]undecan-9-yl)-N-phenylacetamide
2-methyl-9-(2-phenoxyethyl)-4-phenyl-1-oxa-4,9-diazaspiro[5.5]undecan-3-one
2-methyl-4-phenyl-9-(2-(pyridin-3-yl)ethyl)-1-oxa-4,9-diazaspiro[5.5]undecan-3-one
3-(2-(2-methyl-3-oxo-4-phenyl-1-oxa-4,9-diazaspiro[5.5]undecan-9-yl)ethyl)benzo[d]oxazol-2(3H)-one
3-(2-(2-methyl-3-oxo-4-phenyl-1-oxa-4,9-diazaspiro[5,5]undecan-9-yl)ethyl)benzonitrile
4-(2-(2-methyl-3-oxo-4-phenyl-1-oxa-4,9-diazaspiro[5.5]undecan-9-yl)ethyl)benzonitrile
9-(2-(3,5-dimethyl-1H-pyrazol-1-yl)ethyl)-2-methyl-4-phenyl-1-oxa-4,9-diazaspiro[5.5]undecan-3-one
2-methyl-9-(2-morpholino-2-oxoethyl)-4-phenyl-1-oxa-4,9-diazaspiro[5.5]undecen-3-one
9-(2-methoxyphenethyl)-4-(pyridin-2-ylmethyl)-1-oxa-4,9-diazaspiro[5.5]undecan-3-one
4-(2-fluorophenyl)-9-isopentyl-2-methyl-1-oxa-4,9-diazaspiro[5.5]undecan-3-one
9-(cyclopropylmethyl)-4-(2-fluorophenyl)-2-methyl-1-oxa-4,9-diazaspiro[5.5]undecan-3-one
4-(2-fluorophenyl)-9-(3-methoxyphenethyl)-2-methyl-1-oxa-4,9-diazaspiro[5.5]undecan-3-one
9-(2-(pyridin-2-yl)ethyl)-4-(pyridin-2-ylmethyl)-1-oxa-4,9-diazaspiro[5.5]undecan-3-one
9-phenethyl-4-(pyridin-2-ylmethyl)-1-oxa-4,9-diazaspiro[5.5]undecan-3-one
2-methyl-9-phenethyl-4-(thiazol-4-yl)-1-oxa-4,9-diazaspiro[5.5]undecan-3-one
4-(2-fluorophenyl)-9-(2-(6-fluoropyridin-2-yl)ethyl)-2-methyl-1-oxa-4,9-diazaspiro[5.5]undecan-3-one
4-(2-fluorophenyl)-2-methyl-9-(2-(6-(trifluoromethyl)pyridin-3-yl)ethyl)-1-oxa-4,9-diazaspiro[5.5]undecan-3-one
N-methyl-3-(2-(2-methyl-3-oxo-4-phenyl-1-oxa-4,9-diazaspiro[5.5]undecan-9-yl)ethyl)benzenesulfonamide
9-(2-(5-fluoropyridin-2-yl)ethyl)-2-methyl-4-phenyl-1-oxa-4,9-diazaspiro[5.5]undecan-3-one
2-methyl-4-phenyl-9-(2-(thiazol-2-yl)ethyl)-1-oxa-4,9-diazaspiro[5.5]undecan-3-one
9-(2-(3-fluoropyridin-2-yl)ethyl)-2-methyl-4-phenyl-1-oxa-4,9-diazaspiro[5.5]undecan-3-one
9-(2-(pyridin-2-yl)ethyl)-4-((5-(trifluoromethyl)pyridin-2-yl)methyl)-1-oxa-4,9-diazaspiro[5.5]undecan-3-one
9-(2-oxo-2-phenylethyl)-4-((5-(trifluoromethyl)pyridin-2-yl)methyl)-1-oxa-4,9-diazaspiro[5.5]undecan-3-one
N-methyl-3-(2-methyl-3-oxo-4-phenyl-1-oxa-4,9-diazaspiro[5.5]undecan-9-yl)-N-phenylpropanamide
2-methyl-9-(2-(pyridin-2-yl)ethyl)-4-(4-(trifluoromethyl)pyridin-3-yl)-1-oxa-4,9-diazaspiro[5.5]undecan-3-one
9-(2-(6-methoxypyridin-2-yl)ethyl)-2-methyl-4-phenyl-1-oxa-4,9-diazaspiro[5.5]undecan-3-one
9-(3-nitrophenethyl)-4-((5-(trifluoromethyl)pyridin-2-yl)methyl)-1-oxa-4,9-diazaspiro[5.5]undecan-3-one
4-((6-aminopyridin-2-yl)methy)-9-phenethyl-1-oxa-4,9-diazaspiro[5.5]undecan-3-one
4-((5-chloropyridin-2-yl)methyl)-9-phenethyl-1-oxa-4,9-diazaspiro[5.5]undecan-3-one
tert-butyl (4-(2-(3-oxo-4-((5-(trifluoromethyl)pyridin-2-yl)methyl)-1-oxa-4,9-diazaspiro[5.5]undecan-9-yl)ethyl)thiazol-2-yl)carbamate
N-methyl-4-(2-(2-methyl-3-oxo-4-phenyl-1-oxa-4,9-diazaspiro[5.5]undecan-9-yl)ethyl)benzenesulfonamide
4-(2-(2-methyl-3-oxo-4-phenyl-1-oxa-4,9-diazaspiro[5.5]undecan-9-yl)ethyl)benzenesulfonamide
2-methyl-9-(2-(3-nitro-1H-pyrazol-1-yl)ethyl)-4-phenyl-1-oxa-4,9-diazaspiro[5.5]undecan-3-one
9-(2-(6-methoxypyridin-3-yl)ethyl)-2-methyl-4-phenyl-1-oxa-4,9-diazaspiro[5.5]undecan-3-one
2-methyl-4-phenyl-9-(2-(5-(trifluoromethyl)pyridin-3-yl)ethyl)-1-oxa-4,9-diazaspiro[5.5]undecan-3-one
9-(2-(6-chloropyridin-3-yl)ethyl)-2-methyl-4-phenyl-1-oxa-4,9-diazaspiro[5.5]undecan-3-one
9-(2-(5-fluoropyridin-3-yl)ethyl)-2-methyl-4-phenyl-1-oxa-4,9-diazaspiro[5.5]undecan-3-one
9-(2-(5-chloropyridin-3-yl)ethyl)-2-methyl-4-phenyl-1-oxa-4,9-diazaspiro[5.5]undecan-3-one
tert-butyl (1-(2-(2-methyl-3-oxo-4-phenyl-1-oxa-4,9-diazaspiro[5.5]undecan-9-yl)ethyl)-1H-pyrazol-5-yl)carbamate
tert-butyl (4-(2-(4-(2-fluorophenyl)-2-isopropyl-3-oxo-1-oxa-4,9-diazaspiro[5.5]undecan-9-yl)ethyl)thiazol-2-yl)carbamate
tert-butyl (4-(2-(13-oxo-12-{[5-(trifluoromethyl)pyridin-2-yl]methyl}-4-oxa-8,12-diazadispiro[2.1.5.3]tridecan-8-yl)ethyl)thiazol-2-yl)carbamate
tert-butyl (4-(2-(2-methyl-3-oxo-4-(4-(trifluoromethyl)pyridin-3-yl)-1-oxa-4,9-diazaspiro[5.5]undecan-9-yl)ethyl)thiazol-2-yl)carbamate
9-(2-isopropoxyethyl)-2-methyl-4-phenyl-1-oxa-4,9-diazaspiro[5.5]undecan-3-one
6-(2-(2-methyl-3-oxo-4-phenyl-1-oxa-4,9-diazaspiro[5.5]undecan-9-yl)ethyl)picolinonitrile
2-methyl-9-(2-morpholino-2-oxoethyl)-4-((5-(trifluoromethyl)pyridin-2-yl)methyl)-1-oxa-4,9-diazaspiro[5.5]undecan-3-one 9-(2-isopropoxyethyl)-2-methyl-4-((5-(trifluoromethyl)pyridin-2-yl)methyl)-1-oxa-4,9-diazaspiro[5.5]undecan-3-one 9-(2-fluorophenethyl)-2-methyl-4-(4-(trifluoromethyl)pyridin-3-yl)-1-oxa-4,9-diazaspiro[5.5]undecan-3-one (S)-9-(2-fluorophenethyl)-2-methyl-4-(4-(trifluoromethyl)pyridin-3-yl)-1-oxa-4,9-diazaspiro[5.5]undecan-3-one hydrochloride (R)-9-(2-fluorophenethyl)-2-methyl-4-(4-(trifluoromethyl)pyridin-3-yl)-1-oxa-4,9-diazaspiro[5.5]undecan-3-one hydrochloride 2-methyl-9-(2-oxo-2-(piperidin-1-yl)ethyl)-4-((5-(trifluoromethyl)pyridin-2-yl)methyl)-1-oxa-4,9-diazaspiro[5.5]undecan-3-one 2-methyl-9-(2-oxo-2-(piperidin-1-yl)ethyl)-4-phenyl-1-oxa-4,9-diazaspiro[5.5]undecan-3-one 9-(2-fluorophenethyl)-2-methyl-4-(2-(trifluoromethyl)pyridin-3-yl)-1-oxa-4,9-diazaspiro[5.5]undecan-3-one 2-methyl-4-phenyl-9-(2-(tetrahydro-2H-pyran-4-yl)ethyl)-1-oxa-4,9-diazaspiro[5.5]undecan-3-one 9-(3-methoxyphenethyl)-4-phenyl-1-oxa-4,9-diazaspiro[5.5]undecan-3-one 2-methyl-4-phenyl-9-(2-(pyridin-4-yl)ethyl)-1-oxa-4,9-diazaspiro[5.5]undecan-3-one 4-(2-fluorophenyl)-2-(methoxymethyl)-9-(2-(pyridin-2-yl)ethyl)-1-oxa-4,9-diazaspiro[5.5]undecan-3-one 4-(2-fluorophenyl)-2-(methoxymethyl)-9-(2-methoxyphenethyl)-1-oxa-4,9-diazaspiro[5.5]undecan-3-one 9-(2-fluorophenethyl)-4-(2-fluorophenyl)-2-(methoxymethyl)-1-oxa-4,9-diazaspiro[5.5]undecan-3-one 4-(2-fluorophenyl)-2-isopropyl-9-(2-methoxyphenethyl)-1-oxa-4,9-diazaspiro[5.5]undecan-3-one tert-butyl (4-(2-(4-(2-fluorophenyl)-2-methyl-3-oxo-1-oxa-4,9-diazaspiro[5.5]undecan-9-yl)ethyl)thiazol-2-yl)carbamate ethyl 3-(2-(4-(2-fluorophenyl)-2-methyl-3-oxo-1-oxa-4,9-diazaspiro[5.5]undecan-9-yl)ethyl)benzoate 3-(2-methyl-3-oxo-4-phenyl-1-oxa-4,9-diazaspiro[5.5]undecan-9-yl)-N-phenylpropanamide 2-methyl-4-phenyl-9-(2-(pyridin-3-yloxy)ethyl)-1-oxa-4,9-diazaspiro[5.5]undecan-3-one 2-methyl-9-(2-(2-oxopyrrolidin-1-yl)ethyl)-4-phenyl-1-oxa-4,9-diazaspiro[5.5]undecan-3-one 9-(2-(1H-pyrazol-4-yl)ethyl)-2-methyl-4-phenyl-4,9-diazaspiro[5.5]undecan-3-one 2-phenethyl-9-phenyl-6-oxa-2,9-diazaspiro[4.5]decan-8-one 9-(2-hydroxy-2-phenylethyl)-2-methyl-4-phenyl-1-oxa-4,9-diazaspiro[5.5]undecan-3-one (R)-9-((R)-2-hydroxy-2-phenylethyl)-2-methyl-4-phenyl-1-oxa-4,9-diazaspiro[5.5]undecan-3-one (R)-9-((S)-2-hydroxy-2-phenylethyl)-2-methyl-4-phenyl-1-oxa-4,9-diazaspiro[5.5]undecan-3-one (S)-9-((S)-2-hydroxy-2-phenylethyl)-2-methyl-4-phenyl-1-oxa-4,9-diazaspiro[5.5]undecan-3-one (S)-9-((R)-2-hydroxy-2-phenylethyl)-2-methyl-4-phenyl-1-oxa-4,9-diazaspiro[5.5]undecan-3-one 4-benzyl-2-methyl-9-phenethyl-1-oxa-4,9-diazaspiro[5.5]undecan-3-one 4-benzyl-9-phenethyl-1-oxa-4,9-diazaspiro[5.5]undecan-3-one 4-(2-fluorobenzyl)-2-methyl-9-phenethyl-1-oxa-4,9-diazaspiro[5.5]undecan-3-one 4-(3-fluorobenzyl)-2-methyl-9-phenethyl-1-oxa-4,9-diazaspiro[5.5]undecan-3-one 2-methyl-4,9-diphenethyl-1-oxa-4,9-diazaspiro[5.5]undecan-3-one 2-methyl-9-phenethyl-4-(pyridin-2-ylmethyl)-1-oxa-4,9-diazaspiro[5.5]undecan-3-one 4-(4-fluorobenzyl)-2-methyl-9-phenethyl-1-oxa-4,9-diazaspiro[5.5]undecan-3-one 2-methyl-9-phenethyl-4-(pyridin-3-ylmethyl)-1-oxa-4,9-diazaspiro[5.5]undecan-3-one 2-methyl-9-phenethyl-4-(thiazol-2-ylmethyl)-1-oxa-4,9-diazaspiro[5.5]undecan-3-one 2-methyl-9-phenethyl-4-(thiazol-5-ylmethyl)-1-oxa-4,9-diazaspiro[5.5]undecan-3-one 2-methyl-9-phenethyl-4-(pyridin-4-ylmethyl)-1-oxa-4,9-diazaspiro[5.5]undecan-3-one 2-methyl-9-phenethyl-4-((tetrahydro-2H-pyran-4-yl)methyl)-1-oxa-4,9-diazaspiro[5.5]undecan-3-one 2-methyl-9-phenethyl-4-(thiazol-4-ylmethyl)-1-oxa-4,9-diazaspiro[5.5]undecan-3-one 9-phenethyl-4-(pyridin-4-ylmethyl)-1-oxa-4,9-diazaspiro[5.5]undecan-3-one 4-(3-methoxybenzyl)-9-phenethyl-1-oxa-4,9-diazaspiro[5.5]undecan-3-one 9-phenethyl-4-(thiazol-4-ylmethyl)-1-oxa-4,9-diazaspiro[5.5]undecan-3-one 4-((1-benzyl-1H-imidazol-2-yl)methyl)-9-phenethyl-1-oxa-4,9-diazaspiro[5.5]undecan-3-one 9-phenethyl-4-(2-(pyridin-2-yl)ethyl)-1-oxa-4,9-diazaspiro[5.5]undecan-3-one 2-methyl-4-(2-morpholino-2-oxoethyl)-9-phenethyl-1-oxa-4,9-diazaspiro[5.5]undecan-3-one 2-methyl-4-((1-methyl-1H-pyrazol-3-yl)methyl)-9-phenethyl-1-oxa-4,9-diazaspiro[5.5]undecan-3-one 2-methyl-4-((1-methyl-1H-imidazol-2-yl)methyl)-9-phenethyl-1-oxa-4,9-diazaspiro[5.5]undecan-3-one 4-((3-fluoropyridin-2-yl)methyl)-2-methyl-9-phenethyl-1-oxa-4,9-diazaspiro[5.5]undecan-3-one 2-methyl-9-phenethyl-4-((6-(trifluoromethyl)pyridin-2-yl)methyl)-1-oxa-4,9-diazaspiro[5.5]undecan-3-one 2-methyl-9-phenethyl-4-(2-(pyridin-3-yl)ethyl)-1-oxa-4,9-diazaspiro[5.5]undecan-3-one 4-((5-fluoropyridin-2-yl)methyl)-9-phenethyl-1-oxa-4,9-diazaspiro[5.5]undecan-3-one 9-phenethyl-4-((5-(trifluoromethyl)pyridin-2-yl)methyl)-1-oxa-4,9-diazaspiro[5.5]undecan-3-one 9-phenethyl-4-(2-(pyridin-4-yl)ethyl)-1-oxa-4,9-diazaspiro[5.5]undecan-3-one 4-(3-nitrobenzyl)-9-phenethyl-1-oxa-4,9-diazaspiro[5.5]undecan-3-one 4-(2-hydroxy-2-methylpropyl)-2-methyl-9-phenethyl-1-oxa-4,9-diazaspiro[5.5]undecan-3-one 9-benzyl-4-(4-fluorophenyl)-1-oxa-4,9-diazaspiro[5.5]undecan-3-one 4-(2-fluorophenyl)-9-phenethyl-1-oxa-4,9-diazaspiro[5.5]undecan-3-one 4-(4-fluorophenyl)-9-phenethyl-1-oxa-4,9-diazaspiro[5.5]undecan-3-one 4-(3-fluorophenyl)-9-phenethyl-1-oxa-4,9-diazaspiro[5.5]undecan-3-one 4-(2-fluorophenyl)-2-methyl-9-phenethyl-1-oxa-4,9-diazaspiro[5.5]undecan-3-one 4-(2-chlorophenyl)-2-methyl-9-phenethyl-1-oxa-4,9-diazaspiro[5.5]undecan-3-one 2-methyl-9-phenethyl-4-(pyridin-3-yl)-1-oxa-4,9-diazaspiro[5.5]undecan-3-one 2-methyl-9-phenethyl-4-(pyrazin-2-yl)-1-oxa-4,9-diazaspiro[5.5]undecan-3-one 2-methyl-9-phenethyl-4-(pyridin-2-yl)-1-oxa-4,9-diazaspiro[5.5]undecan-3-one ethyl 3-(2-methyl-3-oxo-9-phenethyl-1-oxa-4,9-diazaspiro[5.5]undecan-4-yl)benzoate
2-methyl-4-(3-nitrophenyl)-9-phenethyl-1-oxa-4,9-diazaspiro[5.5]undecan-3-one
2-methyl-4-(1-methyl-1H-indazol-3-yl)-9-phenethyl-1-oxa-4,9-diazaspiro[5.5]undecan-3-one
2-methyl-4-(1-methyl-1H-indazol-6-yl)-9-phenethyl-1-oxa-4,9-diazaspiro[5.5]undecan-3-one
4-(benzo[d][1,3]dioxol-5-yl)-2-methyl-9-phenethyl-1-oxa-4,9-diazaspiro[5.5]undecan-3-one
4-(benzo[d]thiazol-6-yl)-2-methyl-9-phenethyl-1-oxa-4,9-diazaspiro[5.5]undecan-3-one
4-(benzo[d]thiazol-2-yl)-2-methyl-9-phenethyl-1-oxa-4,9-diazaspiro[5.5]undecan-3-one
2-methyl-9-phenethyl-4-(pyridin-4-yl)-1-oxa-4,9-diazaspiro[5.5]undecan-3-one
4-(2-methoxyphenyl)-2-methyl-9-phenethyl-1-oxa-4,9-diazaspiro[5.5]undecan-3-one
2-methyl-9-phenethyl-4-(6-(trifluoromethyl)pyridin-2-yl)-1-oxa-4,9-diazaspiro[5.5]undecan-3-one
4-(3-fluoropyridin-2-yl)-2-methyl-9-phenethyl-1-oxa-4,9-diazaspiro[5.5]undecan-3-one
2-methyl-9-phenethyl-4-(thiazol-2-yl)-1-oxa-4,9-diazaspiro[5.5]undecan-3-one
2-methyl-4-(1-methyl-1H-pyrazol-4-yl)-9-phenethyl-1-oxa-4,9-diazaspiro[5.5]undecan-3-one
4-(6-methoxypyridin-2-yl)-2-methyl-9-phenethyl-1-oxa-4,9-diazaspiro[5.5]undecan-3-one
2-methyl-9-phenethyl-4-(6-(trifluoromethyl)pyridin-3-yl)-1-oxa-4,9-diazaspiro[5.5]undecan-3-one
4-(2-fluoropyridin-3-yl)-2-methyl-9-phenethyl-1-oxa-4,9-diazaspiro[5.5]undecan-3-one
2-methyl-9-phenethyl-4-(4-(trifluoromethyl)pyridin-3-yl)-1-oxa-4,9-diazaspiro[5.5]undecan-3-one
2-methyl-9-phenethyl-4-(2-(trifluoromethyl)pyridin-3-yl)-1-oxa-4,9-diazaspiro[5.5]undecan-3-one
4-(5-fluoropyridin-3-yl)-2-methyl-9-phenethyl-1-oxa-4,9-diazaspiro[5.5]undecan-3-one
2-methyl-9-phenethyl-4-(5-(trifluoromethyl)pyridin-3-yl)-1-oxa-4,9-diazaspiro[5.5]undecan-3-one
2-methyl-9-phenethyl-4-(3-(trifluoromethyl)pyridin-2-yl)-1-oxa-4,9-diazaspiro[5.5]undecan-3-one
9-(2-fluorophenethyl)-2-methyl-4-(3-(trifluoromethyl)pyridin-2-yl)-1-oxa-4,9-diazaspiro[5.5]undecan-3-one
(R)-9-(2-fluorophenethyl)-2-methyl-4-(3-(trifluoromethyl)pyridin-2-yl)-1-oxa-4,9-diazaspiro[5.5]undecan-3-one hydrochloride
(S)-9-(2-fluorophenethyl)-2-methyl-4-(3-(trifluoromethyl)pyridin-2-yl)-1-oxa-4,9-diazaspiro[5.5]undecan-3-one hydrochloride
9-(3-aminophenethyl)-2-methyl-4-phenyl-1-oxa-4,9-diazaspiro[5.5]undecan-3-one
4-(3-aminophenyl)-2-methyl-9-phenethyl-1-oxa-4,9-diazaspiro[5.5]undecan-3-one
9-(4-aminophenethyl)-2-methyl-4-phenyl-1-oxa-4,9-diazaspiro[5.5]undecan-3-one
9-(2-aminophenethyl)-2-methyl-4-phenyl-1-oxa-4,9-diazaspiro[5.5]undecan-3-one
9-(2-(5-aminopyridin-2-yl)ethyl)-4-(2-fluorophenyl)-2-methyl-1-oxa-4,9-diazaspiro[5.5]undecan-3-one
9-(2-(3-aminopyridin-2-yl)ethyl)-4-(2-fluorophenyl)-2-methyl-1-oxa-4,9-diazaspiro[5.5]undecan-3-one
4-(3-aminobenzyl)-9-phenethyl-1-oxa-4,9-diazaspiro[5.5]undecan-3-one
9-(2-(2-aminopyridin-3-yl)ethyl)-2-methyl-4-phenyl-1-oxa-4,9-diazaspiro[5.5]undecan-3-one
9-(3-aminophenethyl)-4-((5-(trifluoromethyl)pyridin-2-yl)methyl)-1-oxa-4,9-diazaspiro[5.5]undecan-3-one
9-(2-(5-aminopyridin-2-yl)ethyl)-2-methyl-4-phenyl-1-oxa-4,9-diazaspiro[5.5]undecan-3-one
9-(2-(3-amino-1H-pyrazol-1-yl)ethyl)-2-methyl-4-phenyl-1-oxa-4,9-diazaspiro[5.5]undecan-3-one
9-(2-(2-aminopyridin-3-yl)ethyl)-4-(2-fluorophenyl)-2-isopropyl-1-oxa-4,9-diazaspiro[5.5]undecan-3-one
9-(2-(2-aminopyridin-3-yl)ethyl)-2-methyl-4-(4-(trifluoromethyl)pyridin-3-yl)-1-oxa-4,9-diazaspiro[5.5]undecan-3-one
N-(4-(2-(2-methyl-3-oxo-4-phenyl-1-oxa-4,9-diazaspiro[5.5]undecan-9-yl)ethyl)phenyl)acetamide
N-(3-(2-methyl-3-oxo-9-phenethyl-1-oxa-4,9-diazaspiro[5.5]undecan-4-yl)phenyl)acetamide
N-(3-(2-(2-methyl-3-oxo-4-phenyl-1-oxa-4,9-diazaspiro[5.5]undecan-9-yl)ethyl)phenyl)acetamide
(S)—N-(3-(2-(2-methyl-3-oxo-4-phenyl-1-oxa-4,9-diazaspiro[5.5]undecan-9-yl)ethyl)phenyl)acetamide
(R)—N-(3-(2-(2-methyl-3-oxo-4-phenyl-1-oxa-4,9-diazaspiro[5.5]undecan-9-yl)ethyl)phenyl)acetamide
N-(2-(2-(2-methyl-3-oxo-4-phenyl-1-oxa-4,9-diazaspiro[5.5]undecan-9-yl)ethyl)phenyl)acetamide
N-(3-(2-(2-methyl-3-oxo-4-phenyl-1-oxa-4,9-diazaspiro[5.5]undecan-9-yl)ethyl)phenyl)isobutyramide
1,1-dimethyl-3-(3-(2-(2-methyl-3-oxo-4-phenyl-1-oxa-4,9-diazaspiro[5.5]undecan-9-yl)ethyl)phenyl)urea
N-(3-((3-oxo-9-phenethyl-1-oxa-4,9-diazaspiro[5.5]undecan-4-yl)methyl)phenyl)acetamide
N-(2-(2-(4-(2-fluorophenyl)-2-methyl-3-oxo-1-oxa-4,9-diazaspiro[5.5]undecan-9-yl)ethyl)pyridin-3-yl)acetamide
N-(3-(2-(3-oxo-4-((5-(trifluoromethyl)pyridin-2-yl)methyl)-1-oxa-4,9-diazaspiro[5.5]undecan-9-yl)ethyl)phenyl)acetamide
N-(6-(2-(2-methyl-3-oxo-4-phenyl-1-oxa-4,9-diazaspiro[5.5]undecan-9-yl)ethyl)pyridin-3-yl)acetamide
N-(2-(2-(2-methyl-3-oxo-4-phenyl-1-oxa-4,9-diazaspiro[5.5]undecan-9-yl)ethyl)pyridin-4-yl)acetamide
N-(6-(2-(2-methyl-3-oxo-4-phenyl-1-oxa-4,9-diazaspiro[5.5]undecan-9-yl)ethyl)pyridin-2-yl)acetamide
N-(4-(2-(2-methyl-3-oxo-4-phenyl-1-oxa-4,9-diazaspiro[5.5]undecan-9-yl)ethyl)pyridin-2-yl)acetamide
N-(3-(2-(2-methyl-3-oxo-4-phenyl-1-oxa-4,9-diazaspiro[5.5]undecan-9-yl)ethyl)phenyl)methanesulfonamide
N-(2-(2-(2-methyl-3-oxo-4-phenyl-1-oxa-4,9-diazaspiro[5.5]undecan-9-yl)ethyl)phenyl)methanesulfonamide
N-(4-(2-(2-methyl-3-oxo-4-phenyl-1-oxa-4,9-diazaspiro[5.5]undecan-9-yl)ethyl)phenyl)methanesulfonamide
N-(3-((3-oxo-9-phenethyl-1-oxa-4,9-diazaspiro[5.5]undecan-4-yl)methyl)phenyl)methanesulfonamide
N-(3-(2-(2-methyl-3-oxo-4-phenyl-1-oxa-4,9-diazaspiro[5.5]undecan-9-yl)ethyl)phenyl)propane-2-sulfonamide
1-(3-(2-(2-methyl-3-oxo-4-phenyl-1-oxa-4,9-diazaspiro[5.5]undecan-9-yl)ethyl)phenyl)urea
1-(6-(2-(2-methyl-3-oxo-4-phenyl-1-oxa-4,9-diazaspiro[5.5]undecan-9-yl)ethyl)pyridin-2-yl)urea
N-[3-(2-{2-methyl-3-oxo-4-phenyl-1-oxa-4,9-diazaspiro[5.5]undecan-9-yl}ethyl)phenyl]aminosulfonamide
3-(2-(2-methyl-3-oxo-4-phenyl-1-oxa-4,9-diazaspiro[5.5]undecan-9-yl)ethyl)benzamide
4-(2-(2-methyl-3-oxo-4-phenyl-1-oxa-4,9-diazaspiro[5.5]undecan-9-yl)ethyl)benzoic acid
3-(2-methyl-3-oxo-9-phenethyl-1-oxa-4,9-diazaspiro[5.5]undecan-4-yl)benzoic acid 3-(2-methyl-3-oxo-4-phenyl-1-oxa-4,9-diazaspiro[5.5]
undecan-9-yl)propanoic acid
2-(3-oxo-9-phenethyl-4-phenyl-1-oxa-4,9-diazaspiro
[5.5]undecan-2-yl)acetic acid
N, N-dimethyl-3-(2-methyl-3-oxo-9-phenethyl-1-oxa-4,
9-diazaspiro[5.5]undecan-4-yl)benzamide
N, N-dimethyl-2-(3-oxo-9-phenethyl-4-phenyl-1-oxa-4,
9-diazaspiro[5.5]undecan-2-yl)acetamide
N, N-dimethyl-4-(2-(2-methyl-3-oxo-4-phenyl-1-oxa-4,
9-diazaspiro[5.5]undecan-9-yl)ethyl)benzamide
N-methyl-4-(2-(2-methyl-3-oxo-4-phenyl-1-oxa-4,9-di-
azaspiro[5.5]undecan-9-yl)ethyl)benzamide
3-(2-(4-(2-fluorophenyl)-2-methyl-3-oxo-1-oxa-4,9-diaz-
aspiro[5.5]undecan-9-yl)ethyl)-N-methylbenzamide
9-(2-hydroxy-2-phenylethyl)-4-((5-(trifluoromethyl)pyri-
din-2-yl)methyl)-1-oxa-4,9-diazaspiro[5.5]undecan-3-
one
9-(2-(6-aminopyridin-3-yl)ethyl)-2-methyl-4-phenyl-1-
oxa-4,9-diazaspiro[5.5]undecan-3-one
4-(2-fluorophenyl)-9-(2-(2-hydroxyethoxy)phenethyl)-2-
isopropyl-1-oxa-4,9-diazaspiro[5.5]undecan-3-one
4-(2-fluorophenyl)-9-(3-(2-hydroxyethoxy)phenethyl)-2-
methyl-1-oxa-4,9-diazaspiro[5.5]undecan-3-one
2-(hydroxymethyl)-9-phenethyl-4-phenyl-1-oxa-4,9-di-
azaspiro[5.5]undecan-3-one
4-((1H-imidazol-2-yl)methyl)-9-phenethyl-1-oxa-4,9-di-
azaspiro[5.5]undecan-3-one
9-benzyl-4-(2-hydroxyphenyl)-1-oxa-4,9-diazaspiro[5.5]
undecan-3-one
4-(2-hydroxyphenyl)-9-phenethyl-1-oxa-4,9-diazaspiro
[5.5]undecan-3-one
9-benzyl-4-(3-hydroxyphenyl)-1-oxa-4,9-diazaspiro[5.5]
undecan-3-one
4-(3-hydroxyphenyl)-9-phenethyl-1-oxa-4,9-diazaspiro
[5.5]undecan-3-one
9-(2-hydroxyphenethyl)-4-phenyl-1-oxa-4,9-diazaspiro
[5.5]undecan-3-one
9-(4-hydroxyphenethyl)-4-phenyl-1-oxa-4,9-diazaspiro
[5.5]undecan-3-one
9-(3-hydroxyphenethyl)-4-phenyl-1-oxa-4,9-diazaspiro
[5.5]undecan-3-one
4-(4-hydroxyphenyl)-2-methyl-9-phenethyl-1-oxa-4,9-
diazaspiro[5.5]undecan-3-one
4-(3-hydroxyphenyl)-2-methyl-9-phenethyl-1-oxa-4,9-
diazaspiro[5.5]undecan-3-one
9-(2-hydroxyphenethyl)-2-methyl-4-phenyl-1-oxa-4,9-
diazaspiro[5.5]undecan-3-one
4-(2-hydroxyphenyl)-2-methyl-9-phenethyl-1-oxa-4,9-
diazaspiro[5.5]undecan-3-one
4-(2-fluorophenyl)-9-(2-hydroxyphenethyl)-2-isopropyl-
1-oxa-4,9-diazaspiro[5.5]undecan-3-one
4-(2-fluorophenyl)-9-(3-hydroxyphenethyl)-2-methyl-1-
oxa-4,9-diazaspiro[5.5]undecan-3-one
9-(2-hydroxyphenethyl)-4-(pyridin-2-ylmethyl)-1-oxa-4,
9-diazaspiro[5.5]undecan-3-one
4-(2-fluorophenyl)-2-(hydroxymethyl)-9-(2-hydroxy-
phenethyl)-1-oxa-4,9-diazaspiro[5.5]undecan-3-one
4-(2-fluorophenyl)-2-(3-hydroxypropyl)-9-phenethyl-1-
oxa-4,9-diazaspiro[5.5]undecan-3-one
9-(2-(2-aminothiazol-4-yl)ethyl)-4-(2-fluorophenyl)-2-
methyl-1-oxa-4,9-diazaspiro[5.5]undecan-3-one
9-(2-(2-aminothiazol-4-yl)ethyl)-4-((5-(trifluoromethyl)
pyridin-2-yl)methyl)-1-oxa-4,9-diazaspiro[5.5]unde-
can-3-one
9-(2-(5-amino-1H-pyrazol-1-yl)ethyl)-2-methyl-4-phe-
nyl-1-oxa-4,9-diazaspiro[5.5]undecan-3-one
9-(2-(2-aminothiazol-4-yl)ethyl)-4-(2-fluorophenyl)-2-
isopropyl-1-oxa-4,9-diazaspiro[5.5]undecan-3-one
9-(2-(2-aminothiazol-4-yl)ethyl)-2-methyl-4-(4-(trifluo-
romethyl)pyridin-3-yl)-1-oxa-4,9-diazaspiro[5.5]unde-
can-3-one
4-(2-fluorophenyl)-9-phenethyl-2-((tetrahydro-2H-
pyran-4-yl)methyl)-1-oxa-4,9-diazaspiro[5.5]undecan-
3-one
4-(2-fluorophenyl)-2-isopropyl-9-phenethyl-1-oxa-4,9-
diazaspiro[5.5]undecan-3-one
4-(2-fluorophenyl)-2-isopropyl-9-(2-(pyridin-2-yl)ethyl)-
1-oxa-4,9-diazaspiro[5.5]undecan-3-one
4-(2-fluorophenyl)-2-(3-methoxypropyl)-9-phenethyl-1-
oxa-4,9-diazaspiro[5.5]undecan-3-one
N-methyl-2-(2-methyl-3-oxo-4-phenyl-1-oxa-4,9-diaz-
aspiro[5.5]undecan-9-yl)-N-phenylacetamide
(R)-2-benzyl-9-phenyl-6-oxa-2,9-diazaspiro[4.5]decan-
8-one
(S)-2-benzyl-9-phenyl-6-oxa-2,9-diazaspiro[4.5]decan-8-
one;
optionally as a stereoisomer, including enantiomers and
diastereomers, a racemate or in form of a mixture of at
least two stereoisomers, including enantiomers and/or
diastereomers, in any mixing ratio, or a corresponding
salt thereof.
20. A process for the preparation of a compound of
formula Ia

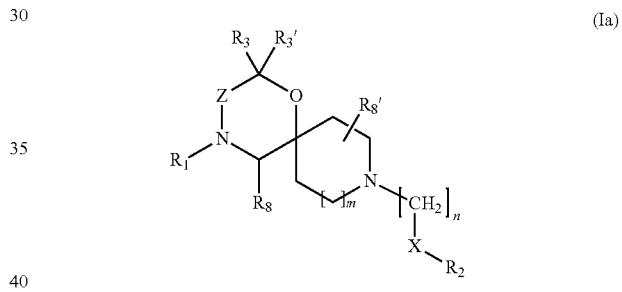

(Ia)

wherein
Z is —C(O)—;
m is 1;
n is 1, 2 or 3;
$R_1$ is substituted or unsubstituted aryl, substituted or
unsubstituted heterocyclyl, substituted or unsubstituted
alkylaryl, substituted or unsubstituted alkylheterocy-
clyl or —(CH$_2$)$_r$—W—$R_1$;
r is 0, 1 or 2;
W is —CH$_2$O—, —CH$_2$C(O)NR$_5$—, —CH$_2$C(O)O—,
—CH$_2$C(O)— or —C(CH$_3$)$_2$O—;
$R_{1'}$ is H, —CN, substituted or unsubstituted heterocyclyl,
substituted or unsubstituted aryl, substituted or unsub-
stituted cycloalkyl or $R_5$;
wherein the aryl, heterocyclyl or cycloalkyl in $R_1$ or $R_{1'}$,
if substituted, also in alkylaryl or alkylheterocyclyl, are
substituted with substituents selected from the group
consisting of —$R_5$, —OR$_5$, halogen, —CN, —NO$_2$,
—NR$_5$R$_{5'''}$, —C(O)OR$_8$, NR$_5$C(O)R$_{5'}$, —C(O)NR$_5$R$_{5'}$,
—NR$_5$S(O)$_2$R$_5$, =O, —OCH$_2$CH$_2$OH, —NR$_5$C(O)
NR$_5$R$_{5'''}$, —S(O)$_2$NR$_5$R$_{5'}$, —NR$_5$S(O)$_2$NR$_5$R$_{5'''}$,
haloalkyl, haloalkoxy, —SR$_5$, —S(O)R$_5$ and —S(O)
$_2$R$_5$;
and wherein "aryl" is a monocyclic aryl and "heterocy-
clyl" is a heterocyclic ring system of one or two
saturated or unsaturated rings of which at least one ring contains one or more heteroatoms from the group consisting of nitrogen, oxygen and/or sulfur in the ring;

X is a bond, —C(O)O—, —C(O)NR$_5$—, —C(O)—, —O— or —C(R$_4$R$_{4'}$)—;

R$_2$ is H, substituted or unsubstituted aryl, substituted or unsubstituted heterocyclyl, substituted or unsubstituted cycloalkyl, substituted or unsubstituted C$_{1-6}$ alkyl, substituted or unsubstituted C$_{2-6}$ alkenyl or substituted or unsubstituted C$_{2-6}$ alkynyl;

wherein the aryl, heterocyclyl or cycloalkyl in R$_2$, if substituted, also in alkylaryl, alkylcycloalkyl or alkylheterocyclyl, is substituted with substituents selected from the group consisting of —R, —OR$_5$, halogen, —CN, —NO$_2$, —NR$_5$R$_{5'''}$, —C(O)OR$_5$, —NR$_5$C(O)R$_{5'}$, —C(O)NR$_5$R$_{5'}$, —NR$_5$S(O)$_2$R$_{5'}$, =O, —OCH$_2$CH$_2$OH, —NR$_5$C(O)NR$_5$R$_{5'''}$, —S(O)$_2$NR$_5$R$_{5'}$, —NR$_5$S(O)$_2$NR$_5$R$_{5'''}$, haloalkyl, -haloalkoxy, —SR$_5$, —S(O)R$_5$ and —S(O)$_2$R$_5$;

and wherein "aryl" is a monocyclic aryl and "heterocyclyl" is a heterocyclic ring system of one or two saturated or unsaturated rings of which at least one ring contains one or more heteroatoms from the group consisting of nitrogen, oxygen and/or sulfur in the ring;

R$_3$ and R$_{3'}$ are independently selected from the group consisting of H, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl, substituted or unsubstituted heterocyclyl, substituted or unsubstituted alkylaryl, substituted or unsubstituted alkylheterocyclyl, and substituted or unsubstituted alkylcycloalkyl; wherein the aryl, cycloalkyl and heterocyclyl as defined in R$_3$, also in alkylaryl, alkylcycloalkyl or alkylheterocyclyl, if substituted, are substituted with substituents selected from the group consisting of —OR$_5$, halogen, —CN, haloalkyl, haloalkoxy, —SR$_5$, —S(O)R$_5$ and —S(O)$_2$R$_5$;

and wherein "aryl" is a monocyclic aryl and "heterocyclyl" is a heterocyclic ring system of one or two saturated or unsaturated rings of which at least one ring contains one or more heteroatoms from the group consisting of nitrogen, oxygen and/or sulfur in the ring;

R$_4$ is H, —OR$_5$, substituted or unsubstituted C$_{1-6}$ alkyl, substituted or unsubstituted C$_{2-6}$ alkenyl, substituted or unsubstituted C$_{2-6}$ alkynyl, —COOR$_5$, —CONR$_5$R$_{5'}$, —NR$_5$COR$_{5'}$, —NR$_5$R$_{5'''}$, or substituted or unsubstituted heterocyclyl, substituted or unsubstituted aryl, or substituted or unsubstituted cycloalkyl, wherein the aryl, cycloalkyl and heterocyclyl as defined in R$_4$, if substituted, are substituted with substituents selected from the group consisting of —OR$_5$, halogen, —CN, haloalkyl, haloalkoxy, —SR$_5$, —S(O)R$_5$ and —S(O)$_2$R$_5$;

and wherein "aryl" is a monocyclic aryl and "heterocyclyl" is a heterocyclic ring system of one or two saturated or unsaturated rings of which at least one ring contains one or more heteroatoms from the group consisting of nitrogen, oxygen and/or sulfur in the ring;

R$_{4'}$ is H, substituted or unsubstituted C$_{1-6}$ alkyl, substituted or unsubstituted C$_{2-6}$ alkenyl or substituted or unsubstituted C$_{2-6}$ alkynyl;

R$_5$, R$_{5'}$, and R$_{5''}$ are independently selected from the group consisting of H, unsubstituted C$_{1-6}$ alkyl, unsubstituted C$_{2-6}$ alkenyl, unsubstituted C$_{2-6}$ alkynyl, and unsubstituted aryl and unsubstituted alkylaryl;

and wherein "aryl" is a monocyclic aryl;

R$_{5'''}$ is H, unsubstituted C$_{1-6}$ alkyl, unsubstituted C$_{2-6}$ alkenyl, unsubstituted C$_{2-6}$ alkynyl or -Boc;

R$_8$ and R$_{8'}$ are independently selected from the group consisting of H, —OR$_5$, halogen, substituted or unsubstituted C$_{1-6}$ alkyl, substituted or unsubstituted C$_{2-6}$ alkenyl and substituted or unsubstituted C$_{2-6}$ alkynyl;

wherein the alkyl, alkenyl and alkynyl as defined in R$_1$, R$_{1'}$, R$_2$, R$_3$, R$_{3'}$, R$_4$, R$_{4'}$, R$_8$, and R$_{8'}$, if substituted, are substituted with substituents selected from the group consisting of —OR$_5$, halogen, —CN, haloalkyl, haloalkoxy, —SR$_5$, —S(O)R$_5$, —S(O)$_2$R$_5$, C(O)OR$_5$ and C(O)NR$_5$R$_{5'}$;

with the proviso that the the following compounds are excluded from formula Ia:

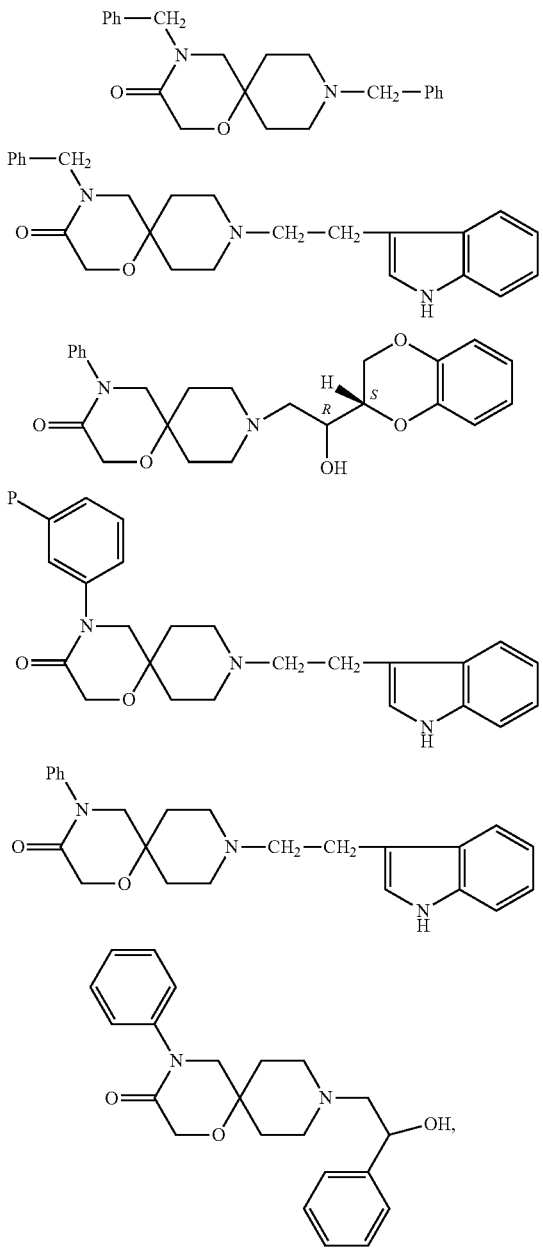

which comprises the steps (a) reacting a compound of formula Va

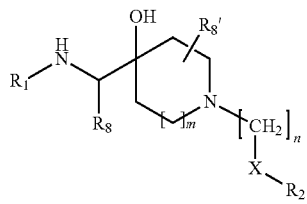

(Va)

with a compound of formula VI

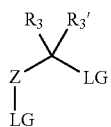

(VI)

wherein LG is a leaving group, to obtain a compound of formula VIIa

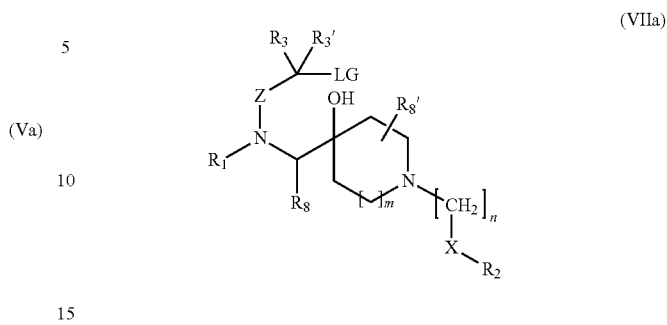

(VIIa)

and (b) Carrying out a cyclisation of the resulting compound in a suitable solvent, in the presence of a strong base and at a temperature comprised between −78° C. and the reflux temperature.

21. A pharmaceutical composition which comprises the compound according to claim 1, or a pharmaceutically acceptable salt thereof, and a pharmaceutically acceptable carrier, adjuvant or vehicle.

22. 3-(2-methyl-3-oxo-9-phenethyl-11-oxa-4,9-diazaspiro[5.5]undecan-4-yl)benzonitrile, optionally as a stereoisomer, including enantiomers and diastereomers, a racemate or in form of a mixture of at least two stereoisomers, including enantiomers and/or diastereomers, in any mixing ratio, or a corresponding salt thereof.

* * * * *

UNITED STATES PATENT AND TRADEMARK OFFICE
CERTIFICATE OF CORRECTION

PATENT NO. : 10,703,765 B2
APPLICATION NO. : 15/314595
DATED : July 7, 2020
INVENTOR(S) : Marina Virgili-Bernado et al.

It is certified that error appears in the above-identified patent and that said Letters Patent is hereby corrected as shown below:

On the Title Page

Item (56), Column 2

Under Foreign Patent Documents: Reference 13: 7/2009 should read 7/2003.

Under Other Publications: Reference 1: Chemicalabstracts should read Chemical Abstracts.

In the Claims

Column 294, Claim 1, Line 48: should read Y is after the formula.

Column 296, Claim 1, Line 48: P should read F.

Column 299, Claim 19, Line 33: delete this line.

Column 301, Claim 19, Lines 55-57: delete these lines.

Column 303, Claim 19, Lines 46-47: delete these lines.

Column 308, Claim 19, Lines 17-20: delete these lines.

Column 310, Claim 20, Line 37: P should read F.

Signed and Sealed this
Twentieth Day of October, 2020

Andrei Iancu
*Director of the United States Patent and Trademark Office*